(12) United States Patent
Matinkhoo et al.

(10) Patent No.: US 12,195,439 B1
(45) Date of Patent: *Jan. 14, 2025

(54) C1-SUBSTITUTED ISOPROPYLAMINE FUSED HETEROCYCLIC MESCALINE DERIVATIVES

(71) Applicant: Enveric Biosciences Canada Inc., Calgary (CA)

(72) Inventors: Kaveh Matinkhoo, Calgary (CA); David James Press, Calgary (CA); Glynnis Elizabeth Jensen, Calgary (CA); Jillian M. Hagel, Calgary (CA); Peter J. Facchini, Calgary (CA)

(73) Assignee: Enveric Biosciences Canada Inc., Calgary (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/494,382

(22) Filed: Oct. 25, 2023

Related U.S. Application Data

(60) Provisional application No. 63/419,157, filed on Oct. 25, 2022.

(51) Int. Cl.
| | | |
|---|---|---|
| *C07D 317/58* | (2006.01) | |
| *A61P 25/00* | (2006.01) | |
| *C07D 319/18* | (2006.01) | |
| *C07D 405/06* | (2006.01) | |

(52) U.S. Cl.
CPC ............ *C07D 317/58* (2013.01); *A61P 25/00* (2018.01); *C07D 319/18* (2013.01); *C07D 405/06* (2013.01)

(58) Field of Classification Search
CPC .................................................. C07D 317/58
See application file for complete search history.

(56) References Cited

U.S. PATENT DOCUMENTS

| 1,964,973 | A | * | 7/1934 | Bockmuhl | ............ | C07D 317/58 |
| | | | | | | 549/520 |
| 8,101,605 | B2 | | 1/2012 | MacKenzie et al. | | |
| 8,765,994 | B2 | | 7/2014 | Andersen et al. | | |
| 9,000,050 | B2 | | 4/2015 | Wang et al. | | |

FOREIGN PATENT DOCUMENTS

WO 2019/140265 A1 7/2019

OTHER PUBLICATIONS

Sharp et al. ("Bases derived from some substituted propenylbenzenes; preparation of pure methylamine," Journal of the Chemical Society, 1931, 1468-1478).*
RN 1893019-18-5 (Apr. 19, 2016).
RN 2794360-21-5 (Jul. 20, 2022).
RN 1346746-92-6 (Dec. 1, 2011).
RN 1881280-15-4 (Mar. 7, 2016).
RN 1346601-54-4 (Nov. 30, 2011).
RN 1225844-34-7 (May 30, 2010).
RN 857543-41-0 (Jul. 29, 2005).
RN 860590-50-7 (Aug. 17, 2005).
RN 856081-72-6 (Jul. 20, 2005).
McMillan, A. E. et al "Stereoretentive Etherification of an α-Aryl-β-amino Alcohol Using a Selective Aziridinium Ring Opening for the Synthesis of AZD7594" Journal of Organic Chemistry 2019, 84(8), 4629-4638 (Jun. 19, 2018).
Kolaczynska, K.E. et al. "The Pharmacological Profile of Second Generation Pyrovalerone Cathinones and Related Cathinone Derivative" International Journal of Molecular Science 2021, 22(15), 8277 (Jul. 30, 2021).
Meetani, M.A. et al. "Enantioseparation of Synthetic Cathinones Enantiomers with Tertiary Amine Structure in Urine and Plasma" Journal of Chromatographic Science, 2019, 57(4), 361-368 (Feb. 7, 2019).
Iversen, L. et al. "Neurochemical Profiles of Some Novel Psychoactive Substances" European Journal of Pharmacology 2013, 700(1-3), 147-151 (Dec. 21, 2012).
Springer, D. et al. "Metabolism and toxicological detection of the new designer drug 3',4'-methylenedioxy-α-pyrrolidinopropiophenone studied in urine using gas chromatography—mass spectrometry" Journal of Chromatography B, 2003, 793(2), 377-388 (Aug. 15, 2003).
Chandrasekhar, S. et al. "Highly efficient synthesis of 3-alkyl/aryl-4-aryl-1,2,3,4-tetrahydroisoquinolines from N,N-dibenzylaminols" Tetrahedron Letters, 2002, 43(10) 1885-1888 (Mar. 4, 2002).
Aoyama, T. et al. "A New Class of Highly Potent Farnesyl Diphosphate-Competitive Inhibitors of Farnesyltransferase" Journal of Medicinal Chemistry, 1998, 41(2), 143-147 (Jan. 15, 1998).

* cited by examiner

*Primary Examiner* — Yong S. Chong
(74) *Attorney, Agent, or Firm* — SMART & BIGGAR LP; Michael Fenwick

(57) ABSTRACT

Disclosed are novel fused mescaline derivative compounds, notably $C_1$-substituted isopropylamine fused heterocyclic mescaline derivatives, including $C_1$-substituted isopropylamine fused dioxolane and fused dioxane mescaline derivatives, and pharmaceutical and recreational drug formulations containing the same. Methods of making and using these compounds are also disclosed.

21 Claims, 24 Drawing Sheets

C1-SUBSTITUTED ISOPROPYLAMINE FUSED HETEROCYCLIC MESCALINE DERIVATIVES

RELATED APPLICATION

This application claims the benefit of U.S. Provisional Application No. 63/419,157 filed Oct. 25, 2022; the entire content of U.S. Patent Application No. 63/419,157 is hereby incorporated by reference.

FIELD OF THE DISCLOSURE

The compositions and methods disclosed herein relate to a chemical compound known as mescaline. Furthermore, the compositions and methods disclosed herein, in particular, relate to fused heterocyclic mescaline derivatives, and more in particular to fused heterocyclic mescaline derivatives possessing a substituted isopropylamine chain.

BACKGROUND OF THE DISCLOSURE

The following paragraphs are provided by way of background to the present disclosure. They are not however an admission that anything discussed therein is prior art or part of the knowledge of a person of skill in the art.

The biochemical pathways in the cells of living organisms may be classified as being part of primary metabolism, or as being part of secondary metabolism. Pathways that are part of a cell's primary metabolism are involved in catabolism for energy production or in anabolism for building block production for the cell. Secondary metabolites, on the other hand, are produced by the cell without having an obvious anabolic or catabolic function. It has long been recognized that secondary metabolites can be useful in many respects, including as therapeutic compounds.

Mescaline (chemical name 3,4,5 trimethoxyphenethylamine), for example, is a secondary metabolite that is naturally produced by certain cactus species belonging to a variety of genera within the plant family of Cactaceae. Cactus species which can produce mescaline include, for example, cactus species belonging to the genus *Lophophora*, including *Lophophora williamsii* (peyote) and *Lophophora diffusa* and cactus species belonging to the genus *Echinopsis/Trichocereus*, including *Echinopsis pachanoi/Trichocereus pachanoi* (also known as San Pedro), *Echinopsis peruviana/Trichocereus peruvianus* (also known as Peruvian torch), (*Echinopsis lageniformis/Trichocereus bridgesihi* (also known as Bolivian torch), and *Echinopsis scopulicola/ Trichocereus scopulicola*.

The interest of the art in mescaline is well established. Thus, for example, mescaline is a psychoactive compound and is therefore used as a recreational drug. Mescaline is also used in Native American religious ceremonies, and for spiritual purposes by Andean indigenous cultures. Furthermore, mescaline has been evaluated for its potential in the treatment of addictions, notably alcohol addiction (Bogenschutz, M. P. and Johnson M. W. (2016), Prog. In Neuro-Psychopharmacol. & Biol. Psychiatry 64; 250-258; Romeu, A. G. et al. (2017), Exp. Clin. Psychopharmacol. 2016 August; 24(4): 229-268).

Although the toxicity of mescaline is low, adverse side effects, including, for example, panic attacks, paranoia, and psychotic states, sometimes together or individually referred to as "a bad trip", are not infrequently experienced by mescaline users. Furthermore, mescaline can induce nausea and vomiting.

There exists therefore a need in the art for improved mescaline compounds.

SUMMARY OF THE DISCLOSURE

The following paragraphs are intended to introduce the reader to the more detailed description, not to define or limit the claimed subject matter of the present disclosure.

In one aspect, the present disclosure relates to mescaline and derivative compounds.

In another aspect, the present disclosure relates to fused heterocyclic mescaline derivatives, and methods of making and using these compounds.

In another aspect, the present disclosure relates to fused heterocyclic mescaline derivatives having a substituted isopropylamine chain and methods of making and using these compounds.

Accordingly, in one aspect, the present disclosure provides, in at least one embodiment, in accordance with the teachings herein, a chemical compound having chemical formula (I) or chemical formula (II):

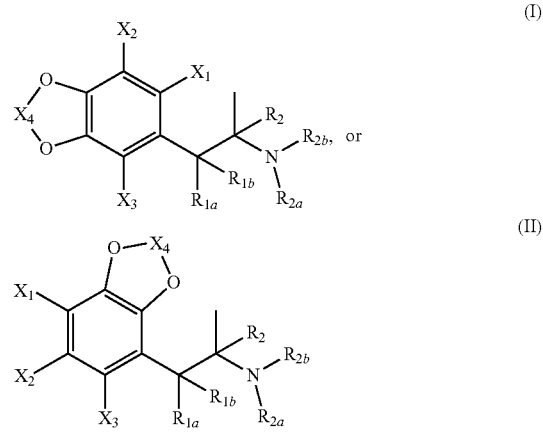

wherein, in chemical formula (I) and chemical formula (II):
  $X_1$, $X_2$, and $X_3$ are independently selected from a hydrogen atom, O-alkyl, N-alkyl, OH, a halogen, or $NH_2$;
  $X_4$ is an alkylene group or substituted alkylene group;
  $R_{1a}$ is an alkyl group, O-alkyl group, a halogen, or OH, $R_{1b}$ is a hydrogen atom or a halogen, or $R_{1a}$ and $R_{1b}$ are joined together to form an oxo group;
  $R_2$ is a hydrogen atom or an O-alkyl group; and
  $R_{2a}$ and $R_{2b}$ are independently selected from an alkyl group, an optionally substituted alkyl-aryl group, or a hydrogen atom, or $R_{2a}$ and $R_{2b}$ are joined together, along with the nitrogen atom to which they are attached, to form a 3-10-membered optionally substituted heterocyclic ring.

In at least one embodiment, in an aspect, $X_4$ can be a $C_1$-$C_3$ alkylene group.

In at least one embodiment, in an aspect, $X_4$ can be an alkylene group having one carbon.

In at least one embodiment, in an aspect, $X_4$ can be an alkylene group having two carbons.

In at least one embodiment, in an aspect, the chemical compound can have a chemical formula ($I_b$) or ($II_b$):

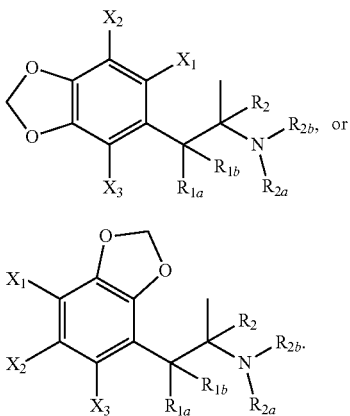

(I_b)

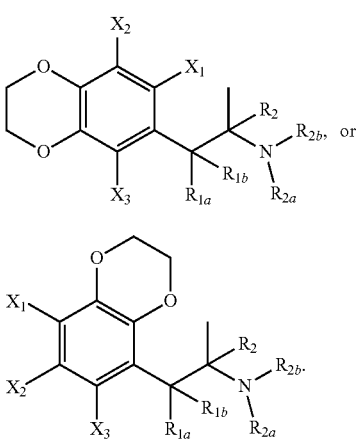

(II_b)

In at least one embodiment, in an aspect, the chemical compound can have a chemical formula (I_c) or (II_c):

(I_c)

(II_c)

In at least one embodiment, in an aspect, the amino group ($-NR_{2a}R_{2b}$) in the compound of formula (I) or formula (II) can be protonated to form ($-N_+HR_{2a}R_{2b}$), and chemical formula (I) or formula (II) further includes a negatively charged anion balancing the positively charged nitrogen atom.

In at least one embodiment, in an aspect, $X_1$, $X_2$, $X_3$, and $R_2$ are each a hydrogen atom (H).

In at least one embodiment, in an aspect, $R_{1a}$ can be an alkyl group, O-alkyl group, a halogen, or OH group, and $R_{1b}$ can be a hydrogen atom.

In at least one embodiment, in an aspect, $R_{1a}$ can be a ($C_1$-$C_6$)-alkyl group and $R_{1b}$ can be a hydrogen atom.

In at least one embodiment, in an aspect, Ria can be a ($C_1$-$C_3$)-alkyl group and $R_{1b}$ can be a hydrogen atom.

In at least one embodiment, in an aspect, $R_{1a}$ can be a methyl or ethyl group and $R_{1b}$ can be a hydrogen atom.

In at least one embodiment, in an aspect, Ria can be fluorine (F) and $R_{1b}$ can be a hydrogen atom.

In at least one embodiment, in an aspect, $R_{1a}$ and $R_{1b}$ can each be fluorine (F).

In at least one embodiment, in an aspect, $R_{1a}$ can be a hydroxy group, and $R_{1b}$ can be a hydrogen atom.

In at least one embodiment, in an aspect, $R_{1a}$ and $R_{1b}$ can be joined together to form an oxo group.

In at least one embodiment, in an aspect, $R_2$ can be a hydrogen atom.

In at least one embodiment, in an aspect, $R_{2a}$ and $R_{2b}$ can be independently selected from a hydrogen atom, an optionally substituted alkyl-aryl group, or an alkyl group, In at least one embodiment, in an aspect, the alkyl group can be a ($C_1$-$C_6$)-alkyl group.

In at least one embodiment, in an aspect, the alkyl group can be a ($C_1$-$C_3$)-alkyl group.

In at least one embodiment, in an aspect, the alkyl group can be a methyl group.

In at least one embodiment, in an aspect, the optionally substituted alkyl-aryl group can be a ($C_1$-$C_6$)-alkyl-aryl group, wherein the aryl group is optionally substituted.

In at least one embodiment, in an aspect, the optionally substituted alkyl-aryl group can be a ($C_1$-$C_6$)-alkyl-phenyl group, wherein the phenyl group is optionally substituted.

In at least one embodiment, in an aspect, the optionally substituted alkyl-aryl group can be a ($C_1$-$C_3$)-alkyl-phenyl group, wherein the phenyl group is optionally substituted.

In at least one embodiment, in an aspect, the optionally substituted alkyl-aryl group can be a $-CH_2$-phenyl group, wherein the phenyl group is optionally substituted.

In at least one embodiment, in an aspect, the optionally substituted alkyl-aryl group can be a ($C_1$-$C_3$)-alkyl-phenyl group, wherein the phenyl group is substituted by at least one of a halogen atom, an O-alkyl group, and additionally two adjacent substituents are joined together, along with the carbon atoms from the phenyl group to form a ($C_5$-$C_{10}$)-heterocycle.

In at least one embodiment, the ($C_5$-$C_{10}$)-heterocycle can be a $C_5$ heterocycle including two oxygen hetero atoms.

In at least one embodiment, in an aspect, the optionally substituted alkyl-aryl group can be a $-CH_2$-phenyl group, wherein the phenyl group is substituted by a halogen atom, and additionally two adjacent substituents are joined together, along with the carbon atoms from the phenyl group to form a ($C_5$)-heterocycle.

In at least one embodiment, in an aspect, the optionally substituted alkyl-aryl group can be a $-CH_2$-phenyl group, wherein the phenyl group is substituted by an ($C_1$-$C_6$)—O—alkyl group, and additionally two adjacent substituents are joined together, along with the carbon atoms from the phenyl group to form a ($C_5$)-heterocycle.

In at least one embodiment, in an aspect, the optionally substituted alkyl-aryl group can be a $-CH_2$-phenyl group, wherein the phenyl group is substituted by an ($C_1$-$C_3$)—O—alkyl group, and additionally two adjacent substituents are joined together, along with the carbon atoms from the phenyl group to form a ($C_5$)-heterocycle.

In at least one embodiment, in an aspect, the optionally substituted alkyl-aryl group can be a $-CH_2$-phenyl group, wherein the phenyl group is substituted by a methoxy group, and additionally two adjacent substituents are joined together, along with the carbon atoms from the phenyl group to form a ($C_5$)-heterocycle.

In at least one embodiment, in an aspect, $R_{2a}$ and $R_{2b}$ can together form a 4-10 membered heterocyclic ring.

In at least one embodiment, in an aspect, the chemical compound having formula (I) can be selected from the group of compounds having chemical formula (A); (B); (C); (D); ($E_x$); and ($E_y$):

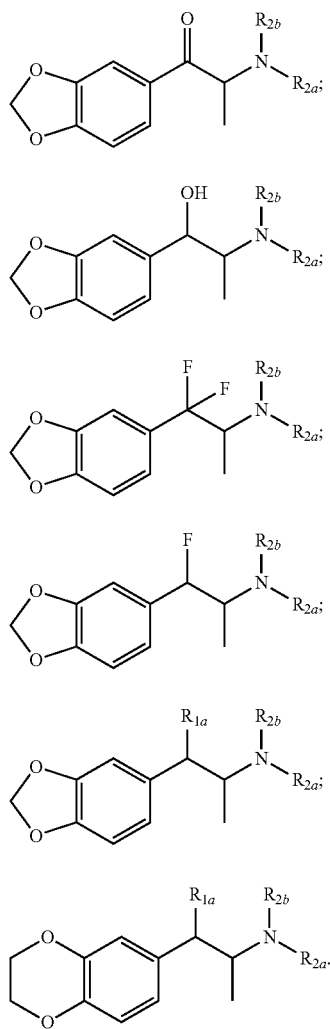
(A)
(B)
(C)
(D)
($E_x$)
($E_y$)
In at least one embodiment, in an aspect, the chemical compound having formula (I) can be selected from the group of compounds having the chemical formula: A(I)-A(III); B(I)-(VI); C(I)-C(VI); D(I)-D(VI); and $E_x$(I)-$E_y$(VIII):
(A): A(I); A(II); and A(III):
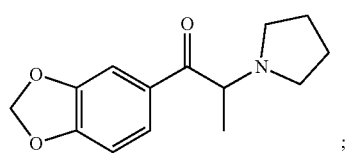
A(I)
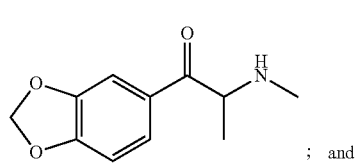
A(II)
; and
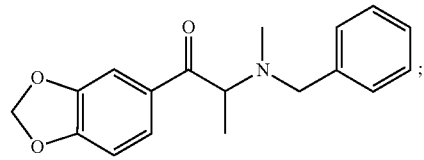
A(III)
(B): B(I); B(II); B(III); B(IV); B(V); and B(VI):
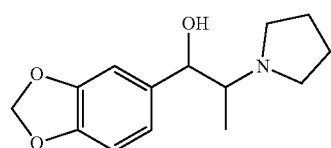
B(I)
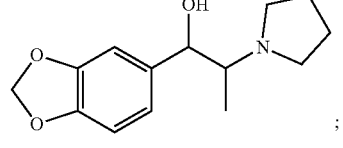
B(II)
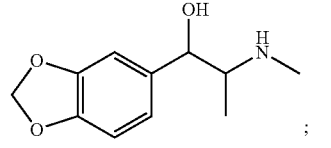
B(III)
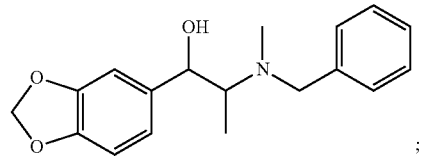
B(IV)
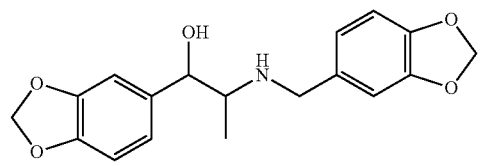
B(V)
; and
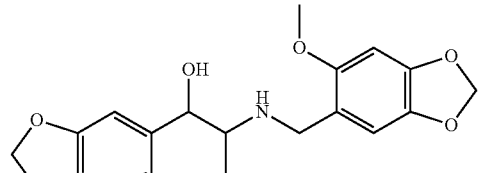
B(VI)
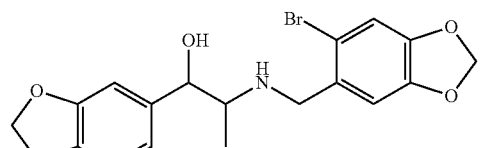

(C): C(I); C(II); C(III); C(IV); C(V); and C(VI):
C(I)
C(II)
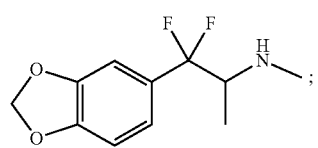
C(III)
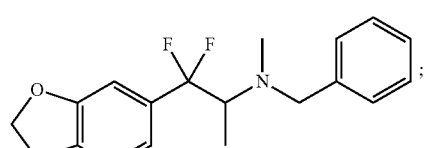
C(IV)
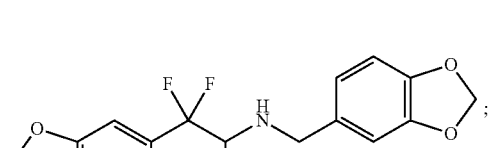
C(V)
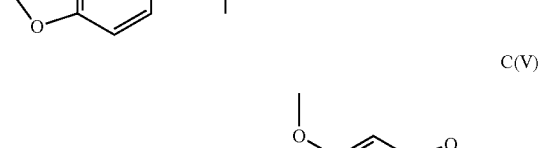
; and
C(VI)
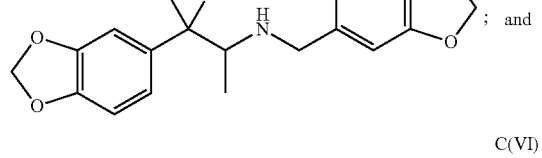
(D): D(I); D(II); D(III); D(IV); D(V); and D(VI):
D(I)
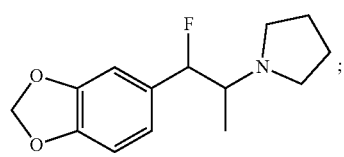
D(II)
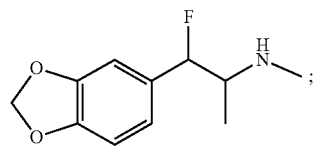
D(III)
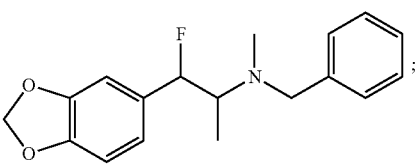
D(IV)
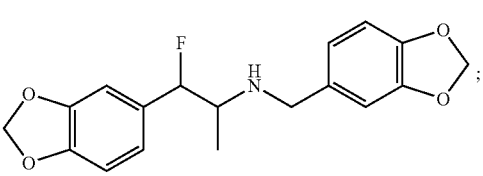
D(V)
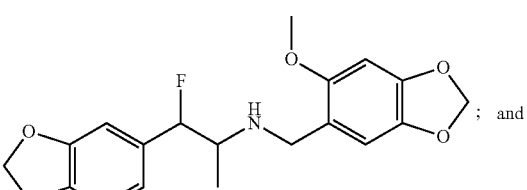
; and
D(VI)
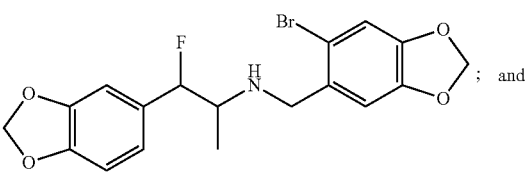
; and
(E): $E_x(I)$; $E_x(II)$; $E_x(III)$; $E_x(IV)$; $E_x(V)$; $E_x(VI)$; $E_x(VII)$; and $E_y(VIII)$:
$E_x(I)$
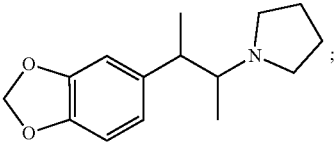
$E_x(II)$
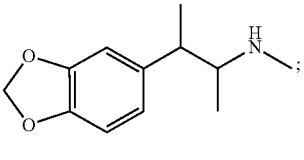
$E_x(III)$
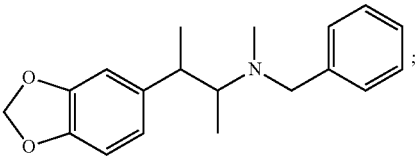
$E_x(IV)$
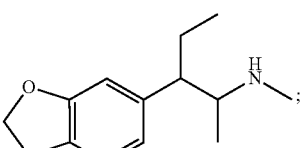

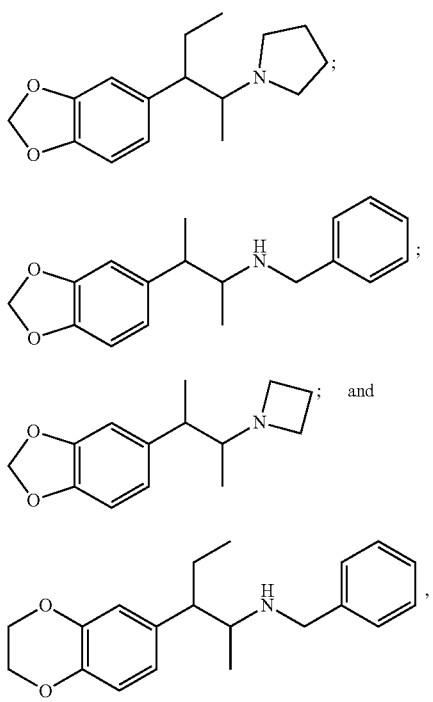

Ex(V);

Ex(VI);

Ex(VII); and

Ey(VIII),

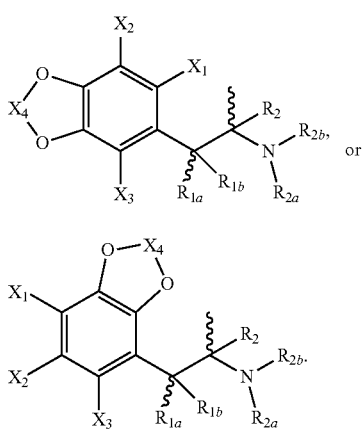

wherein in each of compound A(i) to E_y(VIII), optionally, the nitrogen atom of the isopropylamine portion may be protonated and includes a negatively charged anion balancing the positively charged nitrogen atom.

In at least one embodiment, in an aspect, $R_{1a}$ can be an alkyl group, O-alkyl group, a halogen, or OH, and $R_{1b}$ can be a hydrogen atom or a halogen, provided however, $R_{1a}$ and $R_{1b}$ are not identical halogens, and the compound having chemical formula (I) or formula (II) can have the chemical formula ($I_d$) or ($II_d$):

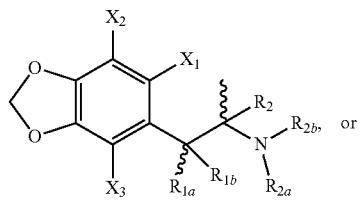

($I_d$)

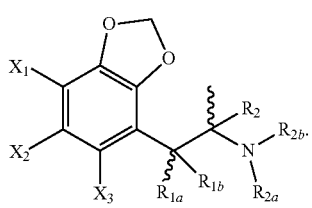

($II_d$)

In at least one embodiment, in an aspect, $R_{1a}$ can be an alkyl group, O-alkyl group, a halogen, or OH, and $R_{1b}$ can be a hydrogen atom or a halogen, provided however, that $R_{1a}$ and $R_{1b}$ are not identical halogens, and the compound having chemical formula (I) or formula (II) can have the chemical formula ($I_e$) or ($II_e$):

($I_e$)

($II_e$)

In at least one embodiment, in an aspect, $R_{1a}$ can be an alkyl group, O-alkyl group, a halogen, or OH, and $R_{1b}$ can be a hydrogen atom or a halogen, provided however, that $R_{1a}$ and $R_{1b}$ are not identical halogens, and the compound having chemical formula (I) or formula (II) can have the chemical formula ($I_f$) or ($II_f$):

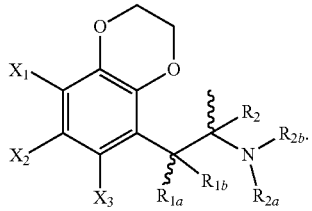

($I_f$)

($II_f$)

In at least one embodiment, in an aspect, Ria and Rib can be identical halogens, or joined together to form an oxo group, and the compound having chemical formula (I) or formula (II) can have the chemical formula ($I_g$) or ($II_g$):

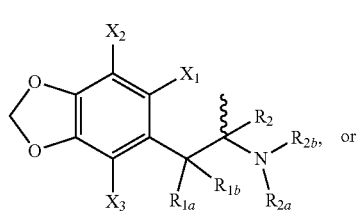

($I_g$)

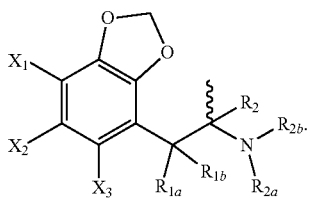
(II_g)

In at least one embodiment, in an aspect, the compound can be a compound included in a mixture of a pair of enantiomeric compounds, the mixture comprising a first and second enantiomeric compound of a pair of enantiomers of formula ($I_d$), ($II_d$), ($I_e$), ($II_e$), ($I_f$), ($II_f$), ($I_g$), or ($II_g$).

In at least one embodiment, in an aspect, the compound can be a first enantiomeric compound of a pair of enantiomers consisting of a first and second enantiomeric compounds of formula ($I_d$), ($II_d$), ($I_e$), ($II_e$), ($I_f$), ($II_f$), ($I_g$), or ($II_g$), wherein the first enantiomeric compound is substantially free of a second enantiomeric compound, the second enantiomeric compound being the other compound of the pair of enantiomers.

In at least one embodiment, in an aspect, the compound can be a compound included in a mixture of a pair of diastereomeric compounds, the mixture comprising a first and second diastereomeric compound of a pair of diastereomers of formula ($I_d$), ($II_d$), ($I_e$), ($II_e$), ($I_f$), or ($II_f$).

In at least one embodiment, in an aspect, the compound can be a first diastereomeric compound of a pair of diastereomers consisting of a first and second diastereomeric compound of formula ($I_d$), ($II_d$), ($I_e$), ($II_e$), ($I_f$), or ($II_f$), wherein the first diastereomeric compound is substantially free of a second diastereomeric compound, the second diastereomeric compound being the other diastereomeric compound of the pair of diastereomers.

In at least one embodiment, in an aspect, the chemical compound having formula ($I_d$) can be selected from the group of compounds selected from a compound having chemical formula ($B_d$); ($D_d$); ($E_{xd}$); and ($E_{yd}$), and the chemical compound having formula ($I_g$) can be selected from the group of compounds having chemical formula ($A_g$); and ($C_g$):

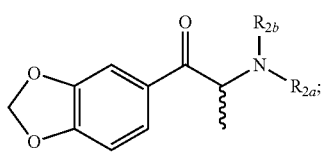
($A_g$)

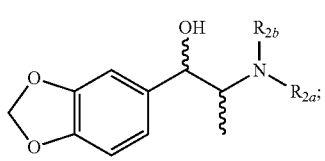
($B_d$)

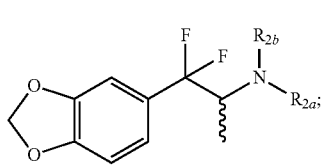
($C_g$)

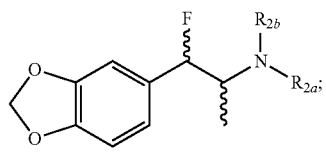
($D_d$)

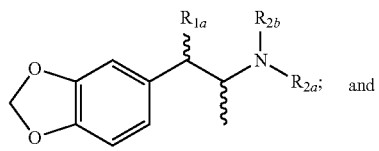
($E_{xd}$); and

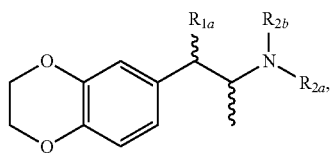
($E_{yd}$)

wherein $R_{1a}$ is an alkyl group; and wherein $R_{2a}$ and $R_{2b}$ are independently selected from an alkyl group, an optionally substituted alkyl-aryl group, or a hydrogen atom, or $R_{2a}$ and $R_{2b}$ are joined together, along with the nitrogen atom to which they are attached, to form a 3-10-membered optionally substituted heterocyclic ring.

In at least one embodiment, in an aspect, the chemical compound having formula ($I_d$) or ($I_g$) can be selected from the group of compounds selected from:

A: A($I_g$); A($II_g$); and A($III_g$):

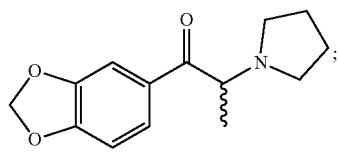
A($I_g$)

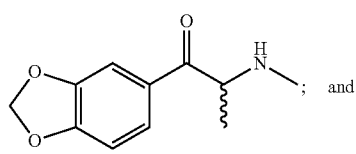
A($II_g$); and

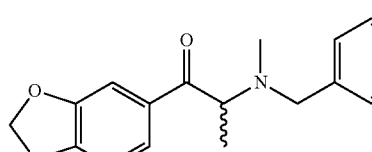
A($III_g$)

(B): B($I_d$); B($II_d$); B($III_d$); B($IV_d$); B($V_d$); and B($VI_d$):

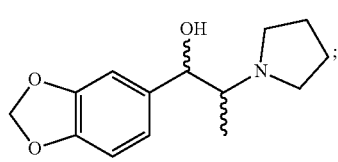
B($I_d$)

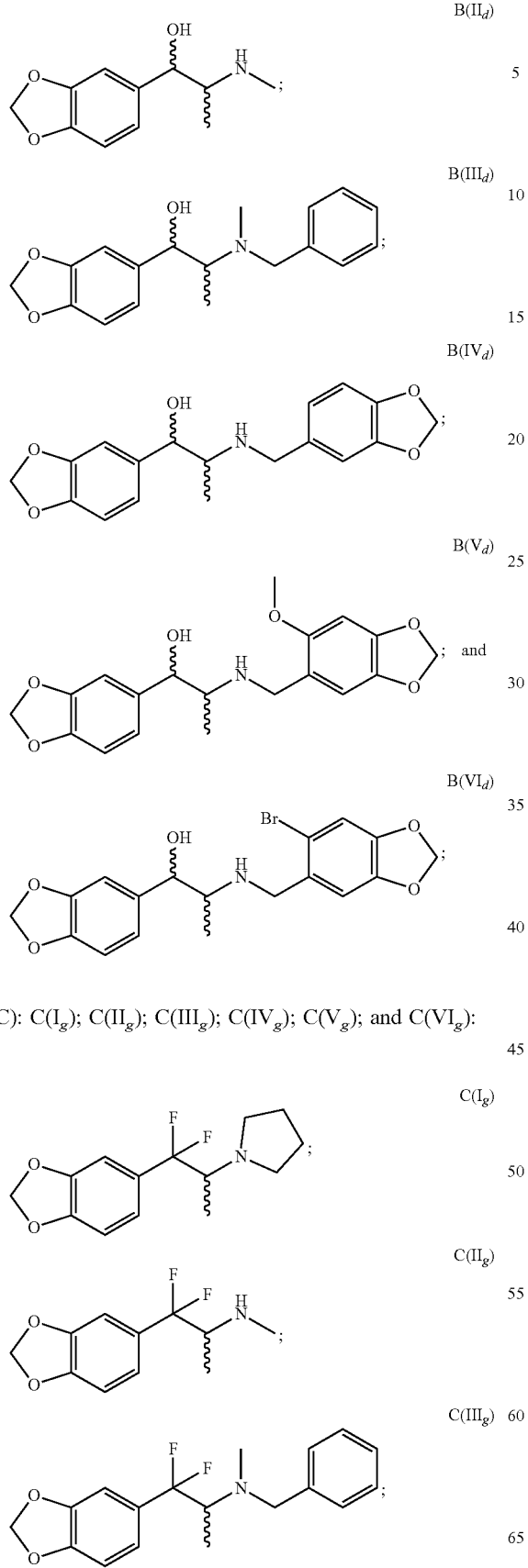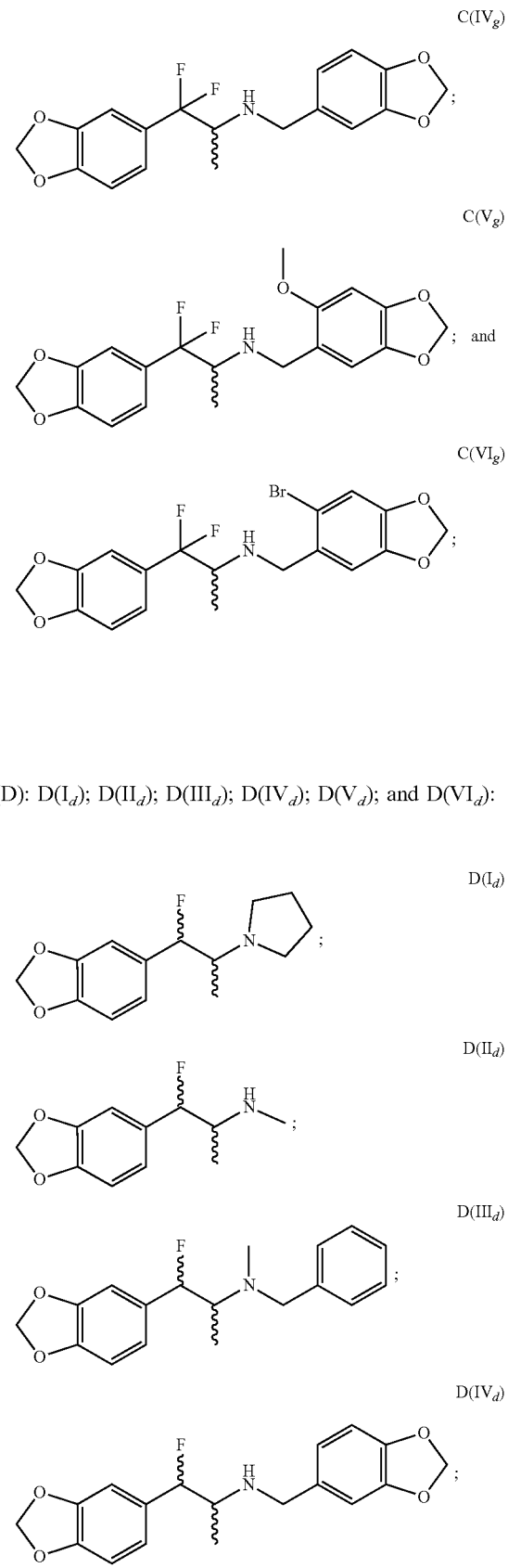

D(V$_d$)

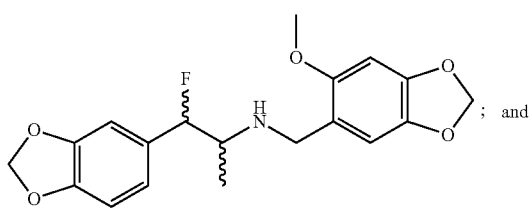
; and

D(VI$_d$)

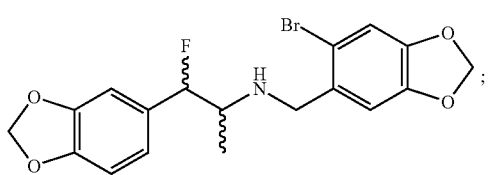
;

and (E): E$_x$(I$_d$); E$_c$(II$_d$); E$_x$(III$_d$); E$_x$(IV$_d$); E$_x$(V$_d$); E$_x$(VI$_d$); E$_x$(VII$_d$); and E$_y$(VIII$_d$):

E$_x$(I$_d$)

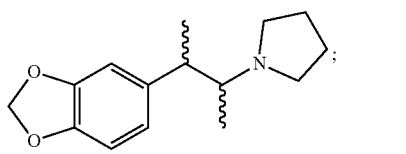

E$_x$(II$_d$)

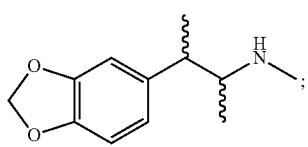

E$_x$(III$_d$)

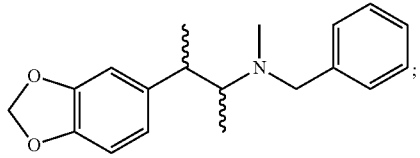

E$_x$(IV$_d$)

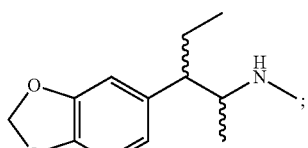

E$_x$(V$_d$)

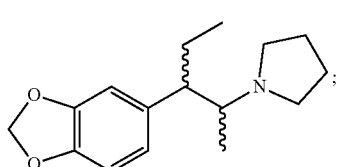

E$_x$(VI$_d$)

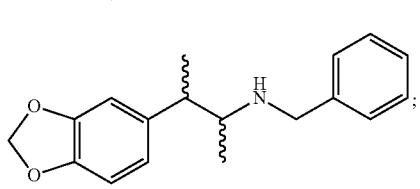

E$_x$(VII$_d$)

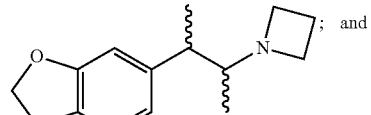
; and

E$_y$(VIII$_d$)

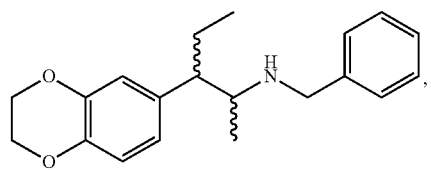
, wherein in each of compound A(I$_g$) to E$_y$(VIII$_d$), optionally, the nitrogen atom of the isopropylamine portion is protonated and includes a negatively charged anion balancing the positively charged nitrogen atom.

In at least one embodiment, in an aspect, the chemical compound having chemical formula (I$_g$), can be a compound selected from the enantiomeric compound pair consisting of A(I$_{ga}$) and A(I$_{gb}$):

A(I$_{ga}$)

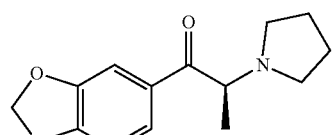

and

A(I$_{gb}$)

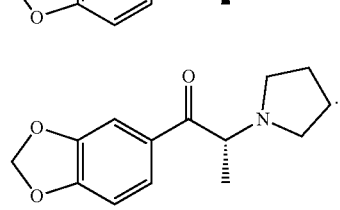

In at least one embodiment, in an aspect, the selected the compound can be in a mixture further comprising the other enantiomeric compound of the enantiomeric compound pair, wherein, optionally, the mixture is a racemic mixture.

In at least one embodiment, in an aspect, the selected compound can be substantially free of the other enantiomeric compound of the enantiomeric compound pair.

In an aspect, the chemical compound having chemical formula (I$_g$) can be a compound selected from the enantiomeric compound pair consisting of A(III$_{ga}$) and A(III$_{gb}$):

A(III$_{ga}$)

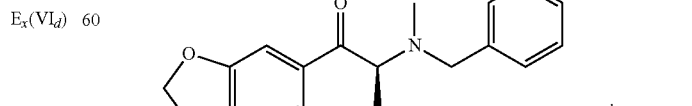

and

-continued

A(III$_{gb}$)

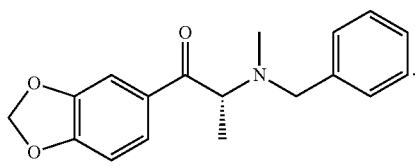

In at least one embodiment, in an aspect, the selected compound can be in a mixture further comprising the other enantiomeric compound of the enantiomeric compound pair, wherein, optionally, the mixture is a racemic mixture.

In at least one embodiment, in an aspect, the selected compound can be substantially free of the other enantiomeric compound of the enantiomeric compound pair.

In at least one embodiment, in an aspect, the chemical compound having formula (I$_d$) can be selected from the group of compounds selected from B(I$_{da}$); B(I$_{db}$); B(I$_{dc}$); B(I$_{dd}$); B(III$_{da}$); B(III$_{db}$); B(III$_{dc}$); and B(III$_{dd}$):

B(I$_{da}$)

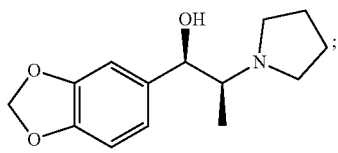

B(I$_{db}$)

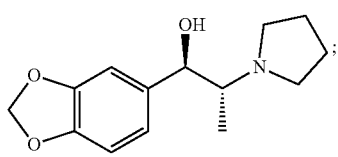

B(I$_{dc}$)

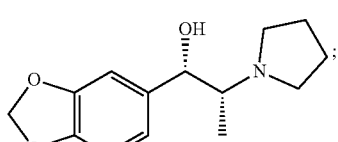

B(I$_{dd}$)

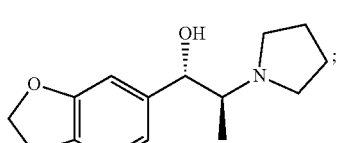

B(III$_{da}$)

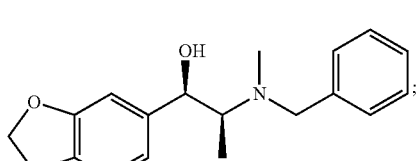

B(III$_{db}$)

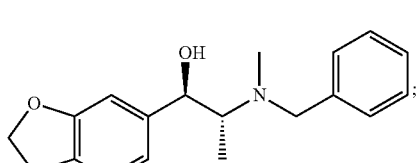

-continued

B(III$_{dc}$)

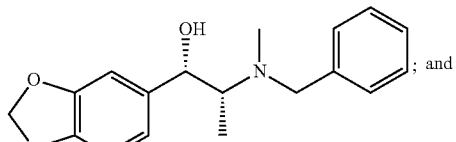
; and

B(III$_{dd}$)

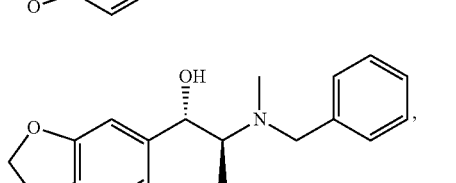
, wherein in each of compound B(I$_{da}$), B(I$_{db}$), B(I$_{dc}$), B(I$_{dd}$), B(III$_{da}$), B(III$_{db}$), B(III$_{dc}$), and B(III$_{dd}$), optionally, the nitrogen atom of the isopropylamine portion is protonated and includes a negatively charged anion balancing the positively charged nitrogen atom.

In at least one embodiment, in an aspect, the chemical compound having formula (I$_d$), can be in a mixture comprising an enantiomeric pair of compounds selected from the syn-enantiomeric pair (B(I$_{da}$), B(I$_{dc}$)) and the anti-enantiomeric pair B(I$_{db}$), B(I$_{dd}$)), wherein, optionally, each pair is a racemic mixture.

In at least one embodiment, in an aspect, the selected enantiomeric pair can be substantially free from the other enantiomeric pair.

In at least one embodiment, in an aspect, the chemical compound having formula (I$_d$), can be in a mixture comprising two enantiomeric pairs (B(I$_{da}$), B(I$_{dc}$)) and (B(I$_{db}$), B(I$_{dd}$)), wherein in the mixture, optionally, each pair is a racemic mixture.

In at least one embodiment, in an aspect, the compound can be selected from B(I$_{da}$); B(I$_{db}$); B(I$_{dc}$); and B(I$_{dd}$), and can be substantially free from its three other isomers.

In at least one embodiment, in an aspect, the chemical compound having formula (I$_d$), can be included in a mixture comprising an enantiomeric pair of compounds selected from the syn-enantiomeric pair (B(III$_{da}$), B(III$_{dc}$)) and the anti-enantiomeric pair B(III$_{db}$), B(III$_{dd}$)), wherein, optionally, each pair is a racemic mixture.

In at least one embodiment, in an aspect, the selected enantiomeric pair can be substantially free from the other enantiomeric pair.

In at least one embodiment, in an aspect, the chemical compound having formula (Id), can be included in a mixture comprising two enantiomeric pairs (B(III$_{da}$), B(III$_{dc}$)) and (B(III$_{db}$), B(III$_{dd}$)), wherein in the mixture, optionally, each pair is a racemic mixture.

In at least one embodiment, in an aspect, the compound can be selected from B(III$_{da}$); B(III$_{db}$); B(III$_{dc}$); and B(III$_{dd}$), and can be substantially free from its three other isomers.

In at least one embodiment, in an aspect, the chemical compound having formula (I$_d$) can be selected from the group of compounds selected from D(I$_{da}$); D(I$_{db}$); D(I$_{dc}$); D(I$_{dd}$); D(II$_{da}$); D(II$_{db}$); D(II$_{dc}$); D(II$_{dd}$); D(III$_{da}$); D(III$_{db}$); D(III$_{dc}$); and D(III$_{dd}$):

D(I$_{da}$) 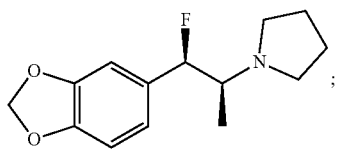;

D(I$_{db}$) 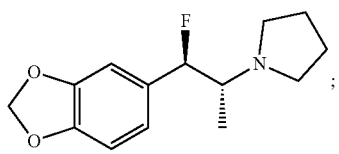;

D(I$_{dc}$) 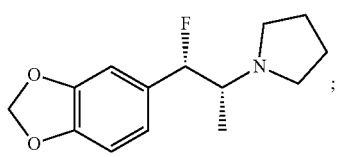;

D(I$_{dd}$) 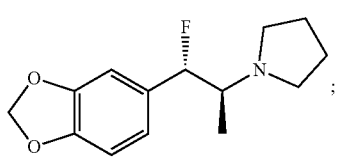;

D(II$_{da}$) 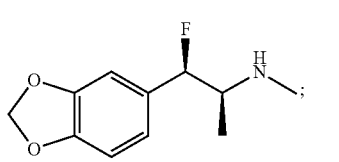;

D(II$_{db}$) 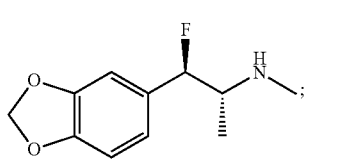;

D(II$_{dc}$) 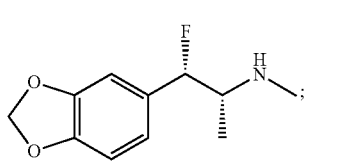;

D(II$_{dd}$) 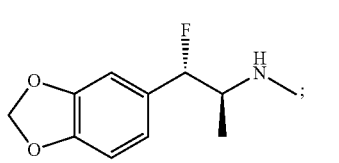;

D(III$_{da}$) 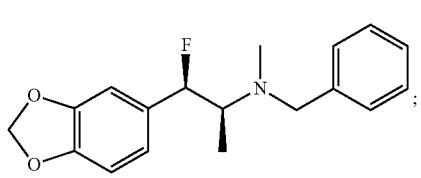;

D(III$_{db}$) 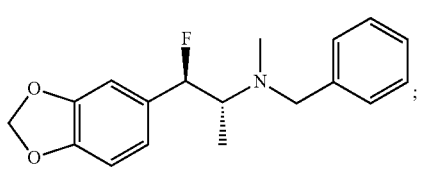;

-continued

D(III$_{dc}$) 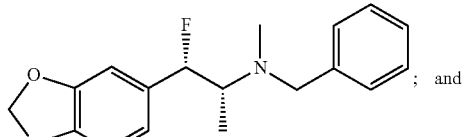; and

D(III$_{dd}$) 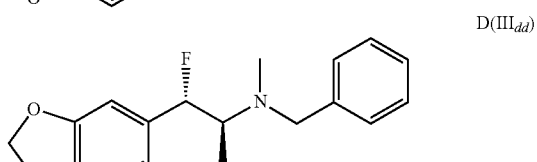, wherein in each of compound D(I$_{da}$), D(I$_{db}$), D(I$_{dc}$), D(I$_{dd}$), D(II$_{da}$), D(II$_{db}$), D(II$_{dc}$), D(II$_{dd}$), D(III$_{da}$), D(III$_{db}$), D(III$_{dc}$), and D(III$_{dd}$), optionally, the nitrogen atom of the isopropylamine portion is protonated and includes a negatively charged anion balancing the positively charged nitrogen atom.

In at least one embodiment, in an aspect, the chemical compound having formula (I$_d$), can be included in a mixture comprising an enantiomeric pair of compounds selected from the syn-enantiomeric pair (D(I$_{da}$), D(I$_{dc}$)) and the anti-enantiomeric pair D(I$_{db}$), D(I$_{dd}$)), wherein, optionally, each pair is a racemic mixture.

In at least one embodiment, in an aspect, the selected enantiomeric pair can be substantially free from the other enantiomeric pair.

In at least one embodiment, in an aspect, the chemical compound having formula (I$_d$), can be included in a mixture comprising two enantiomeric pairs (D(I$_{da}$), D(I$_{dc}$)) and (D(I$_{db}$), D(I$_{dd}$)), wherein in the mixture, optionally, each pair is a racemic mixture.

In at least one embodiment, in an aspect, the compound can be selected from D(I$_{da}$); D(I$_{db}$); D(I$_{dc}$); and D(I$_{dd}$), and can be substantially free from its three other isomers.

In at least one embodiment, in an aspect, the chemical compound having formula (I$_d$), can be included in a mixture comprising an enantiomeric pair of compounds selected from the syn-enantiomeric pair (D(II$_{da}$), D(II$_{dc}$)) and the anti-enantiomeric pair D(II$_{db}$), D(II$_{dd}$)), wherein, optionally, each pair is a racemic mixture.

In at least one embodiment, in an aspect, the selected enantiomeric pair can be substantially free from the other enantiomeric pair.

In at least one embodiment, in an aspect, the chemical compound having formula (I$_d$), can be included in a mixture comprising two enantiomeric pairs (D(II$_{da}$), D(II$_{dc}$)) and (D(II$_{db}$), D(II$_{dd}$)), wherein in the mixture, optionally, each pair is a racemic mixture.

In at least one embodiment, in an aspect, the compound can be selected from D(II$_{da}$); D(II$_{db}$); D(II$_{dc}$); and D(II$_{dd}$), and can be substantially free from its three other isomers.

In at least one embodiment, in an aspect, the chemical compound having formula (I$_d$), can be included in a mixture comprising an enantiomeric pair of compounds selected from the syn-enantiomeric pair (D(III$_{da}$), D(III$_{dc}$)) and the anti-enantiomeric pair D(III$_{db}$), D(III$_{dd}$)), wherein, optionally, each pair is a racemic mixture.

In at least one embodiment, in an aspect, the selected enantiomeric pair can be substantially free from the other enantiomeric pair.

In at least one embodiment, in an aspect, the chemical compound having formula (I$_d$), can be included in a mixture comprising two enantiomeric pairs (D(III$_{da}$), D(III$_{cd}$)) and (D(III$_{db}$), D(III$_{dd}$)), wherein in the mixture, optionally, each pair is a racemic mixture.

In at least one embodiment, in an aspect, the compound can be selected from D(III$_{da}$); D(III$_{db}$); D(III$_{dc}$); and D(III$_{dd}$), and can be substantially free from its three other isomers.

In at least one embodiment, in an aspect, the chemical compound having formula (I$_d$) can be selected from the group of compounds consisting of E$_x$(III$_{da}$); E$_x$(III$_{db}$); E$_x$(III$_{dc}$); E$_x$(III$_{dd}$); E$_x$(VI$_{da}$); E$_x$(VI$_{db}$); E$_x$(VI$_{dc}$); E$_x$(VI$_{dd}$); E$_x$(VII$_{da}$); E$_x$(VII$_{db}$); E$_x$(VII$_{dc}$); E$_x$(VII$_{dd}$); E$_y$(VIII$_{da}$); E$_y$(VIII$_{db}$); E$_y$(VIII$_{dc}$); and E$_y$(VIII$_{dd}$):

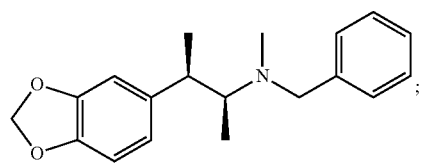

E$_x$(III$_{da}$)

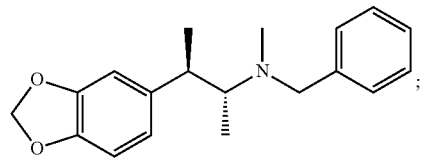

E$_x$(III$_{db}$)

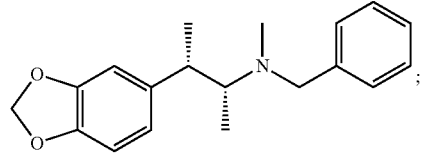

E$_x$(III$_{dc}$)

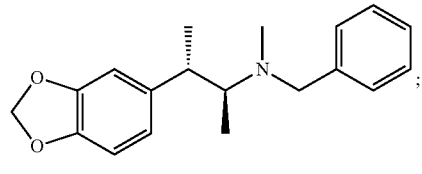

E$_x$(III$_{dd}$)

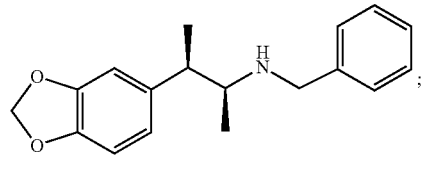

E$_x$(VI$_{da}$)

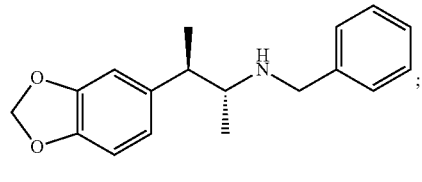

E$_x$(VI$_{db}$)

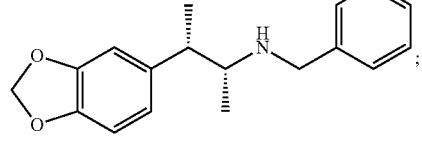

E$_x$(VI$_{dc}$)

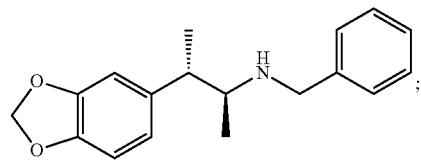

E$_x$(VI$_{dd}$)

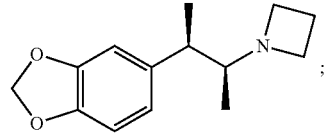

E$_x$(VII$_{da}$)

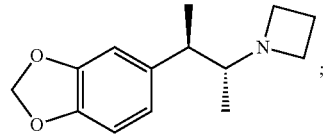

E$_x$(VII$_{db}$)

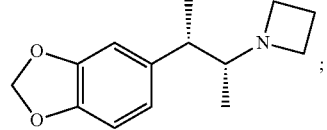

E$_x$(VII$_{dc}$)

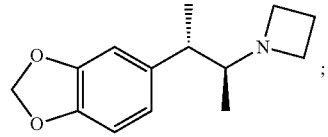

E$_x$(VII$_{dd}$)

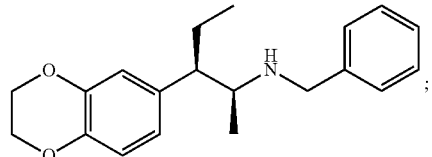

E$_y$(VIII$_{da}$)

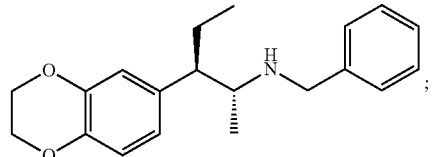

E$_y$(VIII$_{db}$)

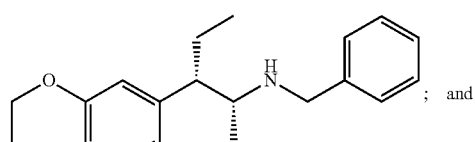

E$_y$(VIII$_{dc}$)

; and

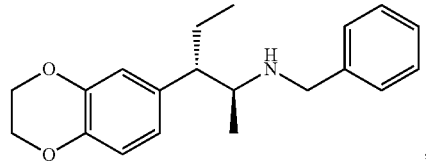

E$_y$(VIII$_{dd}$)

, wherein in compounds E$_x$(III$_{da}$), E$_x$(III$_{db}$), E$_x$(III$_{dc}$), E$_x$(III$_{dd}$), E$_x$(VI$_{da}$), E$_x$(VI$_{db}$), E$_x$(VI$_{dc}$), E$_x$(VI$_{dd}$), E$_x$(VII$_{da}$), E$_x$(VII$_{db}$), E$_x$(VII$_{dc}$), E$_x$(VII$_{dd}$), E$_y$(VIII$_{da}$), E$_y$(VIII$_{db}$), E$_y$(VIII$_{dc}$), and E$_y$(VIII$_{dd}$), optionally, the nitrogen atom of the isopropylamine portion is protonated and includes a negatively charged anion balancing the positively charged nitrogen atom.

In at least one embodiment, in an aspect, the chemical compound having formula ($I_d$), can be included in a mixture comprising an enantiomeric pair of compounds selected from the syn-enantiomeric pair ($E_x(III_{da})$, $E_x(III_{dc})$) and the anti-enantiomeric pair $E_x(III_{db})$, $E_x(III_{dd})$), wherein, optionally, each pair is a racemic mixture.

In at least one embodiment, in an aspect, the selected enantiomeric pair can be substantially free from the other enantiomeric pair.

In at least one embodiment, in an aspect, the chemical compound having formula ($I_d$), can be included in a mixture comprising two enantiomeric pairs ($E_x(III_{da})$, $E_x(III_{dc})$) and ($E_x(III_{db})$, $E_x(III_{dd})$), wherein in the mixture, optionally, each pair is a racemic mixture.

In at least one embodiment, in an aspect, the compound can be selected from $E_x(III_{da})$; $E_x(III_{db})$; $E_x(III_{dc})$; and $E_x(III_{dd})$, and can be substantially free from its three other isomers.

In at least one embodiment, in an aspect, the chemical compound having formula ($I_d$), can be included in a mixture comprising an enantiomeric pair of compounds selected from the syn-enantiomeric pair ($E_x(VI_{da})$, $E_x(VI_{dc})$) and the anti-enantiomeric pair $E_x(VI_{db})$, $E_x(VI_{dd})$), wherein, optionally, each pair is a racemic mixture.

In at least one embodiment, in an aspect, the selected enantiomeric pair can be substantially free from the other enantiomeric pair.

In at least one embodiment, in an aspect, the chemical compound having formula ($I_d$), can be included in a mixture comprising two enantiomeric pairs ($E_x(VI_{da})$, $E_x(VI_{dc})$) and ($E_x(VI_{db})$, $E_x(VI_{dd})$), wherein in the mixture, optionally, each pair is a racemic mixture.

In at least one embodiment, in an aspect, the compound can be selected from $E_x(VI_{da})$; $E_x(VI_{db})$; $E_x(VI_{dc})$; and $E_x(VI_{dd})$, and can be substantially free from its three other isomers.

In at least one embodiment, in an aspect, the chemical compound having formula ($I_d$), can be included in a mixture comprising an enantiomeric pair of compounds selected from the syn-enantiomeric pair ($E_x(VII_{da})$, $E_x(VII_{dc})$) and the anti-enantiomeric pair $E_x(VII_{db})$, $E_x(VII_{dd})$), wherein, optionally, each pair is a racemic mixture.

In at least one embodiment, in an aspect, the selected enantiomeric pair can be substantially free from the other enantiomeric pair.

In at least one embodiment, in an aspect, the chemical compound having formula ($I_d$), can be included in a mixture comprising two enantiomeric pairs ($E_x(VII_{da})$, $E_x(VII_{dc})$) and ($E_x(VII_{db})$, $E_x(VII_{dd})$), wherein in the mixture, optionally, each pair is a racemic mixture.

In at least one embodiment, in an aspect, the compound can be selected from $E_x(VII_{da})$; $E_x(VII_{db})$; $E_x(VII_{dc})$; and $E_x(VII_{dd})$, and can be substantially free from its three other isomers.

In at least one embodiment, in an aspect, the chemical compound having formula ($I_d$), can be included in a mixture comprising an enantiomeric pair of compounds selected from the syn-enantiomeric pair ($E_y(VIII_{da})$, $E_y(VIII_{dc})$) and the anti-enantiomeric pair $E_y(VIII_{db})$, $E_y(VIII_{dd})$), wherein, optionally, each pair is a racemic mixture.

In at least one embodiment, in an aspect, the selected enantiomeric pair can be substantially free from the other enantiomeric pair.

In at least one embodiment, in an aspect, the chemical compound having formula ($I_d$), can be included in a mixture comprising two enantiomeric pairs ($E_y(VIII_{da})$, $E_y(VIII_{dc})$) and ($E_y(VIII_{db})$, $E_y(VIII_{dd})$), wherein in the mixture, optionally, each pair is a racemic mixture.

In at least one embodiment, in an aspect, the compound can be selected from $E_y(VIII_{da})$; $E_y(VIII_{db})$; $E_y(VIII_{dc})$; and $E_y(VIII_{dd})$, and can be substantially free from its three other isomers.

In another aspect, the present disclosure relates to pharmaceutical and recreational drug formulations comprising fused heterocyclic mescaline derivatives. Accordingly, in one aspect, the present disclosure provides, in at least one embodiment, a pharmaceutical or recreational drug formulation comprising an effective amount of a chemical compound selected from a compound having chemical formula (I) or chemical formula (II):

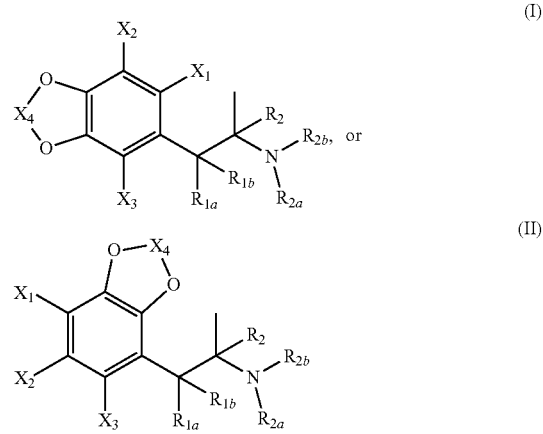

wherein, in chemical formula (I) and chemical formula (II):

$X_1$, $X_2$, and $X_3$ are independently selected from a hydrogen atom, O-alkyl, N-alkyl, OH, a halogen, or $NH_2$;

$X_4$ is an alkylene group or substituted alkylene group;

$R_{1a}$ is an alkyl group, O-alkyl group, a halogen, or OH, $R_{1b}$ is a hydrogen atom or a halogen, or $R_{1a}$ and $R_{1b}$ are joined together to form an oxo group;

$R_2$ is a hydrogen atom or an O-alkyl group; and $R_{2a}$ and $R_{2b}$ are independently selected from an alkyl group, an optionally substituted alkyl-aryl group, or a hydrogen atom, or $R_{2a}$ and $R_{2b}$ are joined together, along with the nitrogen atom to which they are attached, to form a 3-10-membered optionally substituted heterocyclic ring, together with a pharmaceutically acceptable excipient, diluent, or carrier.

In another aspect, the present disclosure relates to methods of treatment of psychiatric disorders. Accordingly, the present disclosure further provides, in one embodiment, a method for treating a brain neurological disorder, the method comprising administering to a subject in need thereof a pharmaceutical formulation comprising a compound having chemical formula (I) or chemical formula (II):

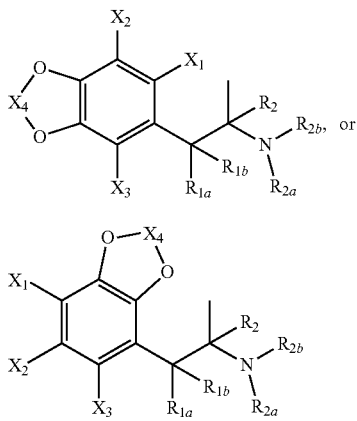

wherein, in chemical formula (I) and chemical formula (II):
- $X_1$, $X_2$, and $X_3$ are independently selected from a hydrogen atom, O-alkyl, N-alkyl, OH, a halogen, or $NH_2$;
- $X_4$ is an alkylene group or substituted alkylene group;
- $R_{1a}$ is an alkyl group, O-alkyl group, a halogen, or OH,
- $R_{1b}$ is a hydrogen atom or a halogen, or $R_{1a}$ and $R_{1b}$ are joined together to form an oxo group;
- $R_2$ is a hydrogen atom or an O-alkyl group; and
- $R_{2a}$ and $R_{2b}$ are independently selected from an alkyl group, an optionally substituted alkyl-aryl group, or a hydrogen atom, or $R_{2a}$ and $R_{2b}$ are joined together, along with the nitrogen atom to which they are attached, to form a 3-10-membered optionally substituted heterocyclic ring, wherein the pharmaceutical formulation is administered in an effective amount to treat the brain neurological disorder in the subject.

In at least one embodiment, in an aspect, upon administration the compound having chemical formula (I) or (II) can interact with a receptor in the subject to thereby modulate the receptor and exert a pharmacological effect.

In at least one embodiment, in an aspect, the receptor can be a G-protein coupled receptor (GPCR).

In at least one embodiment, in an aspect, the receptor can be a 5-HT receptor.

In at least one embodiment, in an aspect, the receptor can be a $5\text{-HT}_{1A}$ receptor, a $5\text{-HT}_{2A}$ receptor, a $5\text{-HT}_{2B}$ receptor, a $5\text{-HT}_{2C}$ receptor, a $5\text{-HT}_7$ receptor, an $\alpha_{2A}$ receptor, or an $MT_1$ receptor.

In at least one embodiment, in an aspect, upon administration the compound having chemical formula (I) or (II) can interact with a transmembrane transport protein in the subject to thereby modulate the transmembrane transport protein and exert a pharmacological effect.

In at least one embodiment, in an aspect, the transmembrane transport protein can be a dopamine active transporter (DAT), a norephedrine transporter (NET), or a serotonin transporter (SERT) transmembrane transport protein.

In at least one embodiment, in an aspect, the disorder can be a G-protein coupled receptor (GPCR)-mediated disorder.

In at least one embodiment, in an aspect, the disorder can be a 5-HT receptor-mediated disorder.

In at least one embodiment, in an aspect, the disorder can be a $5\text{-HT}_{1A}$ receptor-mediated disorder, a $5\text{-HT}_{2A}$ receptor-mediated disorder, a $5\text{-HT}_{2B}$ receptor-mediated disorder, a $5\text{-HT}_{2C}$ receptor-mediated disorder, a $5\text{-HT}_{1D}$ receptor-mediated disorder, a $5\text{-HT}_7$ receptor-mediated disorder, a $\alpha_{2A}$ receptor-mediated disorder, or an $MT_1$ receptor-mediated disorder.

In at least one embodiment, in an aspect, a dose can be administered of about 0.001 mg to about 5,000 mg.

In another aspect, the present disclosure provides, in at least one embodiment, a method for modulating (i) a receptor selected from $5\text{-HT}_{1A}$ receptor, a $5\text{-HT}_{2A}$ receptor, a $5\text{-HT}_{2B}$ receptor, a $5\text{-HT}_{2C}$ receptor, a $5\text{-HT}_7$ receptor, an $\alpha_{2A}$ receptor, or an $MT_1$ receptor; or (ii) a transmembrane transport protein selected from a dopamine active transporter (DAT), a norephedrine transporter (NET) or a serotonin transporter (SERT) transmembrane transport protein, the method comprising contacting (i) the $5\text{-HT}_{1A}$ receptor, the $5\text{-HT}_{2A}$ receptor, the $5\text{-HT}_{2B}$ receptor, the $5\text{-HT}_{2C}$ receptor, the $5\text{-HT}_7$ receptor, the $\alpha_{2A}$ receptor, the $D_2$ receptor, or the $MT_1$ receptor; or (ii) the dopamine active transporter (DAT), the norephedrine transporter (NET), or the serotonin transporter (SERT) transmembrane transport protein with a selected from a first chemical compound having chemical formula (I), and a second chemical compound having chemical formula (II):

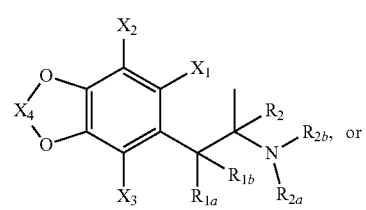

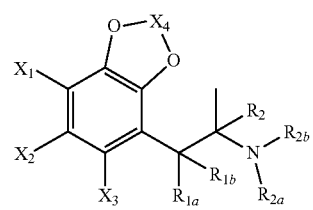

wherein, in chemical formula (I) and chemical formula (II):
- $X_1$, $X_2$, and $X_3$ are independently selected from a hydrogen atom, O-alkyl, N-alkyl, OH, a halogen, or $NH_2$;
- $X_4$ is an alkylene group or substituted alkylene group;
- $R_{1a}$ is an alkyl group, O-alkyl group, a halogen, or OH,
- $R_{1b}$ is a hydrogen atom or a halogen, or $R_{1a}$ and $R_{1b}$ are joined together to form an oxo group;
- $R_2$ is a hydrogen atom or an O-alkyl group; and
- $R_{2a}$ and $R_{2b}$ are independently selected from an alkyl group, an optionally substituted alkyl-aryl group, or a hydrogen atom, or $R_{2a}$ and $R_{2b}$ are joined together, along with the nitrogen atom to which they are attached, to form a 3-10-membered optionally substituted heterocyclic ring, under reaction conditions sufficient to modulate (i) the $5\text{-HT}_{1A}$ receptor, the $5\text{-HT}_{2A}$ receptor, the $5\text{-HT}_{2B}$ receptor, the $5\text{-HT}_{2C}$ receptor, the $5\text{-HT}_7$ receptor, the $\alpha_{2A}$ receptor, or the $MT_1$ receptor; (ii) the dopamine active transporter (DAT), the norephedrine transporter (NET), or the serotonin transporter (SERT) transmembrane transport protein.

In at least one embodiment, in an aspect, the reaction conditions can be in vitro reaction conditions.

In at least one embodiment, in an aspect, the reaction conditions can be in vivo reaction conditions.

In another aspect, the present disclosure relates to methods of making mescaline derivatives. Accordingly, in an aspect, in at least one embodiment, provided herein is a method of making a first chemical compound having chemical formula (I) or chemical formula (II):

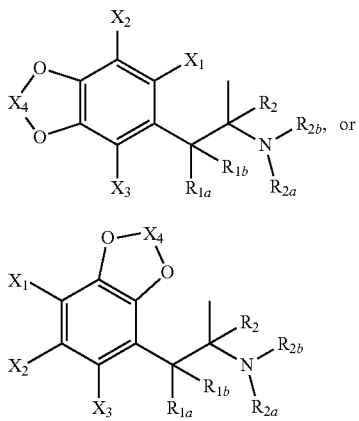

(I)

(II)

wherein, in chemical formula (I) and chemical formula (II):
$X_1$, $X_2$, and $X_3$ are independently selected from a hydrogen atom, O-alkyl, N-alkyl, OH, a halogen, or $NH_2$;
$X_4$ is an alkylene group or substituted alkylene group;
$R_{1a}$ is an alkyl group, O-alkyl group, a halogen, or OH, $R_{1b}$ is a hydrogen atom or a halogen, or $R_{1a}$ and $R_{1b}$ are joined together to form an oxo group;
$R_2$ is a hydrogen atom or an O-alkyl group; and
$R_{2a}$ and $R_{2b}$ are independently selected from an alkyl group, an optionally substituted alkyl-aryl group, or a hydrogen atom, or $R_{2a}$ and $R_{2b}$ are joined together, along with the nitrogen atom to which they are attached, to form a 3-10-membered optionally substituted heterocyclic ring,
wherein the method involves the performance of at least one chemical synthesis reaction selected from the reactions depicted in FIGS. 3A, 3B and 3C.

In at least one embodiment, in an aspect, the compound having chemical formula (I) can be a compound having formula (A):

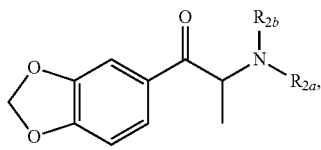

(A)

wherein $R_{2a}$ and $R_{2b}$ are independently selected from an alkyl group, an optionally substituted alkyl-aryl group, or a hydrogen atom, or $R_{2a}$ and $R_{2b}$ are joined together, along with the nitrogen atom to which they are attached, to form a 3-10-membered optionally substituted heterocyclic ring,
and the at least one chemical synthesis reaction is a reaction selected from (c); (b) and (c); and (a), (b), and (c) depicted in FIG. 3A.

In at least one embodiment, in an aspect, the compound having chemical formula (I) can be a compound having formula (B):

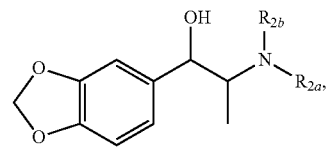

(B)

wherein $R_{2a}$ and $R_{2b}$ are independently selected from an alkyl group, an optionally substituted alkyl-aryl group, or a hydrogen atom, or $R_{2a}$ and $R_{2b}$ are joined together, along with the nitrogen atom to which they are attached, to form a 3-10-membered optionally substituted heterocyclic ring,
and the at least one chemical synthesis reaction is a reaction selected from (e); (c) and (e); (b), (c), and (e); and (a), (b), (c), and (e), depicted in FIG. 3A.

In at least one embodiment, in an aspect, the compound having chemical formula (I) can be a compound having formula (C):

(C)

wherein $R_{2a}$ and $R_{2b}$ are independently selected from an alkyl group, an optionally substituted alkyl-aryl group, or a hydrogen atom, or $R_{2a}$ and $R_{2b}$ are joined together, along with the nitrogen atom to which they are attached, to form a 3-10-membered optionally substituted heterocyclic ring,
and the at least one chemical synthesis reaction is a reaction selected from (d); (c) and (d); (b), (c), and (d); and (a), (b), (c), and (d), depicted in FIG. 3A.

In at least one embodiment, in an aspect, the compound having chemical formula (I) can be a compound having formula (D):

(D)

wherein $R_{2a}$ and $R_{2b}$ are independently selected from an alkyl group, an optionally substituted alkyl-aryl group, or a hydrogen atom, or $R_{2a}$ and $R_{2b}$ are joined together, along with the nitrogen atom to which they are attached, to form a 3-10-membered optionally substituted heterocyclic ring,
and the at least one chemical synthesis reaction is a reaction selected from (f); (e) and (f); (c), (e), and (f); (b), (c), (e), and (f); and (a), (b), (c), (e), and (f), depicted in FIG. 3A.

In at least one embodiment, in an aspect, the compound having chemical formula (I) can be a compound having formula ($E_x$):

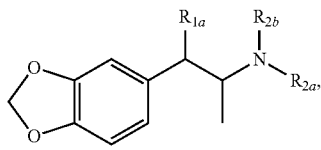

(E$_x$)

wherein R$_{1a}$ is an alkyl group; and wherein R$_{2a}$ and R$_{2b}$ are independently selected from an alkyl group, an optionally substituted alkyl-aryl group, or a hydrogen atom, or R$_{2a}$ and R$_{2b}$ are joined together, along with the nitrogen atom to which they are attached, to form a 3-10-membered optionally substituted heterocyclic ring, and the at least one chemical synthesis reaction is a reaction selected from (e); (d) and (e); (c), (d), and (e); (b), (c), (d), and (e); (a), (b), (c), (d), and (e); (h); (g) and (h); and (f), (g), and (h) depicted in FIG. 3B.

In at least one embodiment, in an aspect, the compound having chemical formula (I) can be a compound having formula (E$_y$):

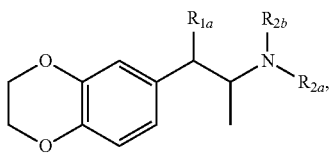

(E$_y$)

wherein R$_{1a}$ is an alkyl group; and wherein R$_{2a}$ and R$_{2b}$ are independently selected from an alkyl group, an optionally substituted alkyl-aryl group, or a hydrogen atom, or R$_{2a}$ and R$_{2b}$ are joined together, along with the nitrogen atom to which they are attached, to form a 3-10-membered optionally substituted heterocyclic ring, and the at least one chemical synthesis reaction is a reaction selected from (e); (d) and (e); (c), (d), and (e); (b), (c), (d), and (e); (a), (b), (c), (d), and (e); (h); (g) and (h); and (f), (g), and (h) depicted in FIG. 3C.

In another aspect, the present disclosure provides, in at least one embodiment, a use of a chemical compound having chemical formula (I) or chemical formula (II):

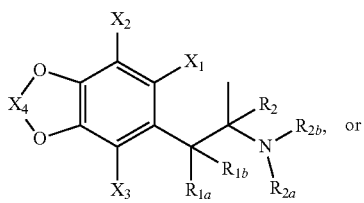

(I)

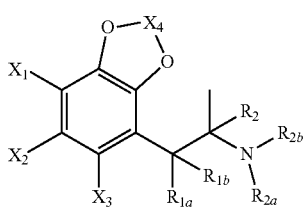

(II)

wherein, in chemical formula (I) and chemical formula (II):

X$_1$, X$_2$, and X$_3$ are independently selected from a hydrogen atom, O-alkyl, N-alkyl, OH, a halogen, or NH$_2$;

X$_4$ is an alkylene group or substituted alkylene group;

R$_{1a}$ is an alkyl group, O-alkyl group, a halogen, or OH, R$_{1b}$ is a hydrogen atom or a halogen, or R$_{1a}$ and R$_{1b}$ are joined together to form an oxo group;

R$_2$ is a hydrogen atom or an O-alkyl group; and

R$_{2a}$ and R$_{2b}$ are independently selected from an alkyl group, an optionally substituted alkyl-aryl group, or a hydrogen atom, or R$_{2a}$ and R$_{2b}$ are joined together, along with the nitrogen atom to which they are attached, to form a 3-10-membered optionally substituted heterocyclic ring, in the manufacture of a pharmaceutical or recreational drug formulation.

In at least one embodiment, in an aspect, the manufacture can comprise formulating the chemical compound with an excipient, diluent, or carrier.

In another aspect, the present disclosure provides, in at least one embodiment, a use of a having chemical formula (I) or chemical formula (II):

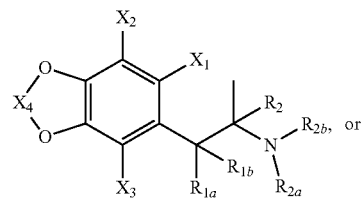

(I)

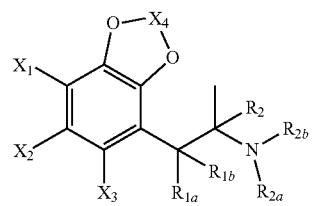

(II)

wherein, in chemical formula (I) and chemical formula (II):

X$_1$, X$_2$, and X$_3$ are independently selected from a hydrogen atom, O-alkyl, N-alkyl, OH, a halogen, or NH$_2$;

X$_4$ is an alkylene group or substituted alkylene group;

R$_{1a}$ is an alkyl group, O-alkyl group, a halogen, or OH, R$_{1b}$ is a hydrogen atom or a halogen, or R$_{1a}$ and R$_{1b}$ are joined together to form an oxo group;

R$_2$ is a hydrogen atom or an O-alkyl group; and

R$_{2a}$ and R$_{2b}$ are independently selected from an alkyl group, an optionally substituted alkyl-aryl group, or a hydrogen atom, or R$_{2a}$ and R$_{2b}$ are joined together, along with the nitrogen atom to which they are attached, to form a 3-10-membered optionally substituted heterocyclic ring, together with a diluent, carrier, or excipient as a pharmaceutical or recreational drug formulation.

Other features and advantages will become apparent from the following detailed description. It should be understood, however, that the detailed description, while indicating preferred implementations of the disclosure, are given by way of illustration only, since various changes and modifications within the spirit and scope of the disclosure will become apparent to those of skill in the art from the detailed description.

BRIEF DESCRIPTION OF THE DRAWINGS

The disclosure is in the hereinafter provided paragraphs described, by way of example, in relation to the attached figures. The figures provided herein are provided for a better understanding of the example embodiments and to show more clearly how the various embodiments may be carried into effect. The figures are not intended to limit the present disclosure.

Figure 1:
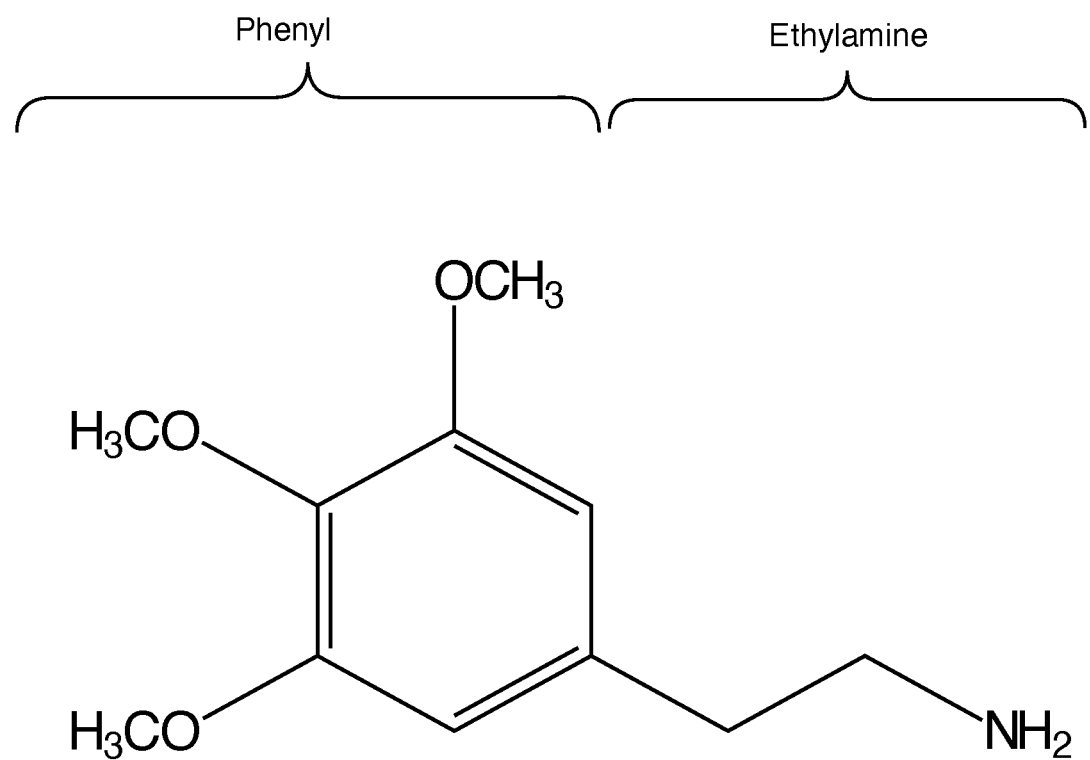
FIG. 1 depicts the chemical structure of mescaline, and identifies a phenyl portion, comprising a substituted phenyl group, and an ethylamine portion of the compound.

The figures together with the following detailed description make apparent to those skilled in the art how the disclosure may be implemented in practice.

DETAILED DESCRIPTION

Various compositions, systems or processes will be described below to provide an example of an embodiment of each claimed subject matter. No embodiment described below limits any claimed subject matter and any claimed subject matter may cover processes, compositions or systems that differ from those described below. The claimed subject matter is not limited to compositions, processes or systems having all of the features of any one composition, system or process described below or to features common to multiple or all of the compositions, systems or processes described below. It is possible that a composition, system, or process described below is not an embodiment of any claimed subject matter. Any subject matter disclosed in a composition, system or process described below that is not claimed in this document may be the subject matter of another protective instrument, for example, a continuing patent application, and the applicant(s), inventor(s) or owner(s) do not intend to abandon, disclaim or dedicate to the public any such subject matter by its disclosure in this document.

As used herein and in the claims, the singular forms, such "a", "an" and "the" include the plural reference and vice versa unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers.

When ranges are used herein for physical properties, such as molecular weight, or chemical properties, such as chemical formulae, all combinations and sub-combinations of ranges and specific embodiments therein are intended to be included. Other than in the operating examples, or where otherwise indicated, all numbers expressing quantities of ingredients or reaction conditions used herein should be understood as modified in all instances by the term "about." The term "about" when referring to a number or a numerical range means that the number or numerical range referred to is an approximation within experimental variability (or within statistical experimental error), and thus the number or numerical range may vary between 1% and 15% of the stated number or numerical range, as will be readily recognized by context. Furthermore, any range of values described herein is intended to specifically include the limiting values of the range, and any intermediate value or sub-range within the given range, and all such intermediate values and sub-ranges are individually and specifically disclosed (e.g., a range of 1 to 5 includes 1, 1.5, 2, 2.75, 3, 3.90, 4, and 5). Similarly, other terms of degree such as "substantially" and "approximately" as used herein mean a reasonable amount of deviation of the modified term such that the end result is not significantly changed. These terms of degree should be construed as including a deviation of the modified term if this deviation would not negate the meaning of the term it modifies.

Unless otherwise defined, scientific and technical terms used in connection with the formulations described herein shall have the meanings that are commonly understood by those of ordinary skill in the art. The terminology used herein is for the purpose of describing particular embodiments only, and is not intended to limit the scope of the present invention, which is defined solely by the claims.

All publications, patents and patent applications are herein incorporated by reference in their entirety to the same extent as if each individual publication, patent, or patent application was specifically and individually indicated to be incorporated by reference in its entirety.

Terms and definitions

The term "mescaline" refers to a chemical compound having the structure set forth in FIG. 1. It is noted that mescaline is also known in the art as 3,4,5 trimethoxyphenethylamine. It is further noted that mescaline includes a phenyl portion comprising a substituted phenyl group, and an ethylamine portion, as shown in FIG. 1.

Figure 2:
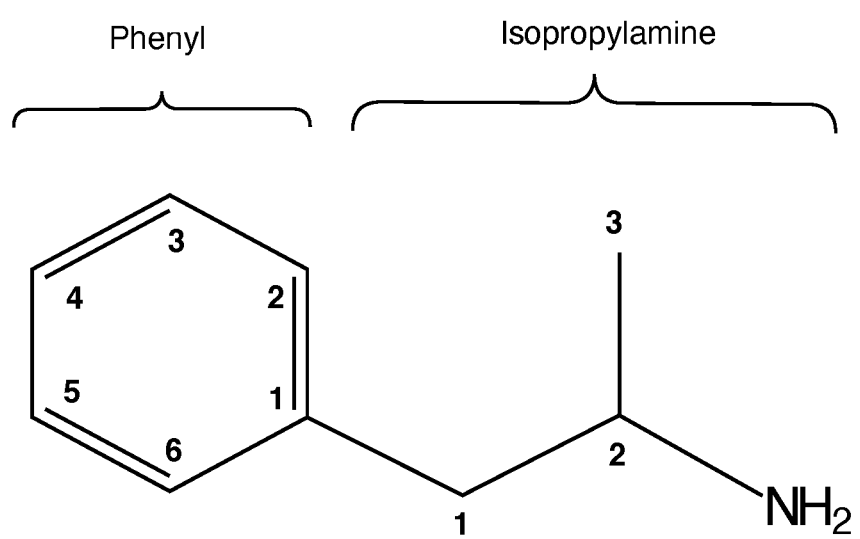
FIG. 2 depicts a certain prototype structure of mescaline derivative compounds. The prototype structure contains a phenyl portion, comprising a substituted phenyl group, and an isopropylamine portion, as indicated. Carbon atoms have been numbered $C_1$, $C_2$, $C_3$ etc. to indicate their position in the phenyl portion or isopropylamine portion, respectively. Thus, for example, it will be clear from FIG. 2 that the isopropylamine chain extends from the $C_1$ carbon of the phenyl group. Furthermore, it is noted that certain compounds may be named in accordance with the same. Thus, for example, in 2,3 (1,3) dioxolanephenisopropylamine, phenyl portion carbon atoms $C_2$ and $C_3$, are each participating in the formation of a (1,3) dioxolane group (i.e., a pentane in which the carbons at positions 1 and 3 have been replaced with an oxygen atom). Similarly, in 3,4,5 trimethoxyphenethylamine (mescaline), phenyl portion carbon atoms $C_3$, $C_4$, and $C_5$ are each bonded to a methoxy group.

The term "mescaline derivative prototype structure" refers to the chemical structure shown in FIG. 2. The mescaline derivatives disclosed herein include the mescaline derivative prototype structure shown in FIG. 2, wherein various atoms may be substituted, as herein described. It is noted that the prototype structure comprises a phenyl portion and an isopropylamine portion (instead of an ethylamine portion as is the case for mescaline, see: FIG. 1). Furthermore, it is noted that specific carbon atoms in the mescaline derivative prototype structure are numbered. In this respect, it is noted that specific carbon atoms in the phenyl portion of the prototype structure are numbered separately from the carbon atoms in the isopropylamine portion. Reference may be made herein to these numbered carbons, for example, $C_1$ of the phenyl portion, $C_2$ of the phenyl portion, or $C_3$ of the isopropylamine portion, and so forth. It is noted that the isopropylamine chain extends from the $C_1$ carbon atom of the phenyl portion of the prototype structure. It is further noted that, in general terms, disclosed herein are mescaline derivatives in which: (i) adjacent carbon atoms $C_2$ and $C_3$ (formula (I)) or $C_4$ and $C_5$ (formula (II)) of the phenyl portion of the prototype structure participate in a fusion to a heterocycle, notably, in some embodiments, a 5-membered or 6-membered heterocycle, and notably, in some embodiments, a (1,3) dioxolane ring or a (1,4) dioxane ring; and (ii) the isopropylamine chain extending from the $C_1$ atom of the phenyl portion of the prototype structure is a $C_1$-substituted isopropylamine chain, notably an isopropylamine chain possessing a substituted $C_1$ carbon atom ($-CR_{1a}R_{1b}$), wherein $R_{1a}$ and/or $R_{1b}$ are a substituent. Thus, the herein disclosed mescaline derivatives can be said to be $C_1$-substituted isopropylamine fused heterocyclic mescaline derivatives.

A straight bond, or a wavy or squiggly bond, drawn to an atom, including, notably, a chiral carbon atom within a structural chemical formula, indicates that the stereochemistry of the atom is undefined. Examples of such chemical structural formulas are structural formulas (a) and (b):

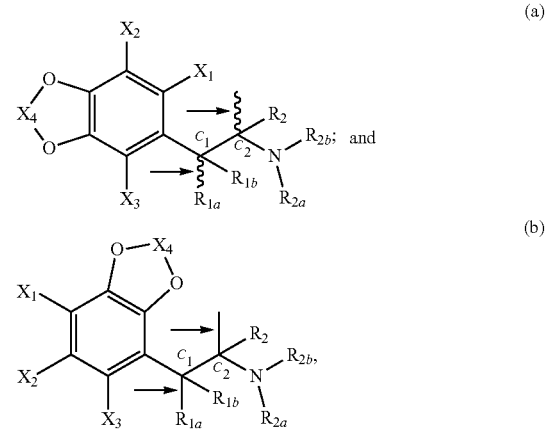

wherein carbon atom $C_1$ and $C_2$ are chiral carbon atoms. Thus, for example, a straight bond, or a wavy or squiggly bond, drawn to a chiral carbon atom is intended to denote the S- or R-configuration, as well as mixtures thereof, in a single figure. When a straight bond, or a wavy or squiggly bond, are attached to a double bond moiety (such as —C═C—), included are the cis- or trans- (or (E)- or (Z)-) geometric isomers, or mixtures thereof. Furthermore, in chemical structural formulas possessing two adjacent chiral carbon atoms (as is the case for structural formula (a) and (b) above, for example) squiggly or straight bonds drawn to such adjacent chiral carbon atoms are intended to denote the syn- or anti-enantiomers, and mixtures thereof in a single figure.

Thus, for example, with respect to chemical structure (a), included are the syn-enantiomeric configurations (a(i)) and (a(ii)):

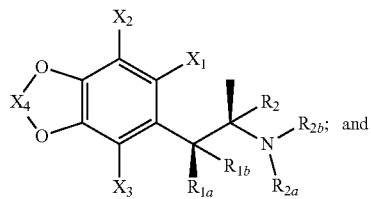
(a(i))

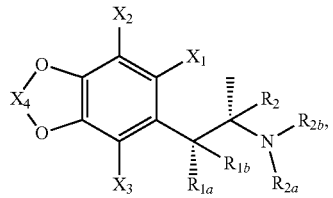
(a(ii))

and mixtures thereof, and the anti-enantiomeric configurations (a(iii)) and (a(iv)):

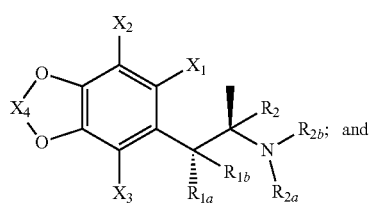
(a(iii))

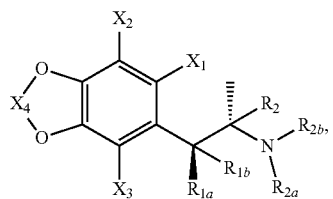
(a(iv))

and mixtures thereof. Mixtures include racemic mixtures, wherein the mixture contains equimolar or approximately equimolar amounts of each (a(i)) and (a(ii)), for example, or equimolar or approximately equimolar amounts of each (a(iii)) and (a(iv)), for example.

The term "chiral carbon atom" as used herein refers to a carbon atom bonded to four different substituents.

The terms "isomer" and "isomeric compound", as used herein, are intended to refer to a chemical compound in reference to another chemical compound, wherein both compounds have the same chemical formula, however they may have a different three dimensional configuration. Isomeric compounds include stereoisomeric compounds and diastereomeric compounds.

The terms "stereoisomer" and "stereoisomeric compound", as used herein, are intended to refer to a chemical compound in reference to another chemical compound, wherein both compounds have the same chemical formula when the structural formula is denoted with straight bonds. However, when the structural formula of the two compounds is denoted with one or more wedge bonds (▲, ⋰) drawn to an atom, to thereby define the three dimensional configuration of the compounds, the compounds are three-dimensionally differently configured. In this respect, the wedge bonds can signify that stereoisomers of a compound exist. A pair of stereoisomers can include two compounds which are configured three-dimensionally such that they are mirror images of one another, or they can be configured three-dimensionally such that they are not mirror images of one another. Thus, for example, compounds (a(i)) and (a(ii)) are stereoisomers which are mirror images of one another,

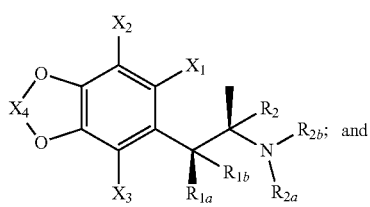
(a(i))

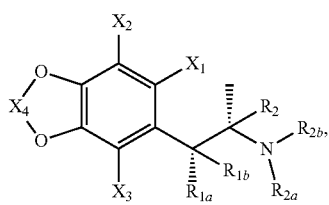
(a(ii))

and compounds (a(i)) and (a(iii)) are stereoisomers which are not mirror images of one another:

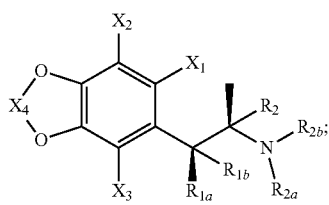
(a(i))

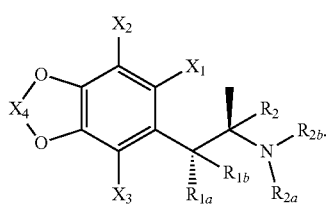
(a(iii))

Furthermore, stereoisomeric compounds may be configured three-dimensionally so that they are superimposable or non-superimposable. Thus, for example, stereoisomeric compounds (a(v)) and (a(vi)), wherein in each compound $R_1$, $R_2$, $R_3$, and $R_4$ denote non-identical substituents:

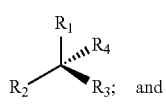
(a(v))

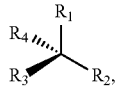
(a(vi))

are mirror images but non-superimposable stereoisomers. By contrast, and byway of example, compounds (a(vii)) and (a(viii)), wherein $R_1$, $R_2$, $R_3$, denote non-identical substituents, and wherein in each compound both substituents labeled $R_3$ denote identical substituents:

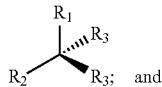

(a(vii))

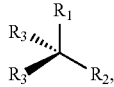

(a(viii))

are mirror images and superimposable depictions and are not stereoisomers but the same compound.

The terms "enantiomer" and "enantiomeric compound", as used herein, are intended to refer to a stereoisomeric compound in reference to another stereoisomeric compound, wherein the two stereoisomeric compounds are non-superimposable. Furthermore, enantiomeric compounds possessing two adjacent chiral carbon atoms may be configured three dimensionally so that two substituents are bonded to the same side of the chiral carbon atoms to be syn-enantiomeric compounds, or so that two substituents are bonded to the opposite side of the chiral carbon atoms to be anti-enantiomeric compounds. Thus, for example, compounds (a(i)) and are (a(ii)):

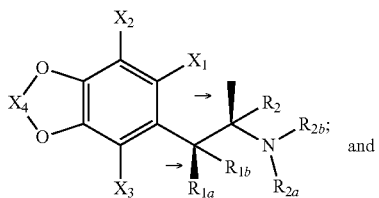

(a(i))

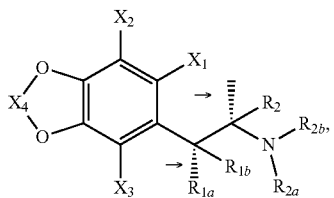

(a(ii))

are syn-enantiomeric compounds. By contrast, compounds (a(iii)) and are (a(iv)):

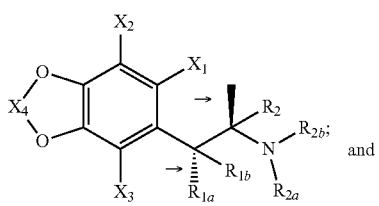

(a(iii))

-continued

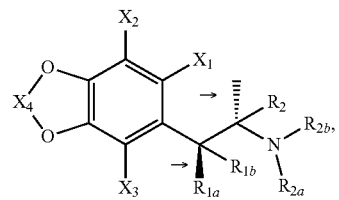

(a(iv))

are anti-enantiomeric compounds.

The terms "diastereomer" and "diastereomeric compound", as used herein, are intended to refer to a stereomeric compound in reference to another stereomeric compound wherein both compounds have the same chemical formula when the structural formula is denoted with straight bonds. However, when the structural formula of the two compounds is denoted with one or more wedge bonds (▲, ⌀⌀⌀) drawn to an atom, to thereby define the three dimensional configuration, they are not mirror images of one another. By way of example, compounds (a(i)) and are (a(iv)):

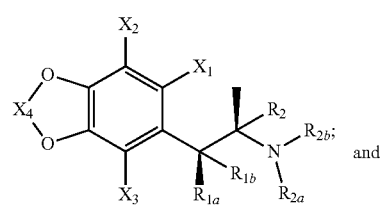

(a(i))

and

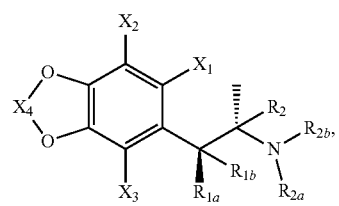

(a(iv))

are diastereomeric compounds.

The terms "hydroxy group", and "hydroxy", as used herein, refers to a molecule containing one atom of oxygen bonded to one atom of hydrogen, and having the chemical formula —OH. A hydroxy group through its oxygen atom may be chemically bonded to another entity.

The terms "amino" and "amino group", as used herein, refers to a molecule containing one atom of nitrogen bonded to hydrogen atoms and having the formula —$NH_2$. An amino group also may be protonated and having the formula —$NH_3^*$. In its protonated form the amino group may form an ammonium salt, for example, a chloride or sulfate ammonium salt, or an organic ammonium salt, all of which may be represented herein as $NH_3^*Z^-$. An amino group through its nitrogen atom may be chemically bonded to another entity. Furthermore, it is noted that an entity attached to an amino group may be referred to herein as an "aminated" entity, e.g., an aminated mescaline derivative is a mescaline derivative possessing an amino group.

The term "oxo group", as used herein, as used herein refers to the group =O, and, for example, can be formed by replacing two hydrogens bonded to the same carbon atom with =O.

The term "carbonyl group", as used herein, as used herein refers to the group —C=O, and can be formed by replacing two hydrogens bonded to the same carbon atom with =O.

The terms "halogen", "halogen group", "halo-" and "halogenated", as used herein, refer to the class of chemical elements consisting of fluorine (F), chlorine (Cl), bromine (Br), and iodine (I). Accordingly, halogenated compounds can refer to "fluorinated", "chlorinated", "brominated", or "iodinated" compounds.

The term "alkyl group", as used herein, refers to a hydrocarbon group arranged in a chain having the chemical formula —$C_nH_{2n+1}$. Alkyl groups include, without limitation, methyl groups (—$CH_3$), ethyl groups (—$C_2H_5$), propyl groups (—$C_3H_7$) and butyl groups (—$C_4H_9$). The alkyl groups (including O-alkyl, and the alkyl groups present in acyl and O-acyl) in any of the embodiments of the disclosure is $C_1$-$C_{20}$-alkyl. In another embodiment, the alkyl group is $C_1$-$C_{10}$-alkyl. In another embodiment, the alkyl group is $C_1$-$C_6$-alkyl. In another embodiment, the alkyl group is methyl, ethyl, propyl, butyl or pentyl.

The terms "O-alkyl group", and "alkoxy group", as used herein interchangeably, refer to a hydrocarbon group arranged in a chain having the chemical formula —O—$C_nH_{2n+1}$. O-alkyl groups include, without limitation, O-methyl groups (—O—$CH_3$) (i.e., methoxy), O-ethyl groups (—O—$C_2H_5$) (i.e., ethoxy), O-propyl groups (—O—$C_3H_7$) (i.e., propoxy) and O-butyl groups (—O—$C_4H_9$) (i.e., butoxy).

The terms "N-alkyl group", as used herein, refers to a hydrocarbon group arranged in a chain having the chemical formula —N—$C_nH_{2n+1}$. N-alkyl groups include, without limitation, N-methyl groups (—N—$CH_3$), N-ethyl groups (—N—$C_2H_5$), N-propyl groups (—N—$C_3H_7$), and N-butyl groups (—N—$C_4H_9$).

The term "acyl group", as used herein, refers to a carbon atom double bonded to an oxygen and single bonded to an alkyl group. The carbon atom further can be bonded to another entity. An acyl group can be described by the chemical formula: —C(=O)—$C_nH_{2n+1}$ or e.g., ($C_1$-$C_6$)-acyl, ($C_1$-$C_3$)-acyl etc. Furthermore, depending on the carbon chain, length specific acyl groups may be termed a formyl group (n=0), an acetyl group (n=1), a propionyl group (n=2), a butyryl group (n=3), a pentanoyl group (n=4), etc.

The term "O-acyl group", as used herein, refers to an acyl group in which the carbon atom is single bonded to an additional oxygen atom. The additional oxygen atom can be bonded to another entity. An O-acyl group can be described by the chemical formula: —O—C(=O)—$C_nH_{2n+1}$ or e.g., —O—($C_1$-$C_6$)-acyl, —O—($C_1$-$C_3$)-acyl etc. Furthermore, depending on the carbon chain, length specific O-acyl groups may be termed an O-formyl group (n=0), an O-acetyl group (n=1), an O-propionyl group (n=2), an O-butyryl group (n=3), an O-pentanoyl group (n=4) etc.

The term "alkylene", as used herein, refers to a divalent alkyl group.

The term "hetero", as used herein, (e.g., "heterocycle", "heterocyclic", "heterocyclic group"), refers to a saturated or partially saturated or aromatic cyclic group, in which one or two ring atoms are a heteroatom selected from N, O, or S, the remaining ring atoms being C. Included are, for example, ($C_3$-$C_{20}$), ($C_3$-$C_{10}$), and ($C_3$-$C_6$) cyclic groups comprising one or two hetero atoms selected from O, S, or N.

The term "aryl group", as used herein, refers to an aromatic ring compound in which at least one hydrogen atom has been removed from the aromatic ring to permit the bonding of a carbon atom in the aromatic ring to another entity. The aryl groups can optionally be a substituted $C_6$-$C_{14}$-aryl. The aryl group can further optionally be substituted $C_6$-$C_{10}$-aryl, or phenyl. Further aryl groups include phenyl, naphthyl, tetrahydronaphthyl, phenanthrenyl, biphenylenyl, indanyl, or indenyl and the like.

The term "alkyl-aryl", as used herein, refers to an alkylene group substituted with an aryl group.

The term "receptor", as used herein, refers to a protein present on the surface of a cell, or in a cell not associated with a cellular surface (e.g., a soluble receptor) capable of mediating signaling to and/or from the cell, or within the cell and thereby affect cellular physiology. Receptors may be classified in classes, such as the G-protein coupled receptors ("GPCRs"), families, such as 5-HT receptors, and sub-families such as 5-$HT_{1A}$ receptors, 5-$HT_{2A}$ receptors, and 5-$HT_{2B}$ receptors, and so on. In this respect, "signaling" refers to a response in the form of a series of chemical reactions which can occur when a molecule, including, for example, the fused heterocyclic mescaline derivatives disclosed herein, interacts with a receptor. Signaling generally proceeds across a cellular membrane and/or within a cell, to reach a target molecule or chemical reaction, and results in a modulation in cellular physiology. Thus, signaling can be thought of as a transduction process by which a molecule interacting with a receptor can modulate cellular physiology, and, furthermore, signaling can be a process by which molecules inside a cell can be modulated by molecules outside a cell. Signaling and interactions between molecules and receptors, including for example, affinity, binding efficiency, and kinetics, can be evaluated through a variety of assays, including, for example, assays known as receptor binding assays (for example, radioligand binding assays, such as e.g., [$^3$H]ketanserin assays may be used to evaluate receptor 5-$HT_{2A}$ receptor activity), competition assays, and saturation binding assays, and the like.

The term "G-protein coupled receptor" or "GPCR", as used herein, refers to a class of evolutionarily related transmembrane receptors capable of interacting with a class of proteins known as G-proteins (guanine nucleotide binding proteins). GPCRs can mediate cellular responses to external stimuli (Weis and Kobilka, 2018, Annual Review of Biochemistry 87: 897-919) and can be activated by interacting with a ligand, including neurotransmitters, such as serotonin or dopamine, for example, which, can then initiate an interaction of the receptor with a G-protein and can elicit dissociation of the G-protein into α and βγ subunits. In turn, these α and βγ subunits can mediate further downstream signaling. GPCRs can also activate other signaling pathways, for example, through arrestin proteins and kinases. Certain ligands can preferentially activate a subset of all GPCR signaling pathways. Signaling pathways downstream of a GPCR can mediate therapeutic efficacy, or can cause drug adverse effects (Bock and Bermudez, 2021, FEBS Journal 288: 2513-2528).

The term "5-HT receptor", as used herein, refers to a family of GPCRs receptors found in the central and peripheral nervous system and include sub-families, such as, 5-$HT_{1A}$ receptors, 5-$HT_{2A}$ receptors, and 5-$HT_{2B}$ receptors. 5-HT receptors can mediate signaling through specific G-proteins, including notably $G\alpha_i$, $G\alpha_{q/11}$, and Gαs and can be involved in the control of multiple physiological processes including cognition, mood, and modulation of sleep-wake cycles, for example (McCorvy and Roth, 2015, Pharmacology and Therapeutics 150: 129-142). 5-HT receptors can further mediate signaling through arrestin as well as G-protein independent signaling pathways. 5-HT-receptors are implicated in multiple brain neurological disorders including migraine headaches, and neuropsychiatric disorders, such as schizophrenia and depression, for example.

The term "5-HT$_{1A}$ receptor", as used herein, refers to a sub-family of a family of receptors for the neurotransmitter and peripheral signal mediator serotonin. 5-HT$_{1A}$ receptors can mediate a plurality of central and peripheral physiologic functions of serotonin. Ligand activity at 5-HT$_{1A}$ is generally not associated with hallucination, although many hallucinogenic compounds are known to modulate 5-HT$_{1A}$ receptors to impart physiological responses (Inserra et al., 2020, Pharmacol. Rev 73: 202). 5-HT$_{1A}$ receptors are implicated in various brain neurological disorders, including depression and anxiety, schizophrenia, and Parkinson's disease (Behav. Pharm. 2015, 26:45-58).

The term "5-HT$_{2A}$ receptor", as used herein, refers to a sub-family of a family of receptors for the neurotransmitter and peripheral signal mediator serotonin. 5-HT$_{2A}$ receptors can mediate a plurality of central and peripheral physiologic functions of serotonin. Central nervous system effects can include mediation of hallucinogenic effects of hallucinogenic compounds. 5-HT$_{2A}$ receptors are implicated in various brain neurological disorders (Nat. Rev. Drug Discov. 2022, 21:463-473; Science 2022, 375:403-411).

The term "5-HT$_{2B}$ receptor" (also referred to herein as "HT2B" and "HTR2B"), as used herein, refers to a sub-family of a family of receptors for the neurotransmitter and peripheral signal mediator serotonin. 5-HT$_{2B}$ receptors can mediate a plurality of central and peripheral physiologic functions of serotonin. Central nervous system effects can include mediation of hallucinogenic effects of hallucinogenic compounds. 5-HT$_{2B}$ receptors are implicated in various brain neurological disorders, including schizophrenia (Pharmacol. Ther. 2018, 181:143-155) and migraine (Cephalalgia 2017, 37:365-371).

The term "5-HT$_{2C}$ receptor" (also referred to herein as "HT2C" and "HTR2C"), as used herein, refers to a sub-family of a family of receptors for the neurotransmitter and peripheral signal mediator serotonin. Antagonism of 5-HT$_{2C}$ receptors by drugs such as agomelatine can increase availability of norepinephrine and dopamine in the prefrontal cortex, and can lead to antidepressant and nootropic effects (Savino et al., 2023, Brain Science 13: 734). Further, 5-HT$_{2C}$ receptors can play a role in food intake and body weight control (Przegalinski et al., 2023, Nutrients 15:1449).

The term "5-HT$_7$ receptor" (also referred to herein as "HT7" and "HTR7"), as used herein, refers to a sub-family of a family of receptors for the neurotransmitter and peripheral signal mediator serotonin. 5-HT$_{1D}$ receptors are implicated in various brain neurological disorders, including Alzheimer's, dementia, and associated depressive disorders (Quintero-Villegas and Valdes-Ferrer, 2022, Molecular Medicine 28: 70).

The term "α$_{2A}$ receptor" (also referred to herein as "α-2A", and "alpha2A") as used herein, refers to a sub-family of a family of receptors for catecholamine neurotransmitters and signal mediators such as norepinephrine (noradrenaline) and epinephrine (adrenaline). α-2A receptors are implicated in various brain neurological disorders, including schizophrenia, bipolar disorders, and post-traumatic stress disorder (PTSD) (Saggu et al., 2023, Molecular Psychiatry 28: 588-600).

The term "MT$_1$ receptor" (also referred to herein as "MT$_1$"), used herein, refers to a sub-family of a family of receptors for the neural transmitter and signal mediator melatonin. MT$_1$ receptors are implicated in various brain neurological disorders, including sleep disorders and depression (Boiko et al., 2022, Neurochemical Research 47: 2909-2924).

The term "DAT", as used herein, refers to a transmembrane transport protein also known as "dopamine active transporter", which is involved in transporting dopamine into the cytosol. DAT is implicated in various brain neurological disorders, notably dopamine related disorders such as attention deficit hyperactivity disorder (ADHD), bipolar disorder, and clinical depression, anxiety (Am. J. Med. Genet. B Neuropsychiatr. Genet. 2018, 177:211-231).

The term "NET", as used herein, refers to a transmembrane transport protein also known as "norepinephrine transporter" or "noradrenaline transporter" or "NAT" which is involved in Na$^+$/Cl$^-$ dependent re-uptake of extracellular norepinephrine or noradrenaline. NET is implicated in various brain neurological disorders, including attention deficit hyperactivity disorder (ADHD) and clinical depression (Neurosci. Biobehav. Rev, 2013, 37:1786-800).

The term "SERT", as used herein, refers to a transmembrane transport protein also known as "serotonin transporter" which is involved in neuronal serotonin transport, notably from the synaptic cleft back to the presynaptic neuron, thereby terminating the action of serotonin. SERT is implicated in various brain neurological disorders, including anxiety and depression (Pharmacol. Rep. 2018, 70:37-46).

The term "modulating receptors", as used herein, refers to the ability of a compound disclosed herein to alter the function of receptors. A receptor modulator may activate the activity of a receptor or inhibit the activity of a receptor depending on the concentration of the compound exposed to the receptor. Such activation or inhibition may be contingent on the occurrence of a specific event, such as activation of a signal transduction pathway, and/or maybe manifest only in particular cell types. The term "modulating receptors," also refers to altering the function of a receptor by increasing or decreasing the probability that a complex forms between a receptor and a natural binding partner to form a multimer. A receptor modulator may increase the probability that such a complex forms between the receptor and the natural binding partner, may increase or decrease the probability that a complex forms between the receptor and the natural binding partner depending on the concentration of the compound exposed to the receptor, and or may decrease the probability that a complex forms between the receptor and the natural binding partner. It is further noted that the fused heterocyclic mescaline derivatives of the present disclosure may alter the function of a receptor by acting as an agonist or antagonist of the receptor, and that fused heterocyclic mescaline derivatives according to the present disclosure may alter the function of a receptor by directly interacting therewith or binding thereto, or by indirectly interacting therewith through one or more other molecular entities. In general, the receptor may be any receptor, including any receptor set forth herein, such as, any of a 5-HT$_{1A}$, 5-HT$_{1B}$, 5-HT$_{2A}$, a 5-HT$_{2B}$, 5-HT$_{3A}$, 5-HT$_{2C}$, 5-HT$_{1D}$, 5-HT$_7$, α$_{2A}$, D$_2$, D$_3$, MT$_1$ receptor, for example. Accordingly, it will be clear, that in order to refer modulating specific receptors, terms such as "modulating 5-HT$_{1A}$ receptors", "modulating 5-HT$_{1B}$ receptors", "modulating 5-HT$_{2A}$ receptors", "modulating 5-HT$_{2B}$ receptors", and so forth, may be used herein.

The term "receptor-mediated disorder", as used herein, refers to a disorder that is characterized by abnormal receptor activity. A receptor-mediated disorder may be completely or partially mediated by modulating a receptor. In particular, a receptor-mediated disorder is one in which modulation of the receptor results in some effect on an underlying disorder e.g., administration of a receptor modulator results in some improvement in at least some of the subjects being treated. In general, the receptor may be any receptor, including any receptor set forth herein, such as any of a 5-HT$_{1A}$, 5-HT$_{2A}$, a 5-HT$_{2B}$, 5-HT$_{2C}$, 5-HT$_7$, α$_{2A}$, or a MT$_1$ receptor, for example. Accordingly, it will be clear, that in order to refer specific receptor-mediated disorders, terms such as "5-HT$_{1A}$ receptor-mediated disorder", "5-HT$_{2A}$ receptor-mediated disorder", "5-HT$_{2B}$ receptor-mediated disorder", and so forth, may be used.

The term "pharmaceutical formulation", as used herein, refers to a preparation in a form which allows an active ingredient, including a psychoactive ingredient, contained therein to provide effective treatment, and which does not contain any other ingredients which cause excessive toxicity, an allergic response, irritation, or other adverse response commensurate with a reasonable risk/benefit ratio. The pharmaceutical formulation may contain other pharmaceutical ingredients such as excipients, carriers, diluents, or auxiliary agents.

The term "recreational drug formulation", as used herein, refers to a preparation in a form which allows a psychoactive ingredient contained therein to be effective for administration as a recreational drug, and which does not contain any other ingredients which cause excessive toxicity, an allergic response, irritation, or other adverse response commensurate with a reasonable risk/benefit ratio. The recreational drug formulation may contain other ingredients such as excipients, carriers, diluents, or auxiliary agents.

The term "effective for administration as a recreational drug", as used herein, refers to a preparation in a form which allows a subject to voluntarily induce a psychoactive effect for non-medical purposes upon administration, generally in the form of self-administration. The effect may include an altered state of consciousness, satisfaction, pleasure, euphoria, perceptual distortion, or hallucination.

The term "effective amount", as used herein, refers to an amount of an active agent, pharmaceutical formulation, or recreational drug formulation, sufficient to induce a desired biological or therapeutic effect, including a prophylactic effect, and further including a psychoactive effect. Such effect can include an effect with respect to the signs, symptoms or causes of a disorder, or disease or any other desired alteration of a biological system. The effective amount can vary depending, for example, on the health condition, injury stage, disorder stage, or disease stage, weight, or sex of a subject being treated, timing of the administration, manner of the administration, age of the subject, and the like, all of which can be determined by those of skill in the art.

The terms "treating" and "treatment", and the like, as used herein, are intended to mean obtaining a desirable physiological, pharmacological, or biological effect, and includes prophylactic and therapeutic treatment. The effect may result in the inhibition, attenuation, amelioration, or reversal of a sign, symptom or cause of a disorder, or disease, attributable to the disorder, or disease, which includes mental and psychiatric diseases and disorders. Clinical evidence of the prevention or treatment may vary with the disorder, or disease, the subject, and the selected treatment.

The term "pharmaceutically acceptable", as used herein, refers to materials, including excipients, carriers, diluents, or auxiliary agents, that are compatible with other materials in a pharmaceutical or recreational drug formulation and within the scope of reasonable medical judgement suitable for use in contact with a subject without excessive toxicity, allergic response, irritation, or other adverse response commensurate with a reasonable risk/benefit ratio.

The term "substantially free", as used herein to describe a composition, references the substantial absence of a second compound in a composition comprising a first compound. Preferably the composition containing the first compound contains less than 5%, less than 2.5%, less than 1%, less than 0.5%, less than 0.1%, or less than 0.01% by mole percent of the second compound.

The terms "substantially pure" and "isolated", as may be used interchangeably herein to describe a compound, e.g., a mescaline derivative, which has been separated from components that naturally accompany it. Typically, a compound is substantially pure when at least 60%, more preferably at least 75%, more preferably at least 90%, 95%, 96%, 97%, or 98%, and most preferably at least 99% of the total material (by volume, by wet or dry weight, or by mole percent or mole fraction) in a sample is the compound of interest. Purity can be measured by any appropriate method, e.g., in the case of polypeptides, by chromatography, gel electrophoresis or HPLC analysis.

General Implementation

As hereinbefore mentioned, the present disclosure relates to mescaline derivatives. In particular, the present disclosure provides novel heterocyclic mescaline derivatives, wherein the phenyl portion participates in the formation of a heterocyclic ring structure, including, in example embodiments, a dioxolane ring or a dioxane ring, fused to the phenyl portion. Thus, the compounds of the present disclosure can be said to be fused heterocyclic mescaline derivatives. Furthermore, the mescaline derivatives include an isopropylamine chain (instead of an ethylamine chain, as is the case for mescaline). The isopropylamine chain can contain various substituent groups, including, notably C$_1$ substituent groups. In addition, the amine group in the isopropylamine chain can be substituted. Thus, the herein provided novel compounds can be referred to as substituted C$_1$-substituted isopropylamine fused heterocyclic mescaline derivatives. In general, the herein provided novel compounds exhibit functional properties which deviate from the functional properties of mescaline. Thus, for example, the mescaline derivatives of the present disclosure, can exhibit pharmacological properties which deviate from mescaline. Furthermore, the mescaline derivatives may exhibit physico-chemical properties which differ from mescaline. Thus, for example, the fused heterocyclic mescaline derivatives may exhibit superior solubility in a solvent, for example, an aqueous solvent. The fused heterocyclic mescaline derivatives in this respect are useful in the formulation of pharmaceutical and recreational drug formulations. In one embodiment, the fused heterocyclic mescaline derivatives of the present disclosure can conveniently be chemically synthesized. The practice of this method avoids the extraction of mescaline from cactus plants and the performance of subsequent chemical reactions to achieve the fused heterocyclic mescaline derivatives. Furthermore, the growth of cactus plants can be avoided thus limiting the dependence on climate and weather, and potential legal and social challenges associated with the cultivation of cactus plants containing psychoactive compounds. The method can efficiently yield substantial quantities of the fused heterocyclic mescaline derivatives.

In what follows selected embodiments are described with reference to the drawings.

Initially example fused heterocyclic mescaline derivatives will be described. Thereafter example methods of using and making the fused heterocyclic mescaline derivatives will be described.

Accordingly, in one aspect the present disclosure provides derivatives of a compound known as mescaline of which the chemical structure is shown in FIG. 1. The derivatives herein provided are, in particular, fused heterocyclic derivatives of mescaline. It is noted that in this respect, that the term "fused heterocyclic", refers to a derivative wherein a heterocycle is bonded to two adjacent carbon atoms present in the phenyl ring of mescaline. Similarly, the terms "fused dioxolane", and "fused dioxane" refer to a derivative wherein a dioxolane or a dioxane, respectively, is bonded to two adjacent carbon atoms present in the phenyl ring of mescaline. Furthermore, the derivatives are $C_1$-substituted isopropylamine mescaline derivatives. In this respect, referring to FIG. 2, "$C_1$-substituted" refers to a mescaline derivative comprising an isopropylamine chain wherein specifically the $C_1$ atom of the isopropylamine chain is substituted with one or two substituents.

Thus, in one aspect, the present disclosure provides, in accordance with the teachings herein, in at least one embodiment, a chemical compound having chemical formula (I) or chemical formula (II):

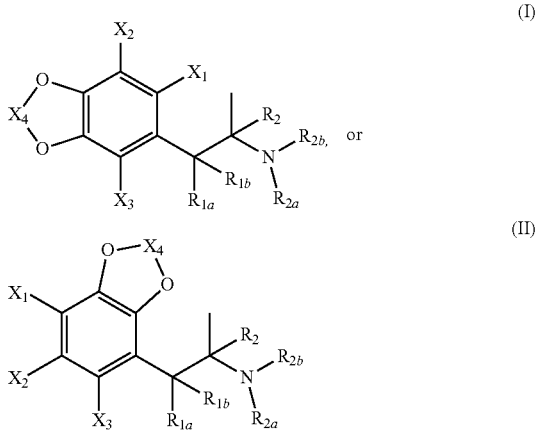

wherein, in chemical formula (I) and chemical formula (II):
 $X_1$, $X_2$, and $X_3$ are independently selected from a hydrogen atom, O-alkyl, N-alkyl, OH, a halogen, or $NH_2$;
 $X_4$ is an alkylene group or substituted alkylene group;
 $R_{1a}$ is an alkyl group, O-alkyl group, a halogen, or OH, $R_{1b}$ is a hydrogen atom or a halogen, or $R_{1a}$ and $R_{1b}$ are joined together to form an oxo group;
 $R_2$ is a hydrogen atom or an O-alkyl group; and
 $R_{2a}$ and $R_{2b}$ are independently selected from an alkyl group, an optionally substituted alkyl-aryl group, or a hydrogen atom, or $R_{2a}$ and $R_{2b}$ are joined together, along with the nitrogen atom to which they are attached, to form a 3-10-membered optionally substituted heterocyclic ring.

Thus, referring to formulae (I), and (II), $X_1$, $X_2$, and $X_3$ can be independently selected from a hydrogen atom, O-alkyl, N-alkyl, OH, a halogen, or $NH_2$. In example embodiments, $X_1$, $X_2$, and $X_3$ can each independently be selected from a hydrogen atom, O-alkyl (e.g., O—($C_1$-$C_{10}$)-alkyl, O—($C_1$-$C_6$)-alkyl, or O—($C_1$-$C_3$)-alkyl (methoxy, ethoxy, propoxy)), N-alkyl (e.g., N—($C_1$-$C_{10}$)-alkyl, N—($C_1$-$C_6$)-alkyl, or N—($C_1$-$C_3$)-alkyl), OH, halogen (C, F, Cl, I), or $NH_2$. In further example embodiments, all three of $X_1$, $X_2$, and $X_3$ can be identical substituents. In further example embodiments, all three of $X_1$, $X_2$, and $X_3$ can be identical O-alkyl groups (e.g., methoxy groups, ethoxy groups), non-identical O-alkyl groups, or partially identical O-alkyl groups (i.e., 2 identical O-alkyl groups, 1 non-identical O-alkyl group); identical N-alkyl groups, non-identical N-alkyl groups, or partially identical N-alkyl groups (i.e., 2 identical N-alkyl groups, 1 non-identical N-alkyl group); identical acyl groups, non-identical acyl groups, or partially identical acyl groups (i.e., 2 identical acyl groups, 1 non-identical acyl group); identical; or identical, non-identical or partially identical halogens (i.e., 2 identical halogens, 1 non-identical halogen). In further example embodiments, two of $X_1$, $X_2$, and $X_3$ can be identical substituents. In yet further example embodiments, all three of $X_1$, $X_2$, and $X_3$ can be non-identical substituents.

Turning to $X_4$, and referring further to formulae (I), and (II), $X_4$ can be an alkylene group or substituted alkylene group. In an example embodiment, $X_4$ can be a non-substituted alkylene, including for example a ($C_1$-$C_{10}$)-alkylene, ($C_1$-$C_6$)-alkylene, or a ($C_1$-$C_3$)-alkylene (methylene (—$CH_2$—), ethylene (—$CH_2CH_2$—), propylene (—$CH_2CH_2CH_2$—)).

In an example embodiment, $X_4$ can be a substituted alkylene, including, for example, a $C_1$-$C_{10}$ substituted alkylene, $C_1$-$C_6$ substituted alkylene or a $C_1$-$C_3$ substituted alkylene (substituted methylene (e.g., —CHR—, wherein R is a substituent), substituted ethylene (e.g., —CHRCH$_2$—, wherein R is a substituent), substituted propylene (e.g., —$CH_2$CHRCH$_2$—, wherein R is a substituent). Substituents can, for example, be selected from an oxo group (forming a carbonyl), hydroxy, halogen (F, Cl, Br, I), O-alkyl (e.g., O—($C_1$-$C_{10}$)-alkyl, O—($C_1$-$C_6$)-alkyl, or —O—($C_1$-$C_3$)-alkyl), N-alkyl (e.g., N—($C_1$-$C_{10}$)-alkyl, N—($C_1$-$C_6$)-alkyl, or N—($C_1$-$C_3$)-alkyl), acyl (e.g., ($C_1$-$C_{10}$)-acyl, ($C_1$-$C_6$)-acyl, or ($C_1$-$C_3$)-acyl), O-acyl (e.g., O—($C_1$-$C_{10}$)-acyl, O—($C_1$-$C_6$)-acyl, or O—($C_1$-$C_3$)-acyl) aryl (e.g., $C_6$-$C_{10}$ aryl, e.g., phenyl, naphthyl), and alkyl-aryl group (e.g., ($C_1$-$C_{10}$)-alkyl-aryl, ($C_1$-$C_6$)-alkyl-aryl, or ($C_1$-$C_3$)-alkyl-aryl).

In an example embodiment, $X_4$ can be a non-substituted alkylene, notably a methylene (—$CH_2$—)), and the compound having chemical formula (I) or chemical formula (II) can have a chemical formula ($I_b$) or ($II_b$):

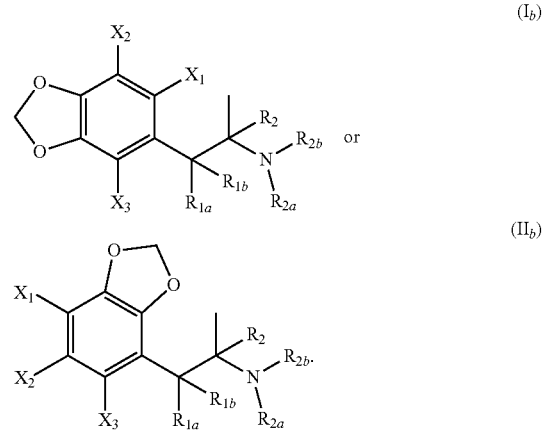

It is noted that in the compounds having formula ($I_b$) and ($II_b$), the 5-membered heterocyclic group fused to the phenyl portion of the compounds having formula ($I_b$) and ($II_b$), is known in the art as a dioxolane ring.

In an example embodiment, $X_4$ can be a non-substituted alkylene, notably an ethylene (—$CH_2$—$CH_2$—)), and the compound having chemical formula (I) or chemical formula (II) can have chemical formula ($I_c$) or ($II_c$):

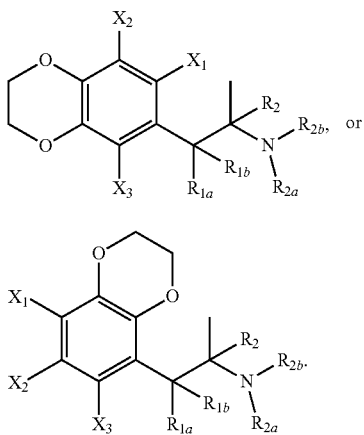

It is noted that in the compounds having formula ($I_c$) and ($II_c$), the 6-membered heterocyclic group fused to the phenyl portion of the compounds having formula ($I_c$) and ($II_c$), is known in the art as a dioxane ring.

As herein before noted, the current disclosure includes, in an aspect, in particular, mescaline derivatives including a $C_1$-substituted isopropylamine chain, notably an isopropylamine chain possessing a substituted $C_1$ carbon atom (—$CR_{1a}R_{1b}$), wherein $R_{1a}$ and/or $R_{1b}$ are a substituent.

Next, further example embodiments of mescaline derivatives including a $C_1$-substituted isopropylamine chain will be described with respect to example selections of $R_{1a}$ and $R_{1b}$ substituents included in the isopropylamine chain. Referring to formulae (I) and (II) $R_{1a}$ can be selected to be an alkyl group, O-alkyl group, a halogen, or OH, and $R_{1b}$ can be selected to be a hydrogen atom or a halogen, or $R_{1a}$ and $R_{1b}$ can be joined together to form an oxo group. Furthermore, referring to formulae (I) and (II), as well as to formulae ($I_b$) and ($II_b$) and ($I_c$) and ($II_c$), it is noted that in particular example embodiments, $X_1$, $X_2$, $X_3$ can each be selected to be H, or $X_1$, $X_2$, $X_3$ and $R_2$ can each be selected to be H, as herein illustrated by example compounds A(I)-$E_y$(VIII). These example embodiments, are in particular, but without limitation, intended to be included in conjunction with the hereinafter described example embodiments with respect to $R_{1a}$ and $R_{1b}$.

Thus, for example, referring to formulae (I), ($I_b$), ($I_c$), (II), ($II_b$) and ($II_c$), in an example embodiment, $R_{1a}$ can be an alkyl group, O-alkyl group, a halogen, or OH group, and $R_{1b}$ can be a hydrogen atom.

Continuing to refer to formulae (I), ($I_b$), ($I_c$), (II), ($II_b$), and ($II_c$), in an example embodiment, $R_{1a}$ can be a ($C_1$-$C_6$)-alkyl group, and $R_{1b}$ can be a hydrogen atom.

Continuing further to refer to formulae (I), ($I_b$), ($I_c$), (II), ($II_b$), and ($II_c$), in an example embodiment, $R_{1a}$ can be a ($C_1$-$C_3$)-alkyl group, and $R_{1b}$ can be a hydrogen atom.

Continuing further to refer to formulae (I), ($I_b$), ($I_c$), (II), ($II_b$), and ($II_c$), in an example embodiment, $R_{1a}$ can be a methyl or ethyl group and $R_{1b}$ can be a hydrogen atom.

Continuing further to refer to formulae (I), ($I_b$), ($I_c$), (II), ($II_b$), and ($II_c$), in an example embodiment, $R_{1a}$ can be fluorine (F) and $R_{1b}$ can be a hydrogen atom.

Continuing further to refer to formulae (I), ($I_b$), ($I_c$), (II), ($II_b$), and ($II_c$), in an example embodiment, $R_{1a}$ and $R_{1b}$ can each be a non-identical halogen.

Continuing further to refer to formulae (I), ($I_b$), ($I_c$), (II), ($II_b$), and ($II_c$), in an example embodiment, $R_{1a}$ and $R_{1b}$ can each be an identical halogen.

Continuing further to refer to formulae (I), ($I_b$), ($I_c$), (II), ($II_b$), and ($II_c$), in an example embodiment, $R_{1a}$ and $R_{1b}$ can each be fluorine (F).

Continuing further to refer to formulae (I), ($I_b$), ($I_c$), (II), ($II_b$), and (II), in an example embodiment, in an aspect, $R_{1a}$ can be hydroxy (OH), and $R_{1b}$ can be a hydrogen atom.

Continuing further to refer to formulae (I), ($I_b$), ($I_c$), (II), ($II_b$), and (II), $R_{1a}$ and $R_{1b}$ can be joined together to form an oxo group.

Turning next to $R_2$, and referring further to formulae (I), ($I_b$), ($I_c$), (II), ($II_b$), and ($II_c$), $R_2$ can be a hydrogen atom or an O-alkyl group.

In an example embodiment, $R_2$ can be a hydrogen atom (H).

In another example embodiment, $R_2$ can be an O-alkyl group, e.g., O—($C_1$-$C_{10}$)-alkyl, O—($C_1$-$C_6$)-alkyl, or O—($C_1$-$C_3$)-alkyl (methoxy, ethoxy, propoxy).

Turning next to $R_{2a}$ and $R_{2b}$, referring further to formulae (I), ($I_b$), ($I_c$), (II), ($II_b$), and ($II_c$), $R_{2a}$ and $R_{2b}$ can be independently selected from an alkyl group, an optionally substituted alkyl-aryl group, or a hydrogen atom, or $R_{2a}$ and $R_{2b}$ can joined together, along with the nitrogen atom to which they are attached, to form a 3-10-membered optionally substituted heterocyclic ring.

In one example embodiment, $R_{2a}$ and $R_{2b}$ can be independently selected from a hydrogen atom, an optionally substituted alkyl-aryl group, or an alkyl group.

In example embodiments, $R_{2a}$ and/or $R_{2b}$ can be an alkyl group, and the alkyl group can be a ($C_1$-$C_6$)-alkyl group, a ($C_1$-$C_3$)-alkyl group, or a methyl group.

In further example embodiments, $R_{2a}$ and/or $R_{2b}$ can be an optionally substituted (i.e., a substituted or non-substituted) alkyl-aryl group, and the optionally substituted alkyl-aryl group can be a ($C_1$-$C_6$)-alkyl-aryl group or a ($C_1$-$C_3$)-alkyl-aryl group, or a —$CH_2$-aryl group, wherein, in each case, the aryl group is optionally substituted, including, for example, a substituted or non-substituted phenyl group.

In further example embodiments, $R_{2a}$ and/or $R_{2b}$ can be a substituted alkyl-aryl group, and the substituted alkyl-aryl group can be a ($C_1$-$C_3$)-alkyl-phenyl group, wherein the phenyl group is substituted by at least one of a halogen atom, an O-alkyl group, and a ($C_5$-$C_{10}$)-heterocycle (including two carbon atoms in the phenyl group) fused to the phenyl group via two adjacent phenyl group substituents, such as alkyl groups. In an example embodiment, the ($C_5$-$C_{10}$)-heterocycle can be $C_6$ heterocycle including two oxygen hetero atoms.

In further example embodiments, $R_{2a}$ and/or $R_{2b}$ can be a substituted alkyl-aryl group, and the substituted alkyl-aryl group can be a substituted —$CH_2$-phenyl group, wherein the phenyl group is substituted by halogen atom, and a ($C_5$)-heterocycle including two oxygen hetero atoms, the ($C_5$)-heterocycle (including two carbon atoms in the phenyl group) fused to the phenyl group via two adjacent phenyl group substituents, such as alkyl groups.

In further example embodiments, $R_{2a}$ and/or $R_{2b}$ can be a substituted alkyl-aryl group, and the substituted alkyl-aryl group can be a substituted —$CH_2$-phenyl group, wherein the phenyl group is substituted by an ($C_1$-$C_6$)—O-alkyl group, and a ($C_5$)-heterocycle (including two carbon atoms in the phenyl group) containing two oxygen hetero atoms, the ($C_5$)-heterocycle fused to the phenyl group via two adjacent phenyl group substituents, such as alkyl groups.

In further example embodiments, $R_{2a}$ and/or $R_{2b}$ can be a substituted alkyl-aryl group, and the substituted alkyl-aryl group can be a substituted —$CH_2$-phenyl group, wherein the phenyl group is substituted by an ($C_1$-$C_3$)—O-alkyl group, and a ($C_5$)-heterocycle (including the two carbon atoms in the phenyl group) containing 2 oxygen hetero atoms, the ($C_5$)-heterocycle fused to the phenyl group via two adjacent phenyl group substituents, such as alkyl groups.

In further example embodiments, $R_{2a}$ and/or $R_{2b}$ can be a substituted alkyl-aryl group, and the substituted alkyl-aryl group can be a substituted —$CH_2$-phenyl group, wherein the phenyl group is substituted by a methoxy group, and a ($C_5$)-heterocycle (including the two carbon atoms in the phenyl group) containing 2 oxygen hetero atoms, the ($C_5$)-heterocycle fused to the phenyl group via two adjacent phenyl group substituents, such as alkyl groups.

In further example embodiments, $R_{2a}$ and $R_{2b}$ can together form a 4-20 membered, 4-14 membered, 4-10 membered, 4-8 membered, 4-6 membered, 6 membered, or 5 membered heterocyclic ring, or 4 membered heterocyclic ring.

In further embodiments, the amino group (—$NR_{2a}R_{2b}$) in the compound of formula (I), ($I_b$), ($I_c$), (II), ($II_b$), and ($II_c$) can be protonated to form (—$N^+HR_{2a}R_{2b}$), and chemical formula (I), ($I_b$), ($I_c$), (II), ($II_b$), and ($II_c$) further include a negatively charged anion balancing the positively charged nitrogen atom, for example, a sulfate ion ($SO_4^{2-}$), a nitrate ion ($NO_3^-$), or a chlorine ion ($Cl^-$).

Next, in order to further exemplify the mescaline derivative compounds that are provided in accordance with the present disclosure, example compounds in accordance with formula (I) are provided. These include compounds having the chemical formula: A(I)-A(III); B(I)-(VI); C(I)-C(VI); D(I)-D(VI); and $E_x$(I)-$E_y$(VIII), as hereinafter set forth.

Thus, the present disclosure provides, in one aspect, example compounds A(I)-A(III):

A(I)
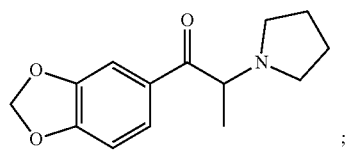

A(II)
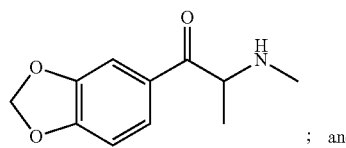
; and

A(III)
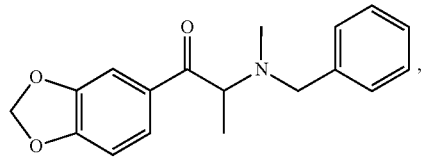
, wherein in each of compound A(I) to A(III), optionally, the nitrogen atom of the isopropylamine portion is protonated and A(I) to A(III) includes a negatively charged anion balancing the positively charged nitrogen atom.

In another aspect, the present disclosure provides example compounds B(I)-B(VI):

B(I)
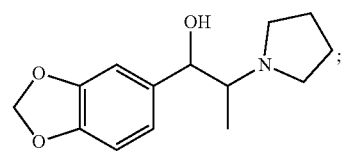
;

B(II)
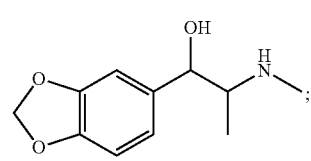
;

B(III)
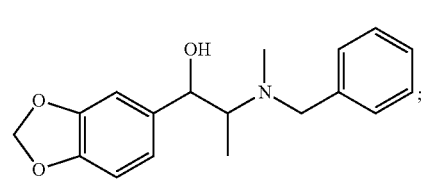
;

B(IV)
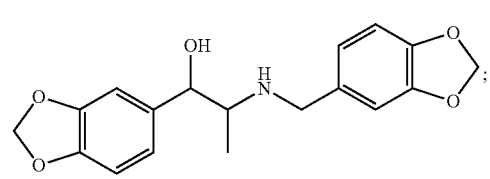
;

B(V)
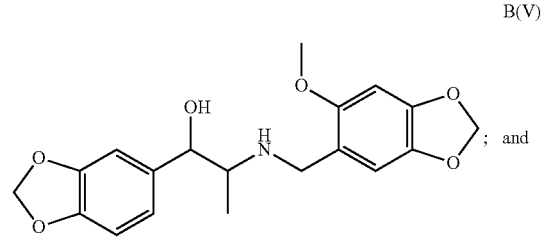
; and

B(VI)
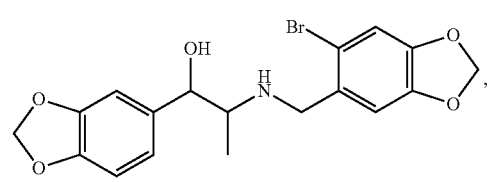
, wherein in each of compound B(I) to B(VI), optionally, the nitrogen atom of the isopropylamine portion is protonated and B(I) to B(VI) includes a negatively charged anion balancing the positively charged nitrogen atom.

In another aspect, the present disclosure provides example compounds C(I)-C(VI):

C(I)
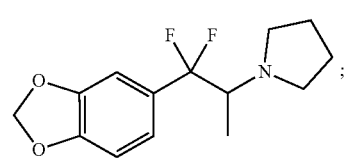
;

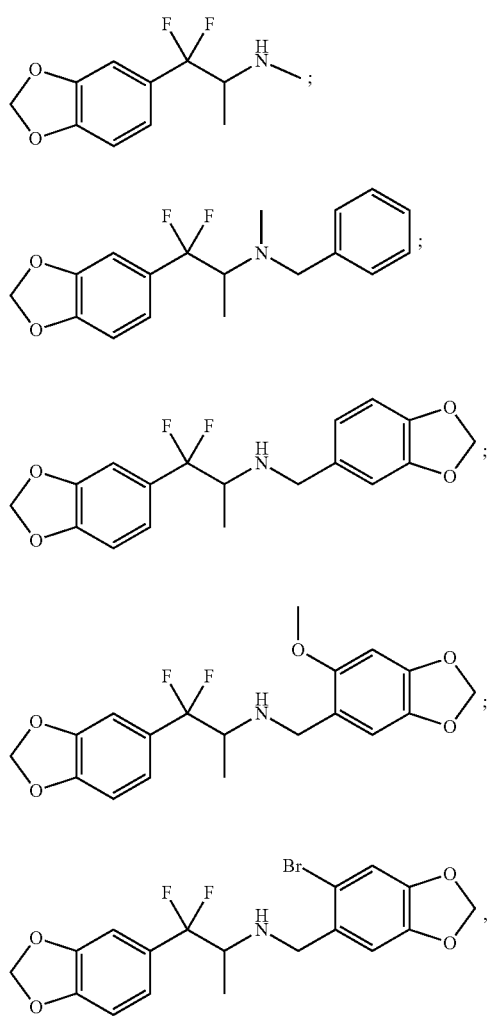

wherein in each of compound C(I) to C(VI), optionally, the nitrogen atom of the isopropylamine portion is protonated and C(I) to C(VI) includes a negatively charged anion balancing the positively charged nitrogen atom.

In another aspect, the present disclosure provides example compounds D(I)-D(VI):

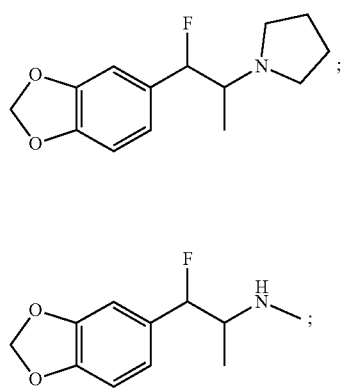

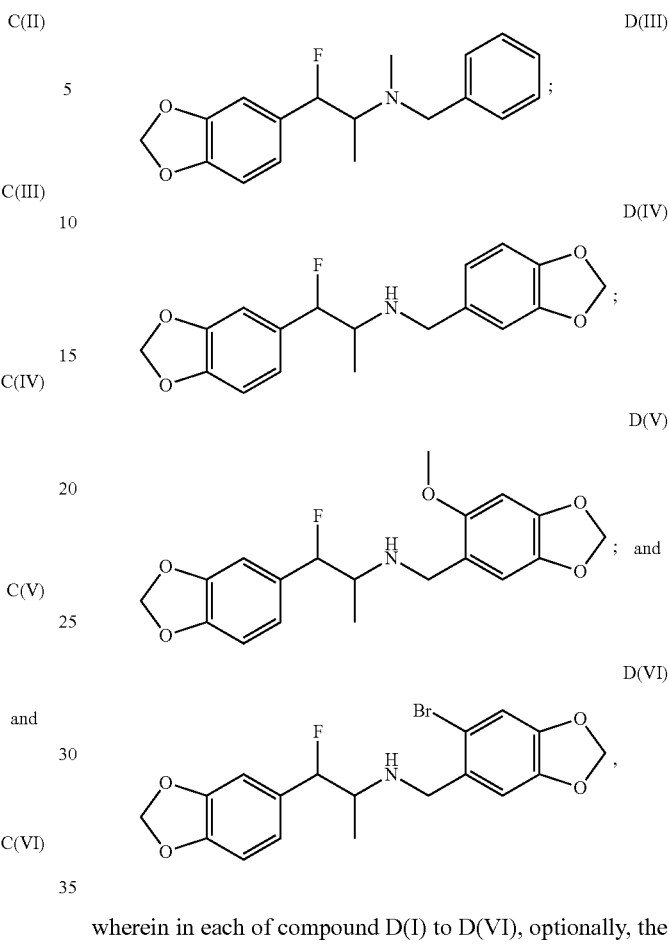

wherein in each of compound D(I) to D(VI), optionally, the nitrogen atom of the isopropylamine portion is protonated and D(I) to D(VI) includes a negatively charged anion balancing the positively charged nitrogen atom.

In another aspect, the present disclosure provides example compounds $E_x(I)$-$E_y(VIII)$:

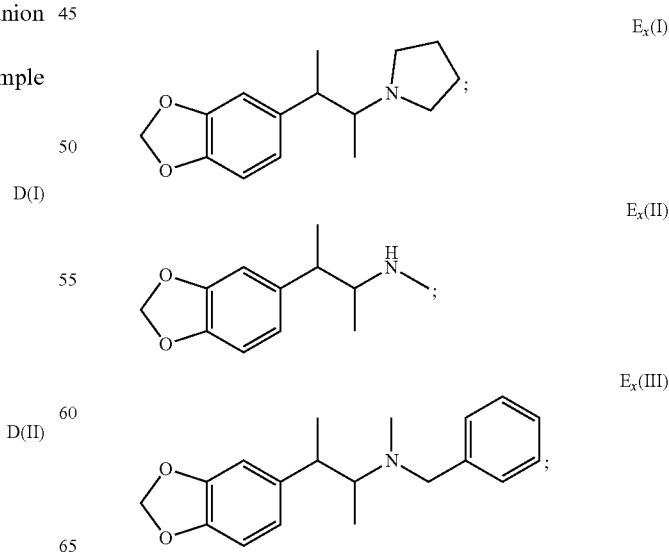

E$_x$(IV)

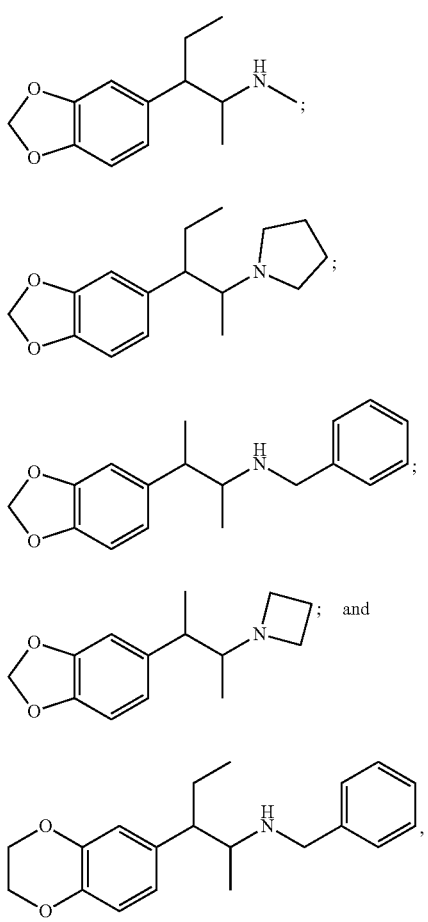

E$_x$(V)

E$_x$(VI)

E$_x$(VII) and

E$_y$(VIII)

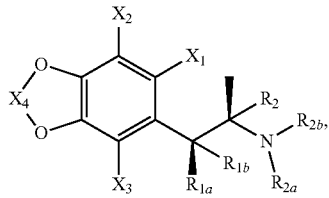 (a(i))

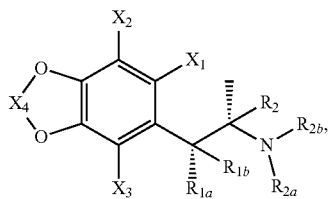 (a(ii))

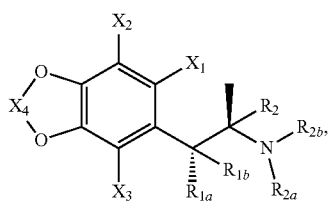 and (a(iii))

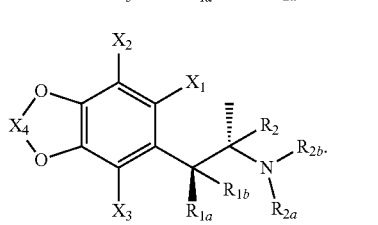 (a(iv))

Referring to example compounds (a(i)), (a(ii)), a(iii)) or (a(iv)), in accordance herewith, in one embodiment, compounds may be prepared as a pair of syn-enantiomers having the chemical formula (a(i)) and (a(ii)), or as a pair of anti-enantiomers (a(iii)) and (a(iv)), for example.

Referring further to example compounds (a(i)), (a(ii)), a(iii)) or (a(iv)), in accordance herewith, in one embodiment, compounds may be prepared as a mixture comprising syn-enantiomer pair (a(i)) and (a(ii)) and anti-enantiomer pair a(iii)) and (a(iv)), for example.

Referring further to example compounds (a(i)), (a(ii)), a(iii)) or (a(iv)), in accordance herewith, in one embodiment, compounds may be prepared as a single enantiomer (a(i)), (a(ii)), a(iii)), or (a(iv)), for example.

When enantiomeric pairs are prepared (e.g., (a(i)) and (a(ii)), or (a(iii)) and (a(iv))) members of each enantiomeric pair may be present in different molar quantities, including, for example, in equimolar or approximately equimolar quantities, as is the case in a so called "racemic mixture", and further, for example, in varying quantities including 10% (mole/mole) of a first member of an enantiomeric pair and 90% (mole/mole) of a second member of an enantiomeric pair; 20% (mole/mole) of a first member of an enantiomeric pair and 80% (mole/mole) of a second member of an enantiomeric pair; 30% of a first member of an enantiomeric pair and 70% (mole/mole) of a second member of an enantiomeric pair; 40% of a first member of an enantiomeric pair and 60% (mole/mole) of a second member of an enantiomeric pair; 60% of a first member of an enantiomeric pair and 40% (mole/mole) of a second member of an enantiomeric pair; 70% of a first member of an enantiomeric wherein in each of compound E$_x$(I) to E$_y$(VIII), optionally, the nitrogen atom of the isopropylamine portion is protonated and E$_x$(I) to E$_y$(VIII) includes a negatively charged anion balancing the positively charged nitrogen atom.

Negatively charged anions in each of the foregoing include, for example, a chloride or sulfate ion.

It is noted that certain example compounds disclosed herein may be prepared in various stereochemical configurations, notably, in particular the C$_1$ and C$_2$ carbon atoms of the isopropyl amine chain, in certain embodiments, may be stereochemical centers (and chiral carbon atoms). Thus, example compounds of the present disclosure may be prepared in various diastereomeric forms (e.g., an anti-diastereomeric form, or a syn-diastereomeric form), or as diastereomeric mixtures, for example. Furthermore, the compounds of the present disclosure may be prepared as a single enantiomer (a single syn-enantiomer or a single anti-enantiomer), or as a pair of enantiomers, for example, a pair of syn-enantiomers, a pair of anti-enantiomers, or as a mixture of a pair of syn-enantiomers and a pair of anti-enantiomers. To further illustrate the foregoing, example compounds (a(i)), (a(ii)), a(iii)) or (a(iv)) may be considered:

pair and 30% (mole/mole) of a second member of an enantiomeric pair; 80% of a first member of an enantiomeric pair and 20% (mole/mole) of a second member of an enantiomeric pair; or 90% of a first member of an enantiomeric pair and 10% (mole/mole) of a second member of an enantiomeric pair.

Furthermore, when mixtures of pairs of enantiomers are prepared, (e.g., a mixture containing (a(i)) (a(ii)), (a(iii)) and (a(iv))) the pairs may be present in different ratios, for example, 10% (mole/mole) syn-enantiomers and 90% (mole/mole) anti-enantiomers; 20% (mole/mole) syn-enantiomers and 80% (mole/mole) anti-enantiomers; 30% (mole/mole) syn-enantiomers and 70% (mole/mole) anti-enantiomers; 40% (mole/mole) syn-enantiomers and 60% (mole/mole) anti-enantiomers; 50% (mole/mole) syn-enantiomers and 50% (mole/mole) anti-enantiomers; 60% (mole/mole) syn-enantiomers and 40% (mole/mole) anti-enantiomers; 70% (mole/mole) syn-enantiomers and 30% (mole/mole) anti-enantiomers; 80% (mole/mole) syn-enantiomers and 20% (mole/mole) anti-enantiomers; or 90% (mole/mole) syn-enantiomers and 10% (mole/mole) anti-enantiomers.

Referring now again to the compounds (I) and (II), in one example embodiment, $R_{1a}$ can be an alkyl group, O-alkyl group, a halogen, or OH, and $R_{1b}$ can be a hydrogen atom or a halogen, provided however, Ria and Rib are not identical halogens and the compound having chemical formula (I) or (II) can have the chemical formula $(I_d)$ or $(II_d)$:

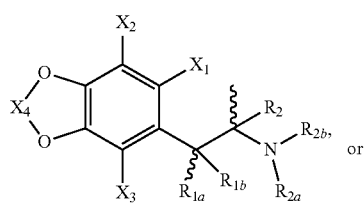

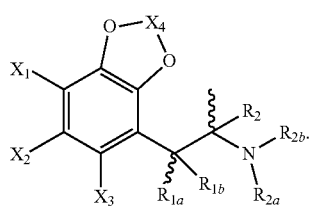

In a further embodiment, in an aspect, $R_{1a}$ can be an alkyl group, O-alkyl group, a halogen, or OH, and $R_{1b}$ can be a hydrogen atom or a halogen, provided however, that $R_{1a}$ and $R_{1b}$ are not identical halogens, and the compound having chemical formula (I) or (II) can have the chemical formula $(I_e)$ or $(II_e)$:

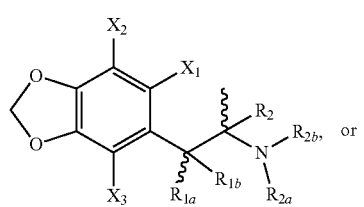

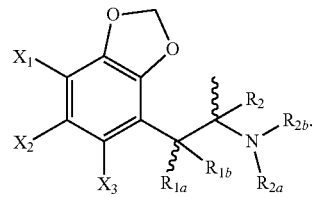

Referring now again further to the compounds (I) and (II), in one example embodiment $R_{1a}$ can be an alkyl group, O-alkyl group, a halogen, or OH, and $R_{1b}$ can be a hydrogen atom, or a halogen, provided however, that $R_{1a}$ and $R_{1b}$ are not identical halogens and the compound having chemical formula (I) or formula (II) can have the chemical formula $(I_f)$ or $(II_f)$:

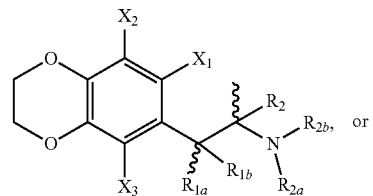

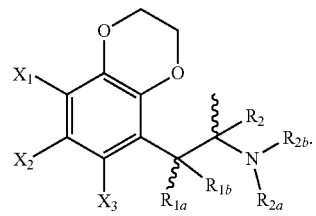

In a further embodiment, $R_{1a}$ and $R_{1b}$ can be identical halogens, or joined together to form an oxo group, and the compound having chemical formula (I) or formula (II) can have the chemical formula $(I_g)$ or $(II_g)$:

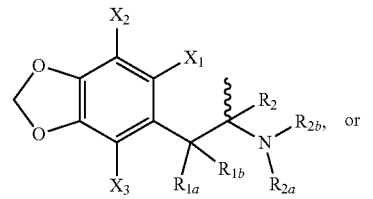

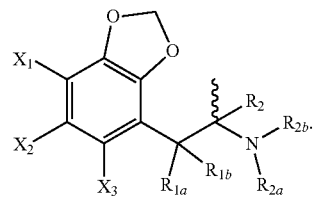

In one embodiment, the compound can be included in a mixture of a pair of diastereomeric compounds, the mixture comprising a pair of diastereomer compounds of formula $(I_d)$, $(II_d)$, $(I_e)$, $(II_e)$, $(I_f)$ or $(II_f)$. The terms "pair of diastereomeric compounds", and "pair of diastereomers", as used herein, are intended to refer to a first and second chemical compound having the same molecular formula, wherein the first and second diastereomer are three-dimensionally configured in a non-identical manner, namely in such a manner that they are not mirror images of one another. The diastereomeric compounds of the present disclosure possess two stereocenters, chiral carbon atoms $C_1$ and $C_2$. The mixture can have varying molar quantities of the first and second diastereomeric compounds of a pair of diastereomeric compounds, for example, at least 10% (mole/mole) of a first diastereomeric compound and 90% (mole/mole) of a second diastereomeric compound, or 20% (mole/mole) of a first diastereomeric compound and 80% (mole/mole) of a second diastereomeric compound, or 30% (mole/mole) of a first diastereomeric compound and 70% (mole/mole) of a second diastereomeric compound, or 40% (mole/mole) of a first diastereomeric compound and 60% (mole/mole) of a second diastereomeric compound, or a equimolar or approximately amounts of a first and of a second diastereomeric compound of a pair of diastereomeric compounds.

In one embodiment, the compound can be a single diastereomeric compound of a pair of diastereomers consisting of a first and second diastereomeric compound of formula ($I_d$), ($II_d$), ($I_e$), ($II_e$), ($I_f$), or ($II_f$) wherein the first diastereomeric compound is substantially free of a second diastereomeric compound, the second diastereomeric compound being the other diastereomeric compound of the pair of diastereomers.

In one embodiment, the compound can be included in a mixture of a pair of enantiomeric compounds, the mixture comprising a pair of enantiomers of formula ($I_d$), ($II_d$), ($I_e$), ($II_e$), ($I_f$), ($II_f$), ($I_g$), or ($II_g$). The mixture can have varying molar quantities of the first and second diastereomeric compounds of a pair of enantiomeric compounds, for example, at least 10% (mole/mole) of a first enantiomeric compound and 90% (mole/mole) of a second enantiomeric compound, or 20% (mole/mole) of a first enantiomeric compound and 80% (mole/mole) of a second enantiomeric compound, or 30% (mole/mole) of a first enantiomeric compound and 70% (mole/mole) of a second enantiomeric compound, or 40% (mole/mole) of a first enantiomeric compound and 60% (mole/mole) of a second enantiomeric compound, or a equimolar or approximately amounts of a first and of a second enantiomeric compound of a pair of diastereomeric compounds.

In one embodiment, the compound can be a single enantiomeric compound of a pair of enantiomers consisting of a first and second enantiomeric compound of formula ($I_d$), ($II_d$), ($I_e$), ($II_e$), ($I_f$), ($II_f$), ($I_g$), or ($II_g$) wherein the first enantiomeric compound is substantially free of a second enantiomeric compound, the second enantiomeric compound being the other enantiomeric compound of the pair of enantiomers.

In another aspect, the present disclosure provides example compounds A($I_g$)-A($III_g$):

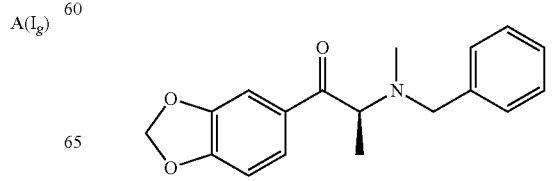

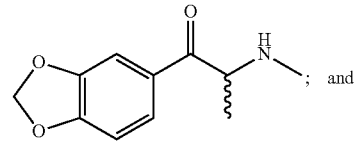

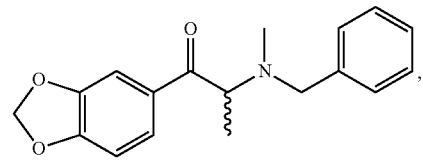

wherein in each of compound A($I_g$) to A($III_g$), optionally, the nitrogen atom of the isopropylamine portion is protonated and A($I_g$) to A($III_g$) includes a negatively charged anion balancing the positively charged nitrogen atom.

In another aspect, the present disclosure provides example compounds A($I_{ga}$) and A($I_{gb}$):

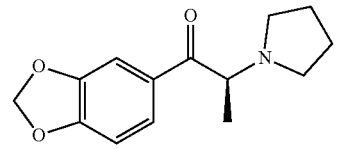

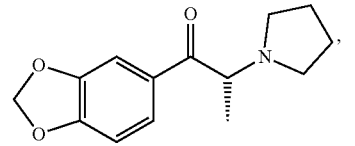

or mixtures thereof, for example, racemic mixtures.

In one aspect, the compound can be provided in a mixture further comprising the other enantiomeric compound of the enantiomeric compound pair i.e., compounds A($I_{ga}$) and A($I_{gb}$), wherein the mixture optionally is a racemic mixture, In one aspect, the selected compound can be substantially free of the other enantiomeric compound of the enantiomeric compound pair, i.e., compound A($I_{ga}$) can be substantially free of compound A($I_{gb}$), or compound A($I_{gb}$) can be substantially free of compound A($I_{ga}$).

In another aspect, the present disclosure provides example compounds A($III_{ga}$) and A($III_{gb}$):

A(III$_{gb}$)

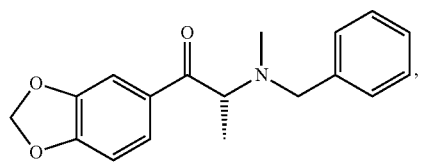

or mixtures thereof, for example, racemic mixtures.

In one aspect, the compound can be provided in a mixture further comprising the other enantiomeric compound of the enantiomeric compound pair i.e., compounds A(I$_{II}$ga) and A(III$_{gb}$), wherein the mixture optionally is a racemic mixture, In one aspect, the selected compound can be substantially free of the other enantiomeric compound of the enantiomeric compound pair, i.e., compound A(I$_{II}$ga) can be substantially free of compound A(III$_{gb}$), or compound A(III$_{gb}$) can be substantially free of compound A(III$_{ga}$).

In another aspect, the present disclosure provides example compounds B(I$_d$)-B(VI$_d$):

B(I$_d$)

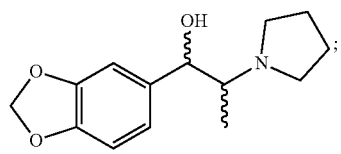

B(II$_d$)

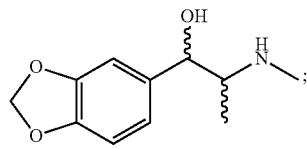

B(III$_d$)

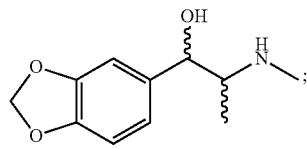

B(IV$_d$)

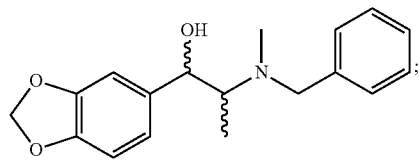

B(V$_d$)

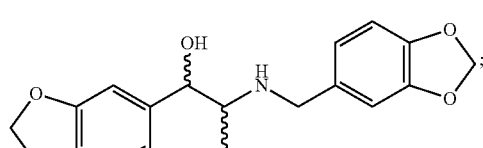

B(VI$_d$)

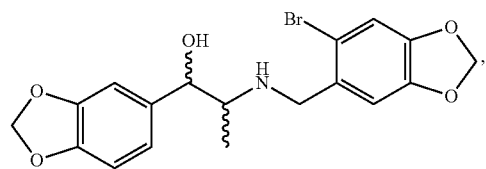

wherein in each of compound B(I$_d$) to B(VI$_d$), optionally, the nitrogen atom of the isopropylamine portion is protonated and B(I$_d$) to B(VI$_d$) includes a negatively charged anion balancing the positively charged nitrogen atom.

Thus, for example, the chemical compound can be selected from the group of compounds consisting of B(I$_{da}$), B(I$_{db}$), B(I$_{dc}$), B(I$_{dd}$), B(III$_{da}$), B(III$_{db}$), B(III$_{dc}$), and B(II-I$_{dd}$):

B(I$_{da}$)

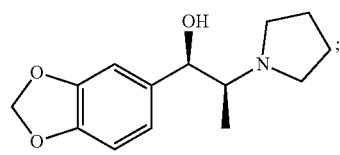

B(I$_{db}$)

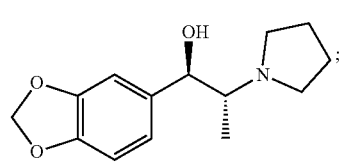

B(I$_{dc}$)

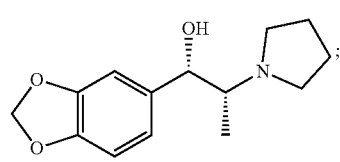

B(I$_{dd}$)

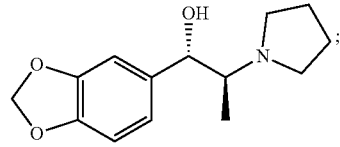

B(III$_{da}$)

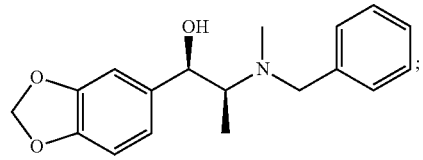

B(III$_{db}$)

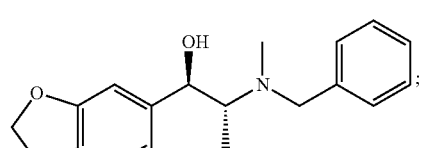

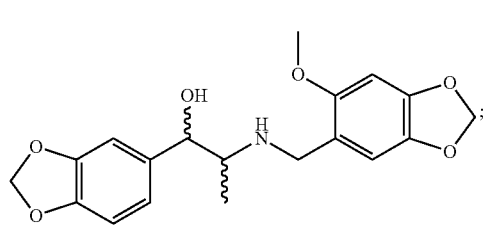

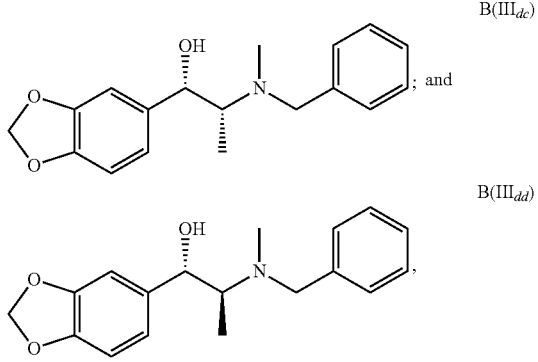

wherein in each of compound B($I_{da}$), B($I_{db}$), B($I_{dc}$), B($I_{dd}$), B(III$_{da}$), B(III$_{db}$), B(III$_{dc}$), and B(III$_{dd}$), optionally, the nitrogen atom of the isopropylamine portion may be protonated and includes a negatively charged anion balancing the positively charged nitrogen atom.

In one embodiment, the chemical compound can be provided in a mixture, for example, a racemic mixture, further comprising an enantiomeric counterpart. In this respect, it will be understood by those of skill in the art, that the enantiomeric counterpart (notably the syn-enantiomeric counterpart) of, for example, compound B($I_{da}$) is compound B($I_{dc}$), and that the enantiomeric counterpart (notably the anti-enantiomeric counterpart) of compound B(Iab) is compound B($I_{dd}$). Thus, in one embodiment, the compound can be provided in a mixture comprising syn-enantiomeric pair (B($I_{da}$), B($I_{dc}$)), or anti-enantiomeric pair (B($I_{db}$), B($I_{dd}$)), or a mixture comprising the syn-enantiomeric pair and the anti-enantiomeric pair. In one embodiment, the compound can be provided in a mixture, for example, a racemic mixture, comprising syn-enantiomeric pair (B($I_{da}$), B($I_{dc}$)), wherein the mixture is substantially free of the anti-enantiomeric pair (B($I_{db}$), B($I_{dd}$)). In one embodiment, the compound can be provided in a mixture, for example, a racemic mixture, comprising anti-enantiomeric pair (B($I_{db}$), B($I_{dd}$)), wherein the mixture is substantially free of the syn-enantiomeric pair (B($I_{da}$), B($I_{dc}$)).

In one embodiment, the chemical compound can be provided in a mixture comprising a diastereomer pair selected from the diastereomer pairs (B($I_{da}$), B($I_{db}$)); (B($I_{da}$), B($I_{dd}$)); (B($I_{db}$), B($I_{dc}$)); and (B($I_{dc}$), B($I_{dd}$)). The mixture can comprise an enantiomeric counterpart pair of the selected diastereomeric pair. Thus, by way of example, a mixture comprising the diastereomer pair (B($I_{da}$), B($I_{db}$)) can also comprise, the enantiomeric counterpart pair (B($I_{dc}$), B($I_{dd}$)). By way of another example, a mixture comprising the diastereomer pair (B($I_{da}$), B($I_{dd}$)) can also comprise, the enantiomeric counterpart pair (B($I_{dc}$), B($I_{db}$)).

In one embodiment, the chemical compound can be a single diastereomer of a selected diastereomer pair selected from the diastereomer pairs (B($I_{da}$), B($I_{db}$)) and (B($I_{dc}$), B($I_{dd}$)), wherein the compound is substantially free of the other diastereomer of the selected diastereomer pair. Thus, for example, B($I_{da}$) can be substantially free of B($I_{db}$).

In one embodiment, the chemical compound can be a single isomer of the isomers B($I_{da}$), B($I_{db}$), B($I_{dc}$), and B($I_{dd}$), wherein the compound is substantially free of the other three isomers. Thus, for example, B($I_{da}$) can be substantially free of B($I_{db}$), B($I_{dc}$), and B($I_{dd}$).

In one embodiment, the chemical compound can be provided in a mixture, for example a racemic mixture, comprising syn-enantiomeric pair (B(III$_{da}$), B(III$_{dc}$)), or anti-enantiomeric pair (B(III$_{db}$), B(III$_{dd}$)), or a mixture of the syn-enantiomeric pair and the anti-enantiomeric pair. In one embodiment, the compound can be provided in a mixture, for example, a racemic mixture, comprising syn-enantiomeric pair (B(III$_{da}$), B(III$_{dc}$)), wherein the mixture is substantially free of the anti-enantiomeric pair (B(III$_{db}$), B(III$_{dd}$)). In one embodiment, the compound can be provided in a mixture, for example, a racemic mixture, comprising anti-enantiomeric pair (B(III$_{db}$), B(III$_{dd}$)), wherein the mixture is substantially free of the syn-enantiomeric pair (B($I_{II}$da), B(III$_{dc}$)).

In one embodiment, the chemical compound can be provided in a mixture comprising a diastereomer pair selected from the diastereomer pairs (B(III$_{da}$), B(III$_{db}$)); (B(III$_{da}$), B(III$_{dd}$)); (B(III$_{db}$), B(III$_{dc}$)); and (B(III$_{dc}$), B(II-I$_{dd}$)). The mixture can comprise an enantiomeric counterpart pair of the selected diastereomeric pair.

In one embodiment, the chemical compound can be a single diastereomer of a selected diastereomer pair selected from the diastereomer pairs (B(III$_{da}$), B(III$_{db}$)) and (B(III$_{dc}$), B(III$_{dd}$)), wherein the compound is substantially free of the other diastereomer of the selected diastereomer pair. Thus, for example, B(III$_{da}$) can be substantially free of B(III$_{dc}$).

In one embodiment, the chemical compound can be a single isomer of the isomers B(III$_{da}$), B(III$_{db}$), B(III$_{dc}$), and B(III$_{dd}$), wherein the compound is substantially free of the other three isomers. Thus, for example, B(III$_{da}$) can be substantially free of B(III$_{db}$), B(III$_{dc}$), and B(III$_{dd}$).

In another aspect, the present disclosure provides example compounds C($I_g$)-C(VI$_g$):

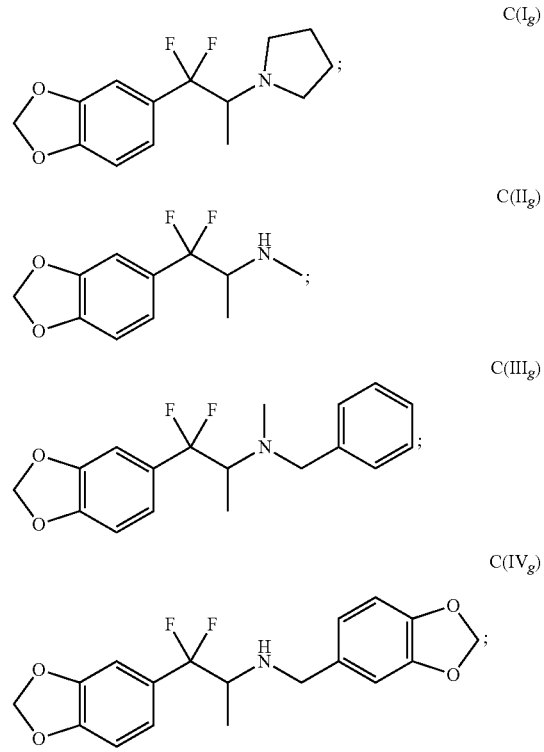

C(V$_g$)

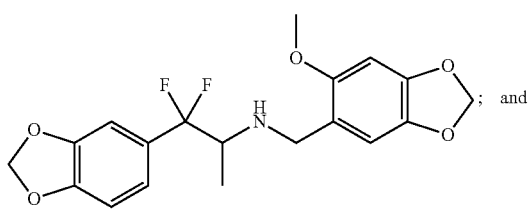

; and

C(VI$_g$)

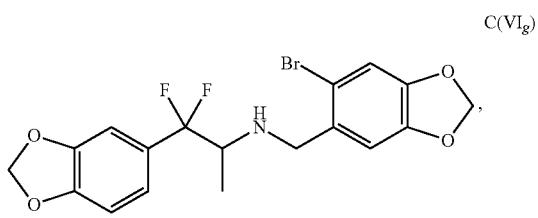

, wherein in each of compound C(I$_g$) to C(IV$_g$), optionally, the nitrogen atom of the isopropylamine portion is protonated and C(I$_g$) to C(VI$_g$) includes a negatively charged anion balancing the positively charged nitrogen atom.

In another aspect, the present disclosure provides example compounds D(I$_d$)-D(VI$_d$):

D(I$_d$)

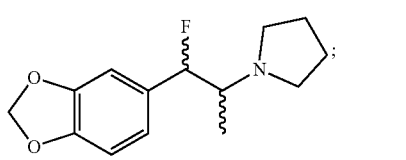

D(II$_d$)

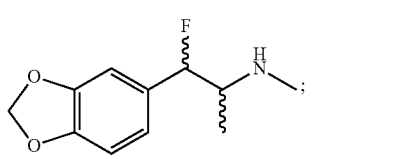

D(III$_d$)

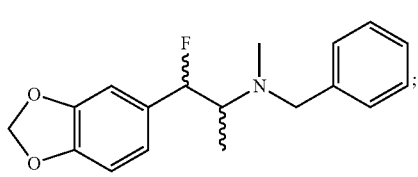

D(IV$_d$)

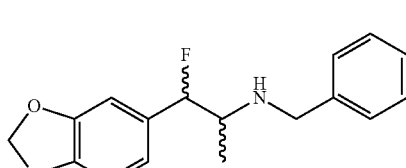

D(V$_d$)

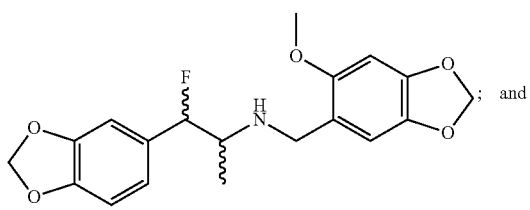

; and

D(VI$_d$)

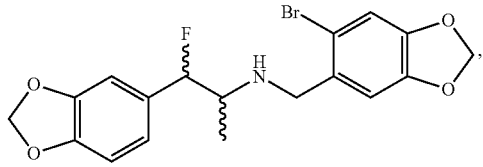

;

wherein in each of compound D(I$_d$) to D(VI$_d$), optionally, the nitrogen atom of the isopropylamine portion is protonated and D(I$_d$) to D(VI$_d$) includes a negatively charged anion balancing the positively charged nitrogen atom.

Thus, for example, in one embodiment, the chemical compound can be selected from the group of compounds consisting of D(I$_{da}$); D(I$_{db}$); D(I$_{dc}$); D(I$_{dd}$); D(II$_{da}$), D(II$_{db}$); D(II$_{dc}$); D(II$_{dd}$); D(III$_{da}$); D(III$_{db}$); D(III$_{dc}$); and D(III$_{dd}$):

D(I$_{da}$)

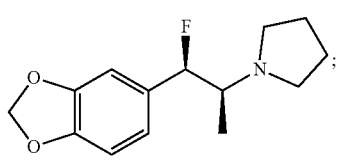

;

D(I$_{db}$)

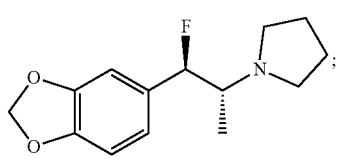

;

D(I$_{dc}$)

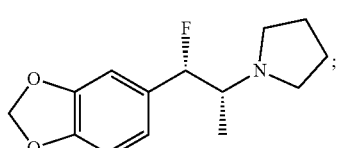

;

D(I$_{dd}$)

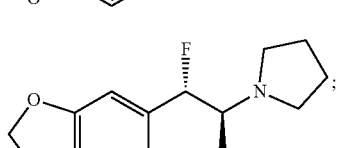

;

D(II$_{da}$)

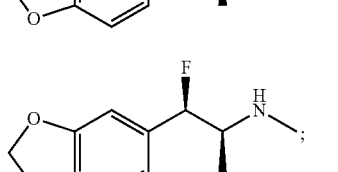

;

D(II$_{db}$)

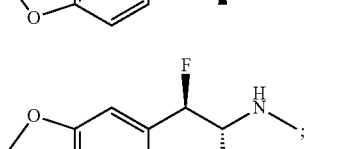

;

D(II$_{dc}$)

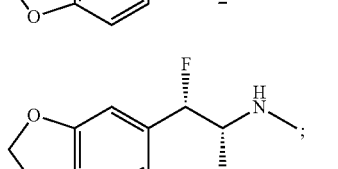

;

-continued

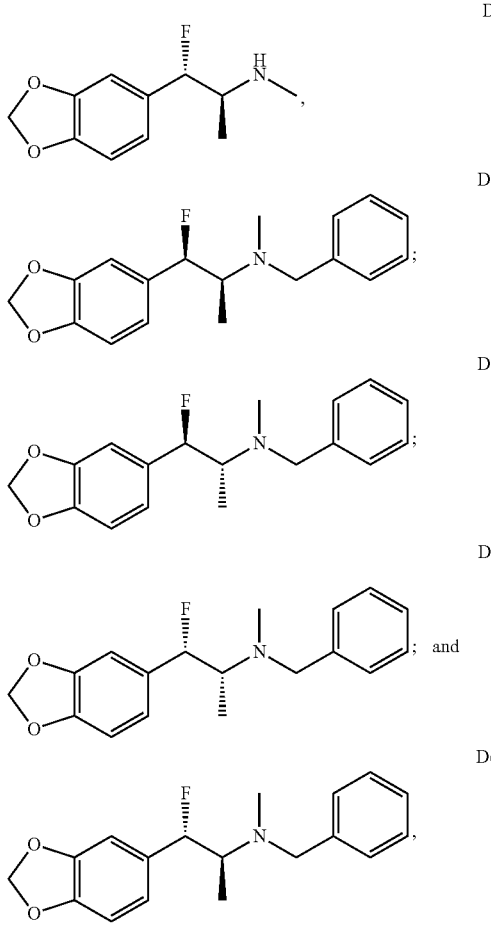

wherein in each of compound $D(I_{da})$, $D(I_{db})$, $D(I_{dc})$, $D(I_{dd})$, $D(II_{da})$, $D(II_{db})$, $D(II_{dc})$, $D(II_{dd})$, $D(III_{da})$, $D(III_{db})$, $D(III_{dc})$, and $D(III_{dd})$, optionally, the nitrogen atom of the isopropylamine portion may be protonated and includes a negatively charged anion balancing the positively charged nitrogen atom.

In one embodiment, the chemical compound can be provided in a mixture, for example a racemic mixture, comprising syn-enantiomeric pair ($D(I_{da})$, $D(I_{dc})$), or anti-enantiomeric pair ($D(I_{db})$, $D(I_{dd})$), or a mixture of the syn-enantiomeric pair and the anti-enantiomeric pair. In one embodiment, the compound can be provided in a mixture, for example, a racemic mixture, comprising syn-enantiomeric pair ($D(I_{da})$, $D(I_{dc})$), wherein the mixture is substantially free of the anti-enantiomeric pair ($D(I_{db})$, $D(I_{dd})$). In one embodiment, the compound can be provided in a mixture, for example, a racemic mixture, comprising anti-enantiomeric pair ($D(I_{db})$, $D(I_{dd})$), wherein the mixture is substantially free of the syn-enantiomeric pair ($D(I_{da})$, $D(I_{dc})$).

In one embodiment, the chemical compound can be provided in a mixture comprising a diastereomer pair selected from the diastereomer pairs ($D(I_{da})$, $D(I_{db})$); ($D(I_{da})$, $D(I_{dd})$); ($D(I_{db})$, $D(I_{dc})$); and ($D(I_{dc})$, $D(I_{dd})$). The mixture can comprise an enantiomeric counterpart pair of the selected diastereomeric pair.

In one embodiment, the chemical compound can be a single diastereomer of a selected diastereomer pair selected from the diastereomer pairs ($D(I_{da})$, $D(I_{db})$) and ($D(I_{dc})$, $D(I_{dd})$), wherein the compound is substantially free of the other diastereomer of the selected diastereomer pair. Thus, for example, $D(I_{da})$ can be substantially free of $D(I_{dc})$.

In one embodiment, the chemical compound can be a single isomer of the isomers $D(I_{da})$, $D(I_{db})$, $D(I_{dc})$, and $D(I_{dd})$, wherein the compound is substantially free of the other three isomers. Thus, for example, $D(I_{da})$ can be substantially free of $D(I_{db})$, $D(I_{dc})$, and $D(I_{dd})$.

In one embodiment, the chemical compound can be provided in a mixture, for example a racemic mixture, comprising syn-enantiomeric pair ($D(II_{da})$, $D(II_{dc})$), or anti-enantiomeric pair ($D(II_{db})$, $D(II_{dd})$), or a mixture of the syn-enantiomeric pair and the anti-enantiomeric pair. In one embodiment, the compound can be provided in a mixture, for example, a racemic mixture, comprising syn-enantiomeric pair ($D(II_{da})$, $D(II_{dc})$), wherein the mixture is substantially free of the anti-enantiomeric pair ($D(II_{db})$, $D(II_{dd})$). In one embodiment, the compound can be provided in a mixture, for example, a racemic mixture, comprising anti-enantiomeric pair ($D(II_{db})$, $D(II_{dd})$), wherein the mixture is substantially free of the syn-enantiomeric pair ($D(II_{da})$, $D(II_{dc})$).

In one embodiment, the chemical compound can be provided in a mixture comprising a diastereomer pair selected from the diastereomer pairs ($D(II_{da})$, $D(II_{db})$); ($D(II_{da})$, $D(II_{dd})$); ($D(II_{db})$, $D(II_{dc})$); and ($D(II_{dc})$, $D(II_{dd})$). The mixture can comprise an enantiomeric counterpart pair of the selected diastereomeric pair.

In one embodiment, the chemical compound can be a single diastereomer of a selected diastereomer pair selected from the diastereomer pairs ($D(II_{da})$, $D(II_{db})$) and ($D(II_{dc})$, $D(II_{dd})$), wherein the compound is substantially free of the other diastereomer of the selected diastereomer pair. Thus, for example, $D(II_{da})$ can be substantially free of $D(II_{dc})$.

In one embodiment, the chemical compound can be a single isomer of the isomers $D(II_{da})$, $D(II_{db})$, $D(II_{dc})$, and $D(II_{dd})$, wherein the compound is substantially free of the other three isomers. Thus, for example, $D(II_{da})$ can be substantially free of $D(II_{db})$, $D(II_{dc})$, and $D(II_{dd})$.

In one embodiment, the chemical compound can be provided in a mixture, for example, a racemic mixture, comprising syn-enantiomeric pair ($D(III_{da})$, $D(III_{dc})$), or anti-enantiomeric pair ($D(III_{db})$, $D(III_{dd})$), or a mixture of the syn-enantiomeric pair and the anti-enantiomeric pair. In one embodiment, the compound can be provided in a mixture, for example, a racemic mixture, comprising syn-enantiomeric pair ($D(III_{da})$, $D(III_{dc})$), wherein the mixture is substantially free of the anti-enantiomeric pair ($D(III_{db})$, $D(III_{dd})$). In one embodiment, the compound can be provided in a mixture, for example, a racemic mixture, comprising anti-enantiomeric pair ($D(III_{db})$, $D(III_{dd})$), wherein the mixture is substantially free of the syn-enantiomeric pair ($D(III_{da})$, $D(III_{dc})$).

In one embodiment, the chemical compound can be provided in a mixture comprising a diastereomer pair selected from the diastereomer pairs ($D(III_{da})$, $D(III_{db})$); ($D(III_{da})$, $D(III_{dd})$); ($D(III_{db})$, $D(III_{dc})$); and ($D(III_{dc})$, $D(III_{dd})$). The mixture can comprise an enantiomeric counterpart pair of the selected diastereomeric pair.

In one embodiment, the chemical compound can be a single diastereomer of a selected diastereomer pair selected from the diastereomer pairs ($D(III_{da})$, $D(III_{db})$) and ($D(III_{dc})$, $D(III_{dd})$), wherein the compound is substantially free of the other diastereomer of the selected diastereomer pair. Thus, for example, $D(I_{II}da)$ can be substantially free of $D(III_{dc})$.

In one embodiment, the chemical compound can be a single isomer of the isomers $D(III_{da})$, $D(III_{db})$, $D(III_{dc})$, and $D(III_{dd})$, wherein the compound is substantially free of the other three isomers. Thus, for example, $D(III_{da})$ can be substantially free of $D(III_{db})$, $D(III_{dc})$, and $D(III_{dd})$.

In another aspect, the present disclosure provides example compounds $E_x(I_d)$-$E_y(VIII_d)$:

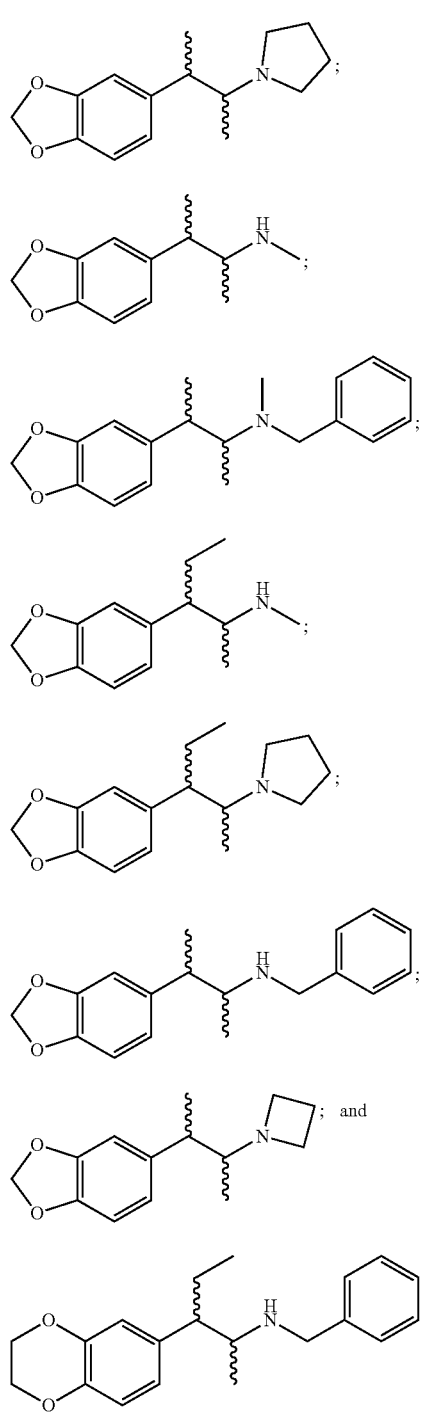

nated and $E_x(I_d)$ to $E_y(VIII_d)$ includes a negatively charged anion balancing the positively charged nitrogen atom.

Thus, for example, the chemical compound having formula $(E_{xd})$ can be selected from the group of compounds consisting of $E_x(III_{da})$, $E_x(III_{db})$, $E_x(III_{dc})$, $E_x(III_{dd})$, $E_x(VI_{da})$, $E_x(VI_{db})$, $E_x(VI_{dc})$, $E_x(VI_{dd})$, $E_x(VII_{da})$, $E_x(VII_{db})$, $E_x(VII_{dc})$, and $E_x(VII_{dd})$:

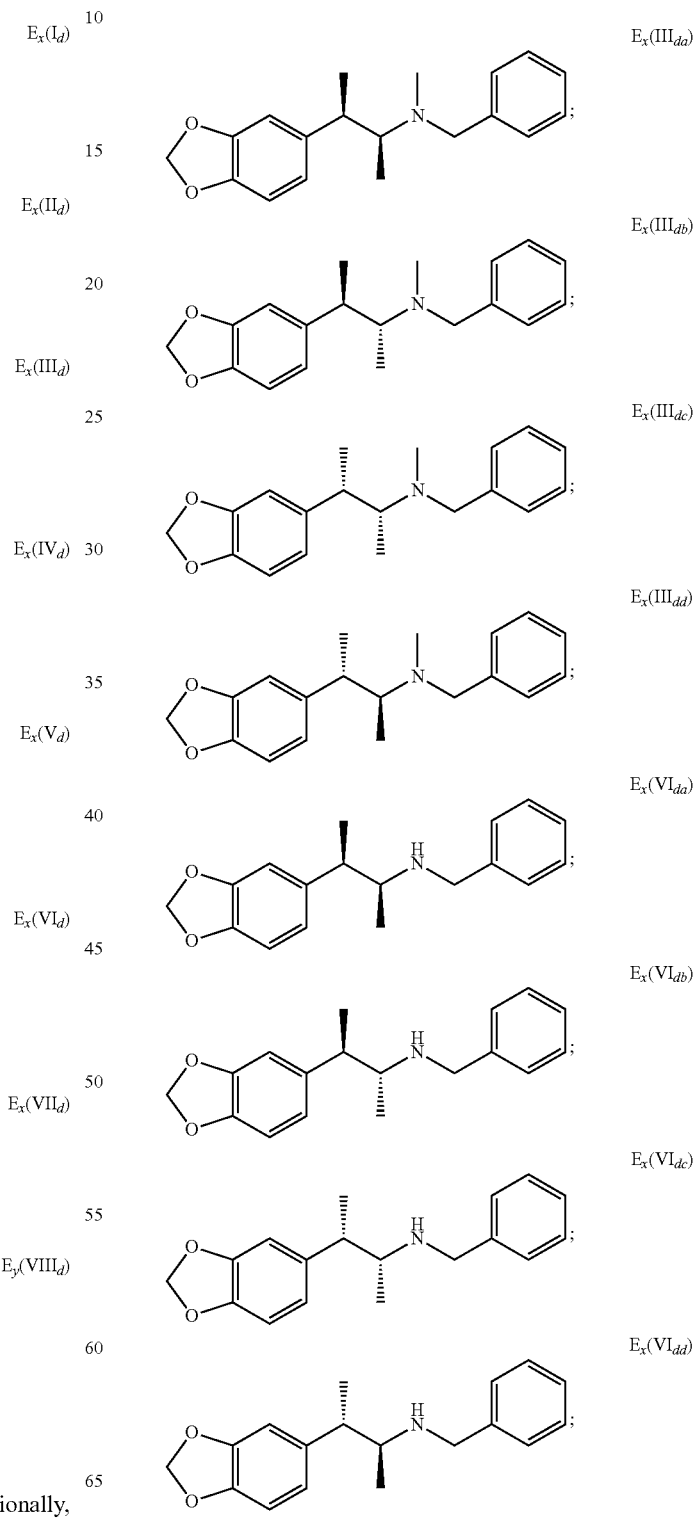

wherein in each of compound $E_x(I_d)$ to $E_y(VIII_d)$, optionally, the nitrogen atom of the isopropylamine portion is proto-

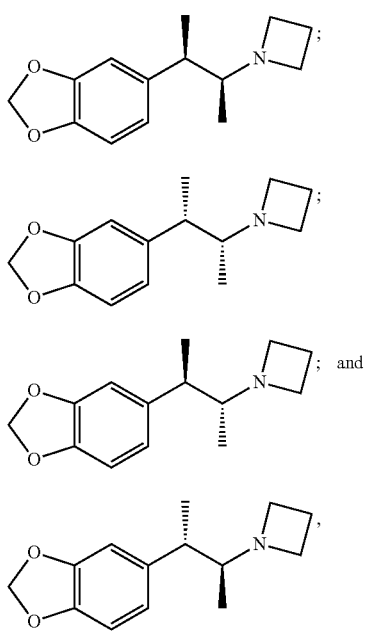

$E_x(VII_{da})$ $E_x(VII_{dc})$ $E_x(VII_{db})$ and $E_x(VII_{dd})$ wherein in each compounds $E_x(III_{da})$, $E_x(III_{db})$, $E_x(III_{dc})$, $E_x(III_{dd})$, $E_x(VI_{da})$ $E_x(VI_{db})$, $E_x(VI_{dc})$, $E_x(VI_{dd})$, $E_x(VII_{da})$, $E_x(VII_{db})$, $E_x(VII_{dc})$, $E_x(VII_{dd})$, optionally, the nitrogen atom of the isopropylamine portion may be protonated and includes a negatively charged anion balancing the positively charged nitrogen atom.

In one embodiment, the chemical compound can be provided in a mixture, for example, a racemic mixture, comprising syn-enantiomeric pair ($E_x(III_{da})$, $E_x(III_{dc})$), or anti-enantiomeric pair ($E_x(III_{db})$, $E_x(III_{dd})$), or a mixture of the syn-enantiomeric pair and the anti-enantiomeric pair. In one embodiment, the compound can be provided in a mixture, for example, a racemic mixture, comprising syn-enantiomeric pair ($E_x(III_{da})$, $E_x(III_{dc})$), wherein the mixture is substantially free of the anti-enantiomeric pair ($E_x(III_{db})$, $E_x(III_{dd})$). In one embodiment, the compound can be provided in a mixture, for example, a racemic mixture, comprising anti-enantiomeric pair ($E_x(III_{db})$, $E_x(III_{dd})$), wherein the mixture is substantially free of the syn-enantiomeric pair ($E_x(III_{da})$, $E_x(III_{dc})$).

In one embodiment, the chemical compound can be provided in a mixture comprising a diastereomer pair selected from the diastereomer pairs ($E_x(III_{da})$, $E_x(III_{db})$); ($E_x(III_{da})$, $E_x(III_{dd})$); ($E_x(III_{db})$, $E_x(III_{cd})$); and ($E_x(III_{cd})$, $E_x(III_{dd})$). The mixture can comprise an enantiomeric counterpart pair of the selected diastereomeric pair.

In one embodiment, the chemical compound can be a single diastereomer of a selected diastereomer pair selected from the diastereomer pairs ($E_x(III_{da})$, $E_x(III_{db})$) and ($E_x(III_{dd})$, $E_x(III_{dd})$), wherein the compound is substantially free of the other diastereomer of the selected diastereomer pair. Thus, for example, $E_x(III_{da})$ can be substantially free of $E_x(III_{dc})$.

In one embodiment, the chemical compound can be a single isomer of the isomers $E_x(III_{da})$, $E_x(III_{db})$, $E_x(III_{dc})$, and $E_x(III_{dd})$, wherein the compound is substantially free of the other three isomers. Thus, for example, $E_x(III_{da})$ can be substantially free of $E_x(III_{db})$, $E_x(III_{dc})$, and $E_x(III_{dd})$.

In one embodiment, the chemical compound can be provided in a mixture, for example a racemic mixture, comprising syn-enantiomeric pair ($E_x(VI_{da})$, $E_x(VI_{dc})$), or anti-enantiomeric pair ($E_x(VI_{db})$, $E_x(VI_{dd})$), or a mixture of the syn-enantiomeric pair and the anti-enantiomeric pair. In one embodiment, the compound can be provided in a mixture, for example, a racemic mixture, comprising syn-enantiomeric pair ($E_x(VI_{da})$, $E_x(VI_{dc})$), wherein the mixture is substantially free of the anti-enantiomeric pair ($E_x(VI_{db})$, $E_x(VI_{dd})$). In one embodiment, the compound can be provided in a mixture, for example, a racemic mixture, comprising anti-enantiomeric pair ($E_x(VI_{db})$, $E_x(VI_{dd})$), wherein the mixture is substantially free of the syn-enantiomeric pair ($E_x(VI_{da})$, $E_x(VI_{dc})$).

In one embodiment, the chemical compound can be provided in a mixture comprising a diastereomer pair selected from the diastereomer pairs ($E_x(VI_{da})$, $E_x(VI_{db})$); ($E_x(VI_{da})$, $E_x(VI_{dd})$); ($E_x(VI_{db})$, $E_x(VI_{dc})$); and ($E_x(VI_{dc})$, $E_x(VI_{dd})$). The mixture can comprise an enantiomeric counterpart pair of the selected diastereomeric pair.

In one embodiment, the chemical compound can be a single diastereomer of a selected diastereomer pair selected from the diastereomer pairs ($E_x(VI_{da})$, $E_x(VI_{db})$) and ($E_x(VI_{dc})$, $E_x(VI_{dd})$), wherein the compound is substantially free of the other diastereomer of the selected diastereomer pair. Thus, for example, $E_x(VI_{da})$ can be substantially free of $E_x(VI_{dc})$.

In one embodiment, the chemical compound can be a single isomer of the isomers $E_x(VI_{da})$, $E_x(VI_{db})$, $E_x(VI_{dc})$, and $E_x(VI_{dd})$, wherein the compound is substantially free of the other three isomers. Thus, for example, $E_x(VI_{da})$ can be substantially free of $E_x(VI_{db})$, $E_x(VI_{dc})$, and $E_x(VI_{dd})$.

In one embodiment, the chemical compound can be provided in a mixture, for example, a racemic mixture, comprising syn-enantiomeric pair ($E_x(VII_{da})$, $E_x(VII_{dc})$), or anti-enantiomeric pair ($E_x(VII_{db})$, $E_x(VII_{dd})$), or a mixture of the syn-enantiomeric pair and the anti-enantiomeric pair. In one embodiment, the compound can be provided in a mixture, for example, a racemic mixture, comprising syn-enantiomeric pair ($E_x(VII_{da})$, $E_x(VII_{dc})$), wherein the mixture is substantially free of the anti-enantiomeric pair ($E_x(VII_{db})$, $E_x(VII_{dd})$). In one embodiment, the compound can be provided in a mixture, for example, a racemic mixture, comprising anti-enantiomeric pair ($E_x(VII_{db})$, $E_x(VII_{dd})$), wherein the mixture is substantially free of the syn-enantiomeric pair ($E_x(VII_{da})$, $E_x(VII_{dc})$).

In one embodiment, the chemical compound can be provided in a mixture comprising a diastereomer pair selected from the diastereomer pairs ($E_x(VII_{da})$, $E_x(VII_{db})$); ($E_x(VII_{dc})$, $E_x(VII_{dd})$); ($E_x(VII_{db})$, $E_x(VII_{dc})$); and ($E_x(VI-I_{dc})$, $E_x(VII_{dd})$). The mixture can comprise an enantiomeric counterpart pair of the selected diastereomeric pair. Thus, for example, $E_x(VII_{da})$ can be substantially free of $E_x(VI-I_{dc})$).

In one embodiment, the chemical compound can be a single isomer of the isomers $E_x(VII_{da})$, $E_x(VII_{db})$, $E_x(VII_{dc})$, and $E_x(VII_{dd})$, wherein the compound is substantially free of the other three isomers. Thus, for example, $E_x(VII_{da})$ can be substantially free of $E_x(VII_{db})$, $E_x(VII_{dc})$, and $E_x(VII_{dd})$.

Thus, for example, the chemical compound having formula ($E_{yd}$) can be selected from the group of compounds consisting of $E_y(VIII_{da})$, $E_y(VIII_{db})$, $E_y(VIII_{dc})$, and $E_y(VII-I_{dd})$:

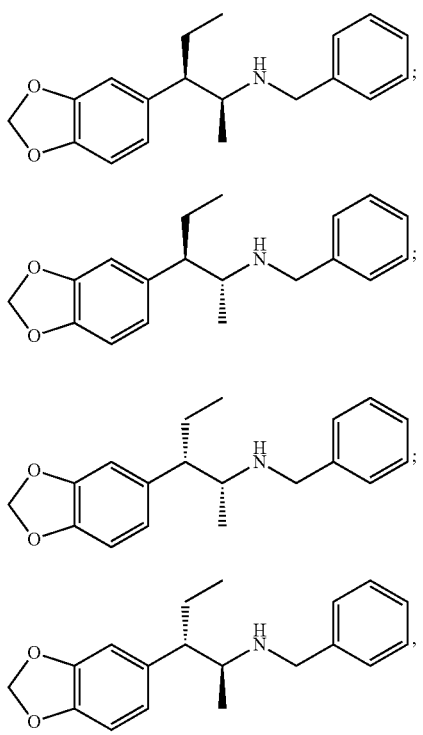

$E_y(VIII_{da})$;

$E_y(VIII_{db})$;

$E_y(VIII_{dc})$; and $E_y(VIII_{dd})$, wherein in each compounds $E_y(VIII_{da})$, $E_y(VIII_{db})$, $E_y(VII-I_{dc})$, and $E_y(VIII_{dd})$, optionally, the nitrogen atom of the isopropylamine portion may be protonated and includes a negatively charged anion balancing the positively charged nitrogen atom.

In one embodiment, the chemical compound can be a single diastereomer of a selected diastereomer pair selected from the diastereomer pairs ($E_y(VIII_{da})$, $E_y(VIII_{dc})$) and ($E_y(VIII_{db})$, $E_y(VIII_{dd})$), wherein the compound is substantially free of the other diastereomer of the selected diastereomer pair. In one embodiment, the chemical compound can be provided in a mixture, for example, a racemic mixture, comprising syn-enantiomeric pair ($E_y(VIII_{da})$, $E_y(VIII_{dc})$), or anti-enantiomeric pair ($E_y(VIII_{db})$, $E_y(VII-I_{dd})$), or a mixture of the syn-enantiomeric pair and anti-enantiomeric pair. In one embodiment, the compound can be provided in a mixture for example a racemic mixture, comprising syn-enantiomeric pair ($E_y(VIII_{da})$, $E_y(VIII_{dc})$), wherein the mixture is substantially free of the anti-enantiomeric pair ($E_y(VIII_{db})$, $E_y(VIII_{dd})$). In one embodiment, the compound can be provided in a mixture, for example, a racemic mixture, comprising anti-enantiomeric pair ($E_y(VII-I_{db})$, $E_y(VIII_{dd})$), wherein the mixture is substantially free of the syn-enantiomeric pair ($E_y(VIII_{da})$, $E_y(VIII_{dc})$).

In one embodiment, the chemical compound can be provided in a mixture comprising a diastereomer pair selected from the diastereomer pairs ($E_y(VIII_{da})$, $E_y(VII-I_{db})$); ($E_y(VIII_{da})$, $E_y(VIII_{dd})$); ($E_y(VIII_{db})$, $E_y(VIII_{dc})$); and ($E_y(VIII_{dc})$, $E_y(VIII_{dd})$). The mixture can comprise an enantiomeric counterpart pair of the selected diastereomeric pair.

In one embodiment, the chemical compound can be a single diastereomer of a selected diastereomer pair selected from the diastereomer pairs ($E_y(VIII_{da})$, $E_y(VIII_{db})$) and ($E_y(VIII_{dc})$, $E_y(VIII_{dd})$), wherein the compound is substantially free of the other diastereomer of the selected diastereomer pair. Thus, for example, $E_y(VIII_{da})$ can be substantially free of $E_y(VIII_{dc})$.

In one embodiment, the chemical compound can be a single isomer of the isomers $E_y(VIII_{da})$, $E_y(VIII_{db})$, $E_y(VII-I_{dc})$, and $E_y(VIII_{dd})$, wherein the compound is substantially free of the other three isomers. Thus, for example, $E_y(VIII_{da})$ can be substantially free of $E_y(VIII_{db})$, $E_y(VIII_{dc})$, and $E_y(VIII_{dd})$.

Thus, to briefly summarize, in an aspect, the present disclosure provides novel chemical compounds which are derivatives of mescaline, fused mescaline derivatives, including in an example embodiment, fused dioxolane mescaline derivatives. The novel chemical compounds have chemical formula (I) or chemical formula (II):

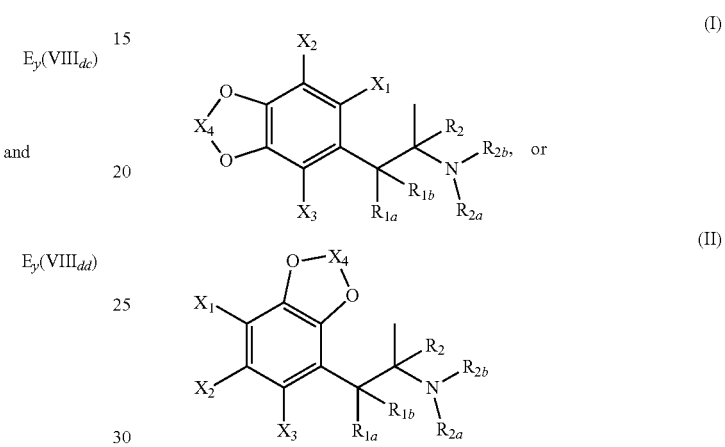

(I)

(II)

wherein, in chemical formula (I) and chemical formula (II):

$X_1$, $X_2$, and $X_3$ are independently selected from a hydrogen atom, O-alkyl, N-alkyl, OH, a halogen, or $NH_2$;

$X_4$ is an alkylene group or substituted alkylene group;

$R_{1a}$ is an alkyl group, O-alkyl group, a halogen, or OH, $R_{1b}$ is a hydrogen atom or a halogen, or $R_{1a}$ and $R_{1b}$ are joined together to form an oxo group;

$R_2$ is a hydrogen atom or an O-alkyl group; and $R_{2a}$ and $R_{2b}$ are independently selected from an alkyl group, an optionally substituted alkyl-aryl group, or a hydrogen atom, or $R_{2a}$ and $R_{2b}$ are joined together, along with the nitrogen atom to which they are attached, to form a 3-10-membered optionally substituted heterocyclic ring.

The fused mescaline derivatives of the present disclosure may be used to prepare a pharmaceutical or recreational drug formulation. Thus, in one embodiment, the present disclosure further provides in another aspect, pharmaceutical and recreational drug formulations comprising fused mescaline derivatives. Accordingly, in one aspect, the present disclosure provides in a further embodiment a pharmaceutical or recreational drug formulation comprising a chemical compound selected from a first chemical compound having chemical formula (I) or chemical formula (II):

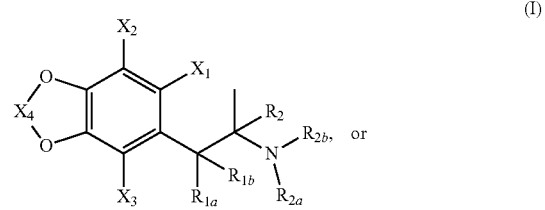

(I)

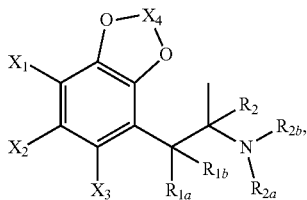

(II)

wherein, in chemical formula (I) and chemical formula (II):
- $X_1$, $X_2$, and $X_3$ are independently selected from a hydrogen atom, O-alkyl, N-alkyl, OH, a halogen, or $NH_2$;
- $X_4$ is an alkylene group or substituted alkylene group;
- $R_{1a}$ is an alkyl group, O-alkyl group, a halogen, or OH, $R_{1b}$ is a hydrogen atom or a halogen, or $R_{1a}$ and $R_{1b}$ are joined together to form an oxo group;
- $R_2$ is a hydrogen atom or an O-alkyl group; and
- $R_{2a}$ and $R_{2b}$ are independently selected from an alkyl group, an optionally substituted alkyl-aryl group, or a hydrogen atom, or $R_{2a}$ and $R_{2b}$ are joined together, along with the nitrogen atom to which they are attached, to form a 3-10-membered optionally substituted heterocyclic ring, together with a diluent, carrier, or excipient.

The pharmaceutical or recreational drug formulations may be prepared as liquids, tablets, capsules, microcapsules, nanocapsules, trans-dermal patches, gels, foams, oils, aerosols, nanoparticulates, powders, creams, emulsions, micellar systems, films, sprays, ovules, infusions, teas, decoctions, suppositories, etc. and include a pharmaceutically acceptable salt or solvate of the fused mescaline derivative compound together with an excipient. The term "excipient" as used herein means any ingredient other than the chemical compound of the disclosure. As will readily be appreciated by those of skill in the art, the selection of excipient may depend on factors such as the particular mode of administration, the effect of the excipient on solubility of the chemical compounds of the present disclosure and methods for their preparation will be readily apparent to those skilled in the art. Such compositions and methods for their preparation may be found, for example, in "Remington's Pharmaceutical Sciences", 22nd Edition (Pharmaceutical Press and Philadelphia College of Pharmacy at the University of the Sciences, 2012).

The pharmaceutical and drug formulations comprising the fused mescaline derivatives of the present disclosure may be administered orally. Oral administration may involve swallowing, so that the compound enters the gastrointestinal tract, or buccal or sublingual administration may be employed by which the compound enters the blood stream directly from the mouth. Formulations suitable for oral administration include both solid and liquid formulations.

Solid formulations include tablets, capsules (containing particulates, liquids, microcapsules, or powders), lozenges (including liquid-filled lozenges), chews, multi- and nano-particulates, gels, solid solutions, liposomal preparations, microencapsulated preparations, creams, films, ovules, suppositories, and sprays.

Liquid formulations include suspensions, solutions, syrups, and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose.

Tablets may also contain diluents, such as lactose (monohydrate, spray-dried monohydrate, anhydrous and the like), mannitol, xylitol, dextrose, sucrose, sorbitol, microcrystalline cellulose, starch, and dibasic calcium phosphate dihydrate.

Tablets may also optionally comprise surface active agents, such as sodium lauryl sulfate and polysorbate 80. When present, surface active agents may comprise from 0.2% (w/w) to 5% (w/w) of the tablet.

Tablets may further contain lubricants such as magnesium stearate, calcium stearate, zinc stearate, sodium stearyl fumarate, and mixtures of magnesium stearate with sodium lauryl sulphate. Lubricants generally comprise from 0.25% (w/w) to 10% (w/w), from 0.5% (w/w) to 3% (w/w) of the tablet.

In addition to the fused heterocyclic mescaline derivative, tablets may contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1% (w/w) to 25% (w/w) or from 5% (w/w) to 20% (w/w) of the dosage form.

Other possible auxiliary ingredients include anti-oxidants, colourants, flavouring agents, preservatives, and taste-masking agents.

For tablet dosage forms, depending on the desired effective amount of the chemical compound, the chemical compound of the present disclosure may make up from 1% (w/w) to 80% (w/w) of the dosage form, more typically from 5% (w/w) to 60% (w/w) of the dosage form.

Exemplary tablets contain up to about 80% (w/w) of the chemical compound, from about 10% (w/w) to about 90% (w/w) binder, from about 0% (w/w) to about 85% (w/w) diluent, from about 2% (w/w) to about 10% (w/w) disintegrant, and from about 0.25% (w/w) to about 10% (w/w) lubricant.

The formulation of tablets is discussed in "Pharmaceutical Dosage Forms: Tablets", Vol. 1-Vol. 3, by CRC Press (2008).

The pharmaceutical and recreational drug formulations comprising the fused heterocyclic mescaline derivatives of the present disclosure may also be administered directly into the blood stream, into muscle, or into an internal organ. Thus, the pharmaceutical and recreational drug formulations can be administered parenterally (for example, by subcutaneous, intravenous, intraarterial, intrathecal, intraventricular, intracranial, intramuscular, or intraperitoneal injection). Parenteral formulations are typically aqueous solutions which may contain excipients such as salts, carbohydrates, and buffering agents (in one embodiment, to a pH of from 3 to 9), but, for some applications, they may be more suitably formulated as a sterile non-aqueous solution or as a dried form to be used in conjunction with a suitable vehicle such as sterile water.

Formulations comprising the fused heterocyclic mescaline derivatives of the present disclosure for parenteral administration may be formulated to be immediate and/or modified release. Modified release formulations include delayed-, sustained-, pulsed-, controlled-, targeted and programmed release. Thus, the chemical compounds of the disclosure may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The pharmaceutical or recreational drug formulations of the present disclosure also may be administered topically to the skin or mucosa, i.e., dermally or transdermally. Example pharmaceutical and recreational drug formulations for this purpose include gels, hydrogels, lotions, solutions, creams, ointments, dusting powders, cosmetics, oils, eye drops, dressings, foams, films, skin patches, wafers, implants, sponges, fibres, bandages and microemulsions. Liposomes may also be used. Example carriers include alcohol, water, mineral oil, liquid petrolatum, white petrolatum, glycerin, polyethylene glycol and propylene glycol. Penetration enhancers may be incorporate (see: for example, Finnin, B. and Morgan, T. M., 1999 J. Pharm. Sci, 88 (10), 955-958).

Other means of topical administration include delivery by electroporation, iontophoresis, phonophoresis, sonophoresis and microneedle or needle-free (e.g., Powderject™, Bioject™, etc.) injection.

Pharmaceutical and recreational drug formulations for inhalation or insufflation include solutions and suspensions in pharmaceutically acceptable, aqueous, or organic solvents, or mixtures thereof, and powders. The liquid or solid pharmaceutical compositions can contain suitable pharmaceutically acceptable excipients. In some embodiments, the pharmaceutical compositions are administered by the oral or nasal respiratory route for local or systemic effect. Pharmaceutical compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder pharmaceutical compositions can be administered, e.g., orally, or nasally, from devices that deliver the formulation in an appropriate manner.

In further embodiments, in which the fused heterocycle mescaline compounds of present disclosure are used as a recreational drug, the compounds may be included in compositions such as a food or food product, a beverage, a food seasoning, a personal care product, such as a cosmetic, perfume or bath oil, or oils (both for topical administration as massage oil, or to be burned or aerosolized). The chemical compounds of the present disclosure may also be included in a "vape" product, which may also include other drugs, such as nicotine, and flavorings.

The pharmaceutical formulations comprising the chemical compounds of the present disclosure may be used to treat a subject, and in particular to treat a brain neurological disorder in a subject. Accordingly, the present disclosure includes in a further embodiment, a method for treating a brain neurological disorder, the method comprising administering to a subject in need thereof a pharmaceutical formulation comprising a chemical compound selected from a first chemical compound having chemical formula (I) or chemical formula (II):

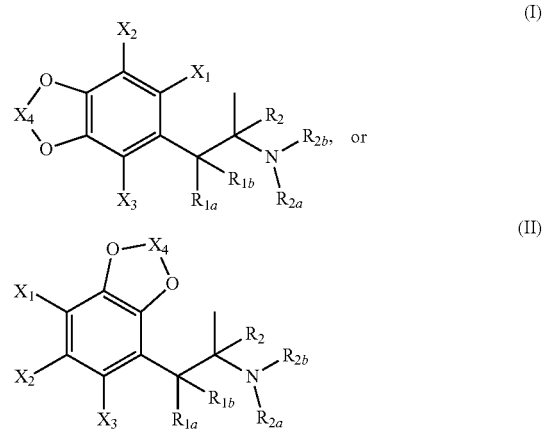

wherein, in chemical formula (I) and chemical formula (II):
  $X_1$, $X_2$, and $X_3$ are independently selected from a hydrogen atom, O-alkyl, N-alkyl, OH, a halogen, or $NH_2$;
  $X_4$ is an alkylene group or substituted alkylene group;
  $R_{1a}$ is an alkyl group, O-alkyl group, a halogen, or OH,
  $R_{1b}$ is a hydrogen atom or a halogen, or $R_{1a}$ and $R_{1b}$ are joined together to form an oxo group;
  $R_2$ is a hydrogen atom or an O-alkyl group; and
  $R_{2a}$ and $R_{2b}$ are independently selected from an alkyl group, an optionally substituted alkyl-aryl group, or a hydrogen atom, or $R_{2a}$ and $R_{2b}$ are joined together, along with the nitrogen atom to which they are attached, to form a 3-10-membered optionally substituted heterocyclic ring, together with a diluent, carrier, or excipient.

Brain neurological disorders, including psychiatric disorders, that may be treated include, for example, neurodevelopmental disorders such as intellectual disability, global development delay, communication disorders, autism spectrum disorder, and attention-deficit hyperactivity disorder (ADHD); bipolar and related disorders, such as mania, and depressive episodes; anxiety disorder, such as generalized anxiety disorder (GAD), agoraphobia, social anxiety disorder, specific phobias (natural events, medical, animal, situational, for example), panic disorder, and separation anxiety disorder; stress disorders, such as acute stress disorder, adjustment disorders, post-traumatic stress disorder (PTSD), and reactive attachment disorder; dissociative disorders, such as dissociative amnesia, dissociative identity disorder, and depersonalization/derealization disorder; somatoform disorders, such as somatic symptom disorders, illness anxiety disorder, conversion disorder, and factitious disorder; eating disorders, such as anorexia nervosa, bulimia nervosa, rumination disorder, pica, and binge-eating disorder; sleep disorders, such as narcolepsy, insomnia disorder, hypersomnolence, breathing-related sleep disorders, parasomnias, and restless legs syndrome; disruptive disorders, such as kleptomania, pyromania, intermittent explosive disorder, conduct disorder, and oppositional defiant disorder; depressive disorders, such as disruptive mood dysregulation disorder, major depressive disorder (MDD), persistent depressive disorder (dysthymia), premenstrual dysphoric disorder, substance/medication-induced depressive disorder, postpartum depression, and depressive disorder caused by another medical condition, for example, psychiatric and existential distress within life-threatening cancer situations (ACS Pharmacol. Transl. Sci. 4: 553-562; J. Psychiatr. Res. 137: 273-282); substance-related disorders, such as alcohol-related disorders, cannabis related disorders, inhalant-use related disorders, stimulant use disorders, and tobacco use disorders; neurocognitive disorders, such as delirium; schizophrenia; compulsive disorders, such as obsessive compulsive disorders (OCD), body dysmorphic disorder, hoarding disorder, trichotillomania disorder, excoriation disorder, substance/medication induced obsessive-compulsive disorder, and obsessive-compulsive disorder related to another medical condition; and personality disorders, such as antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder. Brain neurological disorders that may be treated further include headache disorders, including migraines, including, for example, aural migraine, non-aural migraine, menstrual migraine, chronic migraine, vestibular migraine, abdominal migraine, hemiplegic migraine, and other headache disorders.

In an aspect, the compounds of the present disclosure may be used to be contacted with a receptor to thereby modulate the receptor. Such contacting includes bringing a compound of the present disclosure and receptor together under in vitro conditions, for example, by introducing the compounds in a sample containing a receptor, for example, a sample containing purified receptors, or a sample containing cells comprising receptors. In vitro conditions further include the conditions described in Example 1 hereof. Contacting further includes bringing a compound of the present disclosure and receptor together under in vivo conditions. Such in vivo conditions include the administration to an animal or human subject, for example, of a pharmaceutically effective amount of the compound of the present disclosure, when the compound is formulated together with a pharmaceutically active carrier, diluent, or excipient, as hereinbefore described, to thereby treat the subject. Upon having contacted the receptor, the compound may activate the receptor or inhibit the receptor.

In an aspect, receptors with which the compounds of the present disclosure may be contacted include, for example, the $5\text{-HT}_{1A}$ receptor, the $5\text{-HT}_{2A}$ receptor, the $5\text{-HT}_{2B}$ receptor, the $5\text{-HT}_{2C}$ receptor, the $5\text{-HT}_7$ receptor, the $\alpha_{2A}$ receptor, or the $\text{MT}_1$ receptor.

Thus, in a further aspect, the condition that may be treated in accordance herewith can be any receptor mediated disorder, including, for example, a $5\text{-HT}_{1A}$ receptor-mediated disorder, a $5\text{-HT}_{2A}$ receptor-mediated disorder, a $5\text{-HT}_{2B}$ receptor-mediated disorder, a $5\text{-HT}_{2C}$ receptor-mediated disorder, a $5\text{-HT}_7$ receptor-mediated disorder, a $\alpha_{2A}$ receptor-mediated disorder, or a $\text{MT}_1$ receptor-mediated disorder. Such disorders include, but are not limited to schizophrenia, psychotic disorder, attention deficit hyperactivity disorder, autism, and bipolar disorder.

In some embodiments, upon having contacted a receptor, the compound may modulate the receptor. However, at the same time other receptors may not be modulated, e.g., a compound may activate or inhibit a first receptor, e.g., a $5\text{-HT}_{1A}$ receptor, however the compound may at the same time not modulate a second receptor, e.g., a $5\text{-HT}_{2A}$ receptor, or upon having contacted a first $5\text{-HT}_{2A}$ receptor and a second $5\text{-HT}_{1A}$ receptor, the compound may modulate the first $5\text{-HT}_{2A}$ receptor, e.g., activate or inhibit the $5\text{-HT}_{2A}$ receptor, however the compound may at the same time not modulate the second $5\text{-HT}_{1A}$ receptor.

In one embodiment, in an aspect, upon administration the compounds of the present disclosure can interact with a transmembrane transport protein in the subject to thereby modulate the transmembrane transport protein and exert a pharmacological effect. Such contacting includes bringing a compound of the present disclosure and a transmembrane transport protein together under in vitro conditions, for example, by introducing the compounds in a sample containing a transmembrane transport protein, for example, a sample containing a purified transmembrane transport protein, or a sample containing cells comprising a transmembrane transport protein. Contacting further includes bringing a compound of the present disclosure and a transmembrane transport protein together under in vivo conditions. Such in vivo conditions include the administration to an animal or human subject, for example, of a pharmaceutically effective amount of the compound of the present disclosure, when the compound is formulated together with a pharmaceutically active carrier, diluent, or excipient, as hereinbefore described, to thereby treat the subject.

In one embodiment, in an aspect, the transmembrane transport protein can be a dopamine active transporter (DAT), a norephedrine transporter (NET), or a serotonin transporter (SERT) transmembrane transport protein.

Turning now to methods of making the fused heterocyclic mescaline derivatives of the present disclosure, it is initially noted, by way of general comment that the fused heterocyclic mescaline derivatives of the present disclosure may be prepared in any suitable manner, including by any organic chemical synthesis methods, biosynthetic methods, or a combination thereof.

Figure 3A:
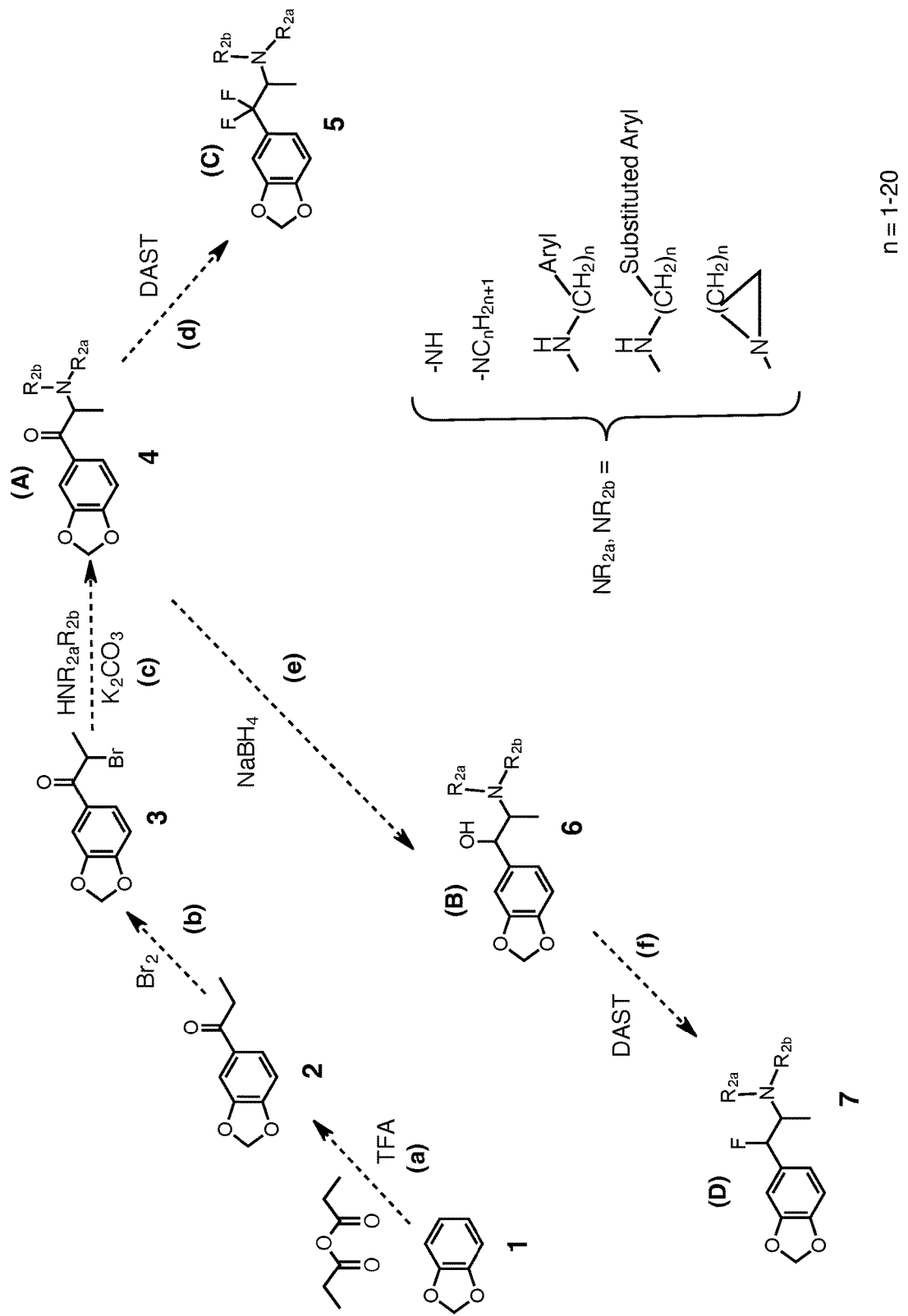
FIGS. 3A, 3B, and 3C show example synthesis pathways and chemical reactions comprising such pathways for certain example mescaline compounds of the present disclosure, notably example mescaline derivative compounds (A), (B), (C), (D) (FIG. 3A), ($E_x$) (FIG. 3B), and ($E_y$) (FIG. 3C). Individual chemical reactions are denoted as (a), (b), (c), (d), (e), and (f) in FIG. 3A, and (a), (b), (c), (d), (e), (f), (g) and (h) in FIGS. 3B and 3C.
Figure 3B:
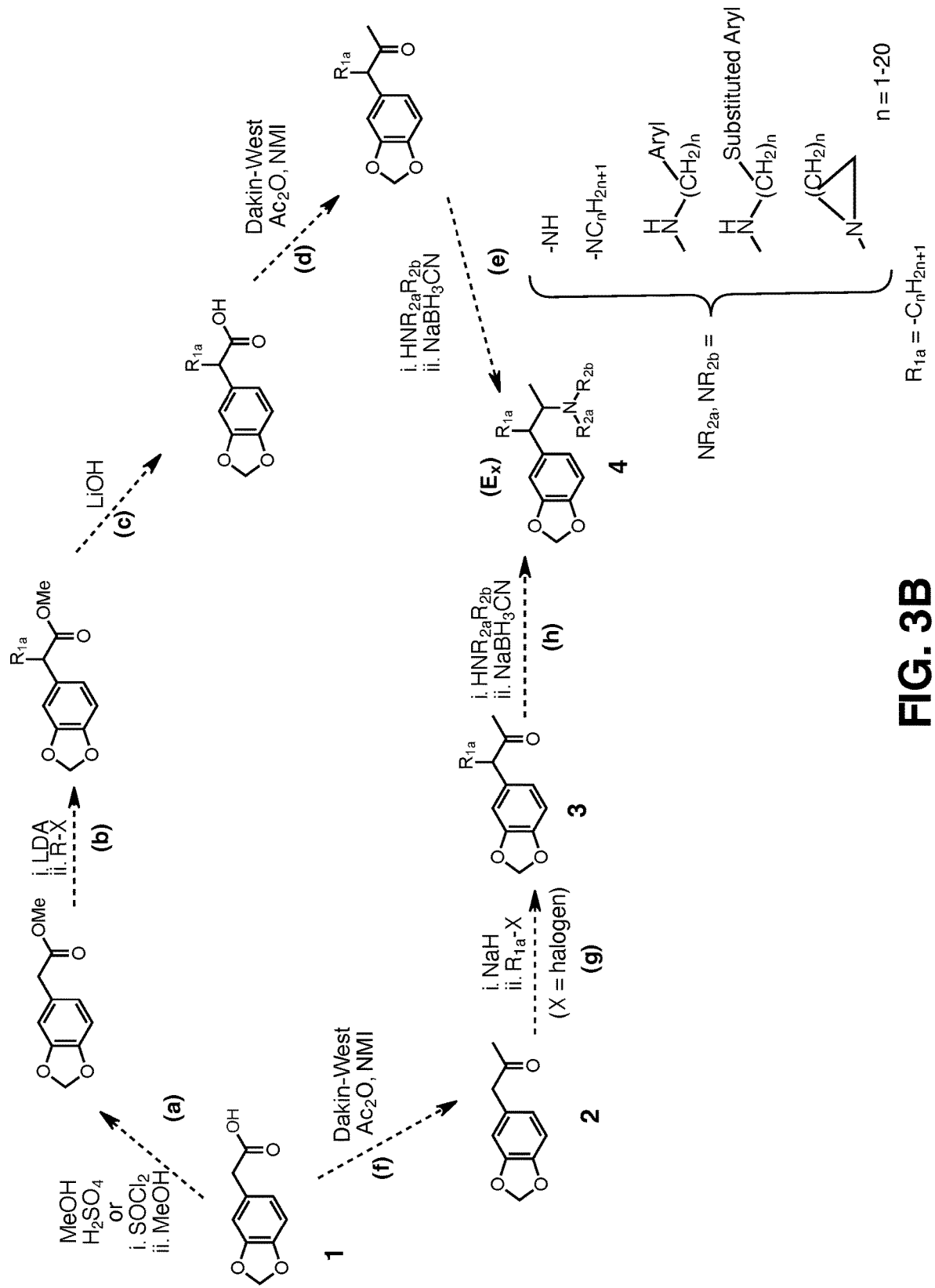
Figure 3C:
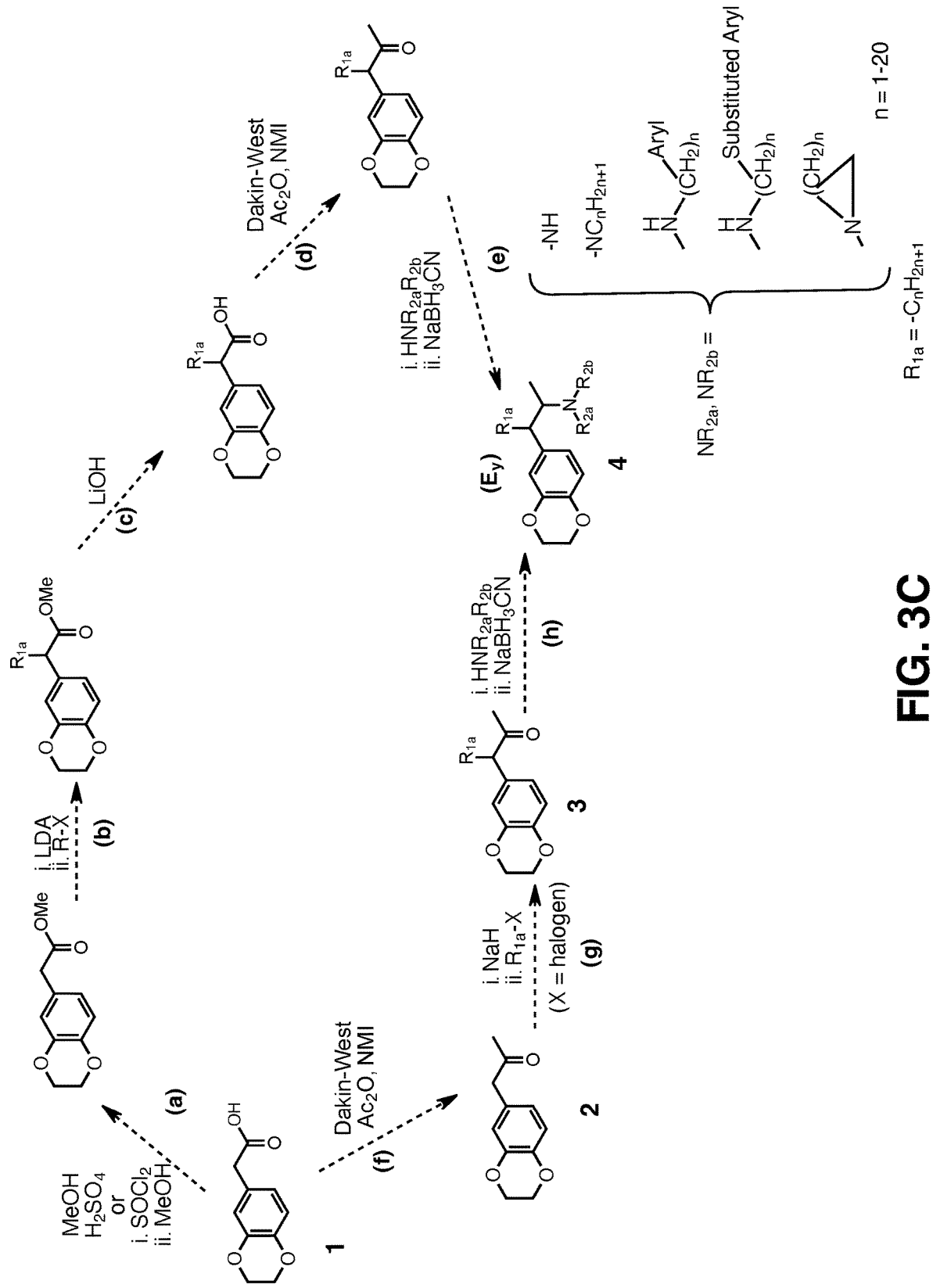

Examples of suitable chemical reactions that may be performed in accordance herewith are depicted in FIGS. 3A, 3B, and 3C, and are further additionally detailed hereinafter in the Example section.

In general, as is known to those of skill in the art, in order to perform chemical synthetic reactions selected reactants are reacted under reaction conditions which permit the reactants to chemically react with each other and form a product, i.e., the heterocyclic mescaline derivatives of the present disclosure. Such reactions conditions may be selected, adjusted, and optimized as known by those of skill in the art. The reactions may be conducted in any suitable reaction vessel (e.g., a tube, bottle). Suitable solvents that may be used are polar solvents such as, for example, dichloromethane, dichloroethane, toluene, and so called participating solvents such as acetonitrile and diethyl ether. Suitable temperatures may range from, for example, e.g., from about −78° C. to about 60° C. Furthermore, catalysts, also known as promoters, may be included in the reaction such as iodonium dicollidine perchlorate (IDCP), any silver or mercury salts, trimethylsilyl trifluoromethanesulfonate (TMS-triflate, TMSOTf), or trifluoronmethanesulfonic acid (triflic acid, TfOH), N-iodosuccinimide, methyl triflate. Furthermore, reaction times may be varied. As will readily be appreciated by those of skill in the art, the reaction conditions may be optimized, for example, by preparing several reactant preparations and reacting these in separate reaction vessels under different reaction conditions, for example, different temperatures, using different solvents etc., evaluating the obtained fused heterocyclic mescaline derivative reaction product, adjusting reaction conditions, and selecting a desired reaction condition. Further general guidance regarding appropriate reaction conditions for performing the reactions may be found in for example: Y. Zou et al., Eur. J. Med. Chem., 138, 199-211 (2017). K. N. Campbell et al., J. Org. Chem., 16, 1736-1740 (1951). D. Ghosh, et al., Tetrahedr. Lett., 58, 2014-2018 (2017). M. G. Cabiddu et al., Tetrahedron 59, 4383-4387 (2003).

In accordance with the foregoing, in an aspect, included herein, in accordance with at least one embodiment, is a method of making a first chemical compound having chemical formula (I) or chemical formula (II):

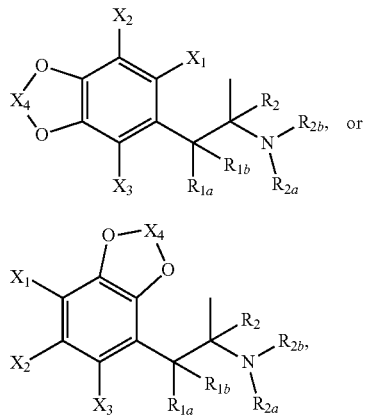

wherein, in chemical formula (I) and chemical formula (II):

$X_1$, $X_2$, and $X_3$ are independently selected from a hydrogen atom, O-alkyl, N-alkyl, OH, a halogen, or $NH_2$;

$X_4$ is an alkylene group or substituted alkylene group;

$R_{1a}$ is an alkyl group, O-alkyl group, a halogen, or OH, $R_{1b}$ is a hydrogen atom or a halogen, or $R_{1a}$ and $R_{1b}$ are joined together to form an oxo group;

$R_2$ is a hydrogen atom or an O-alkyl group; and $R_{2a}$ and $R_{2b}$ are independently selected from an alkyl group, an optionally substituted alkyl-aryl group, or a hydrogen atom, or $R_{2a}$ and $R_{2b}$ are joined together, along with the nitrogen atom to which they are attached, to form a 3-10-membered optionally substituted heterocyclic ring, wherein the method involves the performance of at least one chemical synthesis reaction selected from the reactions depicted in FIGS. 3A, 3B, and 3C.

Referring to FIG. 3A, in one embodiment, the compound having chemical formula (I) can be a compound having formula (A):

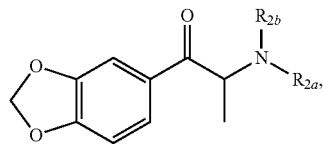

and at least one chemical synthesis reaction is a reaction selected from (c); (b) and (c); and (a), (b), and (c), depicted in FIG. 3A.

Referring to FIG. 3A, in one embodiment, the compound having chemical formula (I) can be a compound having formula (B):

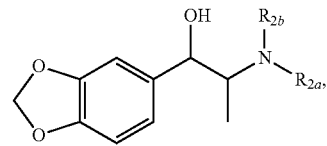

and at least one chemical synthesis reaction is a reaction selected from (e); (c) and (e); (b), (c), and (e); and (a), (b), (c), and (e), depicted in FIG. 3A.

Continuing to refer to FIG. 3A, in one embodiment, the compound having chemical formula (I) can be a compound having formula (C):

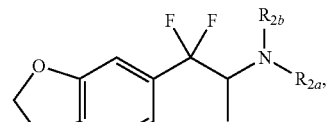

and at least one chemical synthesis reaction is a reaction selected from (d); (c) and (d); (b), (c), and (d); (a), (b), (c), and (d), depicted in FIG. 3A.

Continuing to refer to FIG. 3A, in one embodiment, the compound having chemical formula (I) can be a compound having formula (D):

and at least one chemical synthesis reaction is a reaction selected from (f); (e) and (f); (c), (e), and (f); (b), (c), (e), and (f); and (a), (b), (c), (e), and (f), depicted in FIG. 3A.

Referring to FIG. 3B, in one embodiment, the compound having chemical formula (I) can be a compound having formula ($E_x$):

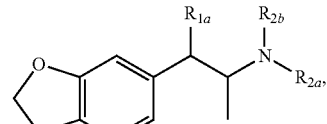

and at least one chemical synthesis reaction is a reaction selected from (e); (d) and (e); (c), (d), and (e); (b), (c), (d), and (e); (a), (b), (c), (d), and (e); (h); (g) and (h); and (f), (g), and (h) depicted in FIG. 3B.

Referring to FIG. 3C, in one embodiment, the compound having chemical formula (I) can be a compound having formula ($E_y$):

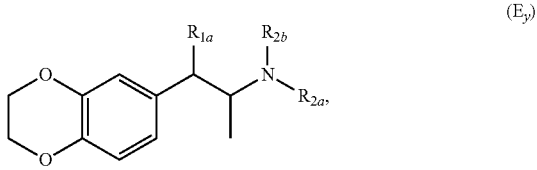

and at least one chemical synthesis reaction is a reaction selected from (e); (d) and (e); (c), (d), and (e); (b), (c), (d), and (e); (a), (b), (c), (d), and (e); (h); (g) and (h); and (f), (g), and (h) depicted in FIG. 3C.

It will now be clear from the foregoing that novel heterocyclic mescaline derivatives are disclosed herein. The heterocyclic mescaline derivatives may be formulated for use as a pharmaceutical drug or recreational drug. Example embodiments and implementations of the present disclosure are further illustrated by the following examples.

EXAMPLES

Example 1—Preparation of a First Fused Heterocyclic Mescaline Derivative

Referring to FIG. 3A, to a solution of compound 1 (4.70 mL, 40.5 mmol) in TFA (40.5 mL) under ambient atmosphere, at 0° C., was added propionic anhydride. (7.91 mL, 60.8 mmol). The reaction mixture was allowed to warm to room temperature—during which it gradually turned a dark pink-purple—and stirred for 24 h until TLC indicated no starting material remained (20% ethyl acetate-hexanes). The reaction mixture was poured over saturated $NaHCO_3$ (500 mL) and extracted with ethyl acetate (3×150 mL). The organic phase was washed with brine (100 mL), dried over anhydrous magnesium sulphate, and concentrated under reduced pressure to yield a crude pink oil. Purification by column chromatography on 80 g normal-phase silica using a 0- to 10% ethyl acetate-hexanes gradient yielded the product, 2, in quantitative yield as a pale-yellow solid.

LRMS-HESI: $[M+H]^+$ calculated 179.07, found 179.09 m/z. $^1$H NMR (400 MHz, $CDCl_3$) δ 7.59 (dd, J=8.1, 1.7 Hz, 1H), 7.47 (d, J=1.7 Hz, 1H), 6.87 (d, J=8.1 Hz, 1H), 6.06 (s, 2H), 2.95 (q, J=7.3 Hz, 2H), 1.23 (t, J=7.3 Hz, 3H).

Continuing to refer to FIG. 3A, to a solution of compound 2 (7.62 g, 42.8 mmol) in chloroform (285 mL) was added a solution of bromine (2.41 mL, 47.1 mmol) in chloroform (7.6 mL). The reaction mixture was allowed to stir overnight at room temperature. Saturated $NaHCO_3$ (200 mL) was added, and the reaction mixture extracted with DCM (3×100 mL). The combined organic layers were washed with brine (15 mL), dried over anhydrous magnesium sulphate, and concentrated under reduced pressure to yield product compound 3 as a pale-brown solid (10.6 g, 96%). No purification was necessary.

LRMS-HESI: $[M+H]^+$ calculated 258.90, found 258.84 m/z. $^1$H NMR (400 MHz, $CDCl_3$) δ 7.66 (dd, J=8.2, 1.8 Hz, 1H), 7.51 (d, J=1.8 Hz, 1H), 6.90 (d, J=8.2 Hz, 1H), 6.09 (s, 2H), 5.24 (q, J=6.6 Hz, 1H), 1.90 (d, J=6.6 Hz, 3H).

Continuing to refer to FIG. 3A, to a solution of compound 3, (962 mg, 3.74 mmol) in dry DMF (24.9 mL) under nitrogen atmosphere was added potassium carbonate (869 mg, 6.29 mmol) and N-methylbenzylamine (2.99 mL, 22.5 mmol). The reaction mixture was allowed to stir for 24 h at room temperature. After MS confirmation of product, the reaction mixture was poured into DI water (300 mL), extracted with DCM (3×100 mL), and the organic phase washed with water (5×100 mL). The organic extracts were dried over anhydrous magnesium sulphate and concentrated under reduced pressure overnight. Purification by column chromatography on 25 g normal-phase silica using a 0 to 8% methanol in dichloromethane eluent system yielded compound 4 (wherein $R_{2a}$=$CH_3$, $R_{2b}$=—$(CH_2)$-phenyl) as a yellow oil (963 mg, 87%).

LRMS-HESI: $[M+H]^+$ calculated 298.14, found 298.14 m/z. $^1$H NMR (400 MHz, $CDCl_3$) δ 7.67 (d, J=8.1 Hz, 1H), 7.52 (s, 1H), 7.34-7.22 (m, 5H), 6.84 (d, J=8.2 Hz, 1H), 6.06 (q, J=1.4 Hz, 2H), 4.27-4.19 (m, 1H), 3.66 (s, 2H), 2.24 (s, 3H), 1.31 (dd, J=12.6, 6.9 Hz, 3H). It is noted that compound 4 (wherein $R_{2a}$=$CH_3$, $R_{2b}$=—$(CH_2)$-phenyl) corresponds with compounds A(III):

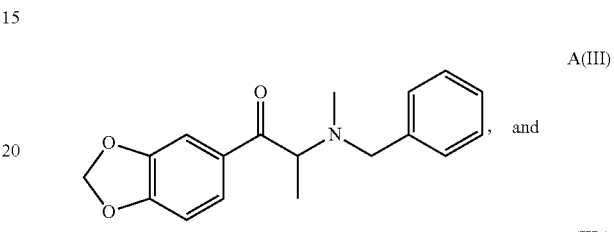

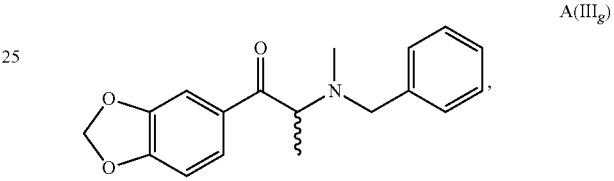

as set forth herein, wherein compound A(III) and A($III_g$) was obtained as a racemic mixture of enantiomers A($III_{ga}$) and A($III_{gb}$):

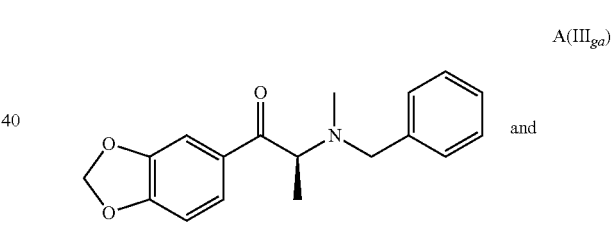

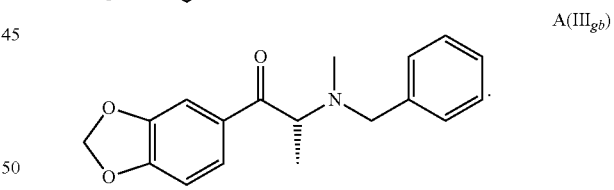

5-HT Receptor Radioligand Competition Assays.

Figure 4A:
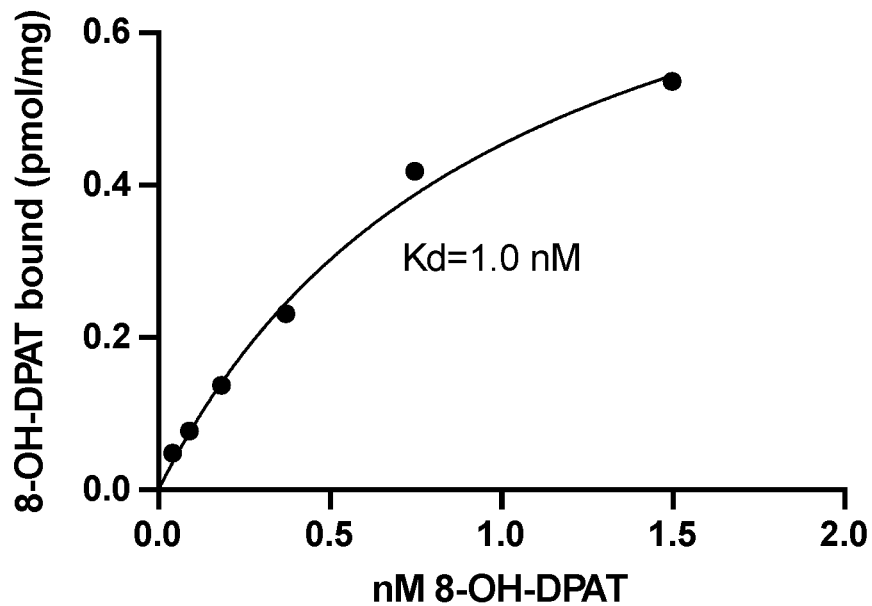
FIGS. 4A, 4B, 4C, 4D, 4E, 4F, 4G, 4H, 4I, 4J, 4K, and 4L depict various graphs representing certain experimental results, notably graphs obtained in the performance of experimental assays to evaluate the pharmaceutical efficacy of an example compound having chemical formula A(III), notably a radioligand 5-$HT_{1A}$ receptor saturation binding assay using radiolabeled 8-hydroxy-DPAT [propyl-2,3-ring-1,2,3-$^3$H] (binding curve) (FIG. 4A); a 5-$HT_{1A}$ receptor competition assay using DMSO (negative control) (FIG. 4B); a 5-$HT_{1A}$ receptor competition assay using tryptophan (negative control) (FIG. 4C); a 5-$HT_{1A}$ receptor competition assay using serotonin (positive control) (FIG. 4D); a 5-$HT_{1A}$ receptor competition assay using mescaline (positive control) (FIG. 4E); a 5-$HT_{1A}$ receptor competition assay using 2C-B (positive control) (FIG. 4F); a 5-$HT_{1A}$ receptor competition assay using MDMA (positive control) (FIG. 4G); a 5-$HT_{1A}$ receptor competition assay using escaline (FIG. 4H); a 5-$HT_{1A}$ receptor competition assay using proscaline (FIG. 4I); a 5-$HT_{1A}$ receptor competition assay using fluoxetine (positive control) (FIG. 4J); a 5-$HT_{1A}$ receptor competition assay using vortioxetine (positive control) (FIG. 4K); a 5-$HT_{1A}$ receptor competition assay using the compound with formula A(III) (FIG. 4L).
Figure 4B:
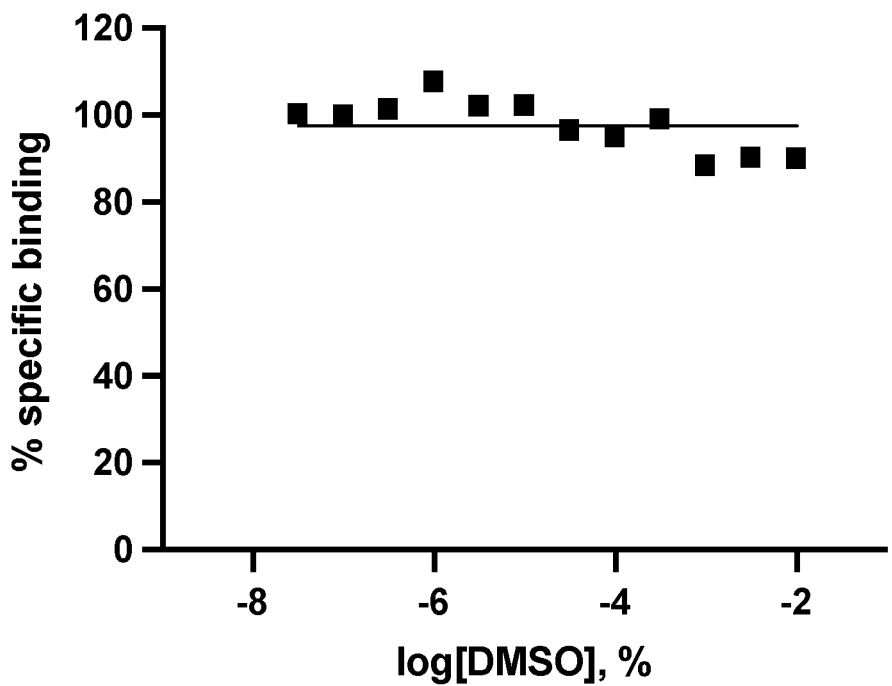
Figure 4C:
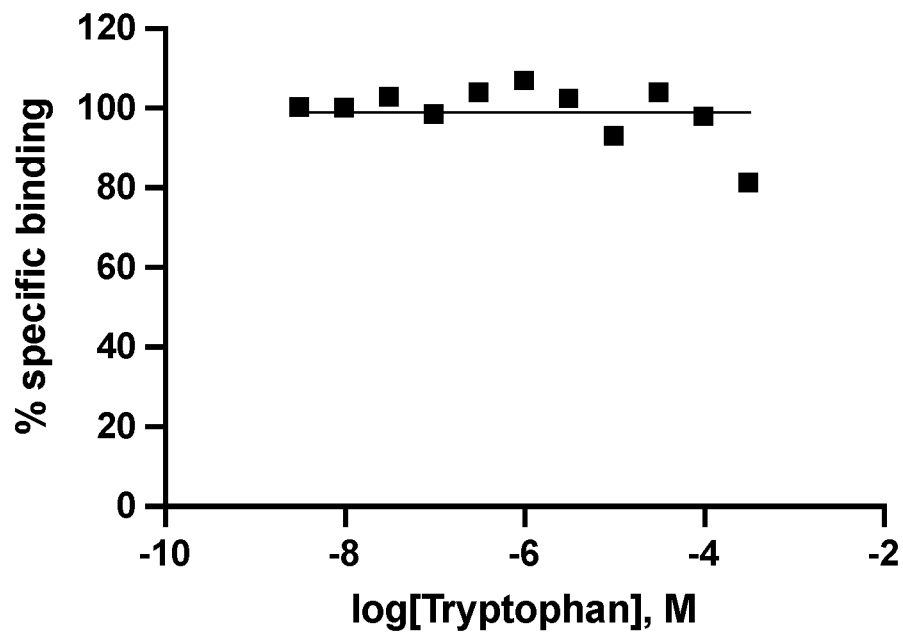
Figure 4D:
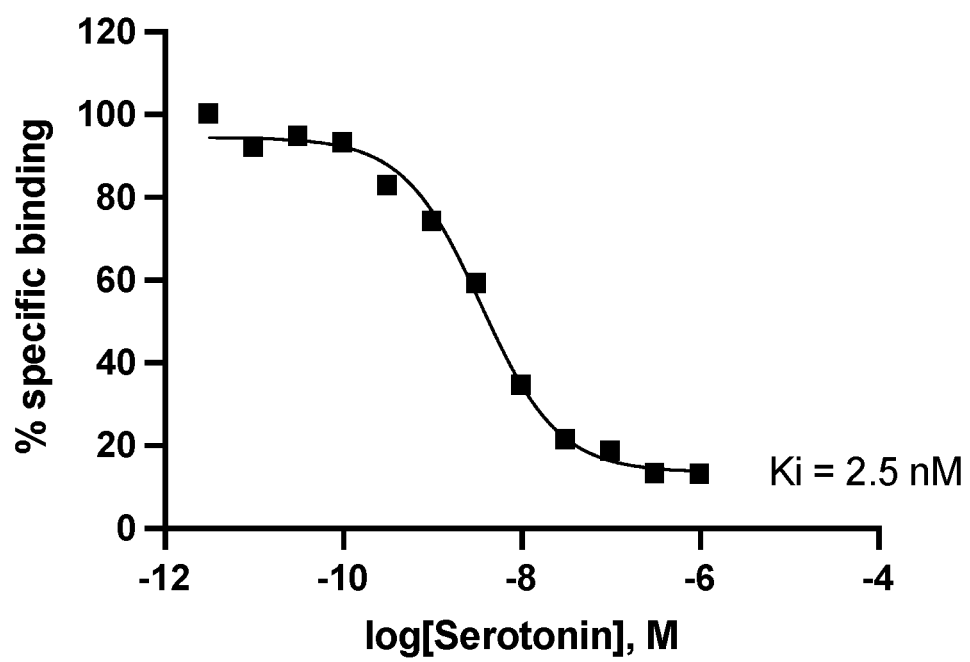
Figure 4E:
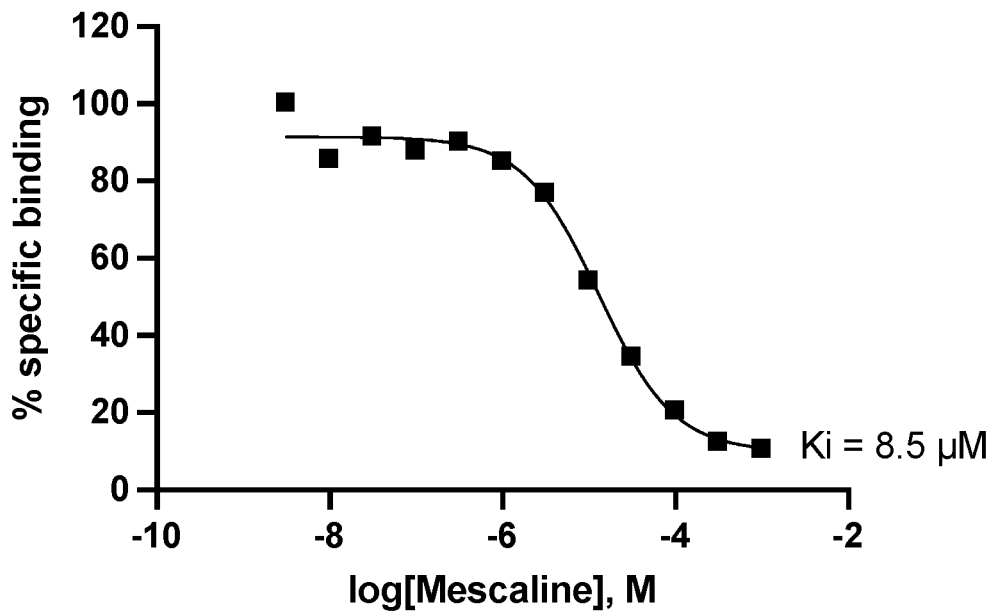
Figure 4F:
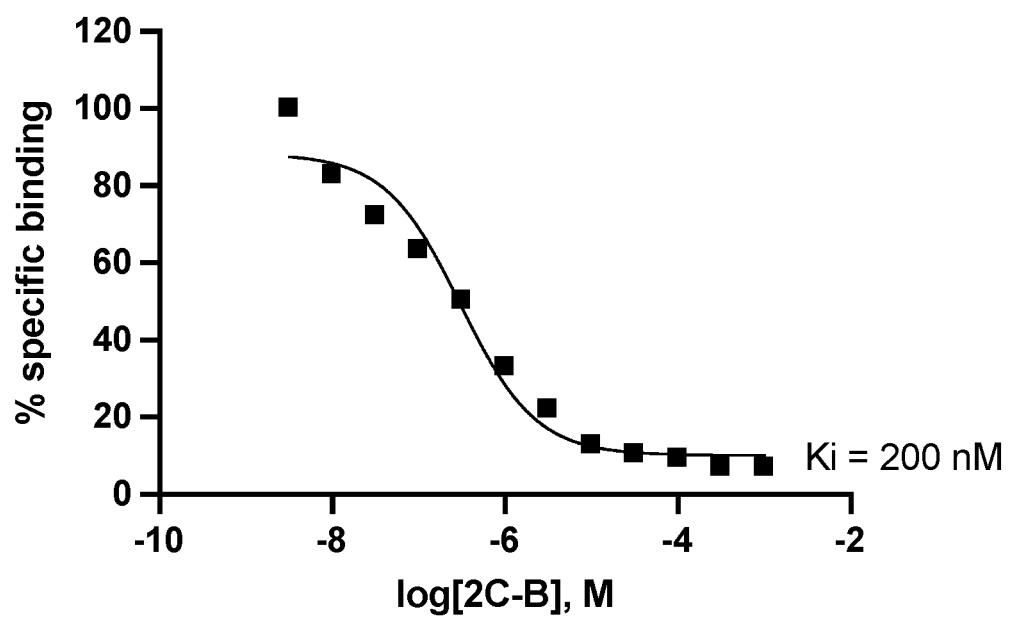
Figure 4G:
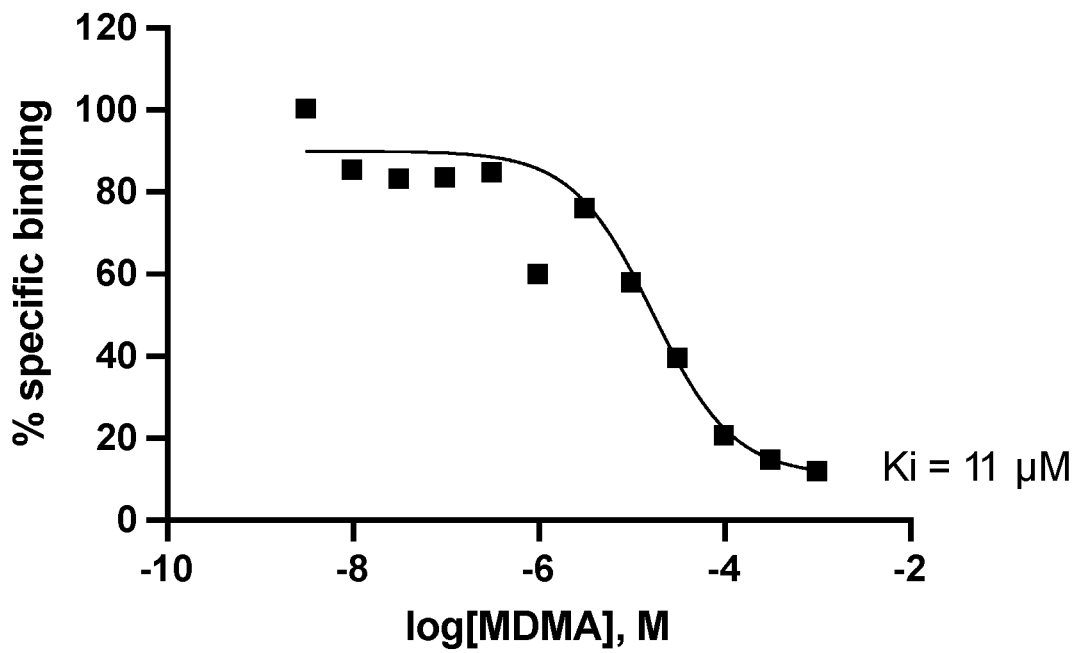
Figure 4H:
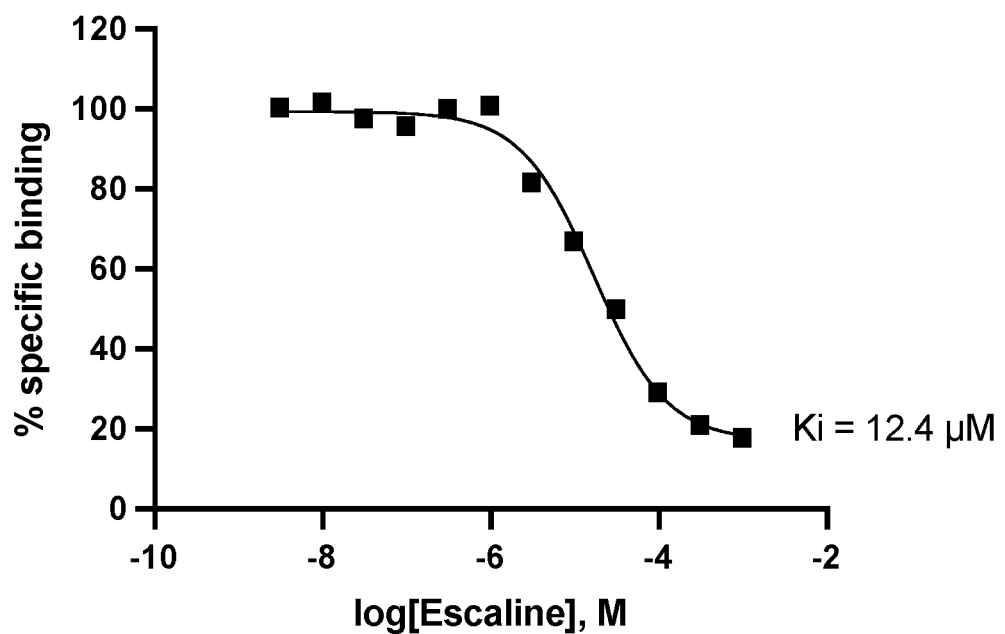
Figure 4I:
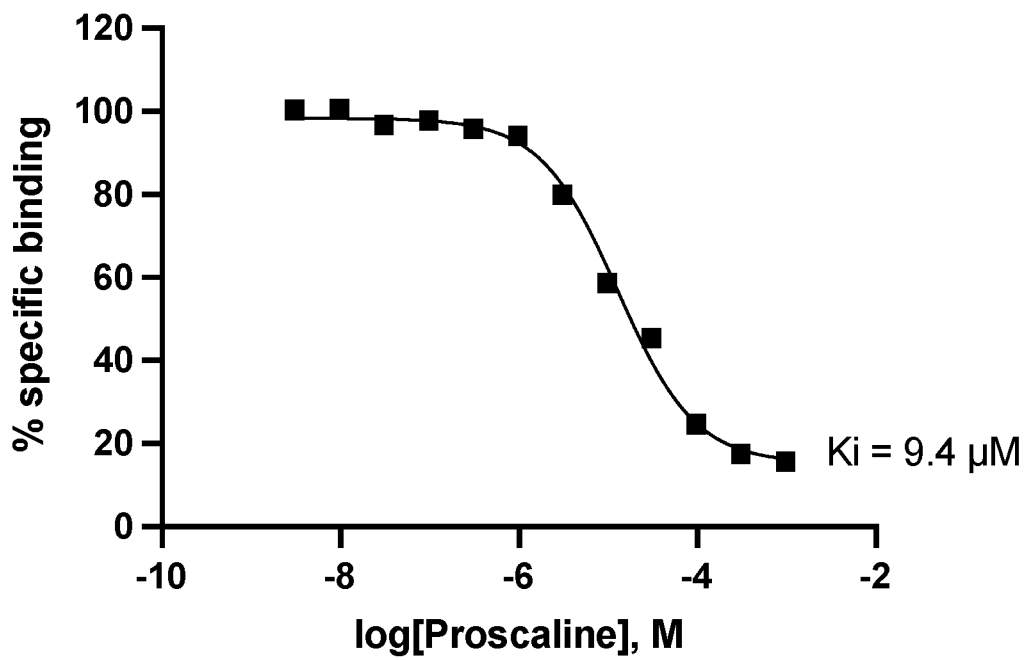
Figure 4J:
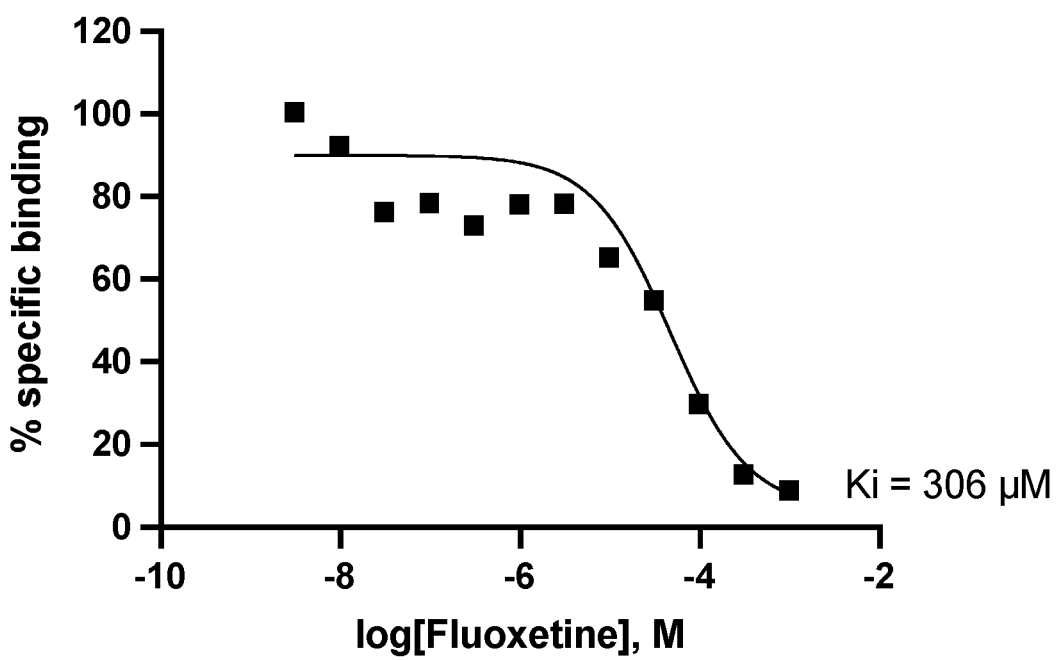
Figure 4K:
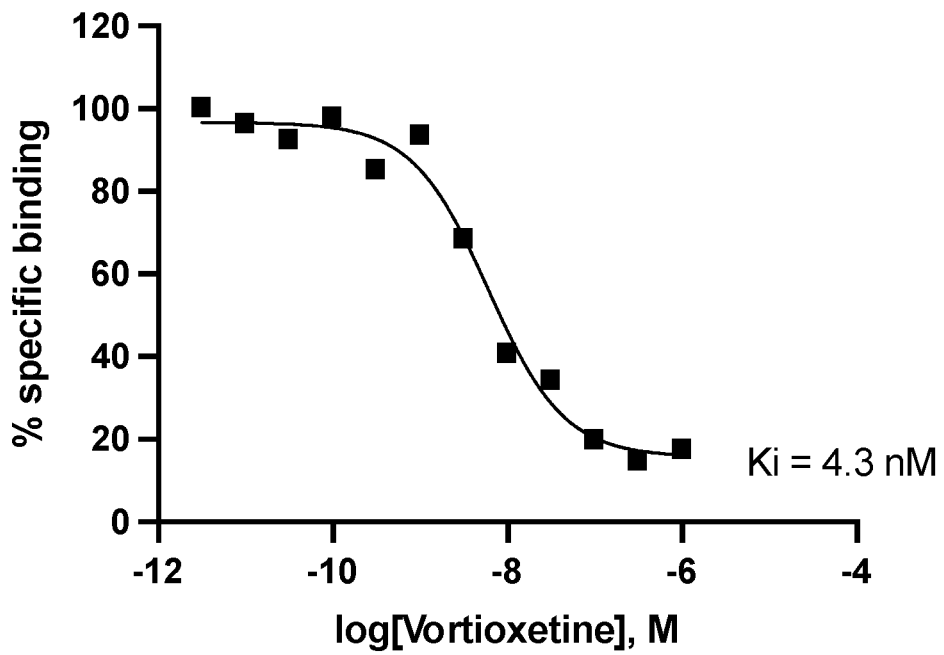
Figure 4L:
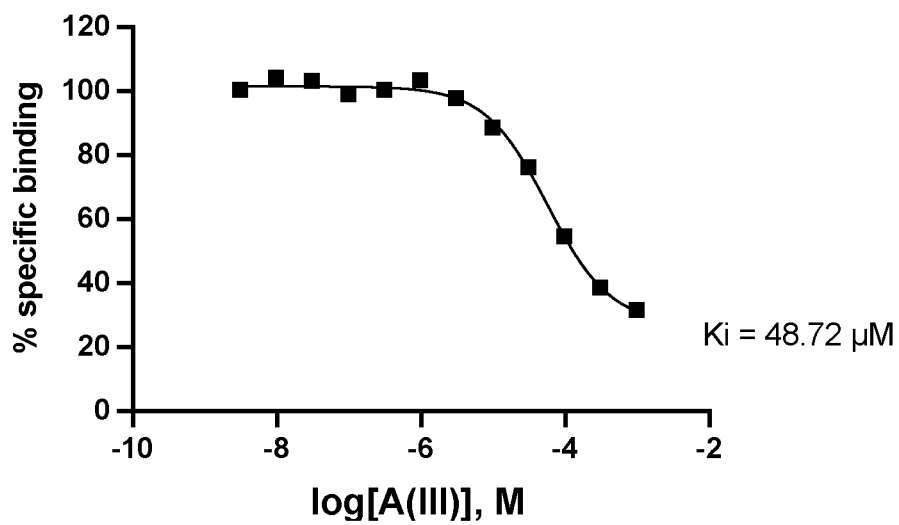

$5-HT_{1A}$ receptor. Competition assays were performed as follows: SPA beads (RPNQ0011), radiolabeled 8-hydroxy-DPAT [propyl-2,3-ring-1,2,3-$^3$H](labelled 7-(dipropylamino)-5,6,7,8-tetrahydronaphthalen-1-ol; NET929250UC), membranes containing $5-HT_{1A}$ (6110501400UA), and isoplate-96 microplate (6005040) were from Perkin Elmer (perkinelmer.com). Radioactive binding assays were carried out using a scintillation proximity assay (SPA; Maguire et al., 2012, Methods in Molecular Biology 897:31-77). For saturation binding assays, mixtures of 10 μg of membrane containing $HT_{1A}$ receptor was pre-coupled to 1 mg of SPA beads at room temperature in a tube rotator for 1 h in binding buffer [50 mM Tris-HCl pH 7.4, 10 mM magnesium sulfate, 0.5 mM EDTA, 3.7% (v/v)

glycerol, 1 mM ascorbic acid, 10 µM pargyline HCl]. After pre-coupling, the beads and membrane were aliquoted in an isoplate-96 microplate with increasing amounts of 8-hydroxy-DPAT [propyl-2,3-ring-1,2,3-$^3$H] (0.1525 nM to 5 nM) and incubated for two hours at room temperature in the dark with shaking. After incubation, the samples were read on a MicroBeta 2 Microplate Counter (perkinelmer.com). Non-specific binding was carried out in the presence of 100 µM of metergoline (M3668-500MG, Sigma-Aldrich). Equilibrium binding constant for 8-hydroxy-DPAT ($K_D$) was determined from a saturation binding curve using one-site saturation binding analysis from GraphPad PRISM software (Version 9.2.0). Test compound was dissolved to 100 mM in dimethylsulfoxide (DMSO), and dilutions were carried out in assay buffer. Competition binding assays were performed using 0.5 nM hot 8-hydroxy-DPAT and different concentrations of DMSO (up to 1%), tryptophan (3 nM to 1 mM), or unlabelled test compounds (3 nM to 1 mM) similar to the saturation binding assay. $K_i$ values were calculated from the competition displacement data using the competitive binding analysis from GraphPad PRISM software. Serotonin was used as a positive control, as it is the natural, endogenous ligand for all serotonergic receptors. 2C-B, MDMA and mescaline were used as positive controls since they are phenylalkylamine-type molecules with relatively strong (2C-B; Rickli et al., 2015, Neuropharmacology 99: 546) or more moderate (MDMA, Simmler et al., 2013, British J. Pharmacol. 168: 458; mescaline, Rickli et al., 2016, Eur. Neuropharm. 26: 1327) 5-HT$_{1A}$ receptor binding activities, respectively. Escaline and proscaline were included in this study for comparative purposes, for although their 5-HT$_{1A}$ receptor binding mode(s) are understudied they are established mescaline-type hallucinogens with therapeutic potential (Shulgin and Shulgin, 1990. *PIHKAL: A Chemical Love Story*. 1$^{St}$ ed., Transform Press). Fluoxetine and vortioxetine were included as positive controls as they are widely prescribed pharmaceuticals with established binding to the 5-HT$_{1A}$ receptor (Owens et al., 1997, Journal of Pharmacology and Experimental Therapeutics 283:1305-1322; Celada et al., 2013, CNS Drugs 27:703-716). FIG. 4A illustrates the binding curve used to determine the $K_D$ of 8-hydroxy-DPAT. FIGS. 4B and 4C illustrate binding curves of negative controls DMSO and tryptophan, respectively. As seen in FIGS. 4B and 4C, data precluded $K_i$ determination (i.e., $K_i$>1000 µM) which indicated no binding for these negative controls. Binding curves illustrated in FIGS. 4D, 4E, 4F, and 4G reveal data permitting $K_i$ determinations for the positive controls: serotonin, mescaline, 2C-B, and MDMA respectively. The sigmoidal curves and $K_i$ values (i.e., $K_i$<1000 µM) in FIGS. 4D, 4E, 4F, and 4G reveal 5-HT$_{1A}$ receptor binding at indicated ligand concentrations. Data in FIGS. 4H and 4I suggest binding to 5-HT$_{1A}$ receptor of escaline and proscaline respectively, at the indicated concentrations. Data in FIGS. 4J and 4K indicate binding to the 5-HT$_{1A}$ receptor of fluoxetine and vortioxetine respectively. Data in FIG. 4L indicates binding to the 5-HT$_{1A}$ receptor of the compound with formula A(III) above levels observed for negative controls (FIGS. 4B and 4C). Resulting $K_i$ data for controls and test compounds in 5-HT$_{1A}$ receptor binding assays is summarized in Table 1.

Figure 5A:
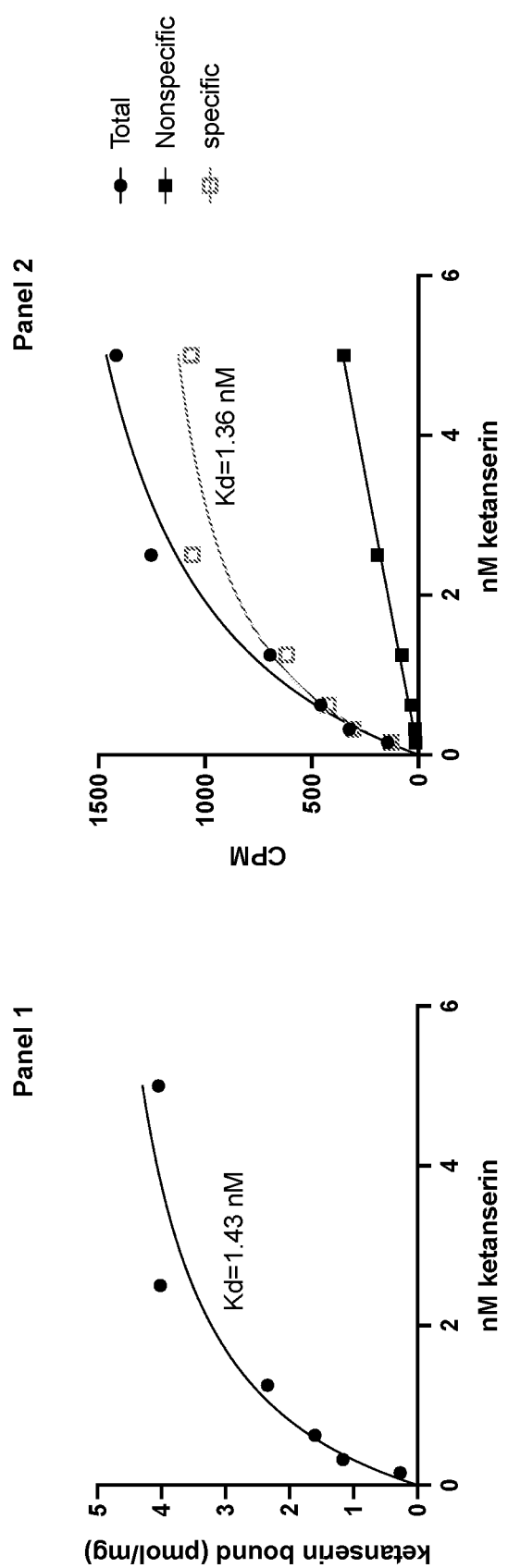
FIGS. 5A, 5B, 5C, 5D, 5E, 5F, 5G, and 5H depict various graphs representing certain experimental results, notably graphs obtained in the performance of experimental assays to evaluate the pharmaceutical efficacy of an example compound having chemical formula A(III), notably a radioligand 5-$HT_{2A}$ receptor saturated binding assay using radiolabeled [$^3$H-ketanserin] (binding curves) (FIG. 5A); a 5-$HT_{2A}$ receptor competition assay using psilocin (positive control) (FIG. 5B); a 5-$HT_{2A}$ receptor competition assay using tryptophan (negative control) (FIG. 5C); a 5-$HT_{2A}$ receptor competition assay using escaline (FIG. 5D); a 5-$HT_{2A}$ receptor competition assay using proscaline (FIG. 5E); a 5-$HT_{2A}$ receptor competition assay using 2C-B (positive control) (FIG. 5F); and a 5-$HT_{2A}$ receptor competition assay using MDMA (positive control) (FIG. 5G), and; a 5-$HT_{2A}$ receptor competition assay using the compound with formula A(III) (FIG. 5H).
Figure 5B:
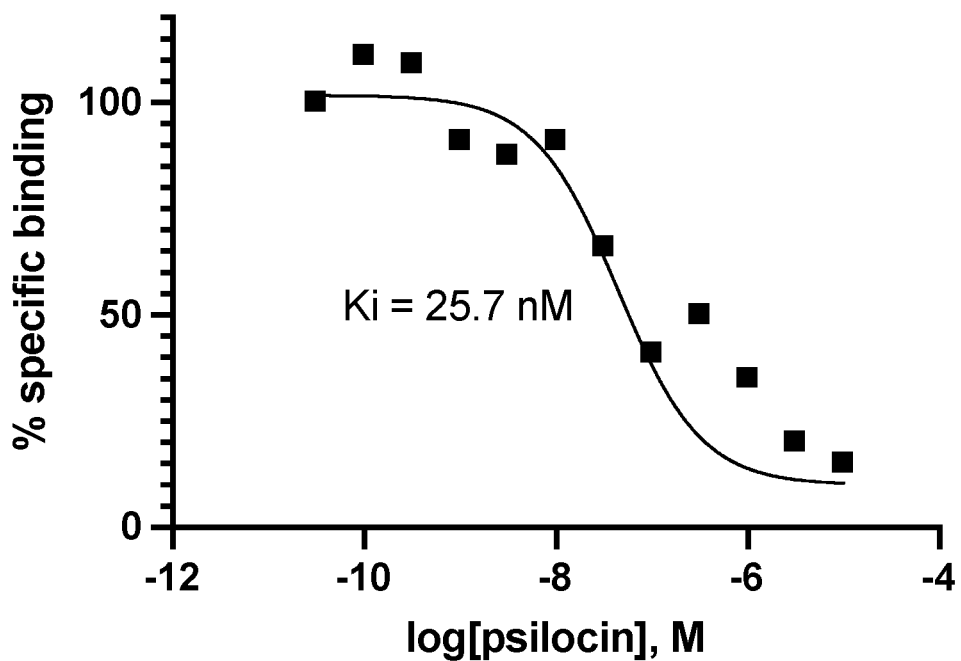
Figure 5C:
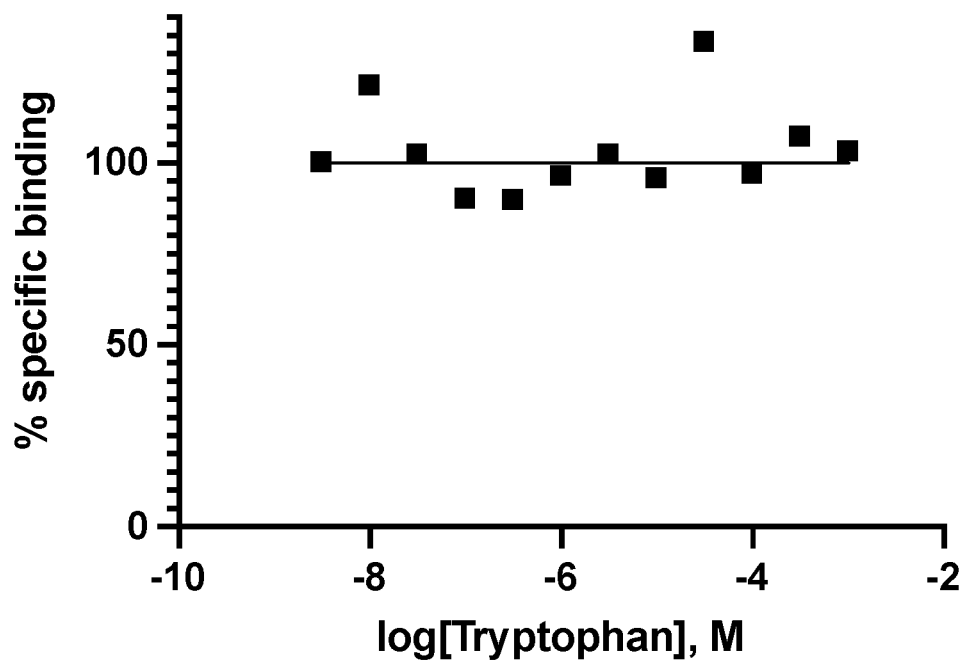
Figure 5D:
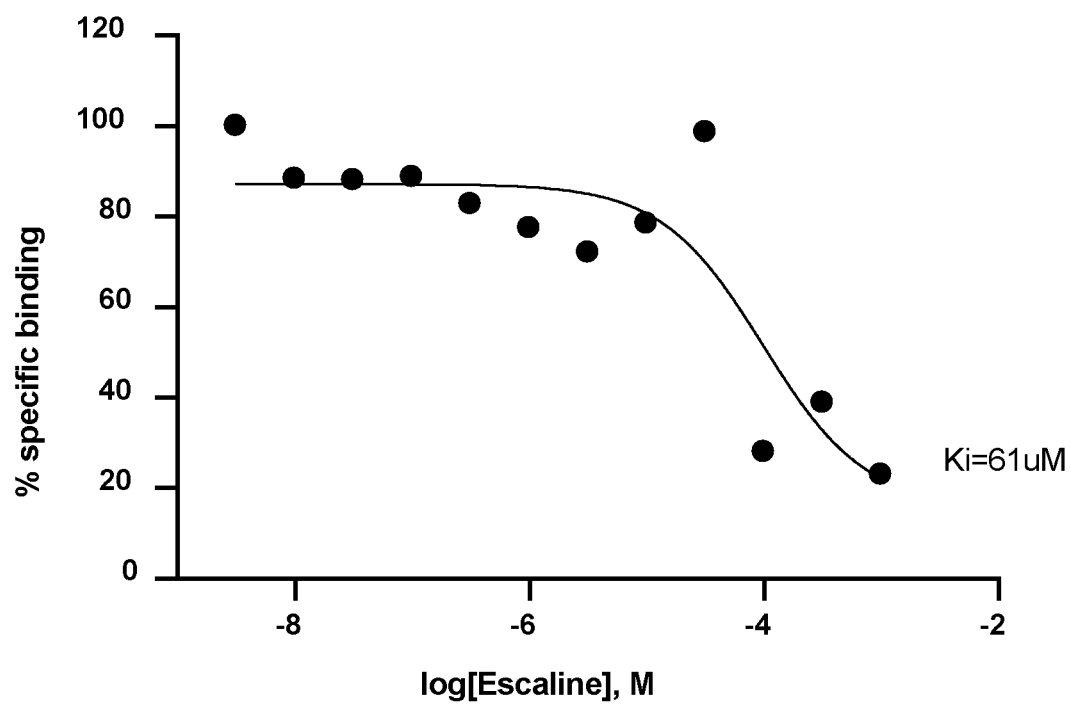
Figure 5E:
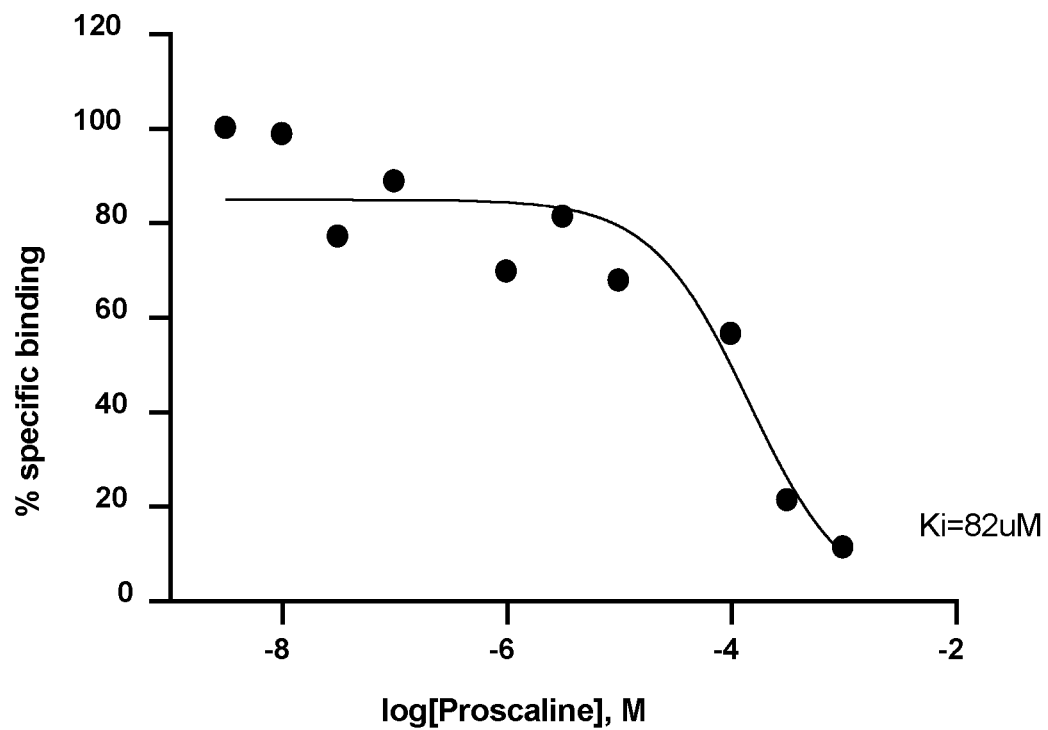
Figure 5F:
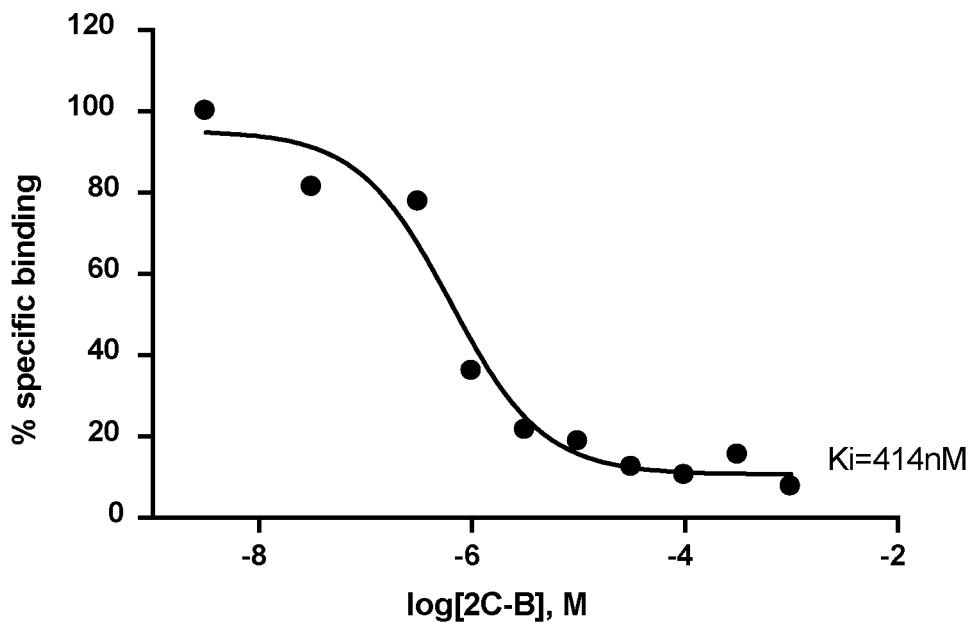
Figure 5G:
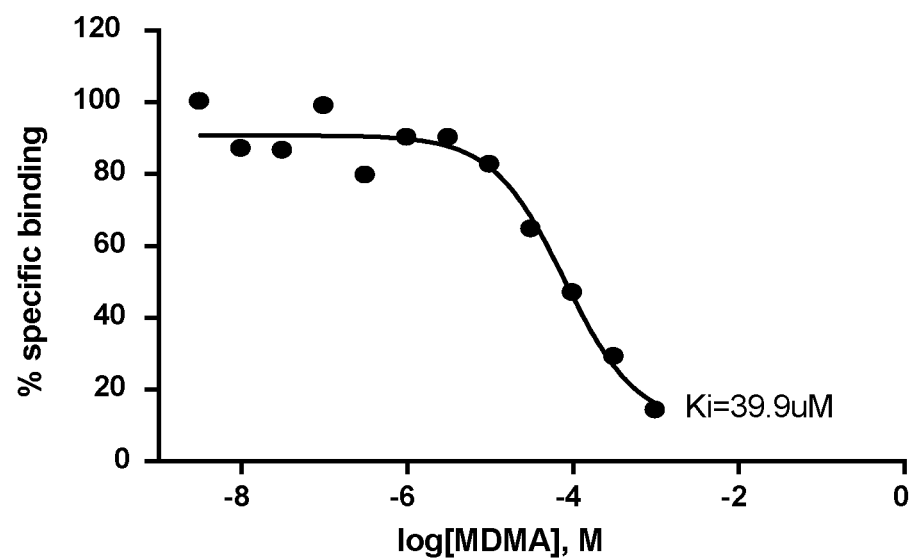
Figure 5H:
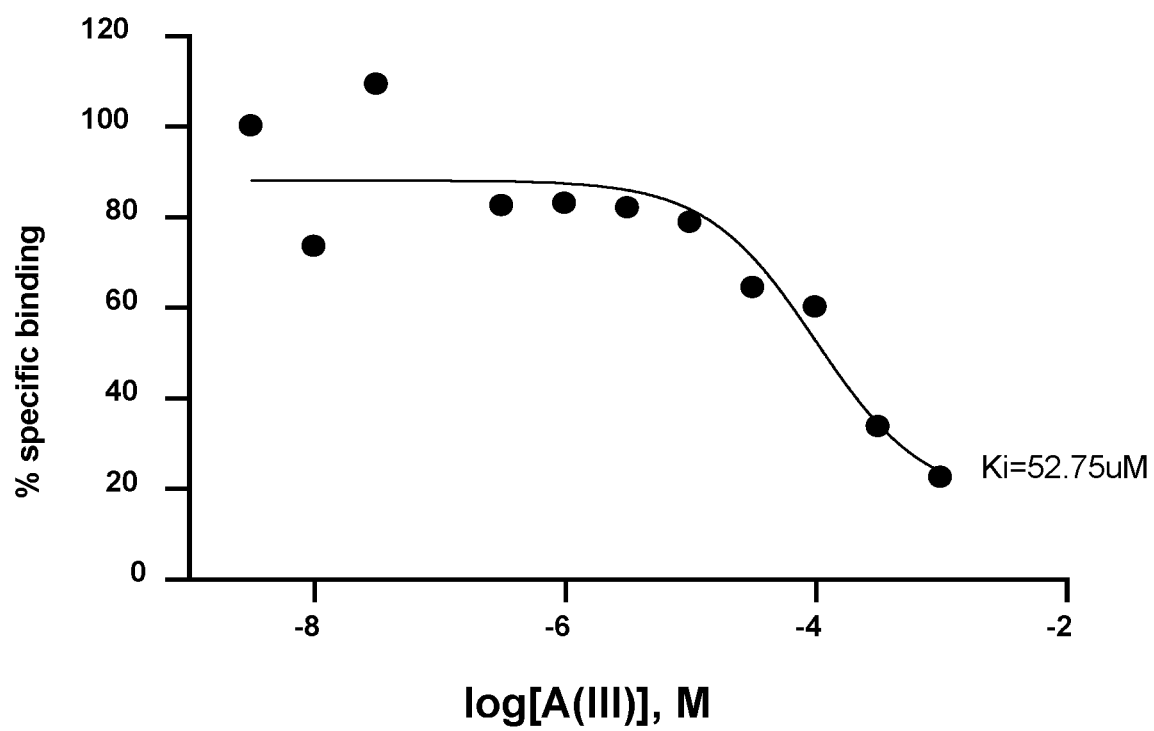

5-HT$_{2A}$ receptor. Competition assays were performed as for 5-HT$_{1A}$ assays with the following differences. SPA beads (RPNQ0010), [$^3$H]ketanserin (NET1233025UC), and membranes containing 5-HT$_{2A}$ (ES-313-M400UA) were from PerkinElmer. After pre-coupling, the beads and membrane were aliquoted in an isoplate-96 microplate with increasing amounts of [$^3$H]ketanserin (0.1525 nM to 5 nM). Determination of non-specific binding was carried out in the presence of 20 mM of spiperone (S7395-250MG, Sigma-Aldrich). Equilibrium binding constant for ketanserin ($K_d$) was determined from saturation binding curves using the 'one-site saturation binding analysis' method in GraphPad PRISM software (Version 9.2.0). Competition binding assays were performed using fixed (1 nM) [$^3$H]ketanserin and different concentrations of unlabeled test compounds (3 nM to 1 mM) similar to the saturation binding assay. Tryptophan was included as a negative control as it has no activity at the 5-HT$_{2A}$ receptor. In contrast, 2C-B and MDMA were used as positive controls since they are phenylalkylamine-type molecules with relatively strong (Marcher-Rorsted et al., 2020, ACS Chem. Neurosci. 11: 1238) or more moderate (Simmler et al., 2013, British J. Pharmacol. 168: 458) 5-HT$_{2A}$ receptor binding activities, respectively. Escaline and proscaline were included in this study for comparative purposes, for although their 5-HT$_{2A}$ receptor binding mode is understudied they are established mescaline-type hallucinogens known to induce head-twitch responses in mice (Halberstadt et al., 2019, J. Psychopharm. 33: 406-414). Mouse head-twitch response has been correlated with 5-HT$_{2A}$ receptor engagement (Halberstadt, 2015, Behav. Brain Res. 277: 99). Psilocin is included as an additional positive control as it exhibits well-established binding to 5-HT$_{2A}$ receptor as a partial agonist. FIG. 5A illustrates data in support of overall $K_D$ determination for ketanserin (Panel 1), in addition to the $K_D$ owed to specific binding (Panel 2). FIG. 5B illustrates data obtained for psilocin and supports binding at the 5-HT$_{2A}$ receptor for this positive control. FIG. 5C illustrates data obtained for tryptophan and supports a lack of binding at the 5-HT$_{2A}$ receptor for this negative control. FIGS. 5D and 5E reveal binding data for escaline and proscaline, respectively, and resulting $K_i$ values (i.e., <1000 µM) reveal binding at the 5-HT$_{2A}$ receptor at indicated concentrations. FIG. 5F reveals binding data for 2C-B and the resulting $K_i$ value (i.e., <1000 µM) reveals binding at the 5-HT$_{2A}$ receptor. FIG. 5G reveals binding data for MDMA and the resulting $K_i$ value (i.e., <1000 µM) reveals binding at the 5-HT$_{2A}$ receptor at the indicated concentrations. Data in FIG. 5H indicates binding to the 5-HT$_{2A}$ receptor of the compound with formula A(III) above levels observed for negative control (FIG. 5C). Resulting $K_i$ data for controls and test compounds in 5-HT$_{2A}$ receptor binding assays is summarized in Table 1.

TABLE 1

Data summary for 5-HT$_{1A}$ and 5-HT$_{2A}$ receptors radioligand competition assays.

| Molecule | 5-HT$_{1A}$, Ki (µM) | 5-HT$_{2A}$, Ki (µM) |
|---|---|---|
| DMSO | >1000 | >1000 |
| tryptophan | >1000 | >1000 |
| serotonin | 0.0025 | N.D. |
| psilocin | N.D. | 0.0257 |
| mescaline | 8.5 | N.D. |
| 2C-B | 0.200 | 0.414 |
| MDMA | 11 | 39.9 |
| escaline | 12.4 | 61 |
| proscaline | 9.4 | 82 |
| fluoxetine | 0.306 | N.D. |
| vortioxetine | 0.0043 | N.D. |
| A(I) | 2.0 | 131 |
| A(III) | 49 | 53 |
| B(I) as diast. (i) | 480 | 4.5 |
| B(I) as diast. (ii) | 37 | 25 |
| B(III) as diast. (iii) | 110 | 44 |
| B(III) as diast. (iv) | 16.9 | N.D. |

TABLE 1-continued

Data summary for $5\text{-}HT_{1A}$ and $5\text{-}HT_{2A}$ receptors radioligand competition assays.

| Molecule | $5\text{-}HT_{1A}$, Ki (µM) | $5\text{-}HT_{2A}$, Ki (µM) |
|---|---|---|
| D(II) as diast. (vi) | 6.0 | N.D. |
| D(III) as diast. (vii) | 11.3 | N.D. |
| D(III) as diast. (viii) | 8.1 | N.D. |
| Ex(VI) as diast. (xi) and (xii) | 65.9 | N.D. |

N.D. = not determined $5\text{-}HT_{1A}$ receptor functional cellular response assay. Functional engagement of the $5\text{-}HT_{1A}$ receptor within an engineered cell system was assessed as described for Example 6, except the compound with formula A(III) was evaluated in place of compounds with formulae $D(III_{da})$ and $D(III_{ab})$. Table 5 shows functional assay results for positive controls, calibrators, and compound with formula A(III), in the form of $EC_{50}$ values. In view of results for controls and calibrator compounds, wherein a negative cellular response corresponded to an $EC_{50}$ value>1000 µM, the $EC_{50}$ value for the compound with formula A(III) in this assay (>1000 µM, Table 5) suggested no ligand-receptor engagement.

In Vitro Survey of Pharmacological Interaction Profiles at Receptors and Transporters Linked to Targeted Health Conditions.

To expand pharmacological profiling to include a broader range of targets with known involvement in, or connection to, brain neurological disorders, the compound with formula A(III) was evaluated with respect to binding and/or interaction at 9 different receptors and transporters. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 6 G-protein coupled receptors (GPCR) receptors: HTR1A ($5\text{-}HTR_{1A}$), HTR2B ($5\text{-}HT_{2B}$), HTR2C ($5\text{-}HT_{2C}$), HTR7 ($5\text{-}HT_7$), alpha2A ($\alpha_{2A}$), MT1 ($MT_1$)) and 3 transporters (SERT, DAT, NET). Assay conditions are summarized in Tables 2 and 3 for GPCR and transporters, respectively. On-site positive controls are routinely applied as part of standard industry practice at Eurofins Cerep (https://www.eurofins.com/contact-us/worldwide-interactive-map/france/eurofins-cerep-france/) to ensure functionality of each assay. To further calibrate each assay specifically for compounds bearing the phenylalkylamine (PAA) structural scaffold, a suite of six, PAA-type calibrator compounds were additionally submitted for assays: MDMA, mescaline, 2C-B, escaline, proscaline, and DOB. Additional tryptamine-type calibrators employed in these assays included serotonin and melatonin. Tryptophan was submitted as a negative control for all assays, as tryptophan is not known to interact with any of the target receptors or transporters. Seven widely marketed pharmaceuticals used in the treatment of mental health disorders with long-established pharmacological profiles were additionally submitted for assay calibration purposes: vortioxetine, trazodone, duloxetine, imipramine, agomelatine, bupropion, and vilazodone. Results for all calibrator compounds, control compounds, and test compounds including the compound with formula A(III) are summarized in Table 4.

TABLE 2

Conditions summary for GPCR (receptor) binding assays. Cold ligand is included in assays to ensure only specific binding is evaluated.

| Receptor | Hot ligand Name | Hot ligand Type | Concentration nM | $K_d$ nM | Cold ligand* Name | Cold ligand* µM | Incubation min/° C. |
|---|---|---|---|---|---|---|---|
| alpha2A | [$^3$H]RX 821002 | Antagonist | 1 | 0.8 | (−)epinephrine | 100 | 60/20 |
| MT1 (ML1A) | [$^{125}$I]2-iodomelatonin | Agonist | 0.01 | 0.04 | melatonin | 1 | 240/20 |
| $5\text{-}HT_{1A}$ | [$^3$H]8-OH-DPAT | Agonist | 0.5 | 0.5 | 8-OH-DPAT | 10 | 60/RT |
| $5\text{-}HT_{2B}$ | [$^3$H]mesulergine | Antagonist | 2 | 2.4 | SB206553 | 10 | 60/20 |
| $5\text{-}HT_{2C}$ | [$^{125}$I](±)DOI | Agonist | 0.1 | 0.9 | (±)DOI | 10 | 60/37 |
| $5\text{-}HT_7$ | [$^3$H]LSD | Agonist | 4 | 2.3 | serotonin | 10 | 120/20 |

TABLE 3

Conditions summary for transporter binding assays. Cold ligand is included in assays to ensure only specific binding is evaluated.

| Transporter | Hot ligand Name | Hot ligand Type | Concentration nM | $K_d$ nM | Cold ligand* Name | Cold ligand* µM | Incubation min/° C. |
|---|---|---|---|---|---|---|---|
| SERT | [$^3$H]imipramine | Antagonist | 2 | 1.7 | imipramine | 10 | 60/RT |
| NET | [$^3$H]nisoxetine | Antagonist | 1 | 2.9 | desipramine | 1 | 120/4 |
| DAT | [$^3$H]BTCP | Antagonist | 4 | 4.5 | BTCP | 10 | 120/4 | i. Competition Assay to Measure Binding Affinity at Alpha2A Receptor.

Assays were conducted according to methodology described by Langin et al., [Eur. J. Pharmacol. 167:95-104, 1989] using conditions summarized in Table 2. As the purpose of this experiment was to gauge general binding potential of test ligand, rather than obtain detailed binding information yielding $K_i$ values, only a single concentration of test ligand was used (10 µM). Briefly, CHO cells were used to express recombinant receptor, and membrane preparation was conducted at 4° C. Binding experiments were conducted using 100 µL membrane suspension incubated with radioligand, cold ligand to ensure specific binding by test ligand, and test molecule (10 µM) in 400 µL final volume of Tris-$Mg^{2+}$ buffer. Incubations were quenched with the addition of 4 mL ice cold washing buffer (10 mM Tris-HCl, 0.5 mM $MgCl_2$). Bound and free radioligand were separated by filtration through GF/C Whatman filters under vacuum. The filters were then washed and subjected to scintillation counting. Results were expressed as a percent of control-specific binding ([measured specific binding/control-specific binding]*100). Results for the compound with formula A(III) are shown in Table 4.

ii. Competition Assay to Measure Binding Affinity at $MT_1$ Receptor.

Assays were conducted according to methodology described by Witt-Endersby and Dubocovich [Mol. Pharmacol. 50:166-174, 1996] using conditions summarized in Table 2. As the purpose of this experiment was to gauge general binding potential of test ligand, rather than obtain detailed binding information yielding $K_i$ values, only a single concentration of test ligand was used (10 µM). Briefly, CHO cells were used to express recombinant receptor, and membrane preparation was conducted at 4° C. Binding experiments were conducted using 100 µL membrane suspension, radioligand, cold ligand to ensure specific binding by test ligand, and test molecule (10 µM) in a final volume of 500 µL. Bound and free radioligand were separated by filtration through GF/C Whatman filters under vacuum. The filters were then washed and subjected to scintillation counting. Results were expressed as a percent of control-specific binding ([measured specific binding/control-specific binding]*100). Results for the compound with formula A(III) are shown in Table 4.

iii. Competition Assay to Measure Binding Affinity at 5-$HT_{1A}$ Receptor.

Assays were conducted according to methodology described by Mulheron et al., [J. Biol. Chem. 269: 12954-12962, 1994] using conditions summarized in Table 2. As the purpose of this experiment was to gauge general binding potential of test ligand, rather than obtain detailed binding information yielding $K_i$ values, only a single concentration of test ligand was used (10 µM). Briefly, HEK-293 cells were used to express recombinant receptor, and membrane preparation was conducted at 4° C. Binding experiments were conducted using radioligand, 30 µg protein (membrane suspension), cold ligand to ensure specific binding by test ligand, and test molecule (10 µM) to final volume of 200 µL. Bound and free radioligand were separated by filtration through glass fiber Whatman filters under vacuum. The filters were then washed and subjected to scintillation counting. Results were expressed as a percent of control-specific binding ([measured specific binding/control-specific binding]*100). Results for the compound with formula A(III) are shown in Table 4.

iv. Competition Assay to Measure Binding Affinity at 5-$HT_{2B}$ Receptor.

Assays were conducted according to methodology described by Kursar et al., [Mol. Pharmacol. 46: 227-234, 1994] using conditions summarized in Table 2. As the purpose of this experiment was to gauge general binding potential of test ligand, rather than obtain detailed binding information yielding $K_i$ values, only a single concentration of test ligand was used (10 µM). Briefly, CHO cells were used to express recombinant receptor, and membrane preparation was conducted at 4° C. Binding experiments were conducted using radioligand, 0.2 mL (~100 µg protein) membrane suspension, cold ligand to ensure specific binding by test ligand, and test molecule (10 µM) in 50 mM Tris pH 7.4. Bound and free radioligand were separated by filtration through glass fiber Whatman filters under vacuum. The filters were then washed and subjected to scintillation counting. Results were expressed as a percent of control-specific binding ([measured specific binding/control-specific binding]*100). Results for the compound with formula A(III) are shown in Table 4.

v. Competition Assay to Measure Binding Affinity at 5-$HT_{2C}$ Receptor.

Assays were conducted according to methodology described by Bryant et al., [Life Sci. 15: 1259-1268, 1996] using conditions summarized in Table 2. As the purpose of this experiment was to gauge general binding potential of test ligand, rather than obtain detailed binding information yielding $K_i$ values, only a single concentration of test ligand was used (10 µM). Briefly, HEK-293 cells were used to express recombinant receptor, and membrane preparation was conducted at 4° C. Binding experiments were conducted using radioligand, 0.2 mL (~100 µg protein) membrane suspension, cold ligand to ensure specific binding by test ligand, and test molecule (10 µM) to final volume of 800 µL with 3 mM $CaCl_2$), 0.1% sodium ascorbate, and 50 mM Tris pH 7.4. Bound and free radioligand were separated by filtration through glass fiber Whatman filters under vacuum. The filters were then washed and subjected to scintillation counting. Results were expressed as a percent of control-specific binding ([measured specific binding/control-specific binding]*100). Results for the compound with formula A(III) are shown in Table 4.

vi. Competition Assay to Measure Binding Affinity at 5-$HT_7$ Receptor.

Assays were conducted according to methodology described by Shen et al., [J. Biol. Chem. 268: 18200-18204, 1993] using conditions summarized in Table 2. As the purpose of this experiment was to gauge general binding potential of test ligand, rather than obtain detailed binding information yielding $K_i$ values, only a single concentration of test ligand was used (10 µM). Briefly, HEK-293 cells were used to express recombinant receptor, and membrane preparation was conducted at 4° C. Binding experiments were conducted using radioligand, 30 µg protein (membrane suspension), cold ligand to ensure specific binding by test ligand, and test molecule (10 µM) to final volume of 200 µL. Bound and free radioligand were separated by filtration through glass fiber Whatman filters under vacuum. The filters were then washed and subjected to scintillation counting. Results were expressed as a percent of control-specific binding ([measured specific binding/control-specific binding]*100). Results for the compound with formula A(III) are shown in Table 4.

vii. Competition Assay to Measure Binding Affinity at Serotonin Transporter (SERT).

Assays were conducted according to methodology described by Tatsumi et al., [Eur J Pharmacol 368: 277-283, 1999] using conditions summarized in Table 3. As the purpose of this experiment was to gauge general binding potential of test ligand, rather than obtain detailed binding information yielding $K_i$ values, only a single concentration of test ligand was used (10 µM). Briefly, CHO cells were used to express recombinant transporter, and membrane preparation was conducted at 4° C. Binding experiments were conducted using radioligand, 30 µg protein (membrane suspension), cold ligand to ensure specific binding by test ligand, and test molecule (10 µM) to final volume of 200 µL. Bound and free radioligand were separated by filtration through Whatman glass fibre filters under vacuum. The filters were then washed and subjected to scintillation counting. Results were expressed as a percent of control-specific binding ([measured specific binding/control-specific binding]*100). Results for the compound with formula A(III) are shown in Table 4.

viii. Competition Assay to Measure Binding Affinity at Norepinephrine Transporter (NET).

Assays were conducted according to methodology described by Pacholczyk et al., [Nature 350: 350-354, 1991] using conditions summarized in Table 3. As the purpose of this experiment was to gauge general binding potential of test ligand, rather than obtain detailed binding information yielding $K_i$ values, only a single concentration of test ligand was used (10 μM). Briefly, CHO cells were used to express recombinant transporter, and membrane preparation was conducted at 4° C. Binding experiments were conducted using radioligand, 30 μg protein (membrane suspension), cold ligand to ensure specific binding by test ligand, and test molecule (10 μM) to final volume of 200 μL. Bound and free radioligand were separated by filtration through Whatman glass fibre filters under vacuum. The filters were then washed and subjected to scintillation counting. Results were expressed as a percent of control-specific binding ([measured specific binding/control-specific binding]*100). Results for the compound with formula A(III) are shown in Table 4.

ix. Competition Assay to Measure Binding Affinity at Dopamine Transporter (DAT).

Assays were conducted according to methodology described by Pristupa et al., [Mol. Pharmacol. 45: 125-135, 1994] using conditions summarized in Table 3. As the purpose of this experiment was to gauge general binding potential of test ligand, rather than obtain detailed binding information yielding $K_i$ values, only a single concentration of test ligand was used (10 μM). Briefly, CHO cells were used to express recombinant transporter, and membrane preparation was conducted at 4° C. Binding experiments were conducted using radioligand, 50 μg protein (membrane suspension), cold ligand to ensure specific binding by test ligand, and test molecule (10 μM) to final volume of 200 μL. Bound and free radioligand were separated by filtration through Whatman glass filters under vacuum. The filters were then washed and subjected to scintillation counting. Results were expressed as a percent of control-specific binding ([measured specific binding/control-specific binding]*100). Results for the compound with formula A(III) are shown in Table 4.

TABLE 4

Results for GPCR and transporter competition-based binding assays. Data is shown as percent of control-specific binding.

| Compound | HT1A | HT2B | HT2C | HT7 | α-2A | SERT | DAT | MT1 | NET |
|---|---|---|---|---|---|---|---|---|---|
| MDMA | 68 | 85 | 96 | 58 | 27 | 46 | 28 | 1 | 3 |
| Mescaline | 65 | 80 | 95 | 38 | 57 | −6 | −1 | 6 | −9 |
| 2C-B | 96 | 99 | 98 | 88 | 88 | 42 | 5 | 86 | 13 |
| Escaline | 44 | 81 | 95 | 16 | 45 | 0 | 0 | 0 | 6 |
| Proscaline | 71 | 85 | 97 | 5 | 40 | 23 | −2 | 3 | −9 |
| DOB | 75 | 97 | 98 | 65 | 66 | 53 | 3 | −3 | 6 |
| Serotonin | 100 | 96 | 102 | 100 | 18 | 80 | 8 | 7 | −3 |
| Melatonin | 46 | 52 | 19 | 8 | −7 | 7 | 4 | 98 | −2 |
| Tryptophan | 6 | 0 | 25 | 11 | −4 | 1 | 1 | −2 | 1 |
| Vortioxetine | 99 | 97 | 99 | 100 | 62 | 101 | 90 | 26 | 99 |
| Trazodone | 97 | 97 | 93 | 99 | 91 | 93 | 24 | 14 | −1 |
| Duloxetine | 95 | 95 | 92 | 94 | 54 | 100 | 94 | 23 | 99 |
| Imipramine | 34 | 94 | 98 | 93 | 57 | 98 | 23 | 29 | 99 |
| Agomelatine | 58 | 93 | 92 | 20 | 2 | 30 | 1 | 99 | 1 |
| Bupropion | −1 | −2 | 1 | 4 | 2 | 25 | 92 | 83 | 12 |
| Vilazodone | 99 | 96 | 92 | 83 | 65 | 100 | 98 | 84 | 99 |
| A(I) | 73 | 19 | 45 | 3 | 24 | 25 | 95 | 5 | 59 |
| B(I) as diast. (i) | 1 | 0 | 0 | 0 | 7 | 28 | 6 | 10 | 0 |
| B(I) as diast. (ii) | 0 | 4 | 15 | 0 | 22 | 10 | 32 | 0 | 1 |
| A(III) | 4 | 32 | 7 | 0 | 42 | 5 | 74 | 77 | 38 |
| B(III) as diast. (iii) | 0 | 3 | 5 | 10 | 7 | 58 | 75 | 0 | 42 |
| B(III) as diast. (iv) | 22 | 28 | 14 | 23 | 42 | 44 | 76 | 15 | 25 |
| D(III) as diast (vii) | 36 | 29 | 36 | 60 | 86 | 35 | 69 | 23 | 50 |
| D(III) as diast (viii) | 50 | 66 | 88 | 57 | 94 | 66 | 75 | 12 | 28 |

Example 2—Preparation of a Second, Third, and Fourth Fused Heterocyclic Mescaline Derivative Compound 3 was prepared as described in Example 1. Referring to FIG. 3A, to a solution of compound 3 (1.00 g, 3.11 mmol) in dry DMF (31.1 mL) under nitrogen atmosphere was added potassium carbonate (645 mg, 4.67 mmol) and pyrrolidine (1.57 mL, 18.7 mmol). The reaction mixture was allowed to stir for 24 h at room temperature. After MS confirmation of product, the reaction mixture was poured into DI water (100 mL), extracted with DCM (3×20 mL) and the organic phase washed with water (5×100 mL). The organic extracts were dried over anhydrous magnesium sulphate and concentrated under reduced pressure. Purification by column chromatography on 12 g normal-phase silica using a 0 to 10% methanol in dichloromethane eluent system yielded compound 4 (wherein $R_{2a}$ and $R_{2b}$ together with the nitrogen atom form a 5-membered heterocycle), as a yellow oil (486 mg, 63%).

LRMS-HESI: $[M+H]^+$ calculated 248.13, found 248.16 m/z. $^1$H NMR (400 MHz, CDCl$_3$) δ 7.79 (dd, J=8.2, 1.7 Hz, 1H), 7.64 (d, J=1.7 Hz, 1H), 6.87 (d, J=8.2 Hz, 1H), 6.06 (s, 2H), 3.93 (s, 1H), 2.67 (d, J=23.5 Hz, 4H), 1.83 (d, J=6.1 Hz, 4H), 1.41 (d, J=6.9 Hz, 3H). It is noted that compound 4, wherein $R_{2a}$ and $R_{2b}$ together with the nitrogen atom form a 5-membered heterocycle, corresponds with compounds A(I) and A($I_g$):

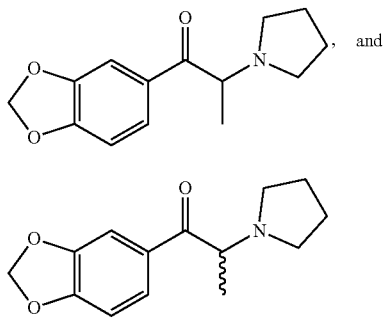

A(I)

, and

A($I_g$)

set forth herein, wherein compound A(I) and A($I_g$) was obtained as a racemic mixture of enantiomers A($I_{ga}$) and A($I_{gb}$):

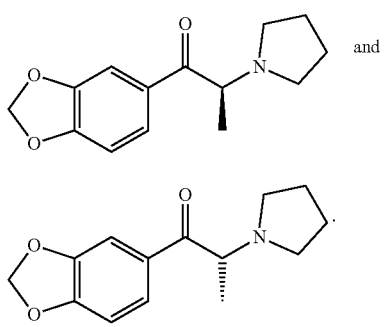

A($I_{ga}$)

and

A($I_{gb}$)

.

Continuing to refer to FIG. 3A, to a solution of compound 4, wherein $R_{2a}$ and $R_{2b}$ together with the nitrogen atom form a 5-membered heterocycle (i.e., compound A(I)), (116 mg, 469 μmol) in methanol (3.87 mL) was slowly added sodium borohydride (92.7 mg, 2.40 mmol). The reaction mixture was allowed to stir for 24 h, after which MS indicated presence of product in high quantity. The reaction mixture was diluted with ethyl acetate (30 mL) and washed with water (2×20 mL) and brine (20 mL). The organic phase was dried over anhydrous magnesium sulphate and concentrated under reduced pressure. Purification by column chromatography using 0 to 10% methanol in dichloromethane yielded compound 6, wherein $R_{2a}$ and $R_{2b}$ together with the nitrogen atom form a 5-membered heterocycle, in the form of a mixture of two separable diastereomers (i) (33.7 mg, 58%) and (ii) (14.1 mg, 24%), as a white powders.

LRMS-HESI: [M+H]$^+$ calculated 250.14, found 250.15 m/z.

Diastereomers (i) and (ii) were separated.

Diastereomer (i): $^1$H NMR (400 MHz, CDCl$_3$) δ 6.91 (d, J=1.6 Hz, 1H), 6.82 (dd, J=8.0, 1.7 Hz, 1H), 6.77 (d, J=7.9 Hz, 1H), 5.96 (s, 2H), 4.16 (d, J=9.6 Hz, 1H), 2.87 (dq, J=9.6, 6.6 Hz, 1H), 2.70 (ttd, J=10.7, 7.9, 5.3 Hz, 4H), 1.88-1.76 (m, 4H), 0.79 (d, J=6.6 Hz, 3H).

Diastereomer (ii): $^1$H NMR (400 MHz, CDCl$_3$) δ 6.89 (q, J=0.8 Hz, 1H), 6.80 (d, J=0.9 Hz, 2H), 5.96 (s, 2H), 4.96 (d, J=3.1 Hz, 1H), 2.83 (dtd, J=8.9, 4.8, 2.2 Hz, 2H), 2.73-2.63 (m, 2H), 2.47 (qd, J=6.6, 3.1 Hz, 1H), 1.85 (td, J=5.5, 3.2 Hz, 4H), 0.84 (d, J=6.6 Hz, 3H).

It is noted that compound 6, wherein $R_{2a}$ and $R_{2b}$ together with the nitrogen atom form a 5-membered heterocycle, corresponds with compounds B(I) and B($I_d$):

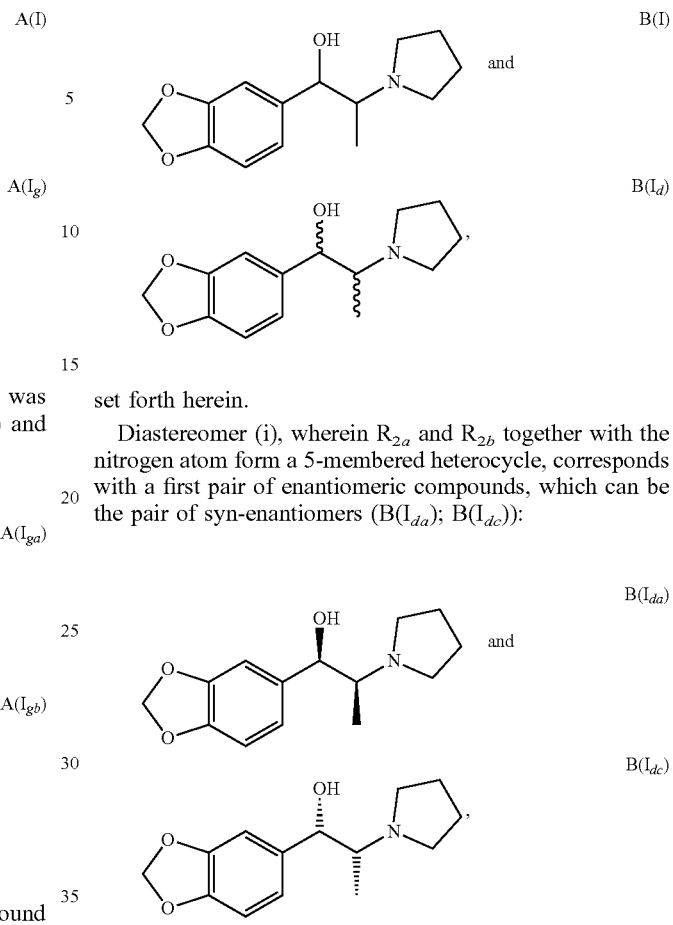

B(I)

and

B($I_d$)

, set forth herein.

Diastereomer (i), wherein $R_{2a}$ and $R_{2b}$ together with the nitrogen atom form a 5-membered heterocycle, corresponds with a first pair of enantiomeric compounds, which can be the pair of syn-enantiomers (B($I_{da}$); B($I_{dc}$)):

B($I_{da}$)

and

B($I_{dc}$)

, which were obtained as a racemic mixture.

Diastereomer (ii), wherein $R_{2a}$ and $R_{2b}$ together with the nitrogen atom form a 5-membered heterocycle, corresponds with a second pair of enantiomeric compounds, which can be the pair of anti-enantiomers (B(Iab); B(Iad)):

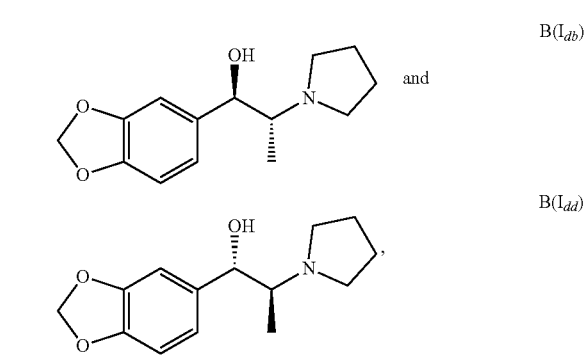

B($I_{db}$)

and

B($I_{dd}$)

, which were obtained as a racemic mixture. It is noted however that the accuracy of the analytical techniques used does leave some room for uncertainty with respect to the distinction between the first and second pair of enantiomers, and thus, alternatively, it is possible that the obtained diastereoisomer (i) corresponds with the anti-enantiomeric pair (B($I_{db}$); B($I_{dd}$)), and diastereoisomer (ii) corresponds with the syn-enantiomeric pair (B($I_{da}$); B($I_{dc}$)).

5-HT Receptor Radioligand Competition Assays.

Activity at 5-HT$_{1A}$ and 5-HT$_{2A}$ receptors were assessed as described for Example 1, except the compounds designated A(I), diastereomer (i) (as a first B(I) enantiomeric pair), and diastereomer (ii) (as a second B(I) enantiomeric pair) were evaluated in place of the compound with formula A(III). Table 1 shows radioligand competition assay results for positive controls, negative controls, and compounds designated A(I), diastereomer (i) (as a first B(I) enantiomeric pair), and diastereomer (ii) (as a second B(I) enantiomeric pair) in the form of K$_i$ values. In view of results for both positive and negative controls, wherein negative controls yield data insufficient for reliable K$_i$ calculations (i.e., K$_i$>1000 mM), the K$_i$ values obtained for compounds with formulae A(I), B(I$_{da}$), and B(I$_{db}$) at the 5-HT$_{1A}$ receptor (2.0 µM, 480 µM and 37 µM, respectively; Table 1) indicate ligand-receptor binding. Similarly, K$_i$ values obtained for compounds with formulae A(I), B(I$_{da}$), and B(I$_{db}$) at the 5-HT$_{2A}$ receptor (131 µM, 4.5 µM, and 25 µM, respectively; Table 1) indicate ligand-receptor binding.

In Vitro Survey of Pharmacological Interaction Profiles at Receptors and Transporters Linked to Targeted Health Conditions.

Compounds designated A(I), diastereomer (i) (as a first B(I) enantiomeric pair), and diastereomer (ii) (as a second B(I) enantiomeric pair) were evaluated with respect to binding and/or interaction at 9 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 6 GPCR receptors: HTR1A (5-HT$_{1A}$), HTR2B (5-HT$_{2B}$), HTR2C (5-HT$_{2C}$), HTR7 (5-HT$_7$), alpha2A ($\alpha_{2A}$), MT1 (MT$_1$), and 3 transporters (SERT, DAT, NET). Assays were conducted using the same materials and procedures outlined in Example 1, except the compounds designated A(I), diastereomer (i) (as a first B(I) enantiomeric pair), and diastereomer (ii) (as a second B(I) enantiomeric pair) were used in place of the compound with formula A(III). Overall assay conditions are summarized in Tables 2 and 3 for GPCR and transporters, respectively. Results for all calibrator compounds, control compounds, and test compounds including compounds designated A(I), diastereomer (i) (as a first B(I) enantiomeric pair), and diastereomer (ii) (as a second B(I) enantiomeric pair) are summarized in Table 4.

Example 3—Preparation of a Fifth and Sixth Fused Heterocyclic Mescaline Derivative Compound 4, wherein R$_{2a}$=CH$_3$, R$_{2b}$=—(CH$_2$)-phenyl, (i.e., compound A(III)) was prepared as described in Example 1. Referring to FIG. 3A, to a solution of compound 4 (488 mg, 1.64 mmol), wherein R$_{2a}$=CH$_3$, R$_{2b}$=—(CH$_2$)-phenyl, dissolved in methanol (8.21 mL) was added sodium borohydride (311 mg, 8.21 mmol) portion-wise. The reaction mixture was stirred overnight under ambient conditions. After being diluted with ethyl acetate (100 mL), the organic phase was washed with water (2×50 mL) and brine (50 mL). The organic phase was dried over anhydrous magnesium sulphate and concentrated under reduced pressure to yield a white crude solid. Purification via column chromatography on 12 g normal-phase silica using a 0 to 4% methanol in dichloromethane eluent gradient yielded compound 6, wherein R$_{2a}$=CH$_3$, R$_{2b}$=—(CH$_2$)-phenyl, in the form of a mixture of diastereomers (iii) (317 mg, 65%) and (iv) (36 mg, 7%, 1:1 mixture with diastereomer (iii)) as a white solids.

LRMS-HESI: [M+H]$^+$ calculated 300.16, found 300.14 m/z.

Diastereomers (iii) and (iv) were isolated.

Diastereomer (iii): $^1$H NMR (400 MHz, CDCl$_3$) δ 7.39 (d, J=4.0 Hz, 4H), 7.35-7.31 (m, 1H), 6.87 (d, J=1.6 Hz, 1H), 6.81 (dd, J=8.0, 1.6 Hz, 1H), 6.78 (dd, J=8.0, 0.5 Hz, 1H), 5.95 (s, 2H), 5.20 (s, 1H), 4.28 (d, J=9.7 Hz, 1H), 3.77 (d, J=13.0 Hz, 1H), 3.53 (d, J=13.0 Hz, 1H), 2.74 (dq, J=9.7, 6.6 Hz, 1H), 2.25 (s, 3H), 0.84 (d, J=6.7 Hz, 3H).

Diastereomer (iv): $^1$H NMR (400 MHz, CDCl$_3$) δ 7.41-7.24 (m, 5H), 6.88-6.83 (m, 1H), 6.82-6.75 (m, 2H), 5.96 (d, J=4.0 Hz, 2H), 4.82 (d, J=4.9 Hz, 1H), 4.26 (d, J=9.7 Hz, OH), 3.76 (d, J=12.9 Hz, OH), 3.65 (s, 1H), 3.52 (d, J=13.0 Hz, OH), 2.89 (qd, J=6.8, 4.9 Hz, 1H), 2.23 (d, J=8.2 Hz, 3H), 1.02 (d, J=6.8 Hz, 2H), 0.83 (d, J=6.6 Hz, 1H).

It is noted that compound 6, wherein R$_{2a}$=CH$_3$, R$_{2b}$=—(CH$_2$)-phenyl, corresponds with compounds B(III) and B(III$_d$):

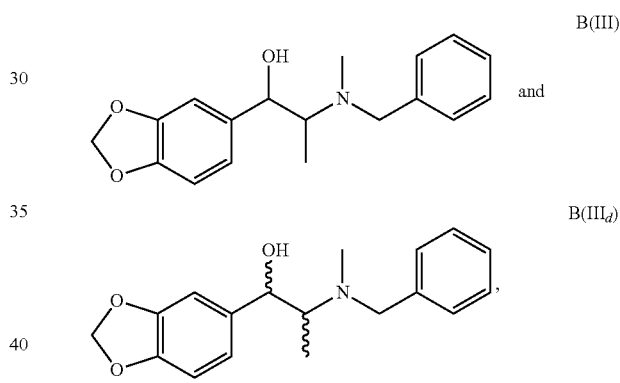

set forth herein.

Diastereomer (iii), wherein R$_{2a}$=CH$_3$, R$_{2b}$=—(CH$_2$)-phenyl, was obtained as a pair of syn-enantiomers (B(III$_{da}$); B(III$_{dc}$)):

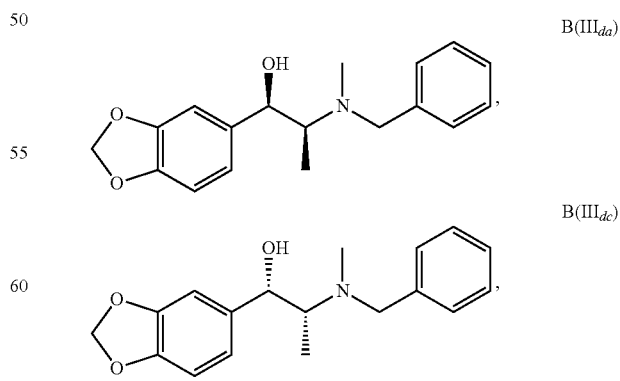

which was obtained as a racemic mixture, or as a pair of anti-enantiomers (B(III$_{ab}$); B(III$_{dd}$)):

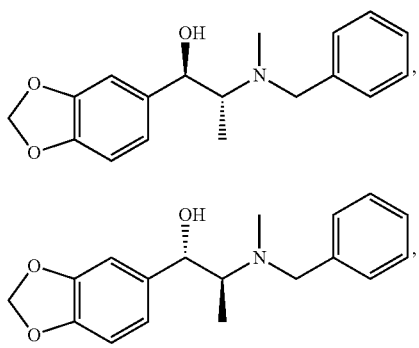

B(III$_{db}$)

B(III$_{dd}$)

which was obtained as a racemic mixture.

Diastereomer (iv), wherein $R_{2a}$=$CH_3$, $R_{2b}$=—($CH_2$)-phenyl, was obtained as a mixture of compound B(III$_{ab}$):

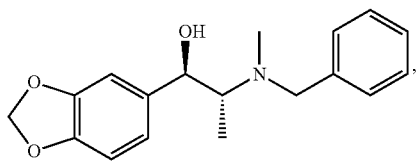

B(III$_{db}$)

and the enantiomeric compound pair (B(III$_{da}$); B(III$_{dc}$)), and compound B(III$_{dd}$), which was obtained as a mixture containing 50% (mole/mole) B(III$_{ab}$), and 50% mole/mole of a mixture of compounds (B(III$_{da}$), B(III$_{dc}$), and B(III$_{ab}$).

5-HT Receptor Radioligand Competition Assays.

Activity at 5-HT$_{1A}$ and 5-HT$_{2A}$ receptors were assessed as described for Example 1, except compounds designated diastereomer (iii) (as a first B(III) enantiomeric pair) and diastereomer (iv) (as a second B(III) diastereomeric mixture) were evaluated in place of the compound with formula A(III). Table 1 shows radioligand competition assay results for positive controls, negative controls, and compounds designated diastereomer (iii) (as a first B(III) enantiomeric pair) and diastereomer (iv) (as a second B(III) diastereomeric mixture) in the form of $K_i$ values. In view of results for both positive and negative controls, wherein negative controls yield data insufficient for reliable $K_i$ calculations (i.e., $K_i$>1000 mM), the $K_i$ values obtained for compounds designated diastereomer (iii) (as a first B(III) enantiomeric pair) and diastereomer (iv) (as a second B(III) diastereomeric mixture) at the 5-HT$_{1A}$ receptor (110 μM and 16.9 μM, respectively; Table 1) indicate ligand-receptor binding. Similarly, the $K_i$ value obtained for compound designated diastereomer (iii) at the 5-HT$_{2A}$ receptor (44 μM; Table 1) indicates ligand-receptor binding. Compound designated diastereomer (iv) was not evaluated for binding at the 5-HT$_{2A}$ receptor.

In Vitro Survey of Pharmacological Interaction Profiles at Receptors and Transporters Linked to Targeted Health Conditions.

Compounds designated diastereomer (iii) (as a first B(III) enantiomeric pair) and diastereomer (iv) (as a second B(III) diastereomeric mixture) were evaluated with respect to binding and/or interaction at 9 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 6 GPCR receptors: HTR1A (5-HT$_{1A}$), HTR2B (5-HT$_{2B}$), HTR2C (5-HT$_{2C}$), HTR7 (5-HT$_7$), alpha2A ($\alpha_{2A}$), MT1 (MT$_1$), and 3 transporters (SERT, DAT, NET). Assays were conducted using the same materials and procedures outlined in Example 1, except compounds designated diastereomer (iii) (as a first B(III) enantiomeric pair) and diastereomer (iv) (as a second B(III) diastereomeric mixture) were used in place of the compound with formula A(III). Overall assay conditions are summarized in Tables 2 and 3 for GPCR and transporters, respectively. Results for all calibrator compounds, control compounds, and test compounds including compounds designated diastereomer (iii) (as a first B(III) enantiomeric pair) and diastereomer (iv) (as a second B(III) diastereomeric mixture) are summarized in Table 4.

Example 4—Preparation of a Seventh Fused Heterocyclic Mescaline Derivative

A single diastereomer, as a racemic pair of enantiomers, of compound 6, wherein $R_{2a}$ and $R_{2b}$ together with the nitrogen atom form a 5-membered heterocycle, in the form of diastereomer (i) was prepared as described in Example 2. Referring to FIG. 3A, compound 6 (236 mg, 947 μmol), wherein $R_{2a}$ and $R_{2b}$ together with the nitrogen atom form a 5-membered heterocycle, was dissolved in anhydrous DCM (9.47 mL), and cooled to −78° C. (Diethylamino)sulfur trifluoride (1.17 mL, 4.73 mmol) was added. The reaction mixture was allowed to stir for 30 min, then warmed to room temperature. After 24 h, saturated NaHCO$_3$ (10 mL) was added dropwise, and the biphasic solution allowed to vigorously stir for 1 h. The mixture was extracted with DCM (3×20 mL), and the combined organic layers washed with brine (20 mL) and dried over anhydrous magnesium sulphate. Purification by column chromatography on 12 g normal-phase silica using a 0-3% methanol in dichloromethane gradient yielded compound 7 (wherein $R_{2a}$ and $R_{2b}$ together with the nitrogen atom form a 5-membered heterocycle) as a white crystalline solid (77.7 mg, 65% with a d.r. of 87:13), diastereomerically enriched in one diastereomer (v).

LRMS-HESI [M+H]$^+$ calculated 252.14, found 252.16 m/z.

Diastereomer (v) was prepared enriched with a d.r. of 87:13.

Diastereomer (v): $^1$H NMR (400 MHz, CDCl$_3$) δ 6.87 (q, J=0.9 Hz, 1H), 6.81 (dd, J=1.9, 0.9 Hz, 2H), 5.98 (s, 2H), 5.33 (dd, J=46.6, 7.4 Hz, 1H), 3.07-2.96 (m, 1H), 2.81-2.71 (m, 4H), 1.85-1.77 (m, 4H), 0.85 (dd, J=6.7, 0.6 Hz, 3H).

It is noted that compound 7, wherein $R_{2a}$ and $R_{2b}$ together with the nitrogen atom form a 5-membered heterocycle, corresponds with compounds D(I) and D(I$_d$):

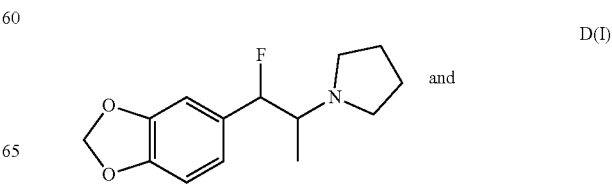

D(I)

and

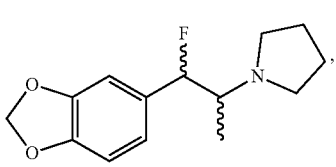
D(I$_d$)

set forth herein.

Diastereomer (v), wherein R$_{2a}$ and R$_{2b}$ together with the nitrogen atom form a 5-membered heterocycle, corresponds with a first pair of enantiomeric compounds, which can be the pair of syn-enantiomers (D(I$_{da}$); D(I$_{dc}$)):

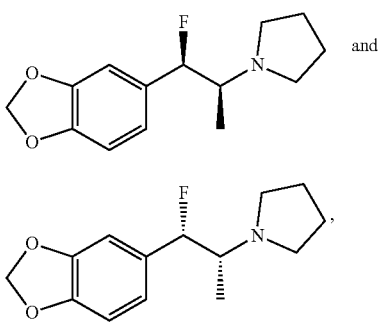
D(I$_{da}$)
and
D(I$_{dc}$)

or with a second pair of enantiomeric compounds which can be the pair of anti-enantiomers (D(I$_{db}$); D(I$_{dd}$)):

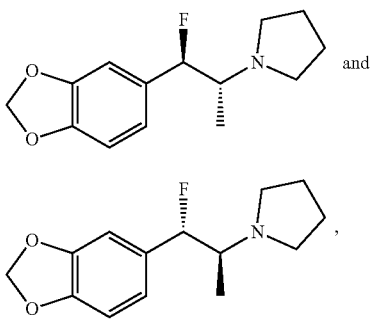
D(I$_{db}$)
and
D(I$_{dd}$)

which was obtained as a racemic mixture. It is noted however that the accuracy of the analytical techniques used does leave some room for uncertainty with respect to the distinction between the first and second pair of enantiomers, and thus, it is possible that the obtained diastereoisomer (v) corresponds with anti-enantiomeric pair (D(I$_{db}$); D(I$_{dd}$)), or with syn-enantiomeric pair (D(I$_{da}$); D(I$_{dc}$)).

5-HT$_{1A}$ receptor functional cellular response assay. Functional engagement of the 5-HT$_{1A}$ receptor within an engineered cell system was assessed as described for Example 6, except the compound designated diastereomer (v) (as a first D(I) enantiomeric pair) was evaluated in place of compounds designated diastereomer (vii) (as a first D(III) enantiomeric pair) and diastereomer (viii) (as a second D(III) enantiomeric pair). Table 5 shows functional assay results for positive controls, calibrators, and compound designated diastereomer (v) (as a first D(I) enantiomeric pair), in the form of EC$_{50}$ values. In view of results for controls and calibrator compounds, wherein a negative cellular response corresponded to an EC$_{50}$ value>1000 μM, the EC$_{50}$ value for the compound designated diastereomer (v) (as a first D(I) enantiomeric pair) in this assay (>1000 μM, Table 5) suggested no ligand-receptor engagement.

Example 5—Preparation of an Eighth Fused Heterocyclic Mescaline Derivative

A single diastereomer, as a racemic pair of enantiomers, of benzylated compound 7, wherein R$_{2a}$=CH$_3$, R$_{2b}$=—(CH$_2$)-phenyl, in the form of diastereomer (viii) was prepared as described in Example 6. Referring to FIG. 3A, to benzylated compound 7 (39.0 mg, 129 μmol), wherein R$_{2a}$=CH$_3$, R$_{2b}$=—(CH$_2$)-phenyl, in the form of diastereomer (viii), in ethanol (1.30 mL), under nitrogen atmosphere was added palladium on carbon 10 wt % (13.8 mg, 0.0129 μmol). H$_2$ gas was bubbled through the solution for 5 minutes, then established as atmosphere for a further 50 minutes. The catalyst was removed through filtration and the filtrate concentrated under reduced pressure. Purification using column chromatography on 4 g normal-phase silica using a 0 to 8% methanol in dichloromethane gradient yielded debenzylated compound 7, wherein R$_{2a}$=CH$_3$, R$_{2b}$=H, as a colourless oil (10.8 mg, 40%) as a single diastereomer (vi).

LRMS-HESI [M+H]$^+$ calculated 212.11, found 212.11 m/z.

Diastereomer (vi) was isolated.

Diastereomer (vi): $^1$H NMR (400 MHz, CDCl$_3$) δ 6.86 (q, J=1.1 Hz, 1H), 6.82 (d, J=0.9 Hz, 2H), 6.00 (s, 2H), 5.12 (dd, J=47.4, 8.0 Hz, 1H), 3.00 (ddq, J=11.6, 8.1, 6.5 Hz, 1H), 2.50 (d, J=0.7 Hz, 3H), 0.89 (dd, J=6.5, 0.9 Hz, 3H).

It is noted that debenzylated compound 7, wherein R$_{2a}$=CH$_3$, R$_{2b}$=H, corresponds with compounds D(II) and D(II$_d$):

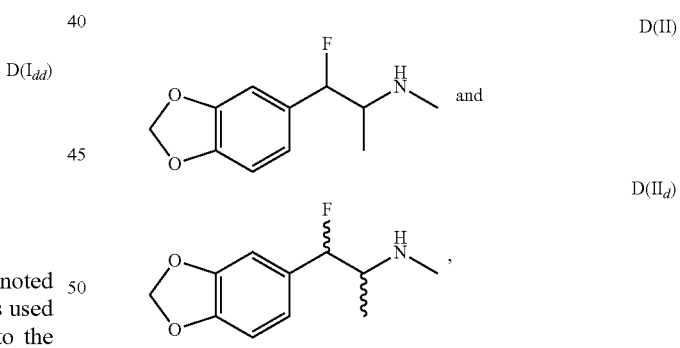
D(II)
and
D(II$_d$)

set forth herein.

Diastereomer (vi), corresponds with a first pair of enantiomeric compounds, which can be the pair of syn-enantiomers (D(II$_{da}$); D(II$_{dc}$)):

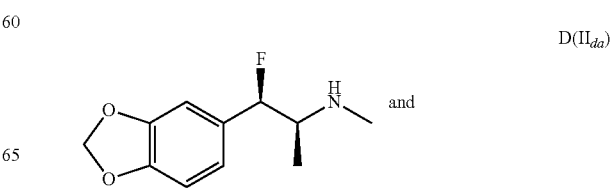
D(II$_{da}$)
and

-continued

D(II$_{dc}$)

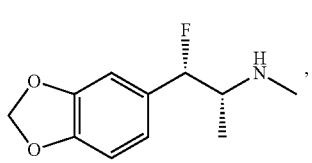

or with a second pair of enantiomeric compounds which can be the pair of anti-enantiomers (D(II$_{db}$); D(II$_{dd}$)):

D(II$_{db}$)

D(II$_{dd}$)

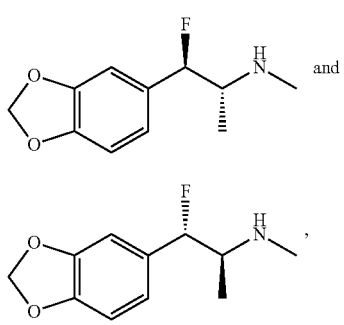

which was obtained as a racemic mixture. It is noted however that the accuracy of the analytical techniques used does leave some room for uncertainty with respect to the distinction between the first and second pair of enantiomers, and thus, it is possible that obtained diastereoisomer (vi) corresponds with anti-enantiomeric pair (D(II$_{db}$); D(II$_{dd}$)), or with syn-enantiomeric pair (D(II$_{da}$); D(II$_{dc}$)).

5-HT Receptor Radioligand Competition Assays.

Activity at the 5-HT$_{1A}$ receptor was assessed as described for Example 1, except the compound designated diastereomer (vi) (as a first D(II) enantiomeric pair) was evaluated in place of the compound with formula A(III). Table 1 shows radioligand competition assay results for positive controls, negative controls, and compound designated diastereomer (vi) (as a first D(II) enantiomeric pair) in the form of K$_i$ values. In view of results for both positive and negative controls, wherein negative controls yield data insufficient for reliable K$_i$ calculations (i.e., K$_i$>1000 mM), the K$_i$ value obtained for the compound designated diastereomer (vi) (as a first D(II) enantiomeric pair) at the 5-HT$_{1A}$ receptor (6.0 µM; Table 1) indicates ligand-receptor binding.

5-HT$_{1A}$ Receptor Functional Cellular Response Assay.

Functional engagement of the 5-HT$_{1A}$ receptor within an engineered cell system was assessed as described for Example 6, except the compound designated diastereomer (vi) (as a first D(II) enantiomeric pair) was evaluated in place of compounds designated diastereomer (vii) (as a first D(III) enantiomeric pair) and diastereomer (viii) (as a second D(III) enantiomeric pair). Table 5 shows functional assay results for positive controls, calibrators, and compound with formula D(II), in the form of EC$_{50}$ values. In view of results for controls and calibrator compounds, wherein a negative cellular response corresponded to an EC$_{50}$ value>1000 µM, the EC$_{50}$ value for the compound with formula D(II) in this assay (>1000 µM, Table 5) suggested no ligand-receptor engagement.

Example 6—Preparation of a Ninth and Tenth Fused Heterocyclic Mescaline Derivative A single diastereomer, as a racemic pair of enantiomers, of compound 6, wherein R$_{2a}$=CH$_3$, R$_{2b}$=—(CH$_2$)-phenyl, in the form of diastereomer (iii) was prepared as described in Example 3. Referring to FIG. 3A, compound 6, wherein R$_{2a}$=CH$_3$, R$_{2b}$=—(CH$_2$)-phenyl, in the form of diastereomer (iii) (250 mg, 835 µmol) was dissolved in dry DCM (10.0 mL) under nitrogen atmosphere and cooled to −78° C. (Diethylamino)sulfur trifluoride (DAST) (1.03 mL, 4.18 mmol) was added, and the reaction mixture was allowed to stir at the same temperature for 30 minutes prior to warming to room temperature and stirring for a further 18 h. Saturated aqueous NaHCO$_3$ (5 mL) was slowly added to quench the reaction, and allowed to stir vigorously for 15 minutes. The biphasic mixture was extracted with DCM (3×20 mL) and the combined organic phases dried over anhydrous magnesium sulphate and concentrated under reduced pressure. Purification on 4 g normal phase silica using a 0%, then slow 5% to 7% ethyl acetate in hexanes eluent system yielded compound 7 in the form of a mixture of two separable diastereomers (vii) (51.6 mg, 41%) and (viii) (63.6 mg, 51%) as white powders.

Diastereomer (vii): LRMS-HESI [M+H]$^+$ calculated 302.16, found 302.14 m/z.

Diastereomer (viii): LRMS-HESI [M+H]$^+$ calculated 302.16, found as fragment 282.15 m/z.

Diastereomer (vii) $^1$H NMR (400 MHz, CDCl$_3$) δ 7.30 (s, 1H), 7.28-7.17 (m, 3H), 6.81 (dd, J=7.9, 0.7 Hz, 1H), 6.79-6.72 (m, 2H), 5.99 (q, J=1.4 Hz, 2H), 5.52 (d, J=47.5 Hz, 1H), 3.72-3.58 (m, 2H), 3.02 (d, J=20.7 Hz, 1H), 2.29 (s, 3H), 1.16 (d, J=6.8 Hz, 3H).

Diastereomer (viii) δ 7.34 (d, J=7.0 Hz, 4H), 7.26 (s, 1H), 6.86-6.75 (m, 3H), 6.00 (s, 2H), 5.33 (dd, J=47.6, 8.5 Hz, 1H), 3.90-3.67 (m, 2H), 3.23-3.10 (m, 1H), 2.38 (s, 3H), 0.88 (d, J=6.9 Hz, 3H).

It is noted that compound 7, wherein R$_{2a}$=CH$_3$, R$_{2b}$=—(CH$_2$)-phenyl, corresponds with compounds D(III) and D(III$_d$):

D(III)

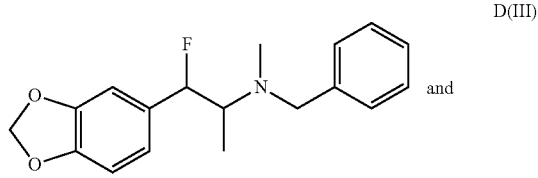

D(III$_d$)

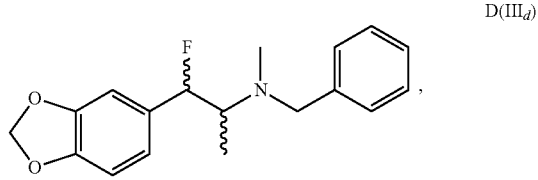 [SMILES: C[C@H]([C@H](O)c1ccc2c(c1)OCO2)N(C)Cc1ccccc1]

set forth herein.

Diastereomer (vii), wherein R$_{2a}$ is —CH$_3$, and R$_{2b}$ is —(CH$_2$)-phenyl, corresponds with a first pair of enantiomeric compounds, which can be the pair of syn-enantiomers (D(III$_{da}$); D(III$_{dc}$)):

D(III$_{da}$)

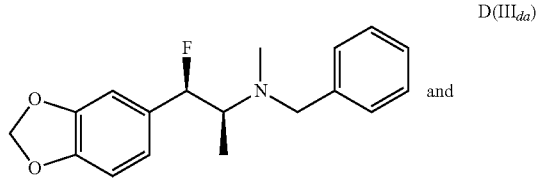

-continued

D(III$_{dc}$)

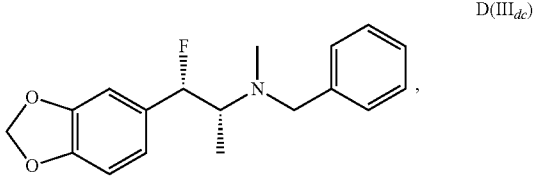

which was obtained as a racemic mixture.

Diastereomer (viii), wherein R$_{2a}$ is —CH$_3$, and R$_{2b}$ is —(CH$_2$)-phenyl, corresponds with a second pair of enantiomeric compounds, which can be the pair of anti-enantiomers (D(III$_{db}$); D(III$_{dd}$)):

D(III$_{db}$)

D(III$_{dd}$)

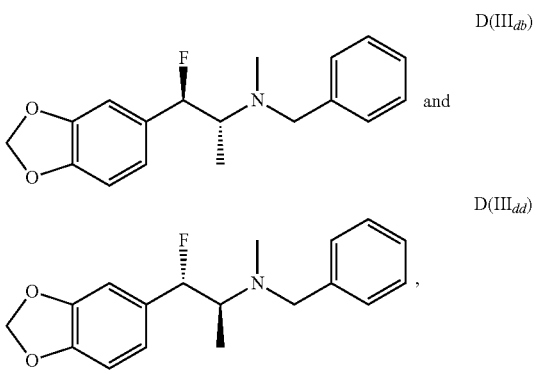

which was obtained as a racemic mixture. It is noted however that the accuracy of the analytical techniques used does leave some room for uncertainty with respect to the distinction between the first and second pair of enantiomers, and thus, alternatively, it is possible that the diastereoisomer (vii) corresponds with the anti-enantiomeric pair (D(III$_{db}$); D(III$_{dd}$)), and diastereoisomer (viii) corresponds with the syn-enantiomeric pair (D(III$_{da}$); D(III$_{dc}$)).

5-HT Receptor Radioligand Competition Assays.

Activity at the 5-HT$_{1A}$ receptor was assessed as described for Example 1, except compounds designated diastereomer (vii) (as a first D(III) enantiomeric pair) and diastereomer (viii) (as a second D(III) enantiomeric pair) were evaluated in place of the compound with formula A(III). Table 1 shows radioligand competition assay results for positive controls, negative controls, and compounds designated diastereomer (vii) (as a first D(III) enantiomeric pair) and diastereomer (viii) (as a second D(III) enantiomeric pair) in the form of K$_i$ values. In view of results for both positive and negative controls, wherein negative controls yield data insufficient for reliable K$_i$ calculations (i.e., K$_i$>1000 mM), the K$_i$ values obtained for compounds designated diastereomer (vii) (as a first D(III) enantiomeric pair) and diastereomer (viii) (as a second D(III) enantiomeric pair) at the 5-HT$_{1A}$ receptor (11.3 µM and 8.1 µM, respectively; Table 1) indicate ligand-receptor binding.

Functional Receptor Potency Assays.

Figure 6A:
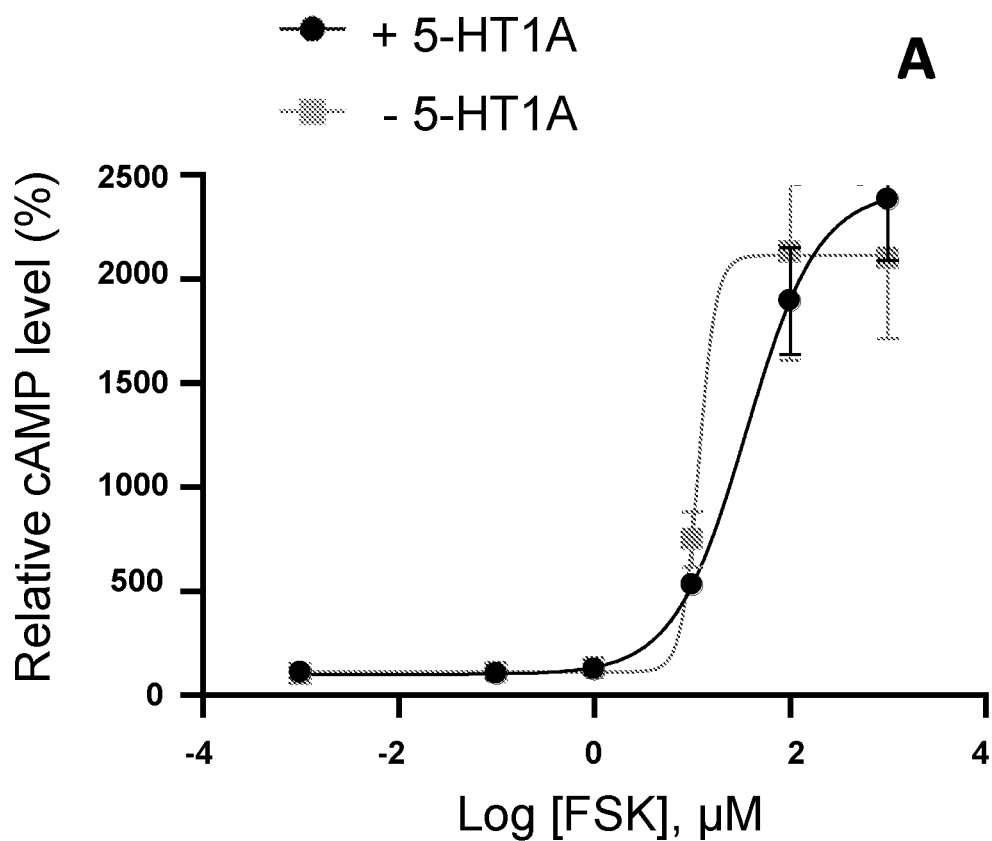
FIGS. 6A, 6B, 6C, 6D, 6E, 6F, 6G, and 6H depict various graphs representing certain experimental results, notably graphs obtained in the performance of experimental assays to evaluate the pharmaceutical efficacy of an example compound comprising enantiomers corresponding with chemical formula D(III), notably a 5-$HT_{1A}$ cAMP receptor assay to detect relative levels of cAMP in cells with (+5-$HT_{1A}$) and without (−5-$HT_{1A}$) 5-$HT_{1A}$ receptors stimulated with varying amounts of forskolin (FIG. 6A); a 5-$HT_{1A}$ cAMP receptor assay to detect relative levels of cAMP in cells with (+5-$HT_{1A}$) and without (−5-$HT_{1A}$) 5-$HT_{1A}$ receptors stimulated with 4 μM forskolin and varying amounts of 8-OH-DPAT (FIG. 6B); a 5-$HT_{1A}$ cAMP receptor assay to detect relative levels of cAMP in cells with (+5-$HT_{1A}$) and without (−5-$HT_{1A}$) 5-$HT_{1A}$ receptors stimulated with 4 μM forskolin and varying amounts of serotonin (FIG. 6C); a 5-$HT_{1A}$ cAMP receptor assay to detect relative levels of cAMP in cells with (+5-$HT_{1A}$) and without (−5-$HT_{1A}$) 5-$HT_{1A}$ receptors stimulated with 4 μM forskolin and varying amounts of psilocin (FIG. 6D); a 5-$HT_{1A}$ cAMP receptor assay to detect relative levels of cAMP in cells with (+5-$HT_{1A}$) and without (−5-$HT_{1A}$) 5-$HT_{1A}$ receptors stimulated with 4 μM forskolin and varying amounts of mescaline (FIG. 6E); a 5-$HT_{1A}$ cAMP receptor assay to detect relative levels of cAMP in cells with (+5-$HT_{1A}$) and without (−5-$HT_{1A}$) 5-$HT_{1A}$ receptors stimulated with 4 μM forskolin and varying amounts of MDMA (FIG. 6F); a 5-$HT_{1A}$ cAMP receptor assay to detect relative levels of cAMP in cells with (+5-$HT_{1A}$) and without (−5-$HT_{1A}$) 5-$HT_{1A}$ receptors stimulated with 4 μM forskolin and varying amounts of 2C-B (FIG. 6G); and a 5-$HT_{1A}$ cAMP receptor assay to detect relative levels of cAMP in cells with (+5-$HT_{1A}$) and without (−5-$HT_{1A}$) 5-$HT_{1A}$ receptors stimulated with 4 μM forskolin and varying amounts of compound D(III$_{enantiomer}$) (FIG. 6H).
Figure 6B:
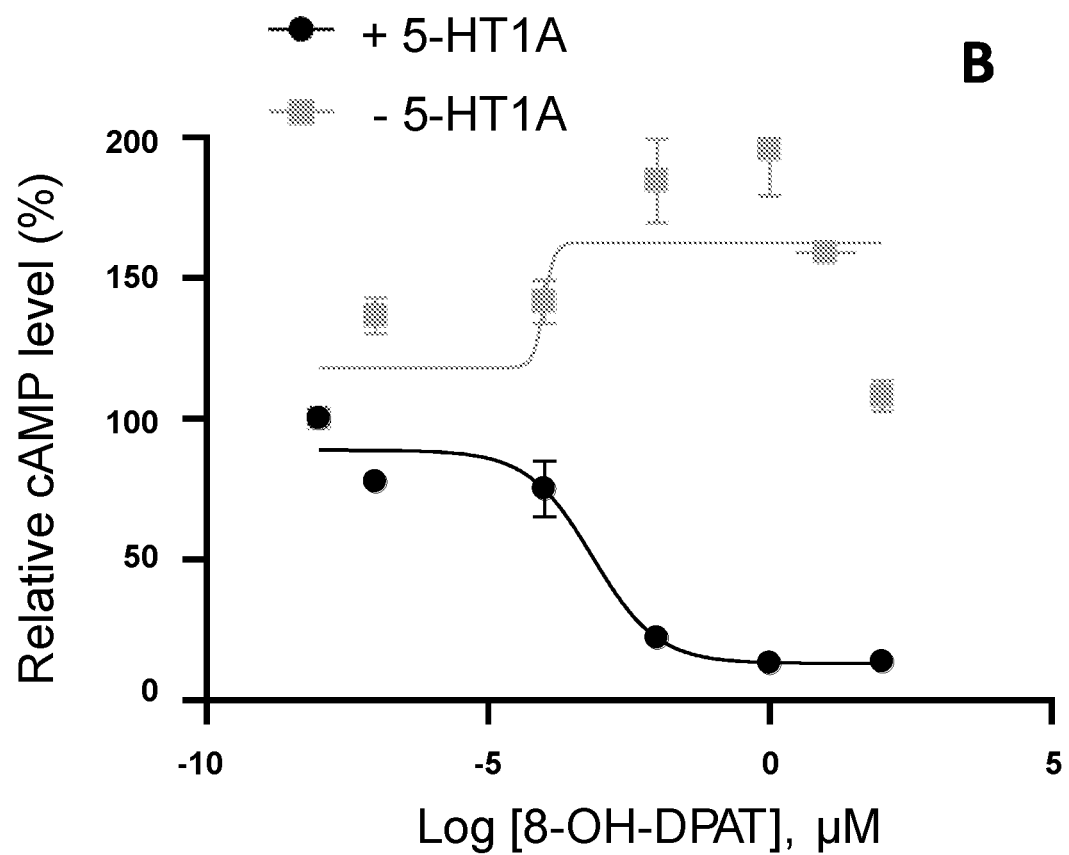
Figure 6C:
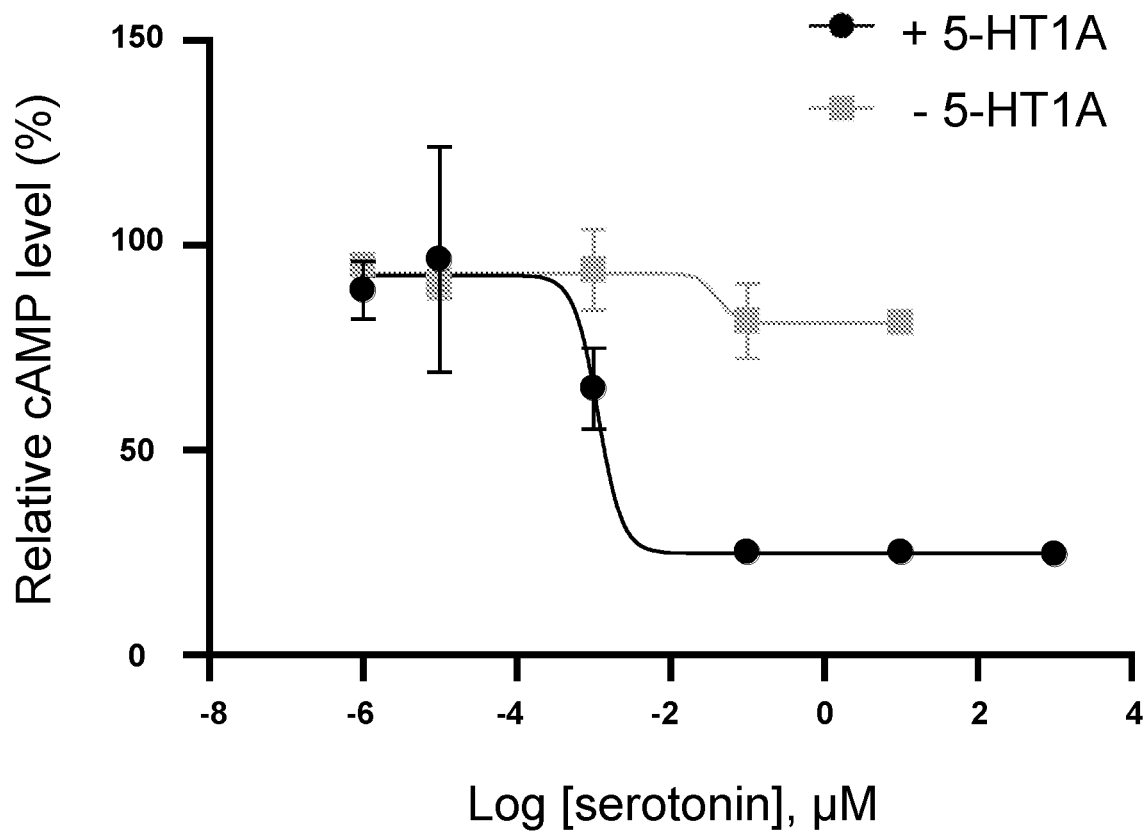
Figure 6D:
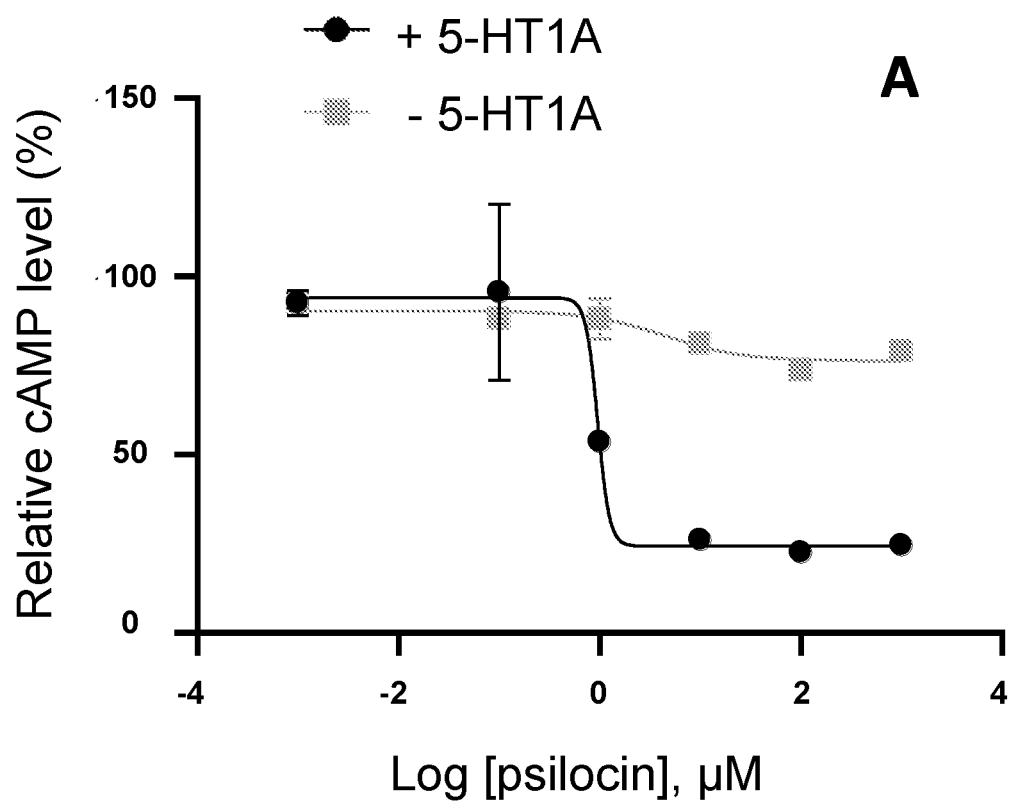
Figure 6E:
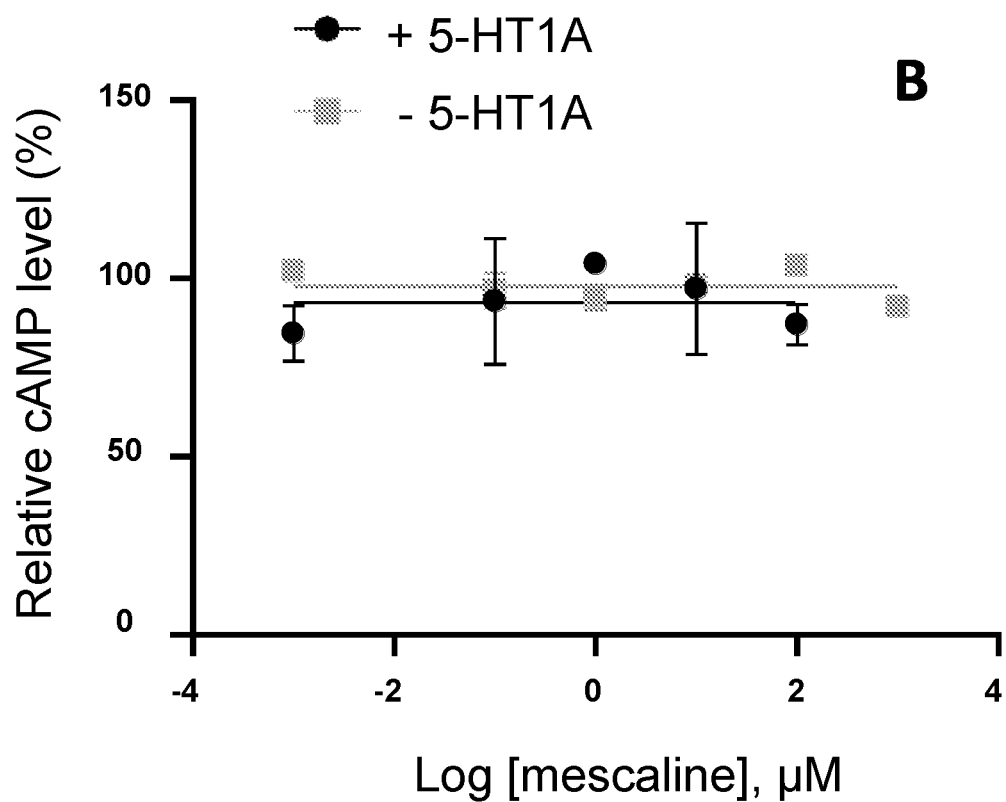
Figure 6F:
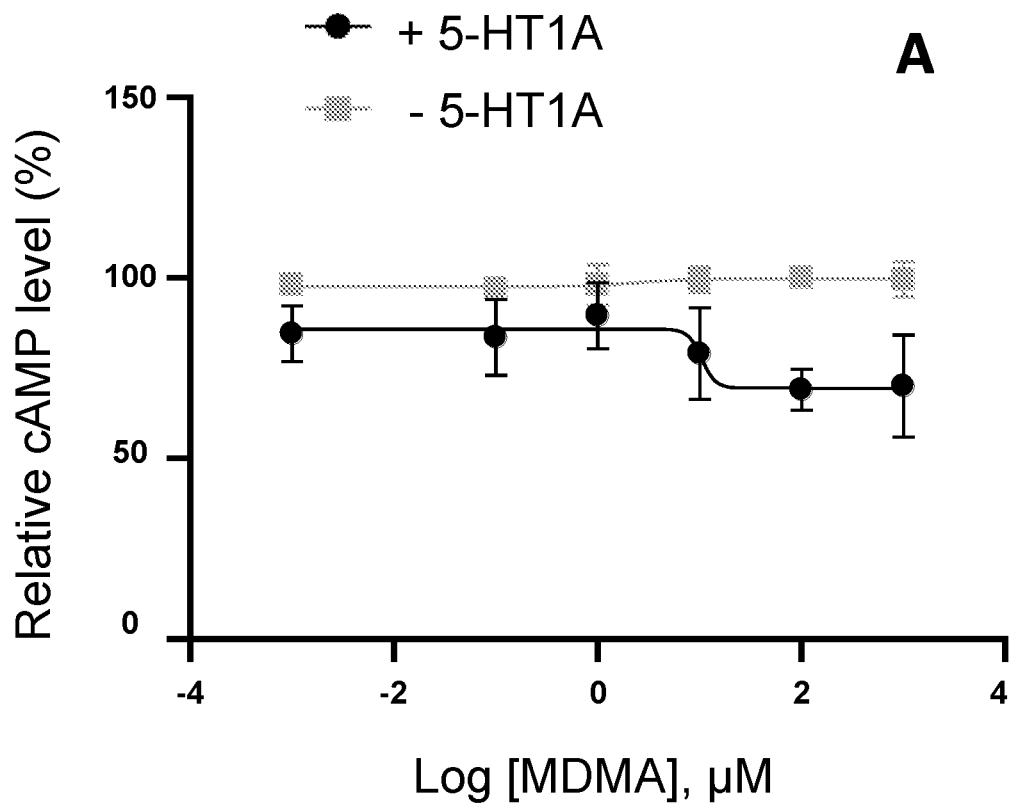
Figure 6G:
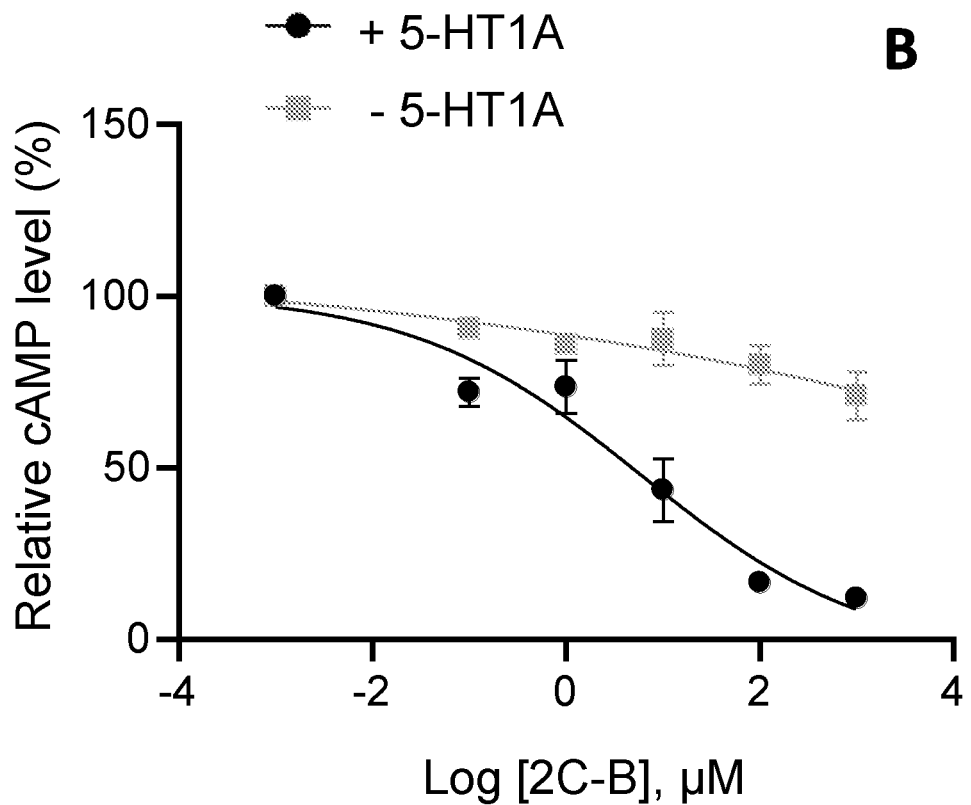
Figure 6H:
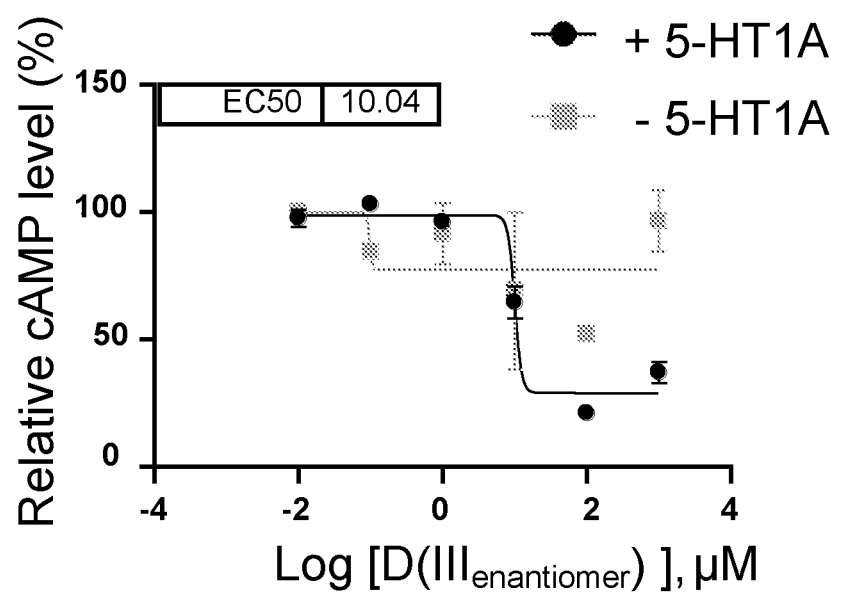

5-HT$_{1A}$ receptor. The Chinese hamster ovary (CHO)-derived cell line, CHO-K1/5-HT$_{1A}$/Gα15 (GenScript M00330), stably transformed to express 5-HT$_{1A}$ serotonin receptor, was used to evaluate specific agonist-mediated stimulation of 5-HT$_{1A}$ signal transduction. In these non-neuronal cells, stimulation of 5-HT$_{1A}$ activates the Gα$_{i/o}$ protein leading to inhibition of adenylyl cyclase (AC) type I (Rojas and Felder, 2016, Frontiers in Cellular Neuroscience 10:272; Polter and Li, 2010, Cell Signalling 22:1406-1412). In cells stimulated with 4 µM forskolin, which directly stimulates AC to elevate intracellular cAMP levels, 5-HT$_{1A}$ activation was assessed quantitatively by measuring reduced intracellular cAMP levels. All cells were grown and maintained as a monolayer in Ham's F12 nutrient mix supplemented with 10% fetal bovine serum (FBS), 200 µg/mL zeocin or 100 µg/mL hygromycin, all obtained from ThermoFisher Scientific and used according to the manufacturer's instructions. Cells were cultured and incubated at 37° C. in a humidified oxygen atmosphere with 5% CO$_2$. To evaluate the activation of 5-HT$_{1A}$ signal transduction, cells were first seeded in tissue culture-treated, white-walled, clear-bottom 96-well plates (Corning, corning.com) at a density of 30,000 cells/well in 100 mL complete growth media. Cells were cultured for 24 h in a humidified incubator at 37° C. and 5% CO$_2$. Cells were then stimulated for 20 min with test compounds, prepared in titration beginning at 1 mM and dissolved in an induction medium (serum-free culture medium containing 4 µM forskolin (Sigma-Aldrich), 500 µM isobutyl-1-methylxanthine (IBMX, Sigma-Aldrich) and 100 µM RO 20-1724 (Sigma-Aldrich). Changes in intracellular cAMP levels were measured using the commercially available cAMP-Glo Assay Kit (Promega, promega.ca) following the manufacturers protocol. The level of luminescence derived from cells stimulated with induction medium alone was used to establish the max level of intracellular cAMP (100%) for each assay run. FIG. 6A shows increasing levels of cAMP in cultured cells incubated with increasing concentrations of forskolin (FSK) independent of 5-HT$_{1A}$ expression. FIG. 6B illustrates reduction in cAMP levels in 5-HT$_{1A}$ receptor expressing cells (+5-HT$_{1A}$) stimulated with 4 µM forskolin as levels of 8-OH-DPAT increase, indicating 5-HT$_{1A}$ receptor binding by 8-OH-DPAT in these cells. Conversely, this trend of decreasing % cAMP levels with increasing 8-OH-DPAT is not observed in cells lacking expression of 5-HT$_{1A}$ receptor. 8-OH-DPAT (7-(dipropylamino)-5,6,7,8-tetrahydronaphthalen-1-ol) is a well-established full agonist of the 5-HT$_{1A}$ receptor (Larsson et al., 1990, Neuropharmacology 29:85-91), and was included as a positive control to ensure functionality of the cellular response system. FIG. 6C illustrates reduction in cAMP levels in 5-HT$_{1A}$ receptor expressing cells (+5-HT$_{1A}$) stimulated with 4 µM forskolin as levels of serotonin increase, indicating 5-HT$_{1A}$ receptor binding by serotonin in these cells. Conversely, this trend of decreasing % cAMP levels with increasing serotonin is not observed in cells lacking expression of 5-HT$_{1A}$ receptor. Serotonin is the innate ligand of the 5-HT$_{1A}$ receptor and was thus included as a positive control. Psilocin, MDMA and 2C-B were included as calibrator compounds, since whereas these compounds are all known to bind 5-HT$_{1A}$ receptor to various degrees (Marcher-Rørsted et al., 2020, ACS Chem. Neurosci. 11: 1238; Simmler et al., 2013, British J. Pharmacol. 168: 458) their ability to elicit a cellular response in this particular functional assay is unknown. The binding mode of mescaline to the 5-HT$_{1A}$ receptor remains understudied but owing to the structural similarity of its phenylethylamine-type backbone to other derivatives within this application, it was included for comparative purposes. FIG. 6D illustrates reduction in cAMP levels in 5-HT$_{1A}$ receptor expressing cells (+5-HT$_{1A}$) stimulated with 4 mM forskolin as levels of psilocin increase, indicating 5-HT$_{1A}$ receptor binding by psilocin in these cells. Conversely, this trend of decreasing % cAMP levels with increasing psilocin is not observed in cells lacking expression of 5-HT$_{1A}$ receptor. FIG. 6E and FIG. 6F illustrate mild or no change in cAMP levels in 5-HT$_{1A}$ receptor expressing cells (+5-HT$_{1A}$) stimulated with 4 μM forskolin as levels of mescaline and MDMA increase, respectively. These results indicate mild or no 5-HT$_{1A}$ receptor engagement by mescaline or MDMA in this cellular system, respectively. FIG. 6G illustrates reduction in cAMP levels in 5-HT$_{1A}$ receptor expressing cells (+5-HT$_{1A}$) stimulated with 4 mM forskolin as levels of 2C-B increase, indicating 5-HT$_{1A}$ receptor engagement by 2C-B in these cells. Conversely, this trend of decreasing % cAMP levels with increasing 2C-B is not observed in cells lacking expression of 5-HT$_{1A}$ receptor. 5-HT$_{1A}$ receptor engagement evaluation for the compound designated diastereomer (viii) (as a second D(III) enantiomeric pair) (designated simply "D(III$_{enantiomer}$)" along the x-axis) is shown in FIG. 6H. Comparison of data acquired in +5-HT$_{1A}$ cultures with those acquired in −5-HT$_{1A}$ cultures indicates receptor modulation at evaluated ligand concentrations (EC$_{50}$=10.04 μM). Table 5 summarizes EC$_{50}$ data for all control, calibrator, and test compounds acquired using this functional 5-HT$_{1A}$ receptor assay. Additionally, the compound designated diastereomer (vii) (as a first D(III) enantiomeric pair) was assessed for 5-HT$_{1A}$ receptor modulation activity in an identical manner to that of compound designated diastereomer (viii). The resulting EC$_{50}$ (156 μM) indicates receptor modulation at higher ligand concentrations (Table 5).

TABLE 5

Data summary for functional 5-HT$_{1A}$ receptor assay.

| Molecule | 5-HT$_{1A}$, EC$_{50}$ (μM) |
|---|---|
| 5-OH-DPAT | 0.0007118 |
| serotonin | 0.001142 |
| psilocin | 0.9567 |
| mescaline | >1000 |
| 2C-B | 5.945 |
| MDMA | >1000 |
| A(III) | >1000 |
| D(I) as diast. (v) | >1000 |
| D(II) as diast. (vi) | >1000 |
| D(III) as diast. (vii) | 156 |
| D(III) as diast. (viii) | 10 |

In Vitro Survey of Pharmacological Interaction Profiles at Receptors and Transporters Linked to Targeted Health Conditions.

Compounds designated diastereomer (vii) (as a first D(III) enantiomeric pair) and diastereomer (viii) (as a second D(III) enantiomeric pair) were evaluated with respect to binding and/or interaction at 9 different receptors and transporters with known or suspected connections to mental health conditions and/or neurological pathologies. This study was conducted by the contracted research organization (CRO) Eurofins Cerep (Cell L'Evescault, France) using standard assay procedures (https://www.eurofinsdiscovery.com/solution/target-based-assays). Data was generated regarding interaction of derivative molecules with the following 6 GPCR receptors: HTR1A (5-HT$_{1A}$), HTR2B (5-HT$_{2B}$), HTR2C (5-HT$_{2C}$), HTR7 (5-HT$_7$), alpha2A ($\alpha_{2A}$), MT1 (MT$_1$), and 3 transporters (SERT, DAT, NET). Assays were conducted using the same materials and procedures outlined in Example 1, except the compounds designated diastereomer (vii) (as a first D(III) enantiomeric pair) and diastereomer (viii) (as a second D(III) enantiomeric pair) were used in place of the compound with formula A(III). Overall assay conditions are summarized in Tables 2 and 3 for GPCR and transporters, respectively. Results for all calibrator compounds, control compounds, and test compounds including compounds designated diastereomer (vii) (as a first D(III) enantiomeric pair) and diastereomer (viii) (as a second D(III) enantiomeric pair) are summarized in Table 4.

Example 7—Preparation of an Eleventh Fused Heterocyclic Mescaline Derivative

Referring to FIG. 3B, 3,4-(methylenedioxy)phenylacetic acid (compound 1) (10.0 g, 55.5 mmol) was dissolved in acetic anhydride (26.8 mL, 278 mmol) at room temperature, and the solution was stirred and purged with nitrogen for several minutes. The reaction was initiated by the dropwise addition of 1-methylimidazole (NMI) (2.23 mL, 27.8 mmol), and was continuously purged with a slow flow of nitrogen at room temperature until the starting material completely disappeared (TLC). After completion (16 h), water (5 mL) was added to the reaction flask. The reaction mixture was extracted with ethyl acetate (3×75 mL). The organic layers were combined and washed with saturated aq. NaHCO$_3$ (50 mL) followed by water, then dried over Na$_2$SO$_4$, filtered and concentrated. The crude product was purified using silica gel (120 g, EA/hex 0:100 to 50:50, 8 CV, product eluting at 20% EA) to afford the pure product compound 2 as a clear colorless oil (7.35 g, 74%).

$^1$H NMR (400 MHz, CDCl$_3$) δ 6.77 (d, J=7.8 Hz, 1H), 6.71-6.66 (m, 1H), 6.64 (ddd, J=7.8, 1.8, 0.5 Hz, 1H), 5.95 (s, 2H), 3.60 (s, 2H), 2.15 (s, 3H).

Continuing to refer to FIG. 3B, to a dry reaction vial was added sodium hydride (60% in mineral oil, 486 mg, 12.1 mmol) and dry THF (28.9 mL). While stirring under nitrogen, to the mixture was added a solution of 2 (2.06 g, 11.6 mmol) in THF (28.9 mL) dropwise, and the resulting mixture was stirred for 10 min (or until gas evolution was complete). Then, iodomethane (796 μL, 12.7 mmol) was added dropwise and the reaction mixture was stirred at RT for 1 h (or until completion). After 1 h, reaction was quenched with H$_2$O, volatiles were removed under reduced pressure and the residue was directly purified by FC on silica gel (40 g, EA/hex 0:100 to 80:20, 10 CV) to afford product 3, wherein R$_{1a}$=CH$_3$, as a light-yellow oil (1.7 g, 77%).

LRMS-HESI: calc'd for C$_{11}$H$_{13}$O$_3$ [M+H]$^+$ 193.09 m/z; observed 193.09.

$^1$H NMR (400 MHz, CDCl$_3$) δ 6.76 (dt, J=6.8, 1.0 Hz, 1H), 6.69-6.66 (m, 2H), 5.94 (s, 2H), 3.65 (q, J=7.0 Hz, 1H), 2.05 (s, 3H), 1.34 (d, J=6.9 Hz, 3H).

Continuing to refer to FIG. 3B, compound 3 (500 mg, 2.60 mmol), wherein R$_{1a}$=CH$_3$, was dissolved in MeOH (13.0 mL) followed by the addition of acetic acid (179 μL, 3.12 mmol). The solution was stirred for a few minutes before the addition of benzylamine (574 μL, 5.20 mmol). The reaction mixture was then heated up to 60° C. and stirred for 3 h. After 3 h, the reaction was cooled to RT and sodium cyanoborohydride (516 mg, 7.80 mmol) was added to the mixture and stirring was continued at room temperature for 18 h. Saturated aq. NaHCO$_3$ was added to the reaction, and the mixture was extracted with DCM (×3). The combined organic layers were washed with brine, dried over anhydrous Na$_2$SO$_4$, filtered, and concentrated to afford the crude product. The crude product was purified by FC on silica gel (25 g, MeOH/DCM 0:100 to 20:80, product eluting at 8% MeOH) to afford the pure product 4, wherein R$_{1a}$ is CH$_3$, R$_{2a}$=H, and R$_{2b}$=—(CH$_2$)-phenyl (mixture of two diastereomers) as a colorless oil (555 mg, 75%, with a d.r.: 2:1).

LRMS-HESI: calc'd for C$_{18}$H$_{22}$NO$_2$ [M+H]$^+$ 284.16 m/z; observed 284.18.

It is noted that the obtained product, compound 4, is a 2:1 mixture comprising of two inseparable diastereomers (ix) and (x), (based on $^1$H-NMR).

Diastereomers (ix) and (x): $^1$H NMR (400 MHz, CDCl$_3$) δ 7.37-7.19 (m, 4H), 7.15-7.11 (m, 1H), 6.74 (dd, J=7.9, 3.4 Hz, 1H), 6.71-6.61 (m, 2H), 5.96-5.92 (m, 2H), 3.84 (dd, J=23.2, 13.3 Hz, 1H), 3.67 (dd, J=44.4, 13.3 Hz, 1H), 2.78-2.60 (m, 2H), 1.24 (dd, J=33.8, 6.7 Hz, 3H), 1.04 (dd, J=56.6, 6.0 Hz, 3H).

It is noted that compound 4, wherein $R_{1a}$=CH$_3$, $R_{2a}$=H, $R_{2b}$=—(CH$_2$)-phenyl, corresponds with compounds $E_x$(VI) and $E_x$(VI$_d$):

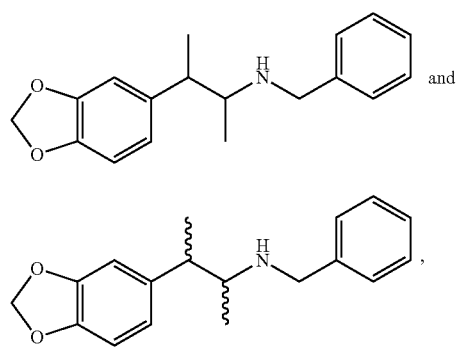

set forth herein.

Diastereomer (ix), wherein $R_{2a}$ is H, and $R_{2b}$ is —(CH$_2$)-phenyl, corresponds with a first pair of enantiomeric compounds, which can be the pair of syn-enantiomers ($E_x$(VI$_{da}$); ($E_x$(VI$_{dc}$)):

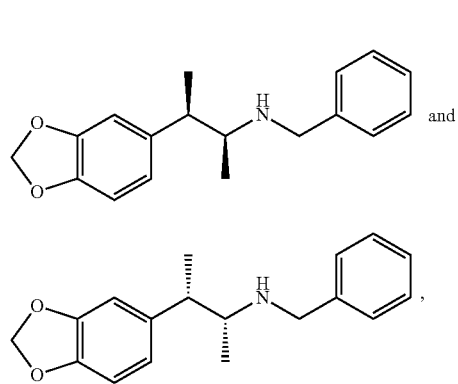

which was obtained as a racemic mixture, and a second pair of anti-enantiomers ($E_x$(VI$_{db}$); $E_x$(VI$_{dd}$)):

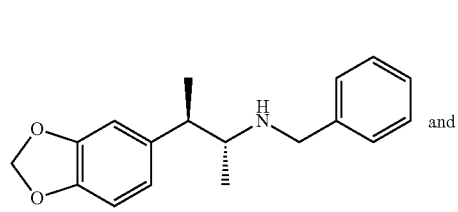

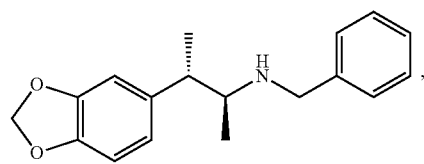

which was obtained as a racemic mixture, wherein in the first pair of enantiomers and second pair of enantiomers were present in the mixture in a molar ratio of 2:1.

Diastereomer (x), wherein $R_{2a}$ is H, and $R_{2b}$ is —(CH$_2$)-phenyl, corresponds with a first pair of enantiomeric compounds, which, can be the pair of syn-enantiomers ($E_x$(VI$_{da}$); ($E_x$(VI$_{dc}$)):

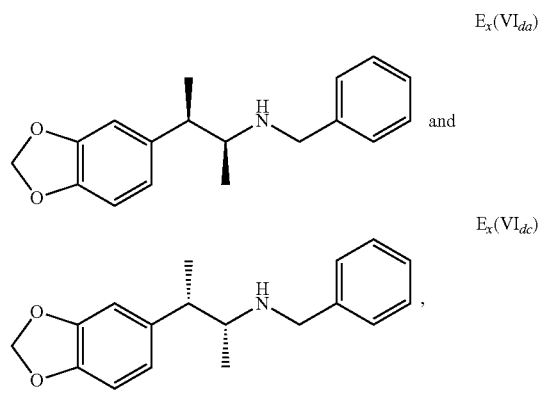

which was obtained as a racemic mixture, and a second pair of anti-enantiomers ($E_x$(VI$_{db}$); $E_x$(VI$_{dd}$)):

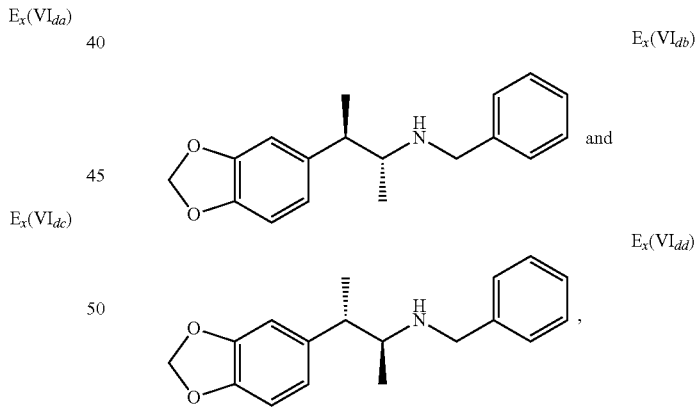

which was obtained as a racemic mixture, wherein in the first pair of enantiomers and second pair of enantiomers were present in the mixture in a molar ratio of 1:2. It is noted however that the accuracy of the analytical techniques used does leave some room for uncertainty with respect to the distinction between the first and second pair of enantiomers, and thus, alternatively, it is possible that the diastereoisomer (ix) corresponds with a mixture wherein in the mixture the first pair of enantiomers ($E_x$(VI$_{da}$); ($E_x$(VI$_{dc}$)) and second pair of enantiomers ($E_x$(VI$_{db}$); $E_x$(Vlad)) was present in a molar ratio of 1:2, respectively; and that diastereoisomer (x) corresponds with a mixture wherein in the mixture the first pair of enantiomers ($E_x(VI_{da})$; ($E_x(VI_{dc})$) and second pair of enantiomers ($E_x(VI_{db})$; $E_x(VI_{dd})$) was present in a molar ratio of 2:1, respectively.

5-HT Receptor Radioligand Competition Assays.

Activity at the 5-HT$_{1A}$ receptor was assessed as described for Example 1, except the compound with formula $E_x(VI)$ (as a 1:1 mixture of diastereomers (ix) and (x)) was evaluated in place of the compound with formula A(III). Table 1 shows radioligand competition assay results for positive controls, negative controls, and the compound with formula $E_x(VI)$ (as a 1:1 mixture of diastereomers (ix) and (x)) in the form of $K_i$ values. In view of results for both positive and negative controls, wherein negative controls yield data insufficient for reliable $K_i$ calculations (i.e., $K_i$>1000 mM), the $K_i$ value obtained for the compound with formula $E_x(VI)$ (as a 1:1 mixture of diastereomers (ix) and (x)) at the 5-HT$_{1A}$ receptor (65.9 µM; Table 1) indicates ligand-receptor binding.

Example 8—Preparation of a Twelfth and Thirteenth Fused Heterocyclic Mescaline Derivative Unmethylated compound 4, wherein $R_{1a}$ is CH$_3$, $R_{2a}$=H, and $R_{2b}$=—(CH$_2$)-phenyl, (i.e., compound $E_x(VI)$) was prepared as described in Example 7. Referring to FIG. 3B, a vial was charged with a 2:1 diastereomeric mixture of unmethylated compound 4 (200 mg, 706 µmol), wherein $R_{1a}$ is CH$_3$, $R_{2a}$=H, and $R_{2b}$=—(CH$_2$)-phenyl, and formic acid (133 µL, 3.53 mmol). To this solution was added formaldehyde (37% in water, 78.8 µL, 2.12 mmol) and the resulting mixture was placed at 90° C. (CAUTION: ensure the vial is vented!). A vigorous evolution of carbon dioxide was observed after 2-3 minutes, then the vial was removed from the heat until the gas evolution notably subsided (15-20 minutes). Then, it was again placed at 90° C. and stirred for 3 hours. The reaction mixture was cooled to room temperature and basified to pH 8-10 (sat'd NaHCO$_3$). The aq. layer was extracted with DCM (×3). The combined organic layers were washed with brine, dried over anhydrous Na$_2$SO$_4$, filtered, and concentrated to afford methylated compound 4 (193 mg, 92% with a d.r. of 2:1), wherein $R_{1a}$ is CH$_3$, $R_{2a}$=CH$_3$, and $R_{2b}$=—(CH$_2$)-phenyl, as a light-yellow oil and an otherwise clean mixture of the two diastereomers, diastereomer (xi) and diastereomer (xii).

LRMS-HESI [M+H]$^+$ 298.17 m/z.

Diastereomer (xi) could not be separated from diastereomer (xii).

Diastereomer (xi) and diastereomer (xii): $^1$H NMR (400 MHz, CDCl$_3$) δ 7.41-7.30 (m, 2H), 7.21-7.14 (m, 2H), 6.99-6.93 (m, 1H), 6.72 (ddd, J=7.6, 7.1, 0.4 Hz, 1H), 6.65-6.57 (m, 2H), 5.96-5.90 (m, 2H), 3.71-3.53 (m, 1H), 3.41 (dd, J=42.4, 13.6 Hz, 1H), 2.81-2.62 (m, 2H), 2.11 (d, J=40.6 Hz, 3H), 1.36-1.14 (m, 3H), 1.08-0.71 (m, 3H).

It is noted that methylated compound 4, wherein $R_{1a}$ is CH$_3$, $R_{2a}$=CH$_3$, and $R_{2b}$=—(CH$_2$)-phenyl, corresponds with compounds $E_x(III)$ and $E_x(III_d)$:

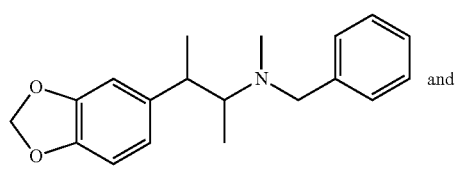

$E_x(III)$ and

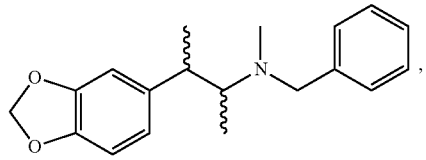

$E_x(III_d)$ set forth herein.

Diastereomer (xi), wherein $R_{2a}$ is —CH$_3$, and $R_{2b}$ is —(CH$_2$)-phenyl, corresponds with a first pair of enantiomeric compounds, which, can be the pair of syn-enantiomers ($E_x(III_{da})$; ($E_x(III_{dc})$):

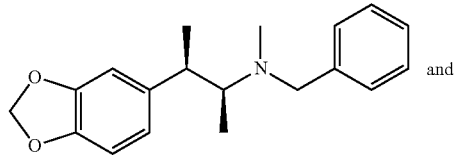

$E_x(III_{da})$ and

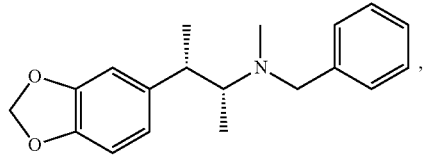

$E_x(III_{dc})$, which was obtained as a racemic mixture, and a second pair of anti-enantiomers ($E_x(III_{db})$; $E_x(III_{dd})$):

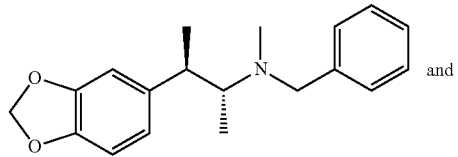

$E_x(III_{db})$ and

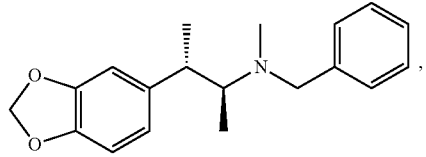

$E_x(III_{dd})$, which was obtained as a racemic mixture, wherein in the first pair of enantiomers and second pair of enantiomers were present in the mixture in a molar ratio of 2:1.

Diastereomer (xii), wherein $R_{2a}$ is —CH$_3$, and $R_{2b}$ is —(CH$_2$)-phenyl, corresponds with a first pair of enantiomeric compounds, which can be the pair of syn-enantiomers ($E_x(III_{da})$; ($E_x(III_{dc})$):

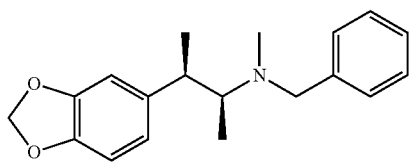

E$_x$(III$_{da}$)

and

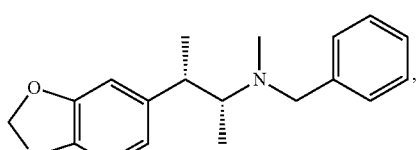

E$_x$(III$_{dc}$)

, which was obtained as a racemic mixture, and a second pair of anti-enantiomers (E$_x$(III$_{db}$); E$_x$(III$_{dd}$)):

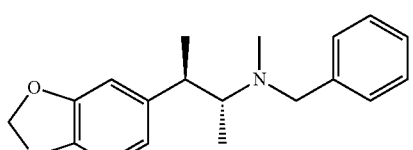

E$_x$(III$_{db}$)

and

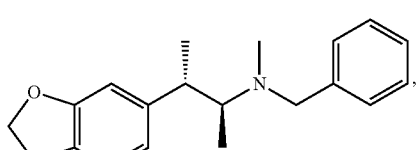

E$_x$(III$_{dd}$)

, which was obtained as a racemic mixture, wherein in the first pair of enantiomers and second pair of enantiomers were present in the mixture in a molar ratio of 1:2. It is noted however that the accuracy of the analytical techniques used does leave some room for uncertainty with respect to the distinction between the first and second pair of enantiomers, and thus, alternatively, it is possible that the diastereoisomer (xi) corresponds with a mixture wherein in the mixture the first pair of enantiomers (E$_x$(III$_{da}$); (E$_x$(III$_{dc}$)) and second pair of enantiomers (E$_x$(III$_{db}$); E$_x$(III$_{dd}$)) was present in a molar ratio of 1:2, respectively; and that diastereoisomer (xii) corresponds with a mixture wherein in the mixture the first pair of enantiomers (E$_x$(III$_{da}$); (E$_x$(III$_{dc}$)) and second pair of enantiomers (E$_x$(III$_{db}$); E$_x$(III$_{dd}$)) was present in a molar ratio of 2:1, respectively.

Example 9—Preparation of a Fourteenth and Fifteenth Fused Heterocyclic Mescaline Derivative Referring to FIG. 3B, compound 2, was prepared as described in Example 7.

Continuing to refer to FIG. 3B, compound 3, wherein R$_{1a}$=CH$_3$, was prepared as described in Example 7.

Continuing to refer to FIG. 3B, compound 3 (109 mg, 567 µmol), wherein R$_{1a}$=CH$_3$, was dissolved in MeOH (2.84 mL) followed by the addition of acetic acid (39.0 µL, 680 µmol), the reaction mixture was stirred for a few minutes before the addition of azetidine (76.5 µL, 1.13 mmol). The reaction mixture was then heated up to 60° C. and stirred for 3 h. The reaction mixture was cooled to RT and sodium cyanoborohydride (113 mg, 1.70 mmol) was added to the mixture and stirring was continued at room temperature for 18 h. Sat'd aq. NaHCO$_3$ was added (10 drops) to the reaction and volatiles were removed in vacuo. The crude residue was directly purified by FC on silica gel (4 g, MeOH/DCM 0:100 to 20:80) to afford the clean product as a dark yellow oil, and as a mixture of two diastereomers. The isolated material was re-purified by FC on silica gel (12 g, MeOH/DCM 0:100 to 20:80, product eluting at 10% MeOH) to afford compound 4, wherein R$_{1a}$ is CH$_3$, R$_{2a}$ and R$_{2b}$ together with the nitrogen atom form a 4-membered heterocycle, as two semi-pure diastereomers (xiii) and (xiv) (each containing 18% of the other diastereomer, d.r.=9:2).

LRMS-HESI: [M+H]$^+$ calculated 234.15, found 234.15 m/z

Diastereomers (xiii) and (xiv) were isolated

Diastereomer (xiii): $^1$H NMR (400 MHz, CDCl$_3$) δ 6.78 (d, J=0.6 Hz, 1H), 6.77 (d, J=1.7 Hz, 1H), 6.74 (d, J=1.6 Hz, 1H), 5.96 (s, 2H), 3.76 (d, J=51.9 Hz, 4H), 3.18 (dt, J=7.8, 6.5 Hz, 1H), 3.04-2.96 (m, 1H), 2.41-2.28 (m, 2H), 1.28 (d, J=7.1 Hz, 3H), 1.22 (d, J=6.6 Hz, 3H).

Diastereomer (xiv): $^1$H NMR (400 MHz, CDCl$_3$): 6.79 (dt, J=7.8, 0.7 Hz, 1H), 6.67-6.63 (m, 2H), 5.97 (s, 2H), 3.98 (dq, J=15.4, 7.8 Hz, 4H), 3.34 (dd, J=6.9, 5.6 Hz, 1H), 3.04 (td, J=7.2, 5.4 Hz, 1H), 2.44 (s, 2H), 1.35 (d, J=7.2 Hz, 3H), 1.19 (d, J=6.7 Hz, 3H).

It is noted that compound 4, wherein R$_{1a}$ is CH$_3$, R$_{2a}$ and R$_{2b}$ together with the nitrogen atom form a 4-membered heterocycle, corresponds with compounds E$_x$(VII) and E$_x$(VII$_d$):

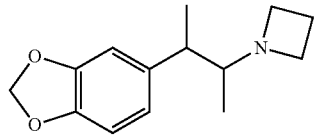

E$_x$(VII)

and

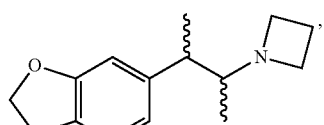

E$_x$(VII$_d$)

, set forth herein.

Diastereomer (xiii), wherein R$_{2a}$ and R$_{2b}$ together with the nitrogen atom form a 4-membered heterocycle, corresponds with a first pair of enantiomeric compounds, which, notably, can be the pair of syn-enantiomers (E$_x$(VII$_{da}$); E$_x$(VII$_{dc}$)):

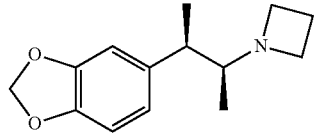

E$_x$(VII$_{da}$)

and

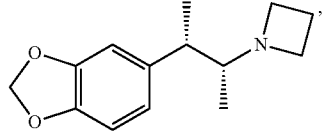

E$_x$(VII$_{dc}$)

, which was obtained as a racemic mixture.

Diastereomer (xiv), wherein $R_{2a}$ and $R_{2b}$ together with the nitrogen atom form a 4-membered heterocycle, corresponds with a second pair of enantiomeric compounds, which can be the pair of anti-enantiomers ($E_x(VII_{db})$; $E_x(VII_{dd})$):

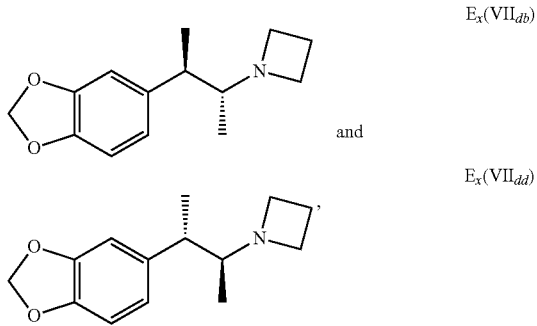

which were obtained as a racemic mixture. It is noted however that the accuracy of the analytical techniques used does leave some room for uncertainty with respect to the distinction between the first and second pair of enantiomers, and thus, alternatively, it is possible that the diastereoisomer (xiii) corresponds with the anti-enantiomeric pair ($E_x(VII_{db})$; $E_x(VII_{dd})$), and diastereoisomer (xiv) corresponds with the syn-enantiomeric pair ($E_x(VII_{da})$; $E_x(VII_{dc})$).

Example 10—Preparation of a Sixteenth Fused Heterocyclic Mescaline Derivative Referring to FIG. 3C, 1,4-benzodioxane-6-acetic acid (compound 1) (2.0 g, 10.3 mmol) was dissolved in acetic anhydride (4.97 mL, 51.5 mmol) at room temperature, and the solution was stirred and purged with nitrogen for several minutes. The reaction was initiated by the dropwise addition of 1-methylimidazole (NMI) (415 µL, 5.15 mmol), and was continuously purged with a slow flow of nitrogen at room temperature until the starting material completely disappeared (TLC). After completion (16 h), water (5 mL) was added to the reaction flask. The reaction mixture was extracted with ethyl acetate (×3). The organic layers were combined and washed with saturated aq. NaHCO₃, followed by water, then dried over Na₂SO₄, filtered and concentrated. The crude product was purified using silica gel (25 g, EA/hex 0:100 to 70:30, 12 CV, product eluting at 30% EA) to afford the pure product compound 2 as a clear colorless oil (760 mg, 38%).

¹H NMR (400 MHz, CDCl₃) δ 6.82 (d, J=8.1 Hz, 1H), 6.72 (d, J=2.1 Hz, 1H), 6.68-6.65 (m, 1H), 4.25 (s, 4H), 3.58 (s, 2H), 2.14 (s, 3H).

Continuing to refer to FIG. 3C, to a dry reaction vial was added sodium hydride (60% in mineral oil, 52.4 mg, 1.31 mmol) and THF (3.12 mL). While stirring under nitrogen, to the mixture was added a solution of compound 2 (240 mg, 1.25 mmol) in THF (3.12 mL) dropwise, and the resulting mixture was stirred for 10 min (or until gas evolution was complete). Then, iodoethane (112 µL, 1.37 mmol) was added dropwise and the reaction mixture was stirred at RT until completion. After 22 h, the reaction was quenched with H₂O (1 mL), volatiles were removed in vacuo and the residue was directly purified by FC on silica gel (12 g, EA/hex 0:100 to 60:40, product eluting at 30% EA) to afford the pure compound 3, wherein $R_{1a}$=CH₂CH₃, as a colorless oil (84 mg, 31%).

Continuing to refer to FIG. 3C, compound 3, wherein $R_{1a}$=CH₂CH₃, (84.0 mg, 381 µmol) was dissolved in MeOH (1.91 mL) followed by the addition of acetic acid (26.2 µL, 458 µmol), and the reaction mixture was stirred for a few minutes before the addition of benzylamine (84.2 µL, 763 µmol). The reaction mixture was then heated up to 60° C. and stirred for 3 h. After 3 h, the reaction was cooled to RT and sodium cyanoborohydride (75.7 mg, 1.14 mmol) was added to the mixture and stirring was continued at room temperature for 18 h. Saturated aq. NaHCO₃ was added (5 mL) to the reaction, and the mixture was extracted with DCM (×3). The combined organic layers were washed with brine, dried over anhydrous Na2SO4, filtered, and concentrated to afford the crude product. The crude product was purified by FC on silica gel (4 g, MeOH/DCM 0:100 to 20:80, product eluting at 13% MeOH) to afford the pure compound 4, wherein $R_{1a}$ is CH₂CH₃, $R_{2a}$=H, and $R_{2b}$=—(CH₂)-phenyl, as a colorless oil and a single unknown diastereomer (28 mg, 24%), diastereomer (xv).

LRMS-HESI: [M+H]⁺ 312.20 m/z.

Diastereomer (xv) was isolated.

Diastereomer (xv): ¹H NMR (400 MHz, CDCl₃) δ 7.29-7.24 (m, 2H), 7.23-7.18 (m, 1H), 7.14-7.10 (m, 2H), 6.78 (d, J=8.2 Hz, 1H), 6.64 (d, J=2.1 Hz, 1H), 6.60 (dd, J=8.2, 2.1 Hz, 1H), 4.25 (s, 4H), 3.69 (dd, J=84.1, 13.5 Hz, 2H), 2.70 (dq, J=7.9, 6.2 Hz, 1H), 2.30 (ddd, J=11.4, 7.9, 3.9 Hz, 1H), 1.79 (dqd, J=13.4, 7.4, 4.0 Hz, 1H), 1.50-1.39 (m, 1H), 1.11 (d, J=6.2 Hz, 3H), 0.69 (t, J=7.4 Hz, 3H).

It is noted that compound 4, wherein $R_{1a}$ is CH₂CH₃, $R_{2a}$=H, and $R_{2b}$=—(CH₂)-phenyl, corresponds with compounds $E_y(VIII)$ and $E_y(VIII_d)$:

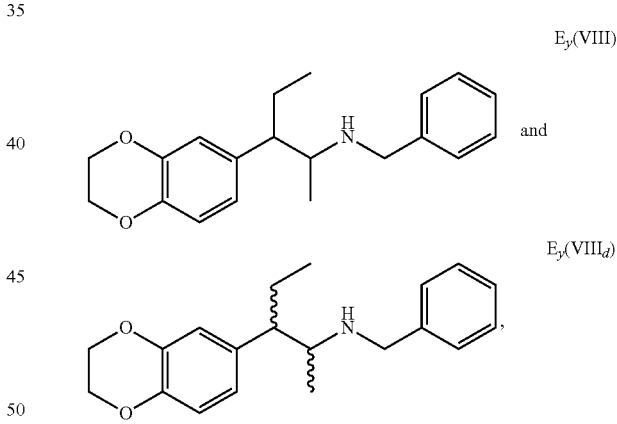

set forth herein.

Diastereomer (xv), corresponds with a first pair of enantiomeric compounds, which can be the pair of syn-enantiomers ($E_y(VIII_{da})$; $E_y(VIII_{dc})$):

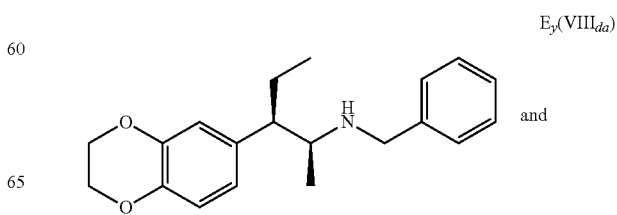

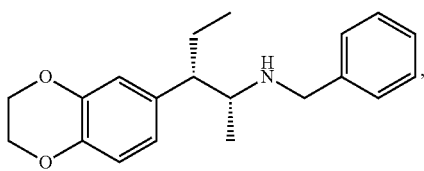

E_y(VIII_dc)

or with a second pair of enantiomeric compounds which can be the pair of anti-enantiomers (E_y(VIII_db); E_y(VIII_dd)):

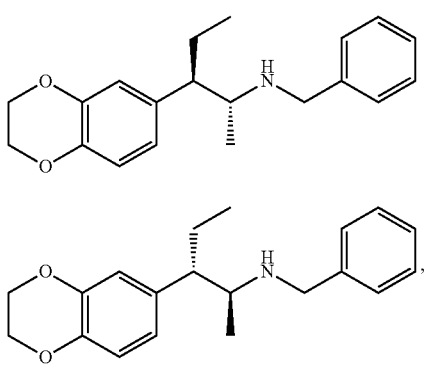

E_y(VIII_db)

and

E_y(VIII_dd)

which was obtained as a racemic mixture. It is noted however that the accuracy of the analytical techniques used does leave some room for uncertainty with respect to the distinction between the first and second pair of enantiomers, and thus, it is possible that obtained diastereoisomer (xv) corresponds with anti-enantiomeric pair (E_y(VIII_db); E_y(VII-I_dd)), or with syn-enantiomeric pair (E_y(VIII_da); E_y(VIII_dc)).

The invention claimed is:

1. A chemical compound having chemical formula (I) or chemical formula (II):

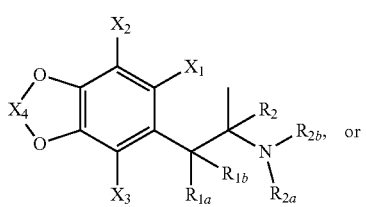

(I)

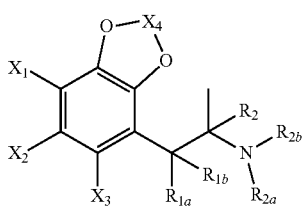

(II)

wherein, in chemical formula (I) and chemical formula (II):

$X_1$, $X_2$, and $X_3$ are independently selected from a hydrogen atom, O-alkyl, N-alkyl, OH, a halogen, or $NH_2$;

$X_4$ is an alkylene group or substituted alkylene group;

$R_{1a}$ is a halogen, and $R_{1b}$ is a hydrogen atom or a halogen;

$R_2$ is a hydrogen atom or an O-alkyl group; and $R_{2a}$ and $R_{2b}$ are independently selected from an alkyl group, an optionally substituted alkyl-aryl group, or a hydrogen atom, or $R_{2a}$ and $R_{2b}$ are joined together, along with the nitrogen atom to which they are attached, to form a 3-10-membered optionally substituted heterocyclic ring.

2. A chemical compound according to claim 1, wherein $X_4$ is a $C_1$-$C_3$ alkylene group.

3. A chemical compound according to claim 1, wherein the chemical compound has a chemical formula ($I_b$) or ($II_b$):

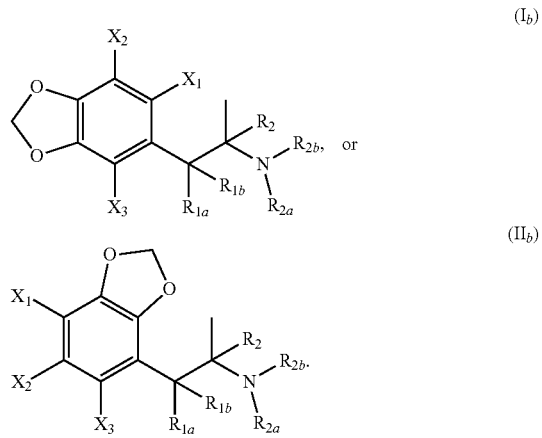

4. A chemical compound according to claim 1, wherein the amino group (—NR_{2a}R_{2b}) in the compound of formula (I) or formula (II) is protonated to form (—N^+HR_{2a}R_{2b}), and chemical formula (I) or formula (II) further includes a negatively charged anion balancing the positively charged nitrogen atom.

5. A chemical compound according to claim 1, wherein $X_1$, $X_2$, $X_3$, and $R_2$ are each a hydrogen atom (H).

6. A chemical compound according to claim 1, wherein $R_2$ is a hydrogen atom.

7. A chemical compound according to claim 1, wherein $R_{2a}$ and $R_{2b}$ is independently selected from a hydrogen atom, an optionally substituted alkyl-aryl group, or an alkyl group, optionally, a ($C_1$-$C_6$)-alkyl group, ($C_1$-$C_3$)-alkyl group.

8. A chemical compound according to claim 1, wherein the optionally substituted alkyl-aryl group is a ($C_1$-$C_6$)-alkyl-aryl group, a ($C_1$-$C_3$)-alkyl-aryl group, or a —$CH_2$-aryl group, wherein the aryl group is optionally substituted by at least one of a halogen atom, an O-alkyl group, optionally a ($C_1$-$C_6$)—O-alkyl group or a ($C_1$-$C_3$)—O-alkyl group, and additionally two adjacent substituents are joined together, along with the carbon atoms from the aryl group to form a ($C_5$-$C_{10}$)-heterocycle, optionally a ($C_5$)-heterocycle, optionally including two oxygen atoms.

9. A chemical compound according to claim 8, wherein the aryl group is a phenyl group.

10. A chemical compound according to claim 1, wherein the chemical compound having formula (I) has the chemical formula (D):

(D)

11. A chemical compound according to claim 1, wherein the chemical compound having formula (I) is selected from the group of compounds having the chemical formula:
(D): D(I); D(II); D(III); D(IV); D(V); and D(VI):

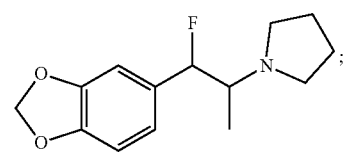
D(I)

D(II)

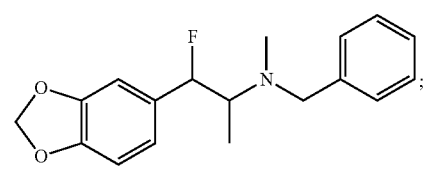
D (III)

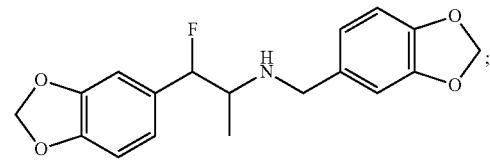
D (IV)

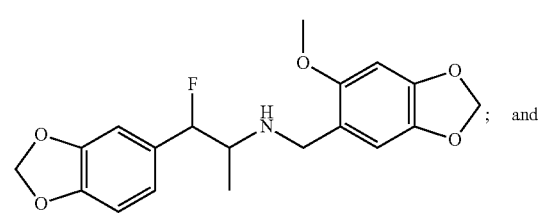
D(V)

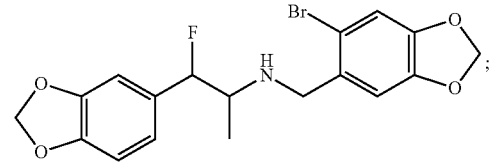
D(VI)

and
wherein in each of compound D(I) to D(VI), optionally, the nitrogen atom of the isopropylamine portion may be protonated and includes a negatively charged anion balancing the positively charged nitrogen atom.

12. A chemical compound according to claim 1, wherein (A) $R_{1a}$ a halogen, and $R_{1b}$ is a hydrogen atom or a halogen, provided however, $R_{1a}$ and $R_{1b}$ are not identical halogens, and the compound having chemical formula (I) or formula (II) has the chemical formula $(I_d)$ or $(III_d)$:

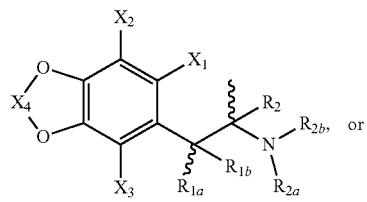
$(I_d)$

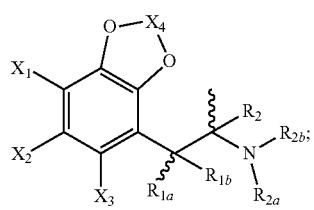
$(II_d)$ or
(B) $R_{1a}$ is a halogen, and $R_{1b}$ is a hydrogen atom or a halogen, provided however, that $R_{1a}$ and $R_{1b}$ are not identical halogens, and the compound having chemical formula (I) or formula (II) has the chemical formula $(I_e)$ or $(II_e)$:

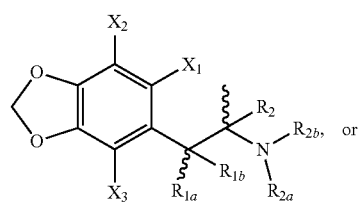
$(I_e)$

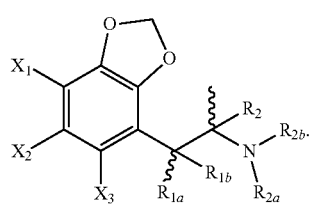
$(II_e)$

13. A chemical compound according to claim 12, wherein the compound is a compound included in a mixture of a pair of enantiomeric compounds, the mixture comprising a first and second enantiomeric compound of a pair of enantiomers of formula $(I_d)$, $(II_d)$, $(I_e)$, or $(II_e)$.

14. A chemical compound according to claim 12, wherein the compound is a first enantiomeric compound of a pair of enantiomers consisting of a first and second enantiomeric compounds of formula $(I_d)$, $(II_d)$, $(I_e)$, or $(II_e)$ wherein the first enantiomeric compound is substantially free of a second enantiomeric compound, the second enantiomeric compound being the other compound of the pair of enantiomers.

15. A chemical compound according to claim 12, wherein the compound is a compound included in a mixture of a pair of diastereomeric compounds, the mixture comprising a first and second diastereomeric compound of a pair of diastereomers of formula $(I_d)$, $(II_d)$, $(I_e)$, or $(II_e)$.

16. A chemical compound according to claim 12, wherein the compound is a first diastereomeric compound of a pair of diastereomers consisting of a first and second diastereomeric compound of formula ($I_d$), ($II_d$), ($I_e$), or ($II_e$), wherein the first diastereomeric compound is substantially free of a second diastereomeric compound, the second diastereomeric compound being the other diastereomeric compound of the pair of diastereomers.

17. A chemical compound according to claim 12, wherein the chemical compound having formula ($I_d$) has chemical formula ($D_d$):

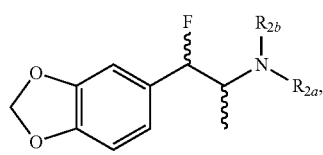

($D_d$)

wherein $R_{2a}$ and $R_{2b}$ are independently selected from an alkyl group, an optionally substituted alkyl-aryl group, or a hydrogen atom, or $R_{2a}$ and $R_{2b}$ are joined together, along with the nitrogen atom to which they are attached, to form a 3-10-membered optionally substituted heterocyclic ring.

18. A chemical compound according to claim 12, wherein the chemical compound having formula ($I_d$) or ($I_g$) is selected from the group of compounds selected from:

(D): D($I_d$); D($II_d$); D($III_d$); D($IV_d$); D($V_d$); and D($VI_d$):

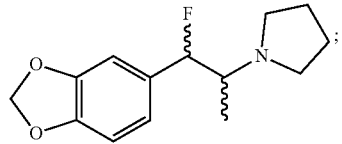

D($I_d$)

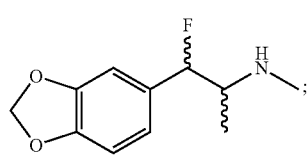

D($II_d$)

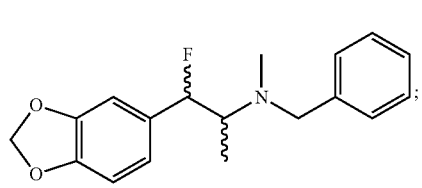

D($III_d$)

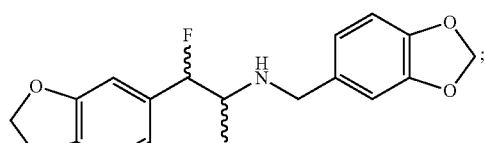

D($IV_d$)

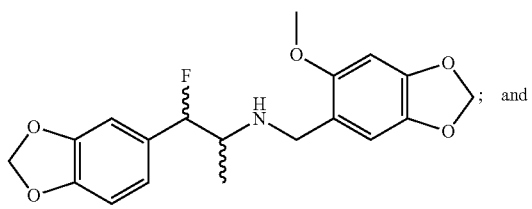

D($V_d$)

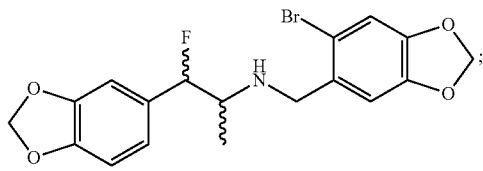

D($VI_d$)

and wherein in each of compound D($I_d$) to D($VI_d$), optionally, the nitrogen atom of the isopropylamine portion is protonated and includes a negatively charged anion balancing the positively charged nitrogen atom.

19. A chemical compound according to claim 12, wherein the chemical compound having formula ($I_d$) is selected from the group of compounds selected from D($I_{da}$); D($I_{db}$); D($I_{dc}$); D($I_{dd}$); D($II_{da}$); D($II_{db}$); D($II_{dc}$); D($II_{dd}$); D($III_{da}$); D($III_{db}$); D($III_{dc}$); and D($III_{dd}$):

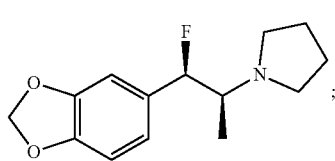

D($I_{da}$)

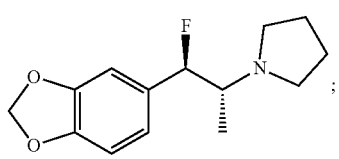

D($I_{db}$)

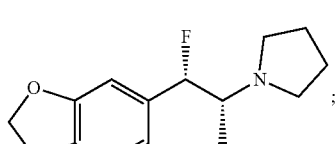

D($I_{dc}$)

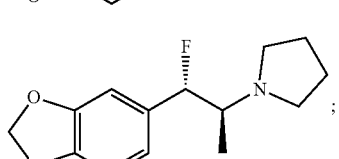

D($I_{dd}$)

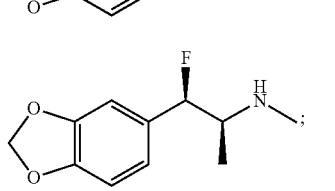

D($II_{da}$)

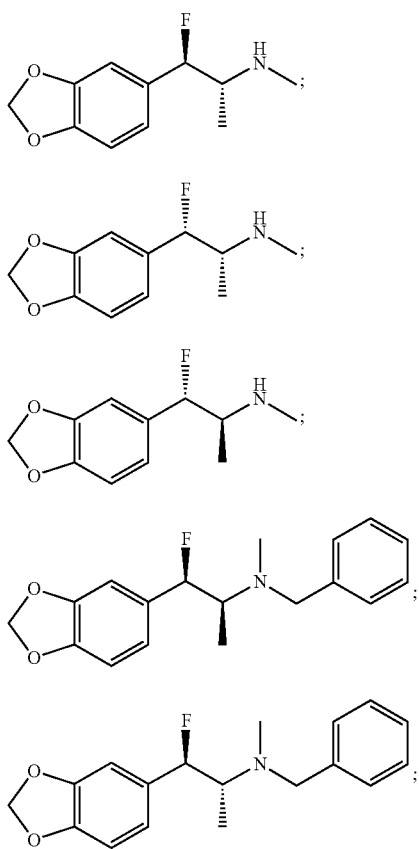

D(II_db)

D(II_dc)

D(II_dd)

D(III_da)

D(III_db)

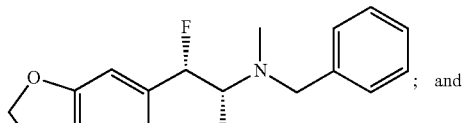

D(III_dc)

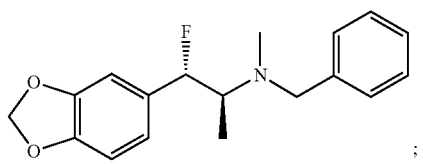

D(III_dd)

wherein in each of compound $D(I_{da})$, $D(I_{db})$, $D(I_{dc})$, $D(I_{dd})$, $D(II_{da})$, $D(II_{db})$, $D(II_{dc})$, $D(II_{dd})$, $D(III_{da})$, $D(III_{db})$, $D(III_{dc})$, and $D(III_{dd})$, optionally, the nitrogen atom of the isopropylamine portion is protonated and includes a negatively charged anion balancing the positively charged nitrogen atom.

20. A pharmaceutical or recreational drug formulation comprising an effective amount of a chemical compound according to claim 1, together with a pharmaceutically acceptable excipient, diluent, or carrier.

21. A pharmaceutical or recreational drug formulation comprising an effective amount of a chemical compound according to claim 19, together with a pharmaceutically acceptable excipient, diluent, or carrier.

\* \* \* \* \*